United States Patent
Sheng et al.

(10) Patent No.: US 12,404,269 B2
(45) Date of Patent: Sep. 2, 2025

(54) AMINOQUINAZOLINONE AND AMINOISOQUINOLINONE DERIVATIVES AND APPLICATION THEREOF

(71) Applicants: ZHEJIANG UNIVERSITY, Hangzhou (CN); SHANGHAI INSTITUTE OF MATERIA MEDICA, CHINESE ACADEMY OF SCIENCES, Shanghai (CN)

(72) Inventors: Rong Sheng, Hangzhou (CN); Jia Li, Shanghai (CN); Dongyan Gu, Hangzhou (CN); Yubo Zhou, Shanghai (CN); Jun Wei, Hangzhou (CN); Mengmeng Zhang, Shanghai (CN); Yongzhou Hu, Hangzhou (CN); Kaixiang Zhang, Shanghai (CN); Jieyu Liu, Shanghai (CN); Weijuan Kan, Shanghai (CN)

(73) Assignees: ZHEJIANG UNIVERSITY, Hangzhou (CN); SHANGHAI INSTITUTE OF MATERIA MEDICA, CHINESE ACADEMY OF SCIENCES, Shanghai (CN)

(*) Notice: Subject to any disclaimer, the term of this patent is extended or adjusted under 35 U.S.C. 154(b) by 1105 days.

(21) Appl. No.: 17/358,002

(22) Filed: Jun. 25, 2021

(65) Prior Publication Data
US 2022/0017505 A1 Jan. 20, 2022

Related U.S. Application Data

(63) Continuation of application No. PCT/CN2019/122973, filed on Dec. 4, 2019.

(30) Foreign Application Priority Data

Dec. 25, 2018 (CN) .......................... 201811593915.2

(51) Int. Cl.
| | | |
|---|---|---|
| C07D 413/14 | (2006.01) | |
| C07D 239/95 | (2006.01) | |
| C07D 401/14 | (2006.01) | |
| C07D 403/12 | (2006.01) | |
| C07D 417/12 | (2006.01) | |

(Continued)

(52) U.S. Cl.
CPC ......... *C07D 413/14* (2013.01); *C07D 239/95* (2013.01); *C07D 401/14* (2013.01); *C07D 403/12* (2013.01); *C07D 417/12* (2013.01); *C07D 471/04* (2013.01);
(Continued)

(58) Field of Classification Search
CPC ................ C07D 413/14; C07D 239/95; C07D 401/14
See application file for complete search history.

(56) References Cited

FOREIGN PATENT DOCUMENTS

| CN | 101631464 A | 1/2010 |
|---|---|---|
| CN | 101965336 A | 2/2011 |

(Continued)

OTHER PUBLICATIONS

International Search Report (PCT/CN2019/122973); Date of Mailing: Mar. 3, 2020.
CN First Office Action(201811593915.2); Date of Mailing: Feb. 6, 2020.
Discovery and SAR of Novel 2,3-Dihydroimidazo[1,2-c]-quinazoline PI3K Inhibitors: Identification of Copanlisib(BAY 80-6946); Date of Mailing: Jun. 16, 2016.

(Continued)

*Primary Examiner* — Sarah Pihonak
*Assistant Examiner* — Mikhail O'Donnel Robinson
(74) *Attorney, Agent, or Firm* — Wiersch Law Group

(57) ABSTRACT

Provided by the present disclosure are an amino quinazolinone and amino isoquinolone derivatives. It is verified by numerous experiments that the compounds provided by the present disclosure have good inhibiting effects on PI3Kα and PI3Kγ, most of the compounds have prominent inhibiting effect on PI3Kα, and show strong growth inhibiting effect on PIK3CA mutant tumor cells such as human breast cancer cell strain (MCF7). Therefore, the amino quinazolinone and amino isoquinolone derivatives according to the present disclosure can be applied in the preparation of anti-tumor and anti-inflammatory medicines, and can be used as PI3Kα inhibitors in the preparation of medicines for treatment of human or animal cell proliferation related tumors, the medicines comprising the derivatives any one or more of pharmaceutically acceptable salts and solvates thereof as well as pharmaceutically acceptable carriers. Formulas a and b are shown as below:

Structural General Formula a

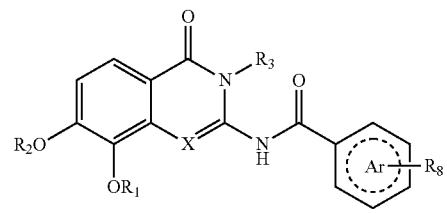

Structural General Formula b

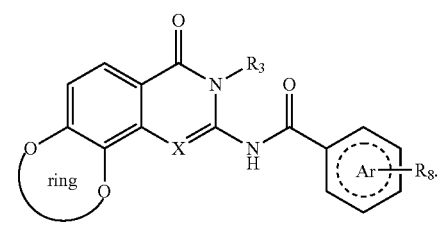

8 Claims, 1 Drawing Sheet

(51) Int. Cl.
 *C07D 471/04* (2006.01)
 *C07D 473/00* (2006.01)
 *C07D 491/056* (2006.01)
 *C07D 491/107* (2006.01)

(52) U.S. Cl.
 CPC ....... *C07D 473/00* (2013.01); *C07D 491/056* (2013.01); *C07D 491/107* (2013.01)

(56) References Cited

FOREIGN PATENT DOCUMENTS

| | | | |
|---|---|---|---|
| CN | 103946226 A | 7/2014 | |
| CN | 103998442 A | 8/2014 | |
| CN | 109516961 A | 3/2019 | |
| IN | 101965335 A | 2/2011 | |
| WO | 2008070150 A1 | 6/2008 | |
| WO | 2008140750 A1 | 11/2008 | |
| WO | 2012037204 A1 | 3/2012 | |
| WO | WO-2012158913 A2 * | 11/2012 | ........... A61K 31/513 |

OTHER PUBLICATIONS

Extended European Search Report (19904796.0), Date of Mailing: Aug. 31, 2022 .

* cited by examiner

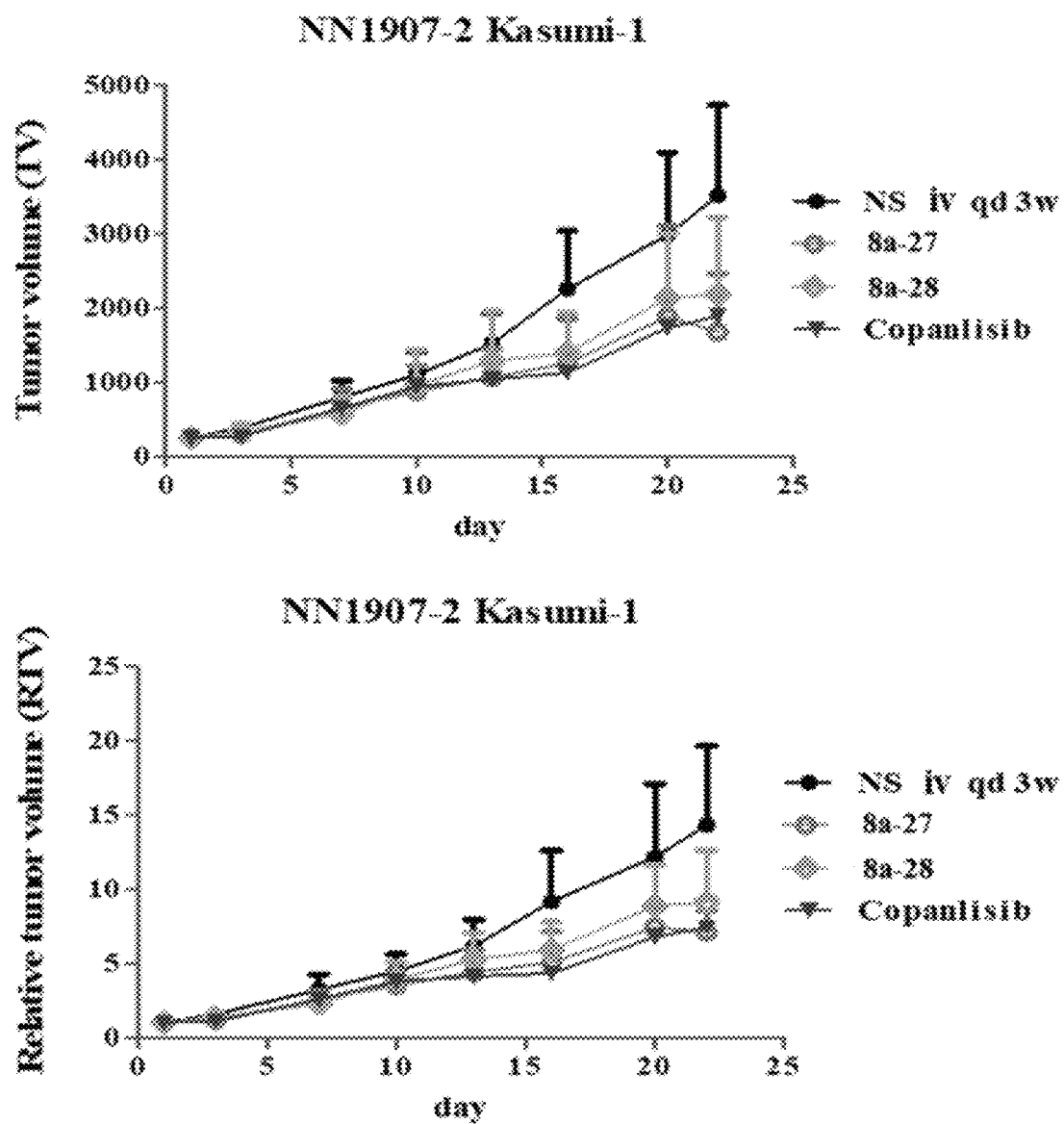

AMINOQUINAZOLINONE AND AMINOISOQUINOLINONE DERIVATIVES AND APPLICATION THEREOF

TECHNICAL FIELD

The present disclosure relates to the technical field of medicine, and in particular, to an aminoquinazolinone and aminoisoquinolinone derivatives, a pharmaceutical composition including the same, and the application thereof in the fields of anti-tumor, anti-inflammatory diseases and the like.

BACKGROUND

In recent years, though significant progress has been made in the field of early diagnosis and treatment of tumors, and anti-tumor drugs have been able to control or delay the development of some tumors, such as leukemia, the treatment of solid tumors that account for more than 90% of malignant tumors is far from satisfactory. The PI3K/Akt/mTOR signaling pathway regulates various cellular processes, such as cell division and growth. It found by research that this signaling pathway is often over-activated in tumor cells, and the key kinase PI3K is often in a state of overexpression in tumor cells. PI3K has a variety of subtypes, and thus the inhibition against PI3K has gradually become an effective means on tumor treatment. On the other hand, the subtypes PI3Kγ and PI3Kδ of PI3K kinase are closely related to inflammation, and thus PI3Kγ and PI3Kδ inhibitors can be used for the treatment of inflammatory diseases, such as arthritis, etc.

As a popular target of anti-tumor drugs, a number of PI3K inhibitors have entered clinical studies, and two of which have been approved for marketing by the FDA: Idelalisib, a PI3Kδ inhibitor developed by Gilead in 2015, was approved for the treatment of relapsed chronic lymphocytic leukemia, follicular lymphoma and small lymphocytic lymphoma; Copanlisib, developed by Bayer in September 2017, also received accelerated approval from the FDA for the treatment of relapsed follicular lymphoma and has received adult patients with at least two systemic therapy.

Though many PI3K inhibitors have been developed, the two drugs that have been marketed still have certain insufficiencies. For example, Idelalisib causes elevated transaminase in CLL patients and has certain toxic side effects on the liver; while Copanlisib has high activity against multiple PI3K subtypes, but the selectivity is poor, and the physicochemical properties of Copanlisib are not good, thus its pharmacokinetic properties are not good, the volume of distribution is large with reaching 32.6 L/kg, which is easy to store in patients, thus triggering corresponding toxic and side effects, therefore the clinical medication is administered by injection on respectively the 1st, 8th and 15th days within a 28-day treatment cycle. Therefore, modifying and optimizing the structure of Copanlisib, and adjusting its physicochemical properties, is expected to improve its pharmacokinetic properties, adjust its selectivity for each subtypes of PI3K, and obtain new anti-tumor and anti-inflammatory drugs that are more suitable for clinical use.

SUMMARY

In view of the insufficiencies of the prior art, the technical problem to be solved by the present disclosure is to provide aminoquinazolinone and aminoisoquinolinone derivatives, which have the structures of General Formulas a and b, or pharmaceutically acceptable salts, stereoisomers or solvates thereof.

Structural General Formula a

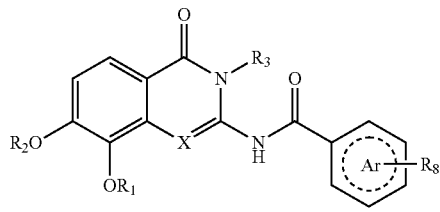

Structural General Formula b

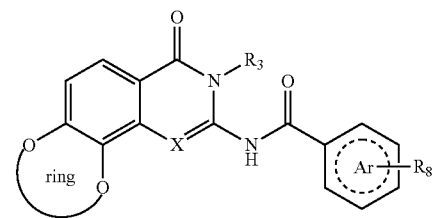

wherein, (1) For Structural General Formula a:

X=N or CH;

$R_1$ is selected from hydrogen, $C_{1-6}$ alkyl, cycloalkyl, or fluoroalkyl, $R_2$ is selected from hydrogen, $C_{1-12}$ alkyl, cycloalkyl, fluoroalkyl, —$(CH_2)_n NR_5 R_6$, —$(CH_2)_n$—$CONR_5 R_6$, —$(CH_2)_n$—$SO_2 NR_5 R_6$, or —$(CH_2)_n OR_5$, wherein n is an integer selected from 1 to 8, $R_5$ and $R_6$ are independent of each other, may be the same or different, and are selected from hydrogen, $C_{1-4}$ alkyl, or $C_{1-4}$ cycloalkyl, or $NR_5 R_6$ is a 4-8 membered cyclic amine, including but not limited to morpholine, piperazine, pyrrolidine, piperidine, or a cyclic amine substituted with $R_7$ which is selected from hydrogen, $C_{1-6}$ alkyl, $C_{1-6}$ alkoxy, $C_{2-6}$ unsaturated aliphatic chain hydrocarbon group, $C_{3-8}$ cycloalkyl, $C_{3-8}$ unsaturated alicyclic group, $C_{3-8}$ saturated aliphatic heterocyclic group, halogen, amino, or cyano;

$R_3$ is selected from $C_{1-6}$ alkyl, cycloalkyl, or fluoroalkyl;

Ar is an aromatic heterocyclic ring, including but not limited to benzene ring, furan ring, thiophene ring, pyrrole ring, thiazole ring, pyrazole ring, oxazole ring, pyridine ring, pyrimidine ring, pyridazine ring, pyrazine ring, purine ring, azapurine ring, azaindole ring, indole ring, quinoline ring, quinazoline ring, quinoxaline ring, or indazole ring;

$R_8$ is selected from hydrogen, halogen, cyano, hydroxyl, $C_{1-6}$ alkoxy, amino, $C_{1-6}$ alkylamino, $C_{1-6}$ dialkylamino, $C_{1-6}$ alkyl, $C_{2-6}$-unsaturated fat chain hydrocarbon group, $C_{3-8}$ cycloalkyl, $C_{3-8}$ unsaturated alicyclic group, $C_{3-8}$ saturated aliphatic heterocyclic group, or $C_{1-6}$ haloalkyl; and (2) For Structural General Formula b:

The two adjacent oxygen atoms on the benzene ring of the quinazoline or quinoline are connected by different chains to form a 5-21 membered ring, and the chain can contain 2-7 oxygen atoms; the rest of the structure has the same definition as the Structural General Formula a:

Furthermore, in the preferred aminoquinazolinone and aminoisoquinolinone compounds of the present disclosure, when $R_1$ in the Structural General Formula a is a methyl, $R_2$ is selected from but not limited to the following groups:

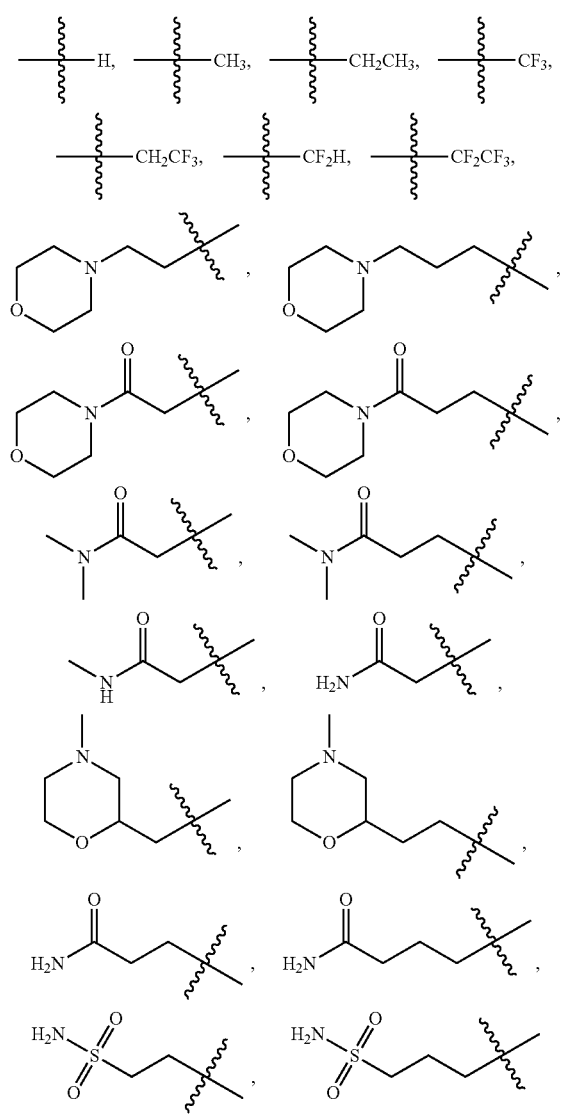

Furthermore, in the preferred aminoquinazolinone and aminoisoquinolinone compounds of the present disclosure, the 5-21 membered ring formed by connecting the two oxygen atoms on the benzene ring by chains described for the Structural General Formula b is selected from but not limited to the following groups:

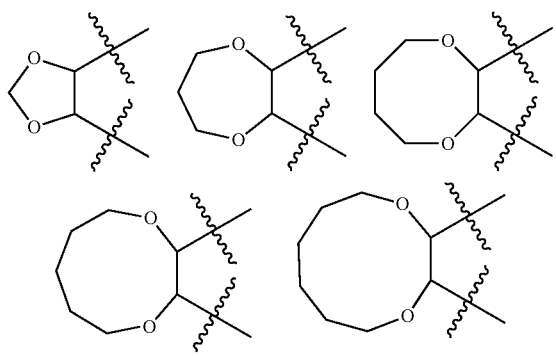

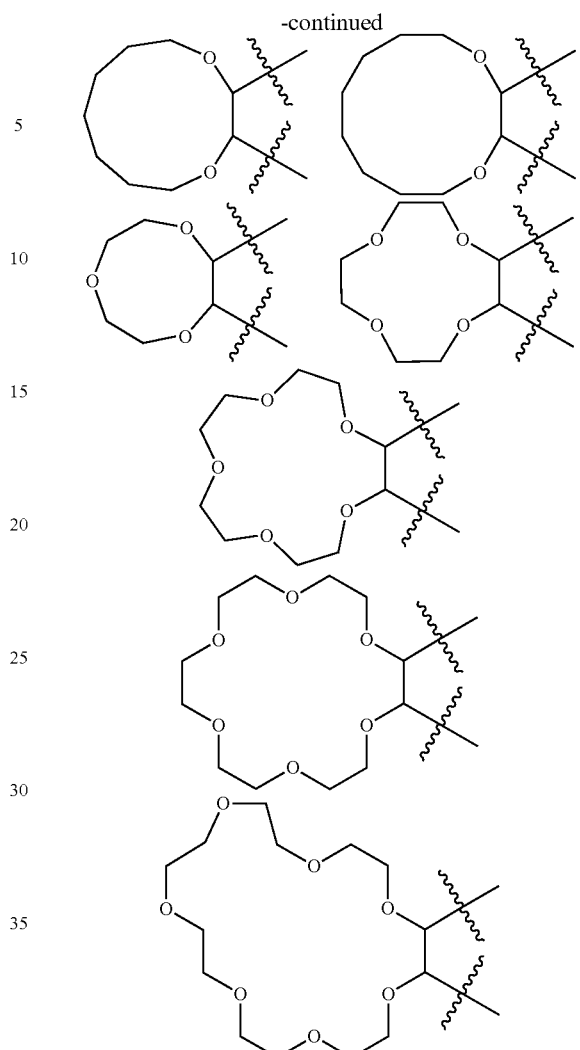

Furthermore, in the preferred aminoquinazolinone and aminoisoquinolinone compounds of the present disclosure, in the Structural General Formula a and the Structural General Formula b, $R_3$ is preferably selected from —$CH_3$, —$CH_2CH_3$, cyclopropyl, —$CH_2CH_2CH_3$, —$CH(CH_3)_2$, —$CH_2CF_3$, or —$CH_2CF_2H$;

Furthermore, in the preferred aminoquinazolinone and aminoisoquinolinone compounds of the present disclosure, in the Structural General Formula a and the Structural General Formula b, Ar is preferably selected from 4-methoxyphenyl, p-aminophenyl, 5-amino-pyrazol-3-yl, 2-amino-imidazol-4-yl, 2-amino-thiazol-4-yl, 2-amino-oxazol-4-yl, pyridin-3-yl, pyridin-2-yl, 2-amino-pyridin-5-yl, 2-amino-pyrimidin-5-yl, 2-amino-pyrazin-5-yl, or 3-amino-pyridazin-6-yl; $R_8$ is selected from amino, methylamino, hydroxyl, methoxy, dimethylamino, cyano, or 3,4-dimethoxy.

It should be noted that, the present disclosure includes all combinations and sub-combinations of the specific groups defined in the present disclosure, and includes the substitutions defined in the above summary, illustrated in the various embodiments throughout the specification and described in the attached claims.

More specifically, the preferred compounds of the aminoquinazolinone and aminoisoquinolinone derivatives having the structures of the General Formula a or b of the present disclosure are as follows:

| Compd. | Structure |
|---|---|
| 7a-1 | 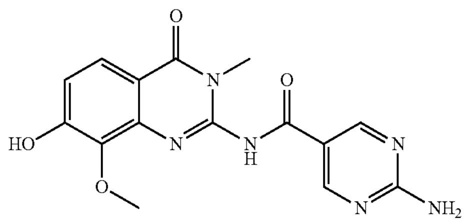 [SMILES: COc1c(O)ccc2c(=O)n(C)c(NC(=O)c3cnc(N)nc3)nc12] |
| 8a-1 | 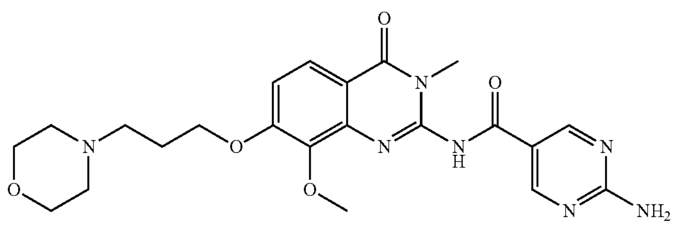 [SMILES: COc1c(OCCCN2CCOCC2)ccc2c(=O)n(C)c(NC(=O)c3cnc(N)nc3)nc12] |
| 8a-2 | 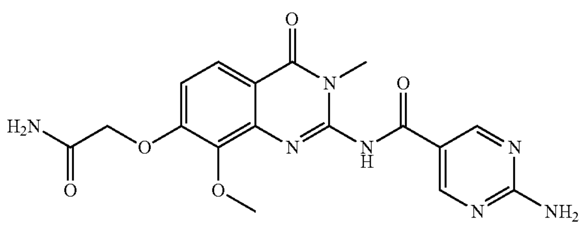 [SMILES: COc1c(OCC(N)=O)ccc2c(=O)n(C)c(NC(=O)c3cnc(N)nc3)nc12] |
| 8a-3 | 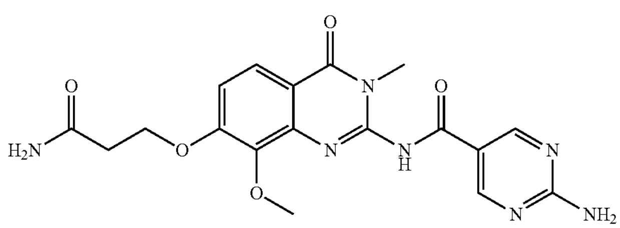 [SMILES: COc1c(OCCC(N)=O)ccc2c(=O)n(C)c(NC(=O)c3cnc(N)nc3)nc12] |
| 8a-4 | 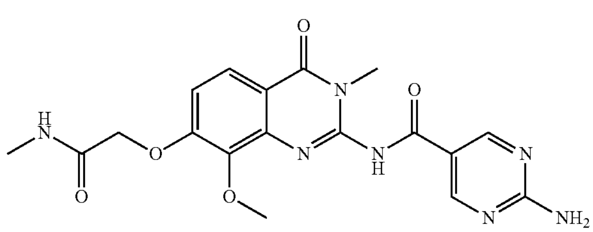 [SMILES: CNC(=O)COc1ccc2c(=O)n(C)c(NC(=O)c3cnc(N)nc3)nc2c1OC] |
| 8a-5 | 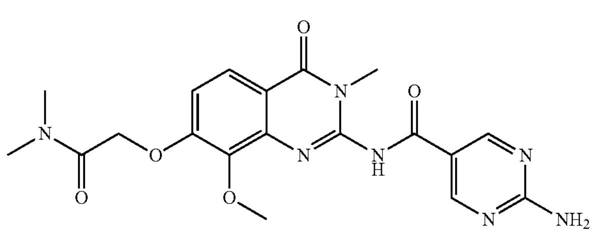 [SMILES: COc1c(OCC(=O)N(C)C)ccc2c(=O)n(C)c(NC(=O)c3cnc(N)nc3)nc12] |

| Compd. | Structure |
|---|---|
| 8a-6 | 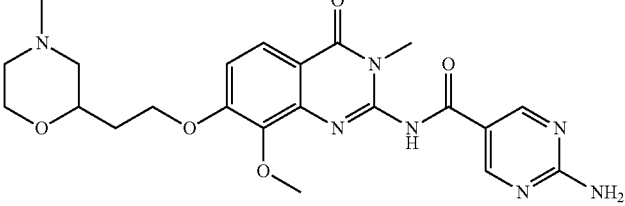 |
| 8a-7 | 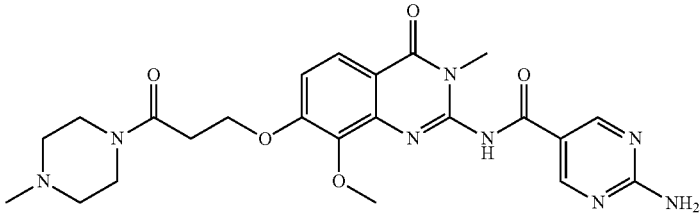 |
| 8a-8 | 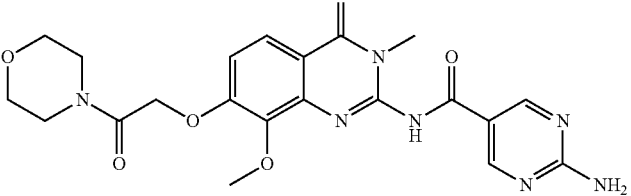 |
| 8a-9 | 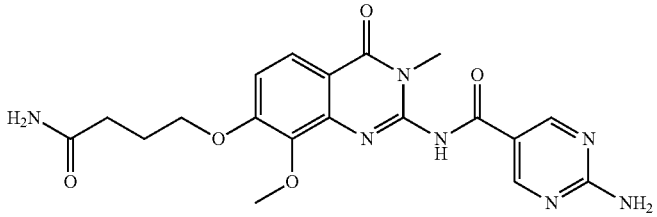 [SMILES: COc1c(OCCCC(N)=O)ccc2c(=O)n(C)c(NC(=O)c3cnc(N)nc3)nc12] |
| 8a-10 | 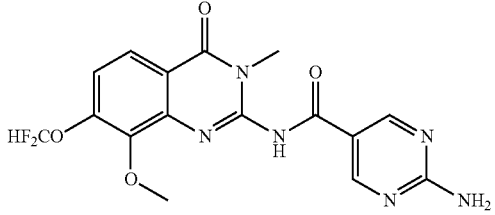 |
| 8a-11 | 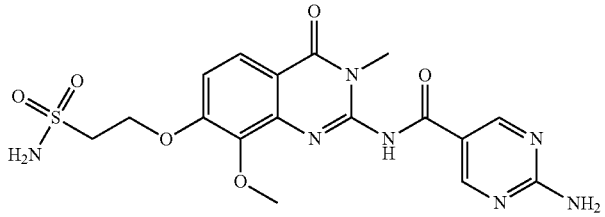 [SMILES: COc1c(OCCS(N)(=O)=O)ccc2c(=O)n(C)c(NC(=O)c3cnc(N)nc3)nc12] |
| 8a-12 | 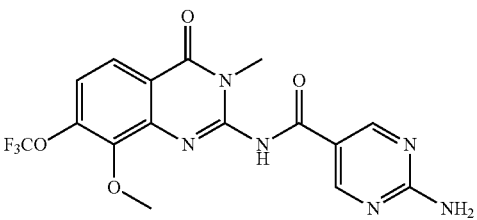 |

| Compd. | Structure |
|---|---|
| 8a-13 | 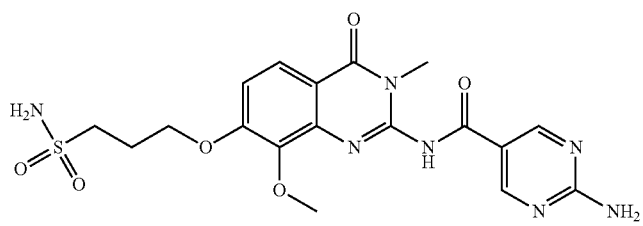 [SMILES: COc1c(OCCCS(N)(=O)=O)ccc2c(=O)n(C)c(NC(=O)c3cnc(N)nc3)nc12] |
| 8a-14 | 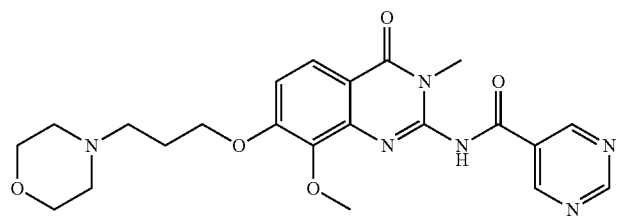 [SMILES: COc1c(OCCCN2CCOCC2)ccc2c(=O)n(C)c(NC(=O)c3cncnc3)nc12] |
| 8a-15 | 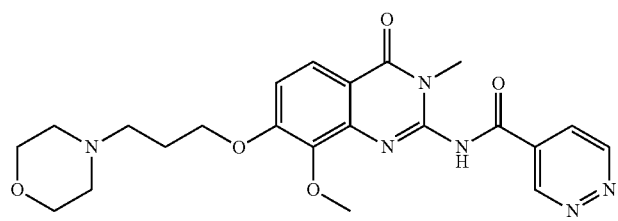 [SMILES: COc1c(OCCCN2CCOCC2)ccc2c(=O)n(C)c(NC(=O)c3ccnnc3)nc12] |
| 8a-16 | 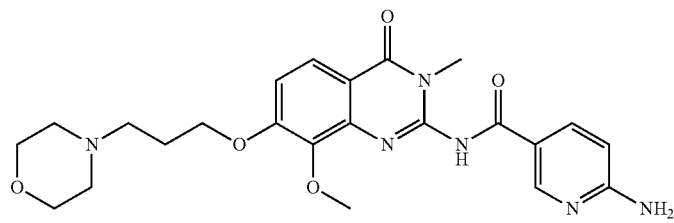 |
| 8a-17 | 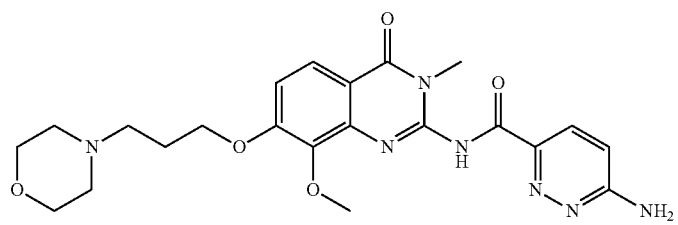 |
| 8a-18 | 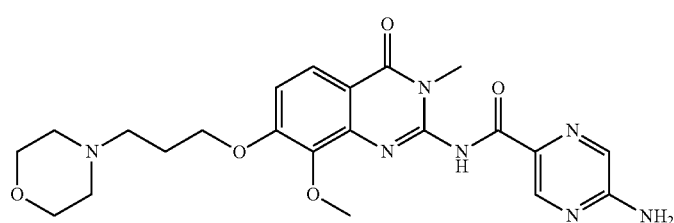 |
| 8a-19 | 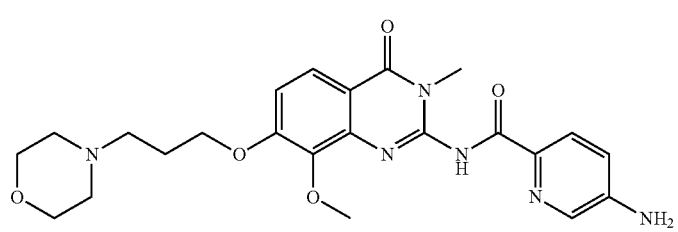 [SMILES: COc1c(OCCCN2CCOCC2)ccc2c(=O)n(C)c(NC(=O)c3ccc(N)cn3)nc12] |

| Compd. | Structure |
|---|---|
| 8a-20 | 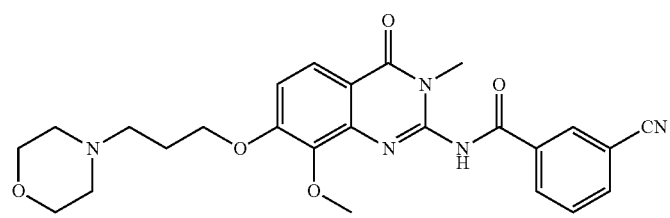 |
| 8a-21 | 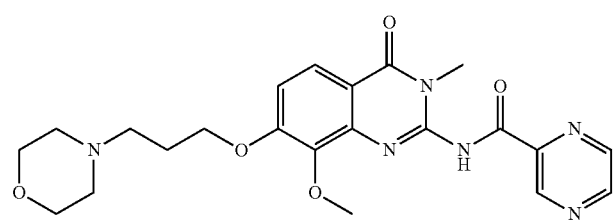 [SMILES: COc1c(OCCCN2CCOCC2)ccc2c(=O)n(C)c(NC(=O)c3cnccn3)nc12] |
| 8a-22 | 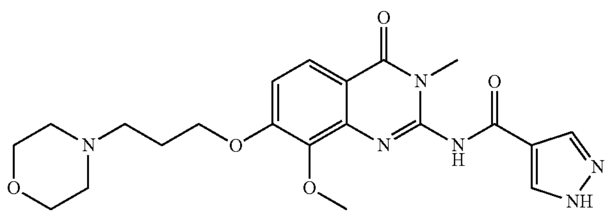 [SMILES: COc1c(OCCCN2CCOCC2)ccc2c(=O)n(C)c(NC(=O)c3cn[nH]c3)nc12] |
| 8a-23 | 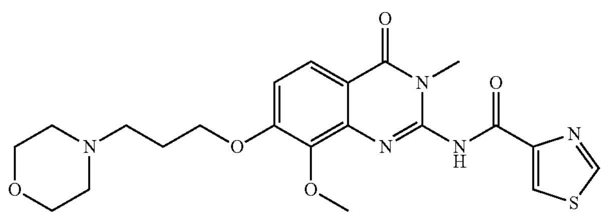 [SMILES: COc1c(OCCCN2CCOCC2)ccc2c(=O)n(C)c(NC(=O)c3cscn3)nc12] |
| 8a-24 | 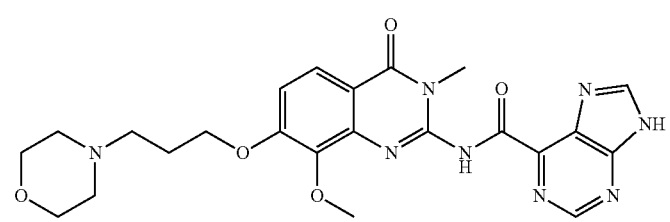 [SMILES: COc1c(OCCCN2CCOCC2)ccc2c(=O)n(C)c(NC(=O)c3ncnc4[nH]cnc34)nc12] |
| 8a-25 | 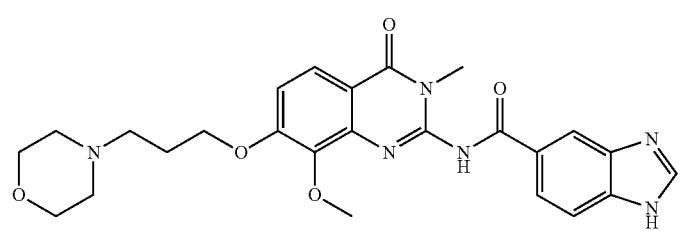 [SMILES: COc1c(OCCCN2CCOCC2)ccc2c(=O)n(C)c(NC(=O)c3ccc4[nH]cnc4c3)nc12] |
| 8a-26 | 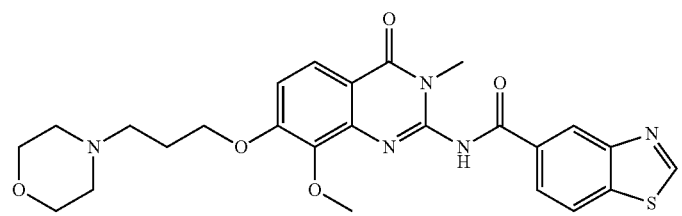 |

-continued

| Compd. | Structure |
|---|---|
| 8a-27 | 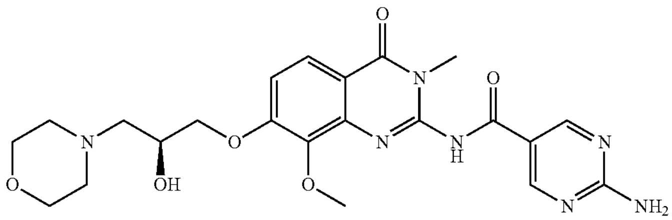 |
| 8a-28 | 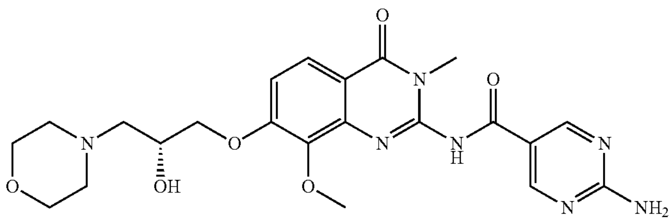 |
| 8a-29 | 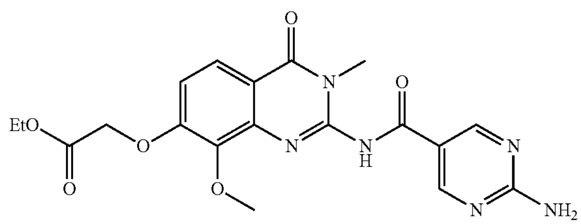 [SMILES: CCOC(=O)COc1ccc2c(=O)n(C)c(NC(=O)c3cnc(N)nc3)nc2c1OC] |
| 8a-30 | 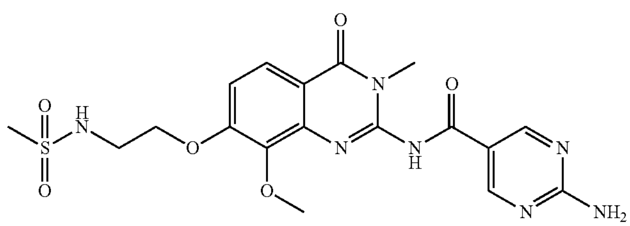 [SMILES: COc1c(OCCNS(C)(=O)=O)ccc2c(=O)n(C)c(NC(=O)c3cnc(N)nc3)nc12] |
| 8a-31 | 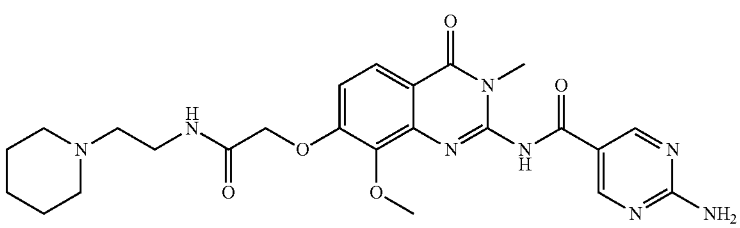 [SMILES: COc1c(OCC(=O)NCCN2CCCCC2)ccc2c(=O)n(C)c(NC(=O)c3cnc(N)nc3)nc12] |
| 8a-32 | 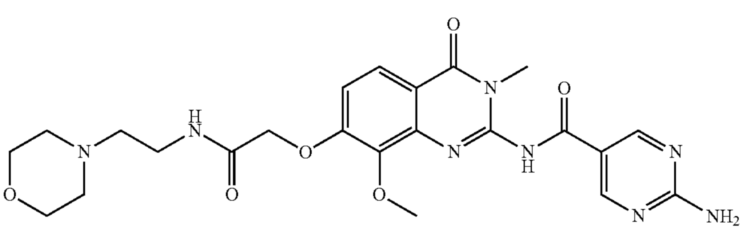 |
| 8a-33 | 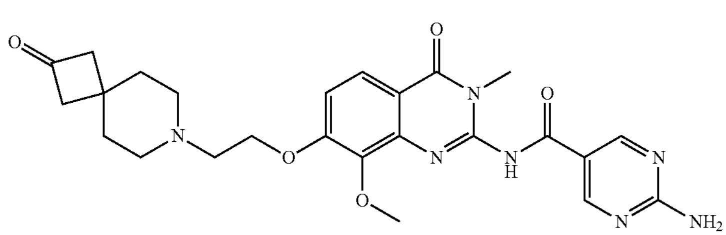 [SMILES: COc1c(OCCN2CCC3(CC2)CC(=O)C3)ccc2c(=O)n(C)c(NC(=O)c3cnc(N)nc3)nc12] |

| Compd. | Structure |
|---|---|
| 8a-34 | 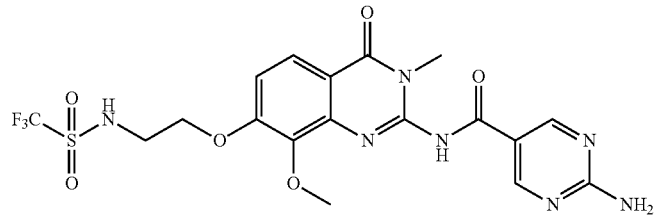 [SMILES: COc1c(OCCNS(=O)(=O)C(F)(F)F)ccc2c(=O)n(C)c(NC(=O)c3cnc(N)nc3)nc12] |
| 8a-35 | 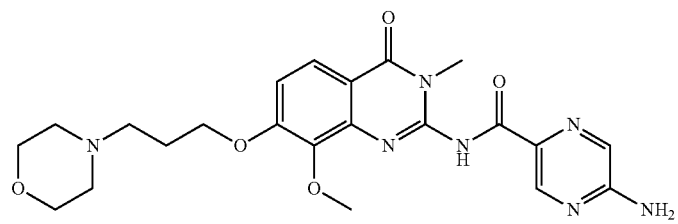 [SMILES: COc1c(OCCCN2CCOCC2)ccc2c(=O)n(C)c(NC(=O)c3cnc(N)cn3)nc12] |
| 8a-36 | 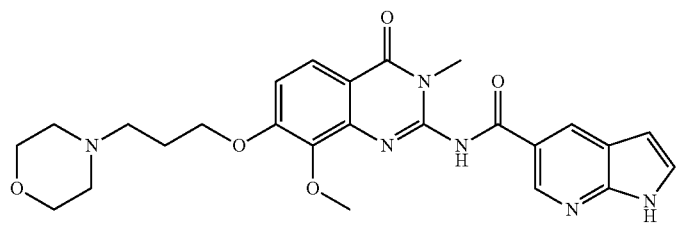 [SMILES: COc1c(OCCCN2CCOCC2)ccc2c(=O)n(C)c(NC(=O)c3cnc4[nH]ccc4c3)nc12] |
| 8a-37 | 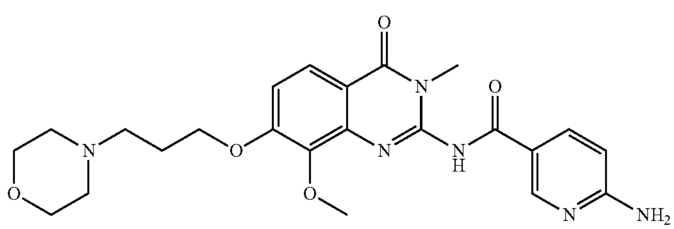 |
| 8a-38 | 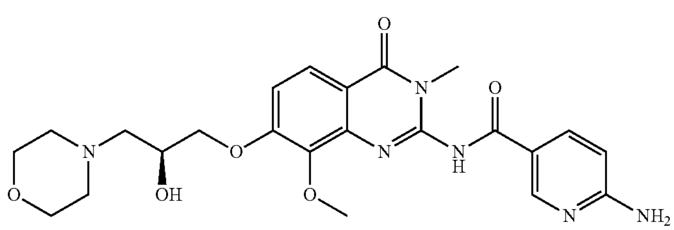 [SMILES: COc1c(OC[C@@H](O)CN2CCOCC2)ccc2c(=O)n(C)c(NC(=O)c3ccc(N)nc3)nc12] |
| 8a-39 | 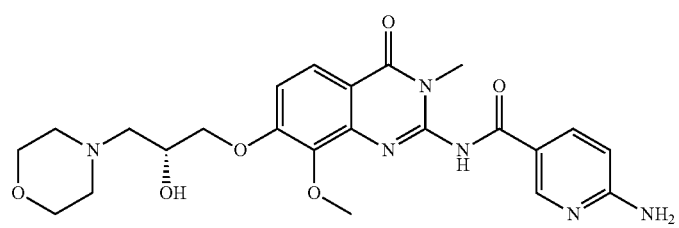 |

| Compd. | Structure |
|---|---|
| 8a-40 | 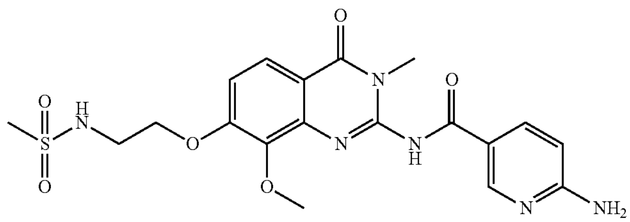 |
| 8a-41 | 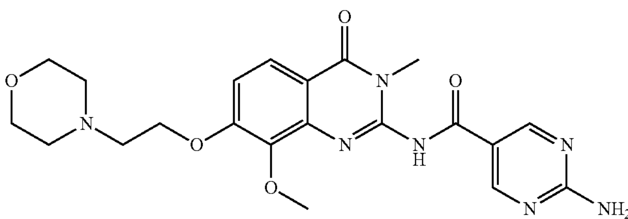 [SMILES: COc1c(OCCN2CCOCC2)ccc2c(=O)n(C)c(NC(=O)c3cnc(N)nc3)nc12] |
| 8a-42 | 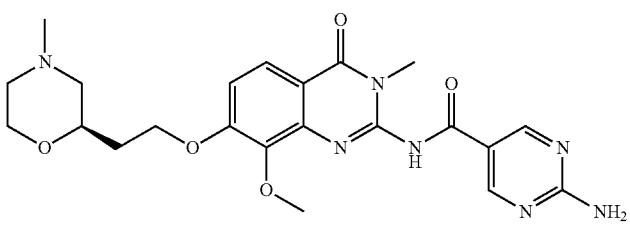 [SMILES: COc1c(OCC[C@@H]2CN(C)CCO2)ccc2c(=O)n(C)c(NC(=O)c3cnc(N)nc3)nc12] |
| 8a-43 | 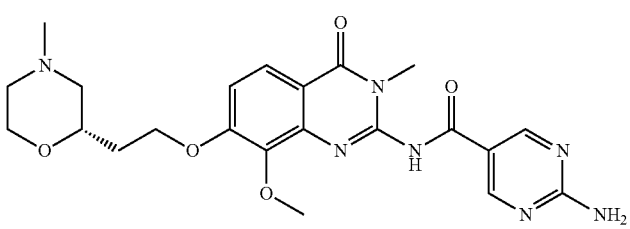 |
| 8a-44 | 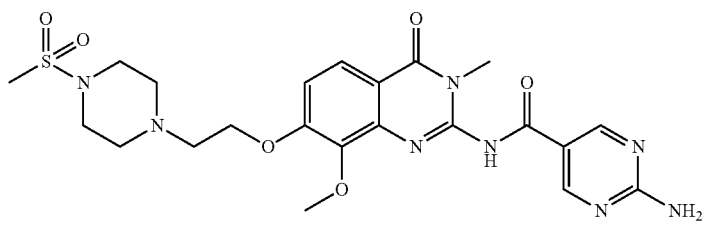 [SMILES: COc1c(OCCN2CCN(S(C)(=O)=O)CC2)ccc2c(=O)n(C)c(NC(=O)c3cnc(N)nc3)nc12] |
| 8a-45 | 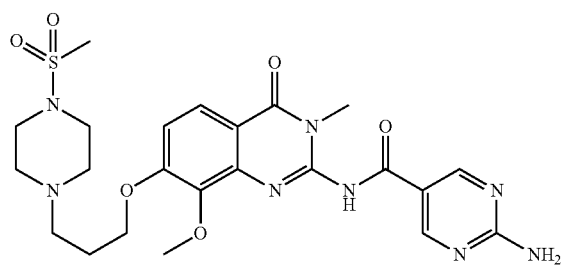 [SMILES: COc1c(OCCCN2CCN(S(C)(=O)=O)CC2)ccc2c(=O)n(C)c(NC(=O)c3cnc(N)nc3)nc12] |

| Compd. | Structure |
|---|---|
| 8a-46 | 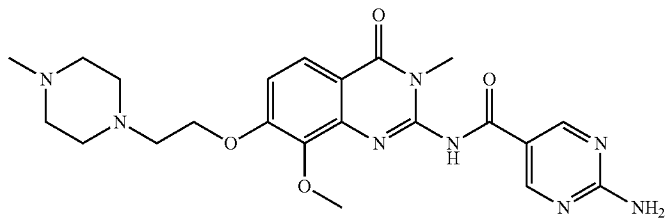 [SMILES: COc1c(OCCN2CCN(C)CC2)ccc2c(=O)n(C)c(NC(=O)c3cnc(N)nc3)nc12] |
| 8a-47 | 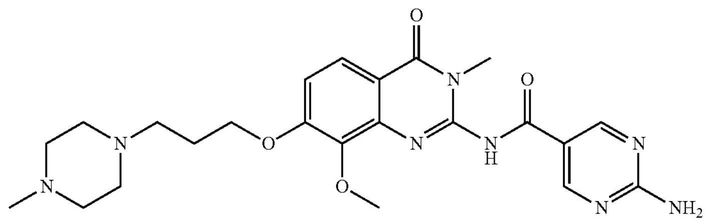 [SMILES: COc1c(OCCCN2CCN(C)CC2)ccc2c(=O)n(C)c(NC(=O)c3cnc(N)nc3)nc12] |
| 8a-48 | 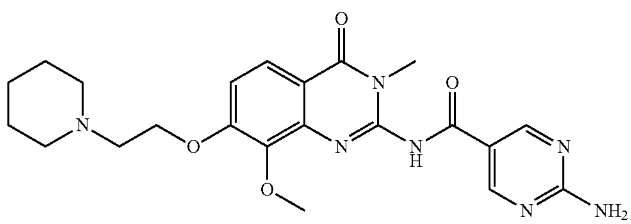 [SMILES: COc1c(OCCN2CCCCC2)ccc2c(=O)n(C)c(NC(=O)c3cnc(N)nc3)nc12] |
| 8a-49 | 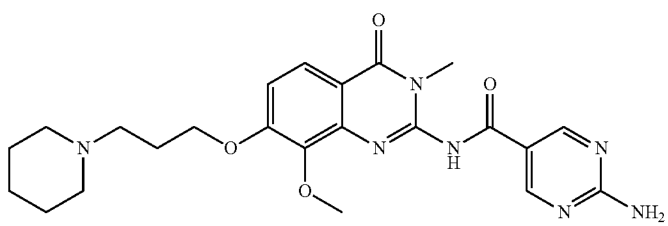 [SMILES: COc1c(OCCCN2CCCCC2)ccc2c(=O)n(C)c(NC(=O)c3cnc(N)nc3)nc12] |
| 8a-50 | 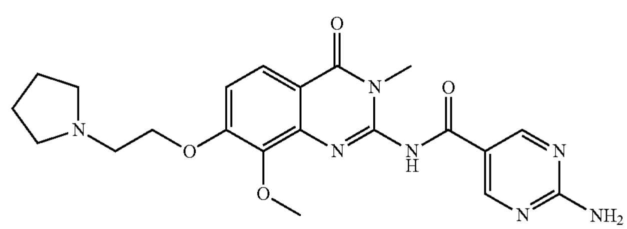 [SMILES: COc1c(OCCN2CCCC2)ccc2c(=O)n(C)c(NC(=O)c3cnc(N)nc3)nc12] |
| 8a-51 | 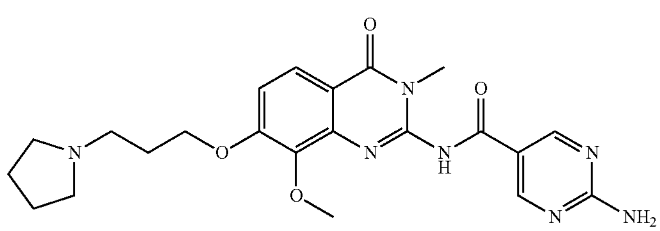 [SMILES: COc1c(OCCCN2CCCC2)ccc2c(=O)n(C)c(NC(=O)c3cnc(N)nc3)nc12] |
| 8a-52 | 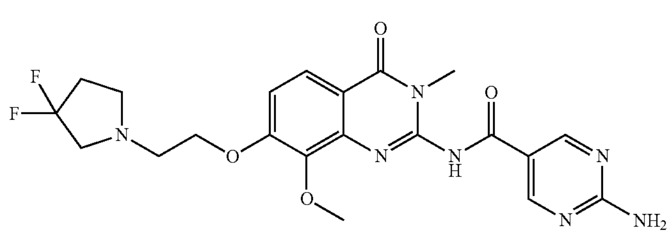 [SMILES: COc1c(OCCN2CCC(F)(F)C2)ccc2c(=O)n(C)c(NC(=O)c3cnc(N)nc3)nc12] |

-continued
| Compd. | Structure |
|---|---|
| 8a-53 | 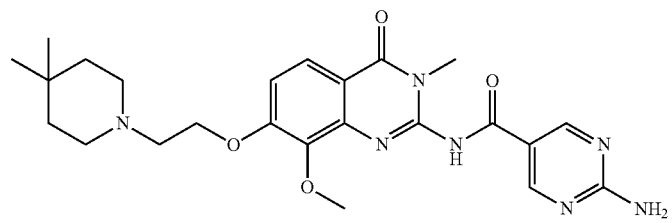 [SMILES: COc1c(OCCN2CCC(C)(C)CC2)ccc2c(=O)n(C)c(NC(=O)c3cnc(N)nc3)nc12] |
| 8a-54 | 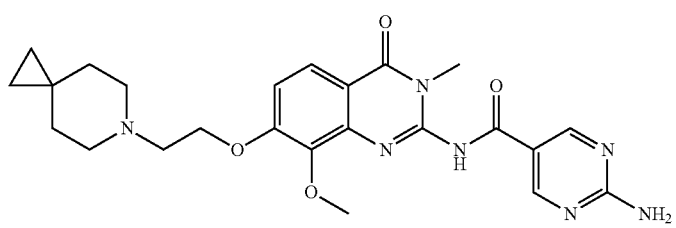 [SMILES: COc1c(OCCN2CCC3(CC2)CC3)ccc2c(=O)n(C)c(NC(=O)c3cnc(N)nc3)nc12] |
| 8a-55 | 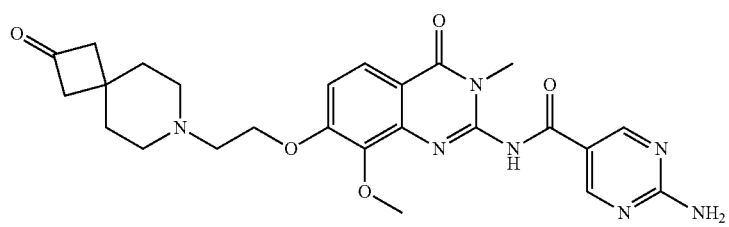 [SMILES: COc1c(OCCN2CCC3(CC2)CC(=O)C3)ccc2c(=O)n(C)c(NC(=O)c3cnc(N)nc3)nc12] |
| 8a-56 | 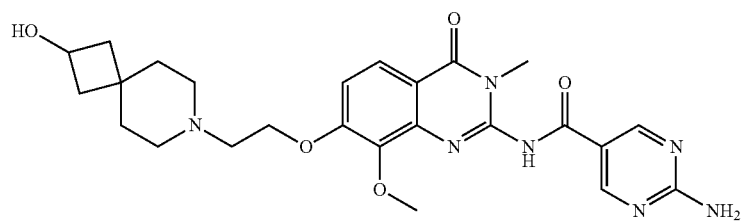 [SMILES: COc1c(OCCN2CCC3(CC2)CC(O)C3)ccc2c(=O)n(C)c(NC(=O)c3cnc(N)nc3)nc12] |
| 8a-57 | 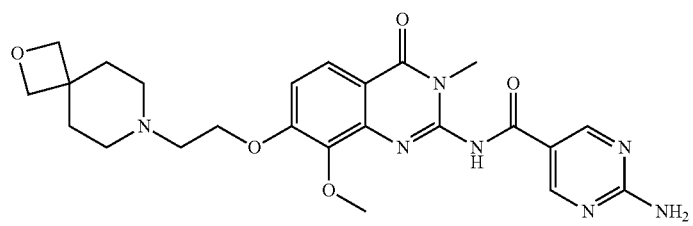 |
| 8a-58 | 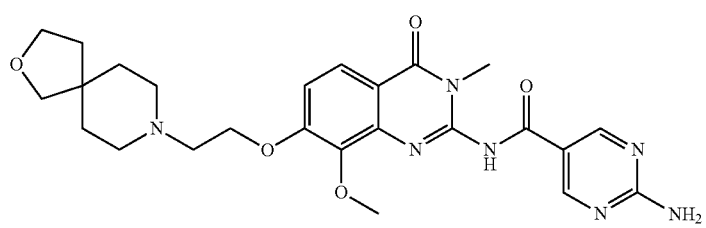 [SMILES: COc1c(OCCN2CCC3(CCOC3)CC2)ccc2c(=O)n(C)c(NC(=O)c3cnc(N)nc3)nc12] |

-continued

| Compd. | Structure |
|---|---|
| 8a-59 | 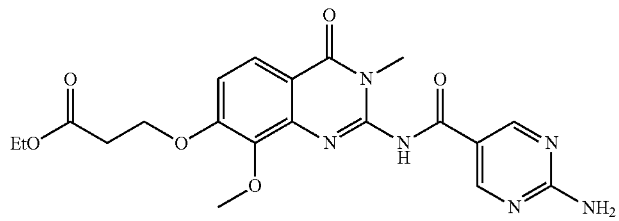 [SMILES: CCOC(=O)CCOc1ccc2c(=O)n(C)c(NC(=O)c3cnc(N)nc3)nc2c1OC] |
| 8a-60 | 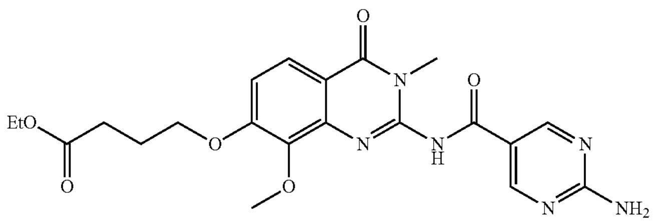 [SMILES: CCOC(=O)CCCOc1ccc2c(=O)n(C)c(NC(=O)c3cnc(N)nc3)nc2c1OC] |
| 8a-61 | 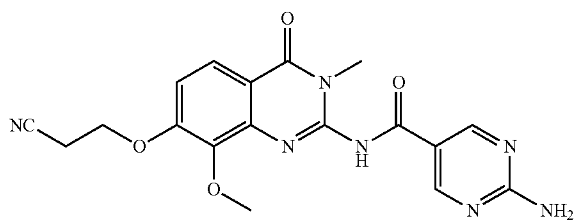 [SMILES: COc1c(OCCC#N)ccc2c(=O)n(C)c(NC(=O)c3cnc(N)nc3)nc12] |
| 8a-62 | 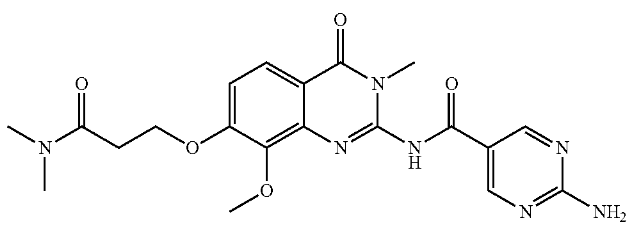 [SMILES: COc1c(OCCC(=O)N(C)C)ccc2c(=O)n(C)c(NC(=O)c3cnc(N)nc3)nc12] |
| 8a-63 | 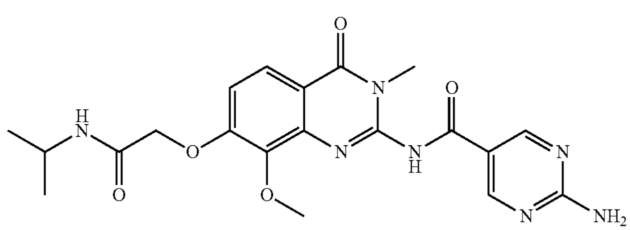 [SMILES: COc1c(OCC(=O)NC(C)C)ccc2c(=O)n(C)c(NC(=O)c3cnc(N)nc3)nc12] |
| 8a-64 | 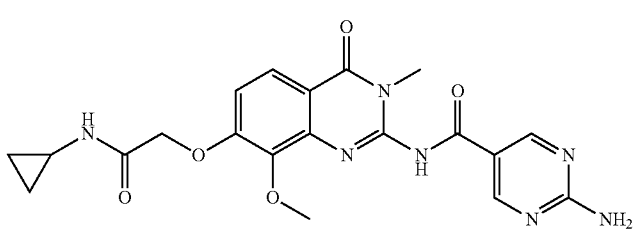 [SMILES: COc1c(OCC(=O)NC2CC2)ccc2c(=O)n(C)c(NC(=O)c3cnc(N)nc3)nc12] |
| 8a-65 | 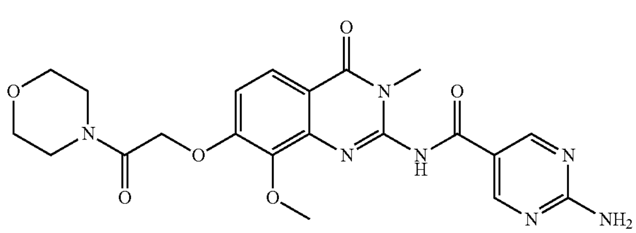 [SMILES: COc1c(OCC(=O)N2CCOCC2)ccc2c(=O)n(C)c(NC(=O)c3cnc(N)nc3)nc12] |

-continued
| Compd. | Structure |
|---|---|
| 8a-66 | 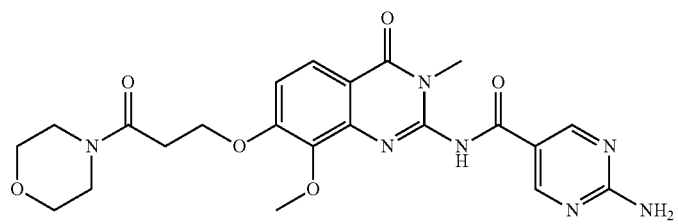 [SMILES: COc1c(OCCC(=O)N2CCOCC2)ccc2c(=O)n(C)c(NC(=O)c3cnc(N)nc3)nc12] |
| 7b-1 | 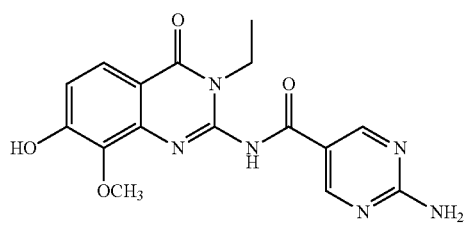 |
| 8b-1 | 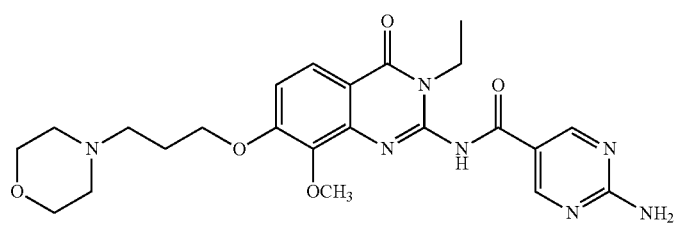 [SMILES: CCn1c(NC(=O)c2cnc(N)nc2)nc2c(OC)c(OCCCN3CCOCC3)ccc2c1=O] |
| 8b-2 | 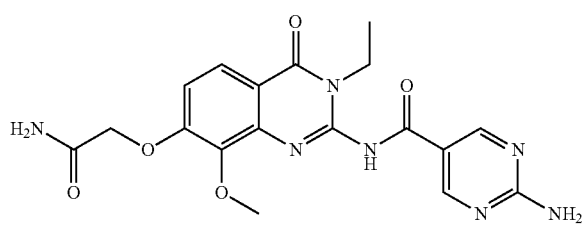 |
| 8b-3 | 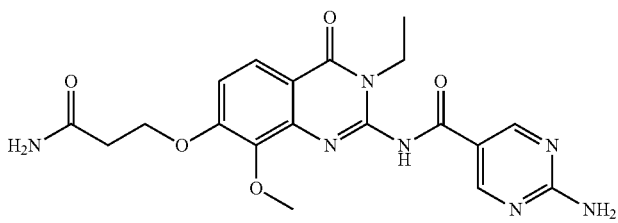 [SMILES: CCn1c(NC(=O)c2cnc(N)nc2)nc2c(OC)c(OCCC(N)=O)ccc2c1=O] |
| 8b-4 | 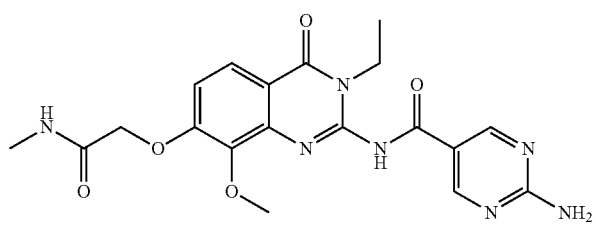 |

-continued

| Compd. | Structure |
|---|---|
| 8b-5 | 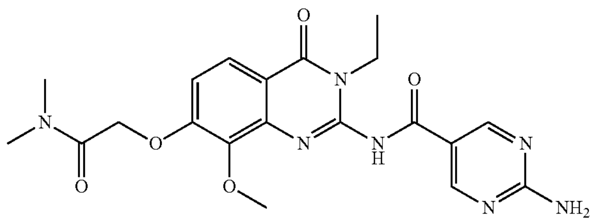 |
| 8b-6 | 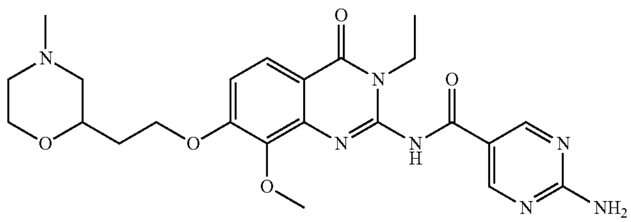 [SMILES: CCn1c(NC(=O)c2cnc(N)nc2)nc2c(OC)c(OCCC3CN(C)CCO3)ccc2c1=O] |
| 8b-7 | 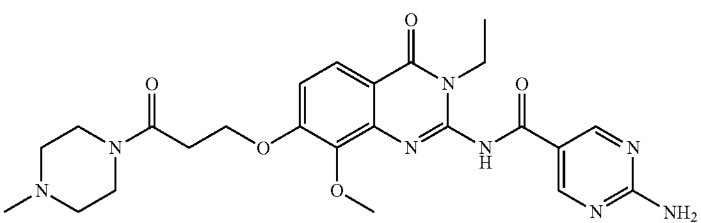 |
| 8b-8 | 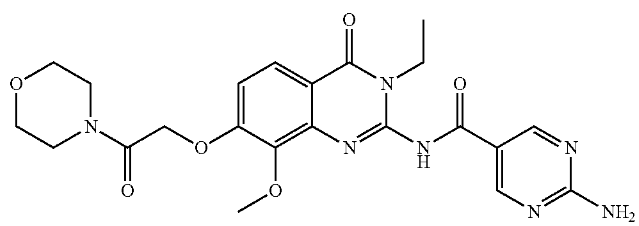 [SMILES: CCn1c(NC(=O)c2cnc(N)nc2)nc2c(OC)c(OCC(=O)N3CCOCC3)ccc2c1=O] |
| 8b-9 | 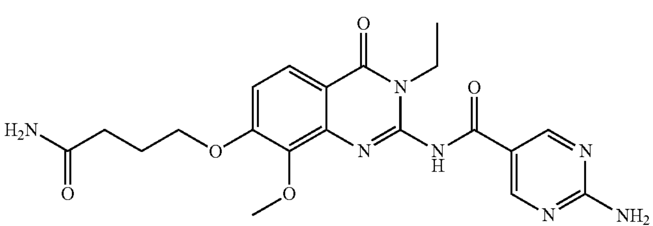 [SMILES: CCn1c(NC(=O)c2cnc(N)nc2)nc2c(OC)c(OCCCC(N)=O)ccc2c1=O] |
| 8b-10 | 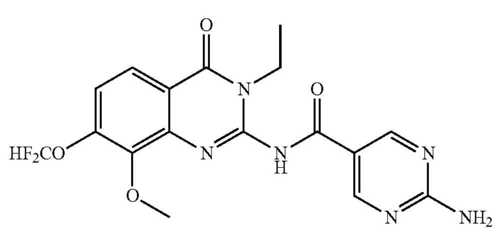 |
| 8b-11 | 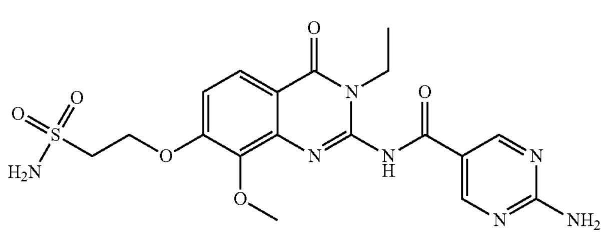 [SMILES: CCn1c(NC(=O)c2cnc(N)nc2)nc2c(OC)c(OCCS(N)(=O)=O)ccc2c1=O] |

| Compd. | Structure |
|---|---|
| 8b-12 | 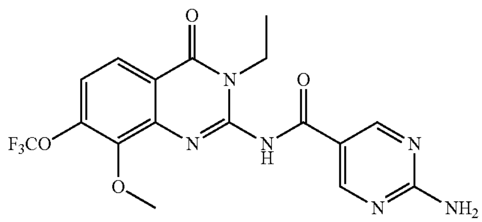 [SMILES: CCn1c(NC(=O)c2cnc(N)nc2)nc2c(OC)c(OC(F)(F)F)ccc2c1=O] |
| 8b-13 | 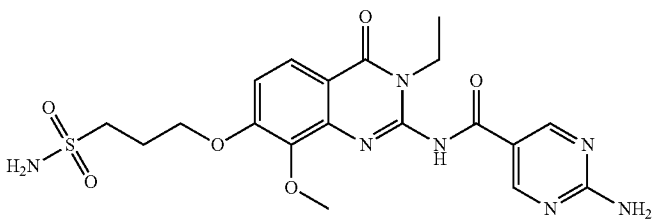 [SMILES: CCn1c(NC(=O)c2cnc(N)nc2)nc2c(OC)c(OCCCS(N)(=O)=O)ccc2c1=O] |
| 8b-14 | 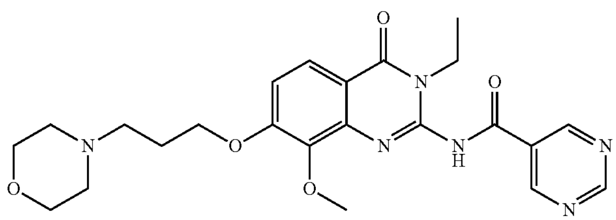 [SMILES: CCn1c(NC(=O)c2cncnc2)nc2c(OC)c(OCCCN3CCOCC3)ccc2c1=O] |
| 8b-15 | 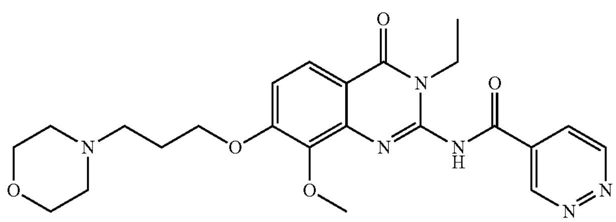 [SMILES: CCn1c(NC(=O)c2ccnnc2)nc2c(OC)c(OCCCN3CCOCC3)ccc2c1=O] |
| 8b-16 | 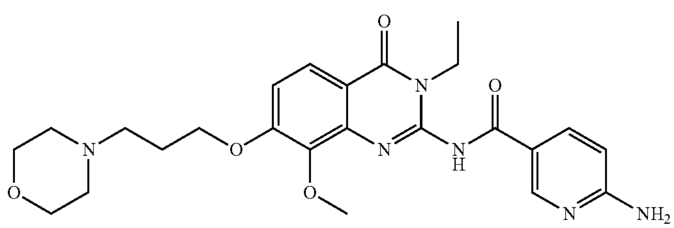 |
| 8b-17 | 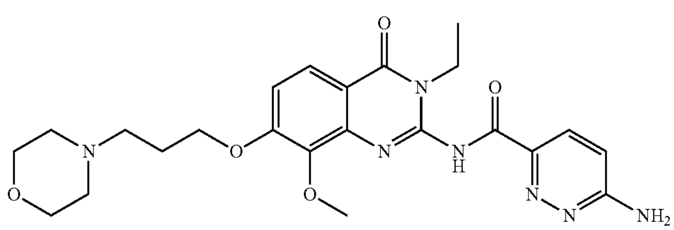 |
| 8b-18 | 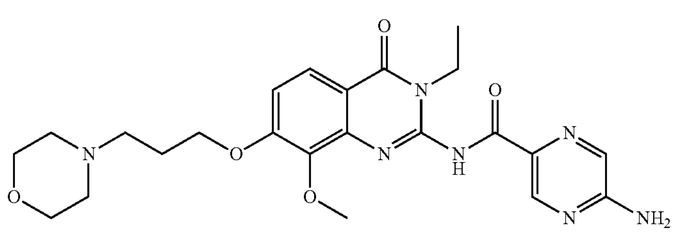 [SMILES: CCn1c(NC(=O)c2cnc(N)cn2)nc2c(OC)c(OCCCN3CCOCC3)ccc2c1=O] |

| Compd. | Structure |
|---|---|
| 8b-19 | 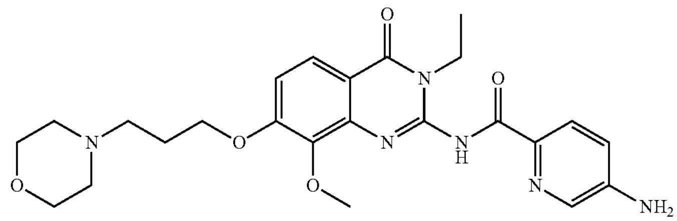 [SMILES: CCn1c(NC(=O)c2ccc(N)cn2)nc2c(OC)c(OCCCN3CCOCC3)ccc2c1=O] |
| 8b-20 | 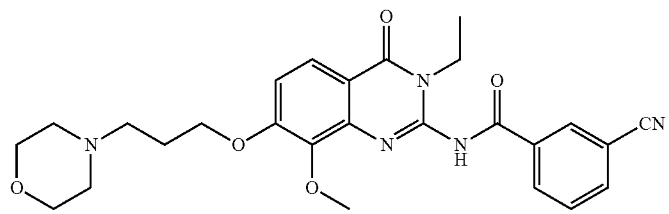 [SMILES: CCn1c(NC(=O)c2cccc(C#N)c2)nc2c(OC)c(OCCCN3CCOCC3)ccc2c1=O] |
| 8b-21 | 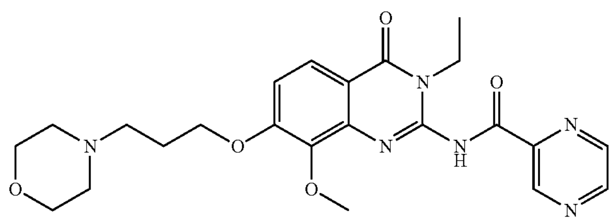 [SMILES: CCn1c(NC(=O)c2cnccn2)nc2c(OC)c(OCCCN3CCOCC3)ccc2c1=O] |
| 8b-22 | 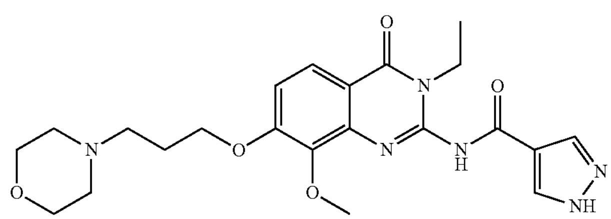 [SMILES: CCn1c(NC(=O)c2cn[nH]c2)nc2c(OC)c(OCCCN3CCOCC3)ccc2c1=O] |
| 8b-23 | 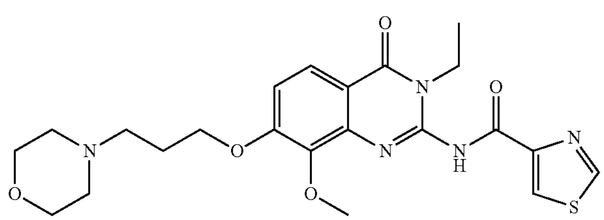 [SMILES: CCn1c(NC(=O)c2cscn2)nc2c(OC)c(OCCCN3CCOCC3)ccc2c1=O] |
| 8b-24 | 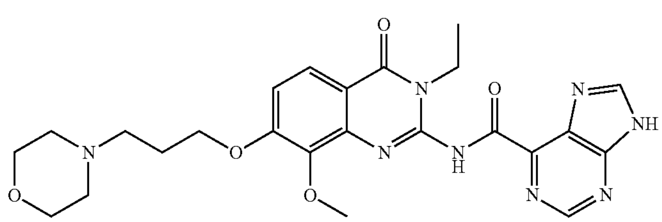 [SMILES: CCn1c(NC(=O)c2ncnc3[nH]cnc23)nc2c(OC)c(OCCCN3CCOCC3)ccc2c1=O] |
| 8b-25 | 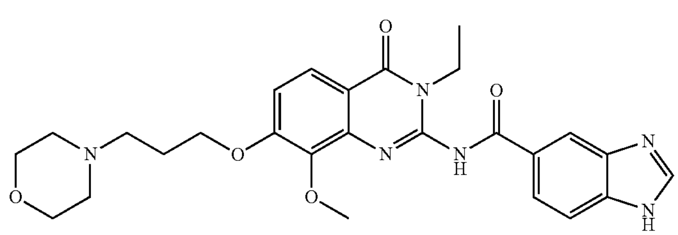 [SMILES: CCn1c(NC(=O)c2ccc3[nH]cnc3c2)nc2c(OC)c(OCCCN3CCOCC3)ccc2c1=O] |

-continued

| Compd. | Structure |
|---|---|
| 8b-26 | 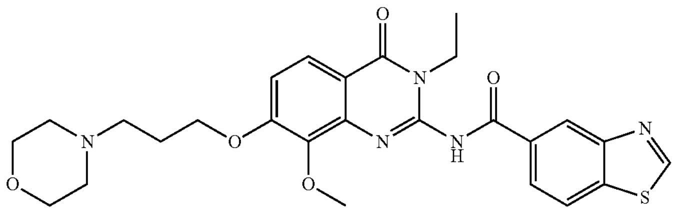 [SMILES: CCn1c(NC(=O)c2ccc3scnc3c2)nc2c(OC)c(OCCCN3CCOCC3)ccc2c1=O] |
| 8b-27 | 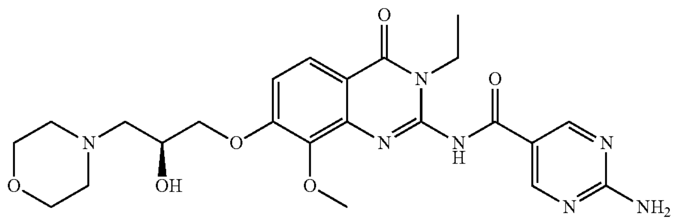 |
| 8b-28 | 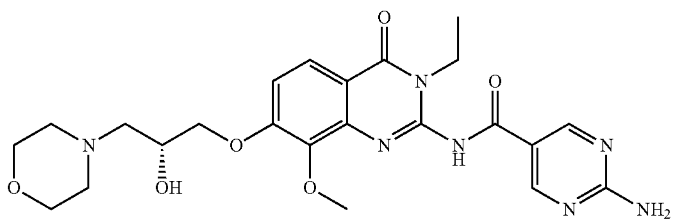 |
| 8b-29 | |
| 8b-29 | |
| 8b-31 | 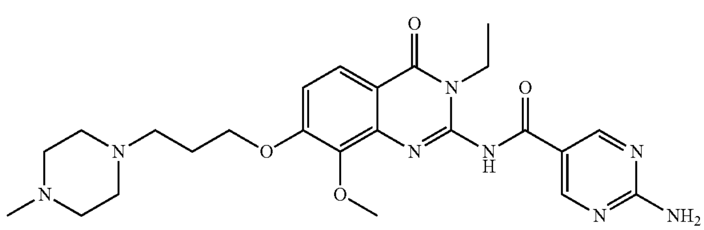 [SMILES: CCn1c(NC(=O)c2cnc(N)nc2)nc2c(OC)c(OCCCN3CCN(C)CC3)ccc2c1=O] |
| 8b-32 | 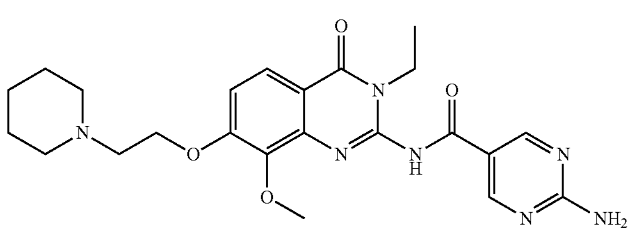 [SMILES: CCn1c(NC(=O)c2cnc(N)nc2)nc2c(OC)c(OCCN3CCCCC3)ccc2c1=O] |

| Compd. | Structure |
|---|---|
| 8b-33 | 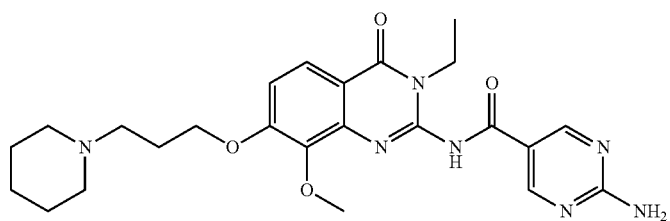 |
| 8b-34 | 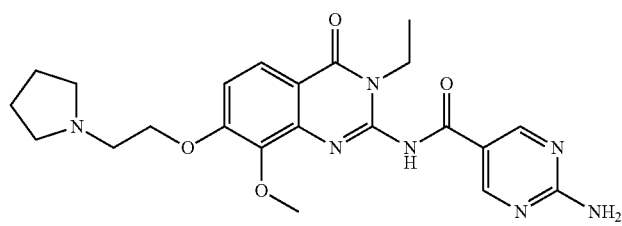 [SMILES: CCn1c(NC(=O)c2cnc(N)nc2)nc2c(OC)c(OCCN3CCCC3)ccc2c1=O] |
| 8b-35 | 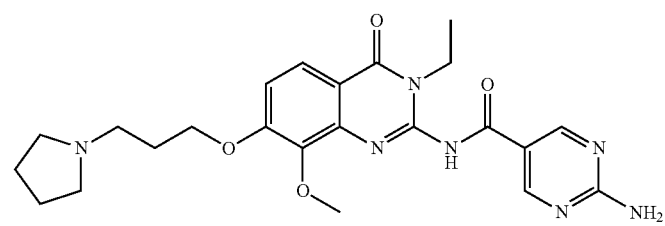 [SMILES: CCn1c(NC(=O)c2cnc(N)nc2)nc2c(OC)c(OCCCN3CCCC3)ccc2c1=O] |
| 8b-36 | 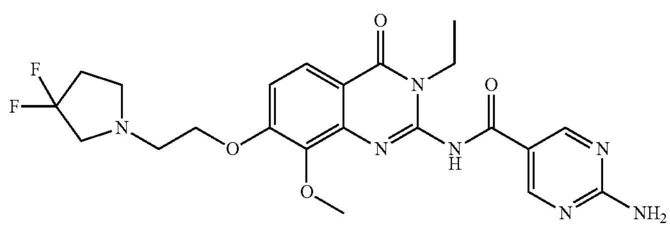 [SMILES: CCn1c(NC(=O)c2cnc(N)nc2)nc2c(OC)c(OCCN3CCC(F)(F)C3)ccc2c1=O] |
| 8b-37 | 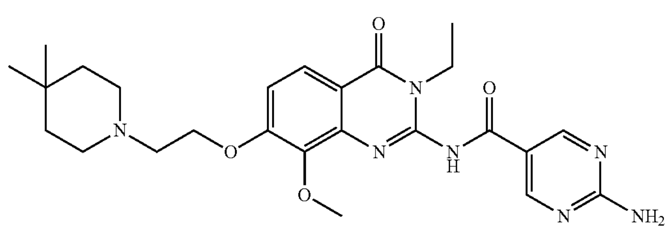 |
| 8b-38 | 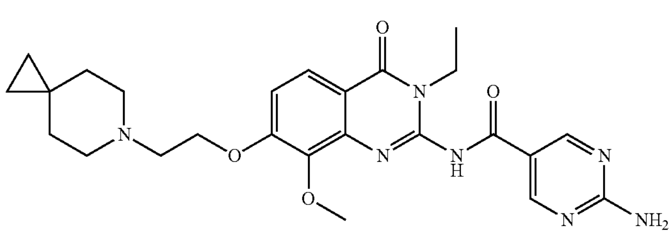 [SMILES: CCn1c(NC(=O)c2cnc(N)nc2)nc2c(OC)c(OCCN3CCC4(CC3)CC4)ccc2c1=O] |

-continued
| Compd. | Structure |
|---|---|
| 8b-39 | 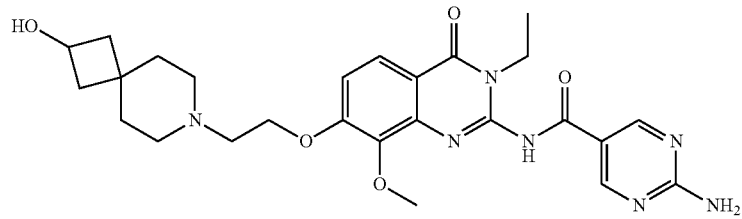 [SMILES: CCn1c(NC(=O)c2cnc(N)nc2)nc2c(OC)c(OCCN3CCC4(CC3)CC(O)C4)ccc2c1=O] |
| 8b-40 | 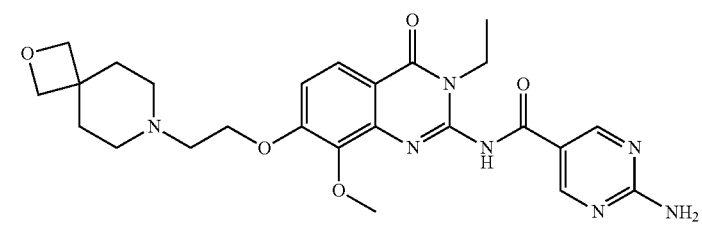 [SMILES: CCn1c(NC(=O)c2cnc(N)nc2)nc2c(OC)c(OCCN3CCC4(CC3)COC4)ccc2c1=O] |
| 8b-41 | 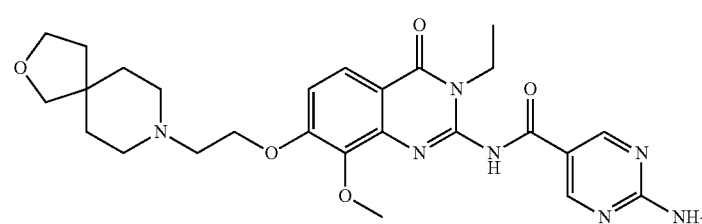 |
| 8b-42 | 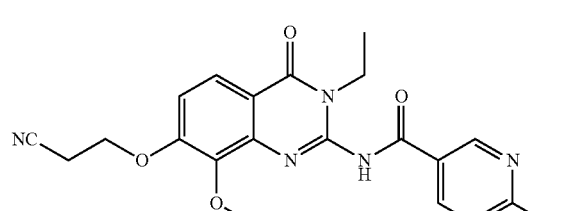 |
| 8b-43 | 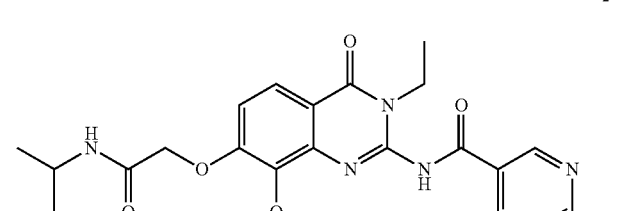 |
| 8b-44 | 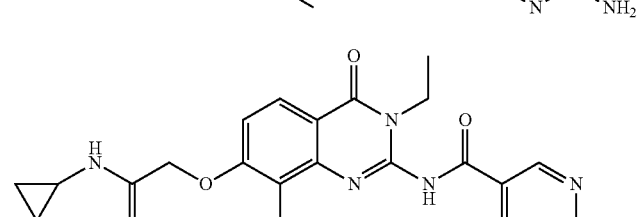 |
| 8b-45 | 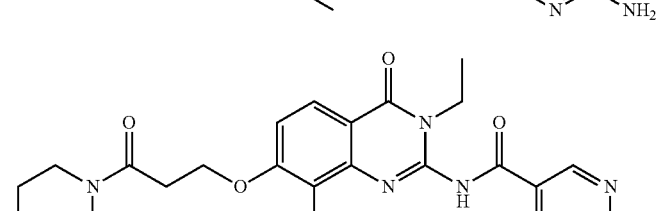 |

| Compd. | Structure |
|---|---|
| 8b-46 | 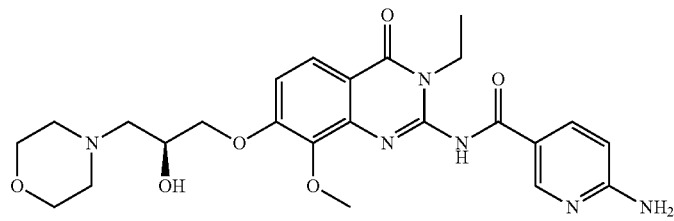 |
| 8b-47 | 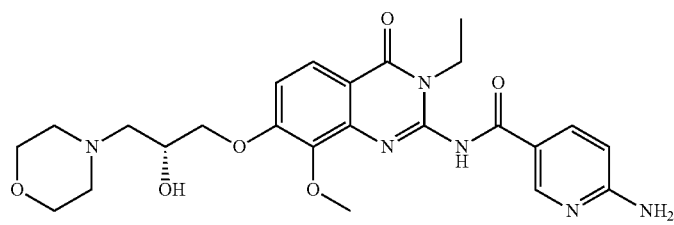 [SMILES: CCn1c(NC(=O)c2ccc(N)nc2)nc2c(OC)c(OC[C@H](O)CN3CCOCC3)ccc2c1=O] |
| 8b-48 | 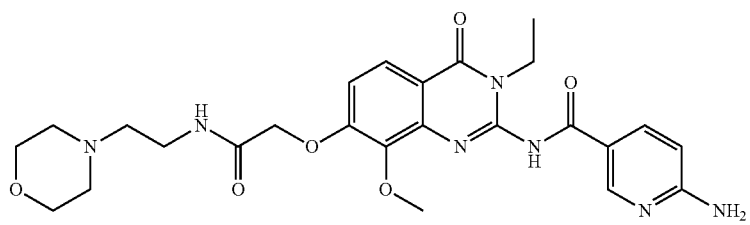 [SMILES: CCn1c(NC(=O)c2ccc(N)nc2)nc2c(OC)c(OCC(=O)NCCN3CCOCC3)ccc2c1=O] |
| 8b-49 | 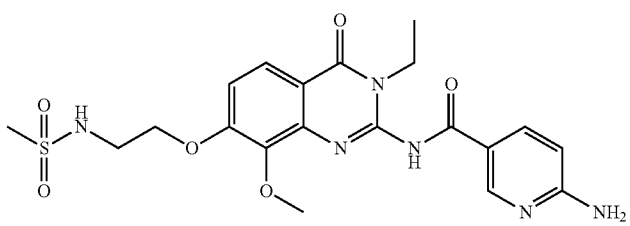 [SMILES: CCn1c(NC(=O)c2ccc(N)nc2)nc2c(OC)c(OCCNS(C)(=O)=O)ccc2c1=O] |
| 8b-50 | 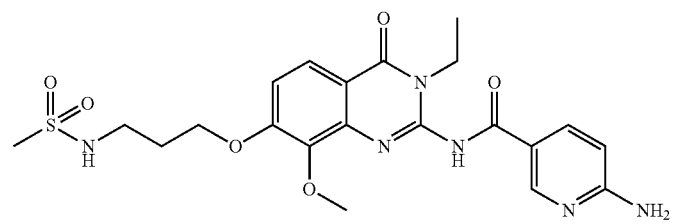 [SMILES: CCn1c(NC(=O)c2ccc(N)nc2)nc2c(OC)c(OCCCNS(C)(=O)=O)ccc2c1=O] |
| 7c-1 | 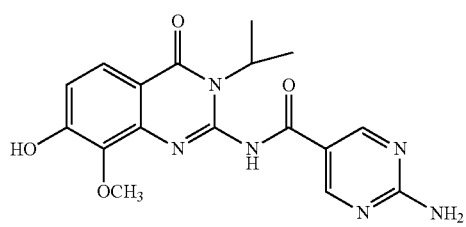 |

-continued

| Compd. | Structure |
|---|---|
| 8c-1 | 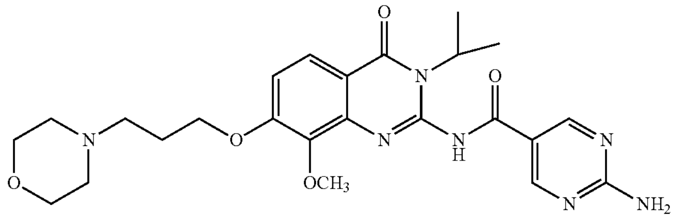 [SMILES: COc1c(OCCCN2CCOCC2)ccc2c(=O)n(C(C)C)c(NC(=O)c3cnc(N)nc3)nc12] |
| 8c-2 | 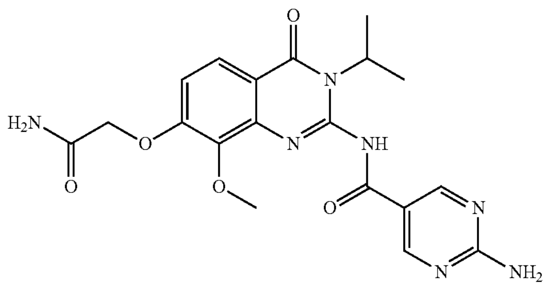 [SMILES: COc1c(OCC(N)=O)ccc2c(=O)n(C(C)C)c(NC(=O)c3cnc(N)nc3)nc12] |
| 8c-3 | 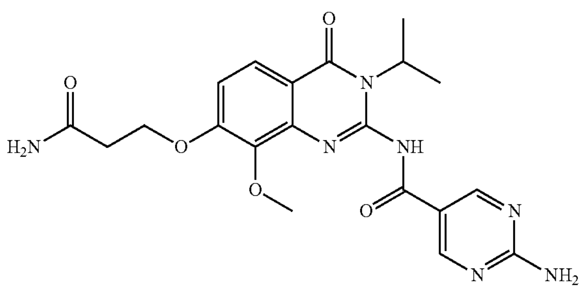 [SMILES: COc1c(OCCC(N)=O)ccc2c(=O)n(C(C)C)c(NC(=O)c3cnc(N)nc3)nc12] |
| 8c-4 | 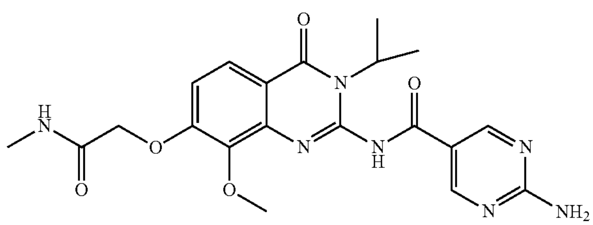 [SMILES: CNC(=O)COc1ccc2c(=O)n(C(C)C)c(NC(=O)c3cnc(N)nc3)nc2c1OC] |
| 8c-5 | 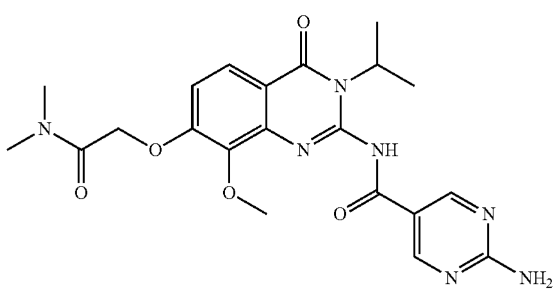 [SMILES: COc1c(OCC(=O)N(C)C)ccc2c(=O)n(C(C)C)c(NC(=O)c3cnc(N)nc3)nc12] |
| 8c-6 | 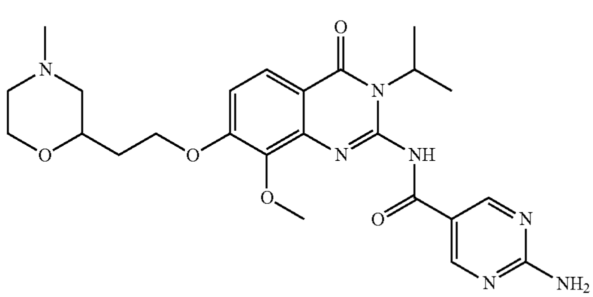 [SMILES: COc1c(OCCC2CN(C)CCO2)ccc2c(=O)n(C(C)C)c(NC(=O)c3cnc(N)nc3)nc12] |

-continued
| Compd. | Structure |
|---|---|
| 8c-7 | 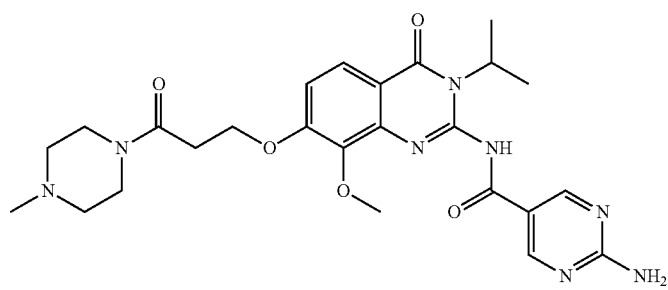 [SMILES: COc1c(OCCC(=O)N2CCN(C)CC2)ccc2c(=O)n(C(C)C)c(NC(=O)c3cnc(N)nc3)nc12] |
| 8c-8 | 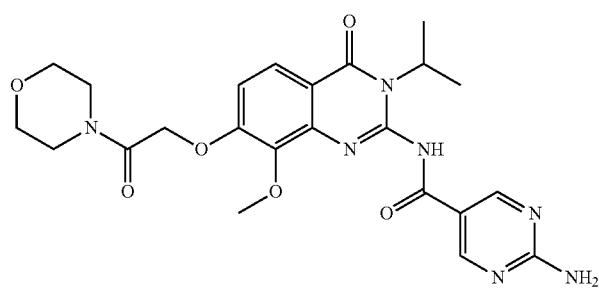 [SMILES: COc1c(OCC(=O)N2CCOCC2)ccc2c(=O)n(C(C)C)c(NC(=O)c3cnc(N)nc3)nc12] |
| 8c-9 | 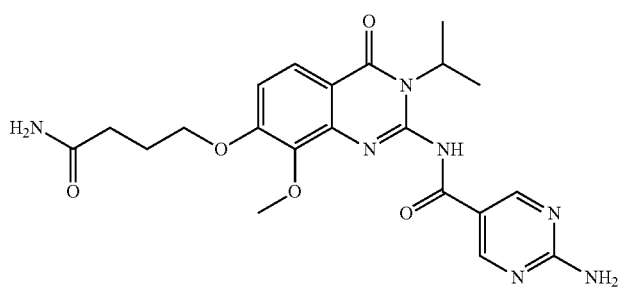 [SMILES: COc1c(OCCCC(N)=O)ccc2c(=O)n(C(C)C)c(NC(=O)c3cnc(N)nc3)nc12] |
| 7d-1 | 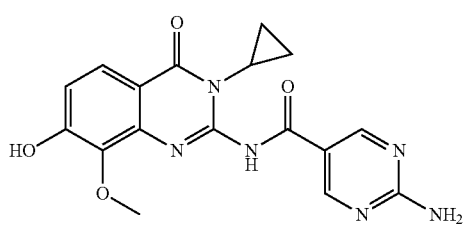 [SMILES: COc1c(O)ccc2c(=O)n(C3CC3)c(NC(=O)c3cnc(N)nc3)nc12] |
| 8d-1 | 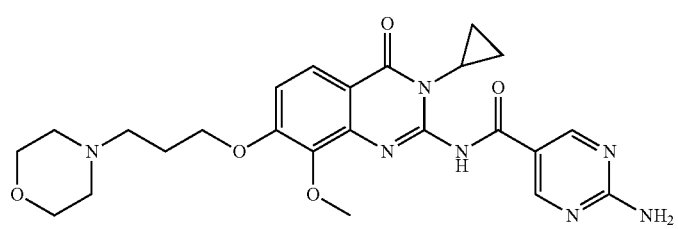 [SMILES: COc1c(OCCCN2CCOCC2)ccc2c(=O)n(C3CC3)c(NC(=O)c3cnc(N)nc3)nc12] |
| 8d-2 | 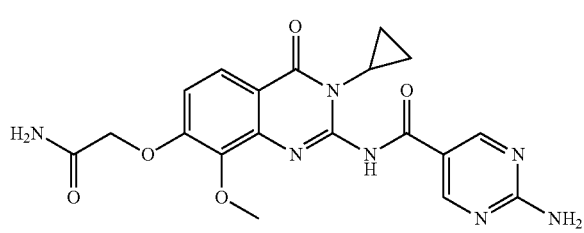 [SMILES: COc1c(OCC(N)=O)ccc2c(=O)n(C3CC3)c(NC(=O)c3cnc(N)nc3)nc12] |

| Compd. | Structure |
|---|---|
| 8d-3 | 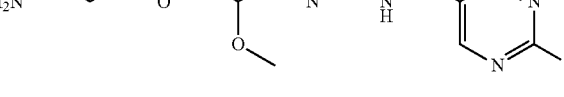 |
| 8d-4 | 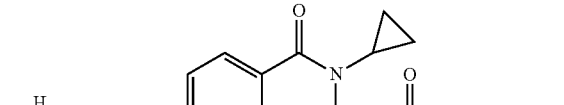 |
| 8d-5 | 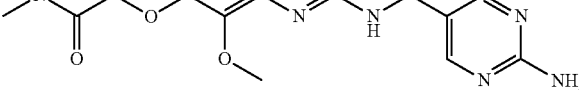 |
| 7e-1 | 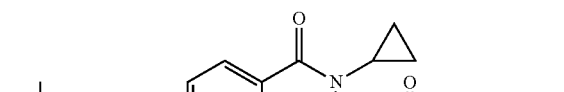 |
| 8e-1 | 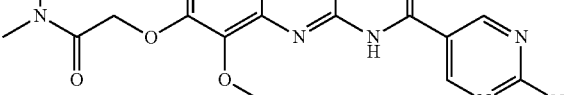 |
| 8e-2 | 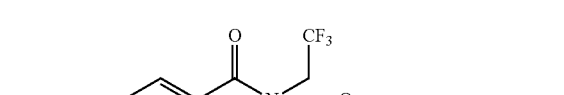 |
| 8e-3 | 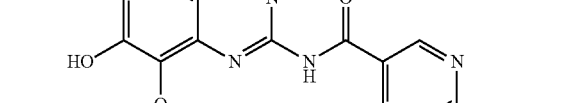 |

| Compd. | Structure |
|---|---|
| 8e-4 | (chemical structure) |
| 8e-5 | (chemical structure) |
| 7f-1 | (chemical structure) |
| 8f-1 | (chemical structure) |
| 8f-2 | (chemical structure) |
| 8f-3 | (chemical structure) |

-continued

| Compd. | Structure |
|---|---|
| 7g-1 | (structure) |
| 8g-1 | (structure) |
| 8g-2 | (structure) |
| 8g-3 | (structure) |
| 8g-4 | (structure) |
| 8g-5 | (structure) |
| 14a-1 | (structure) |

| Compd. | Structure |
|---|---|
| 14a-2 | 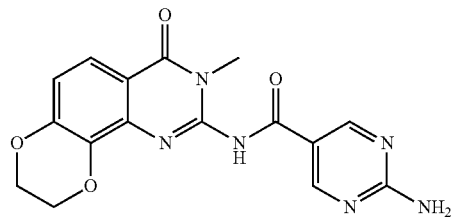 [SMILES: Cn1c(NC(=O)c2cnc(N)nc2)nc2c3c(ccc2c1=O)OCCO3] |
| 14a-3 | 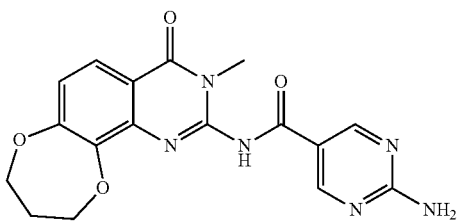 |
| 14a-4 | 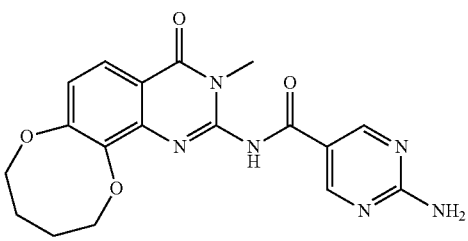 [SMILES: Cn1c(NC(=O)c2cnc(N)nc2)nc2c3c(ccc2c1=O)OCCCCO3] |
| 14a-5 | 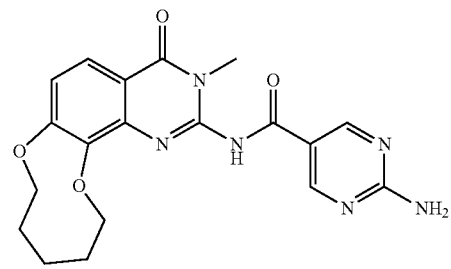 [SMILES: Cn1c(NC(=O)c2cnc(N)nc2)nc2c3c(ccc2c1=O)OCCCCCO3] |
| 14a-6 | 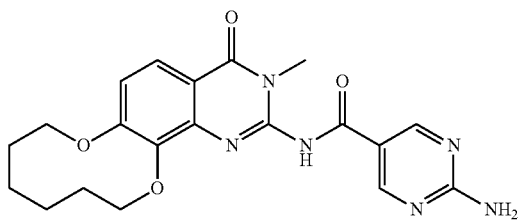 |
| 14a-7 | 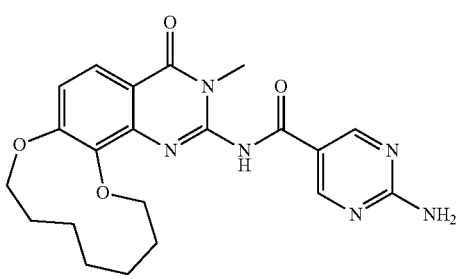 [SMILES: Cn1c(NC(=O)c2cnc(N)nc2)nc2c3c(ccc2c1=O)OCCCCCCCO3] |

| Compd. | Structure |
|---|---|
| 14a-8 | 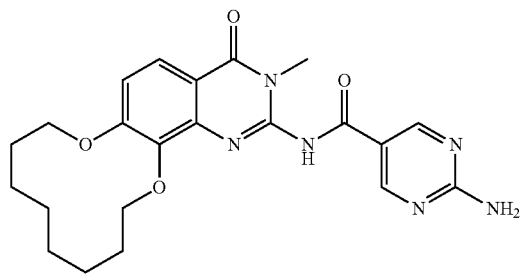 [SMILES: Cn1c(NC(=O)c2cnc(N)nc2)nc2c3c(ccc2c1=O)OCCCCCCCCO3] |
| 14a-9 | 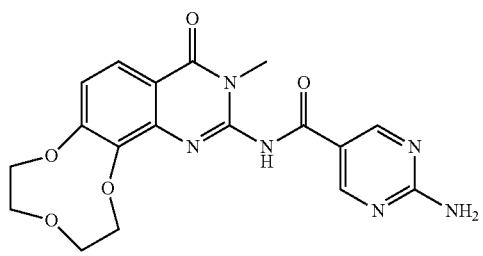 [SMILES: Cn1c(NC(=O)c2cnc(N)nc2)nc2c3c(ccc2c1=O)OCCOCCO3] |
| 14a-10 | 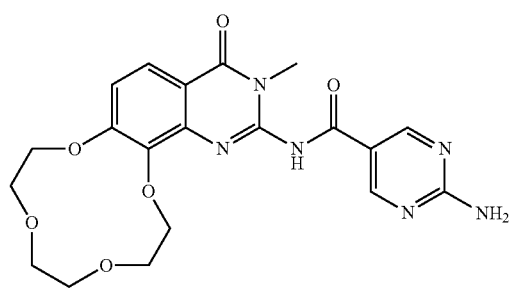 |
| 14a-11 | 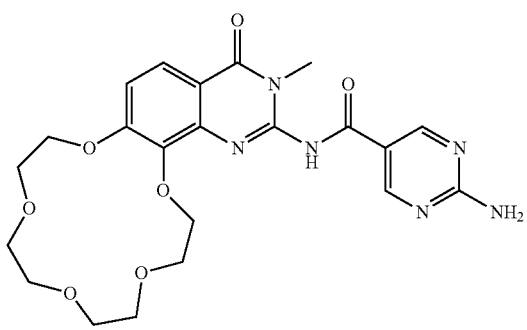 |
| 14a-12 | 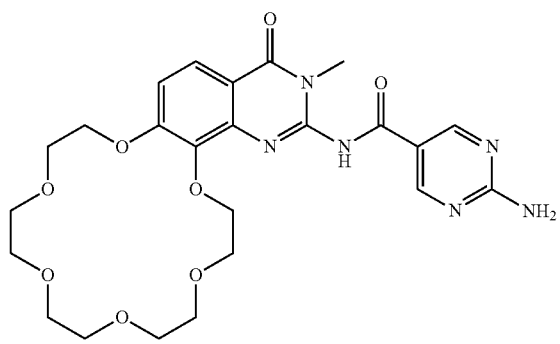 |

-continued

| Compd. | Structure |
|---|---|
| 14b-1 | 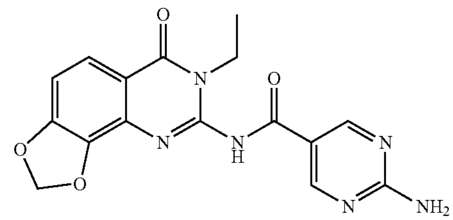 [SMILES: CCn1c(NC(=O)c2cnc(N)nc2)nc2c3c(ccc2c1=O)OCO3] |
| 14b-2 | 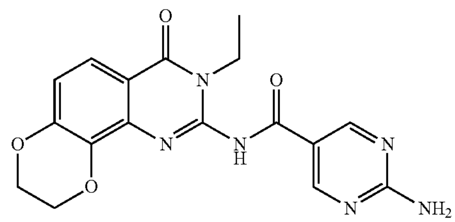 [SMILES: CCn1c(NC(=O)c2cnc(N)nc2)nc2c3c(ccc2c1=O)OCCO3] |
| 14b-3 | 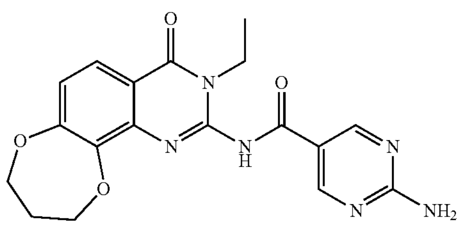 |
| 14b-4 | 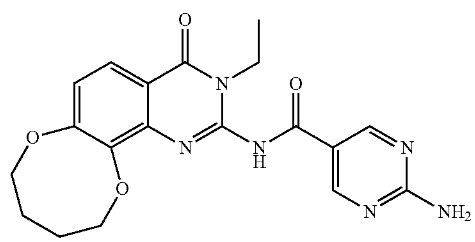 |
| 14b-5 | 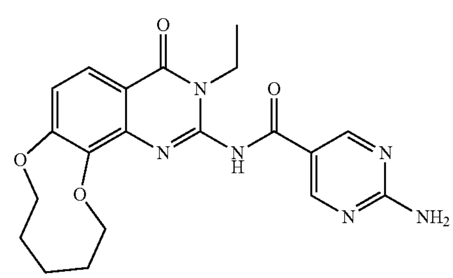 [SMILES: CCn1c(NC(=O)c2cnc(N)nc2)nc2c3c(ccc2c1=O)OCCCCCO3] |
| 14b-6 | 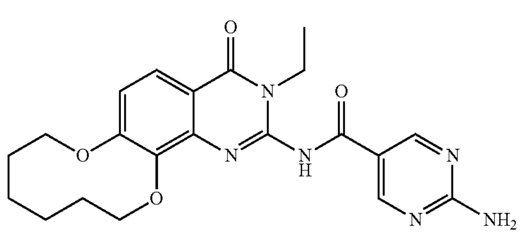 [SMILES: CCn1c(NC(=O)c2cnc(N)nc2)nc2c3c(ccc2c1=O)OCCCCCCO3] |

| Compd. | Structure |
|---|---|
| 14b-7 | 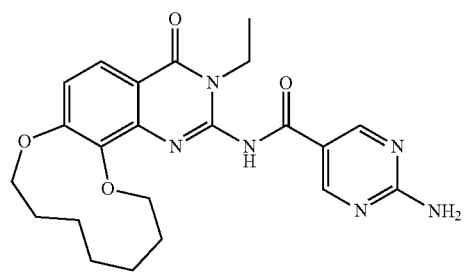 [SMILES: CCn1c(NC(=O)c2cnc(N)nc2)nc2c3c(ccc2c1=O)OCCCCCCCO3] |
| 14b-8 | 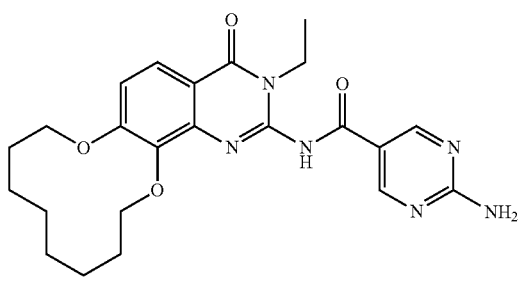 [SMILES: CCn1c(NC(=O)c2cnc(N)nc2)nc2c3c(ccc2c1=O)OCCCCCCCCO3] |
| 14b-9 | 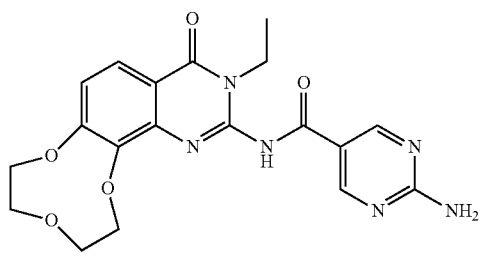 [SMILES: CCn1c(NC(=O)c2cnc(N)nc2)nc2c3c(ccc2c1=O)OCCOCCO3] |
| 14b-10 | 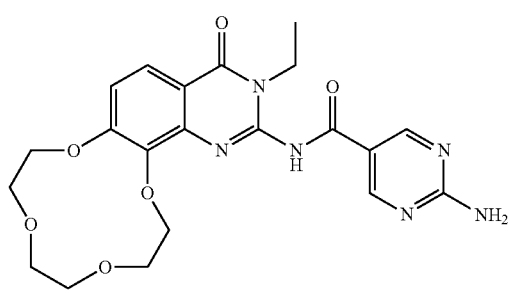 |
| 14b-11 | 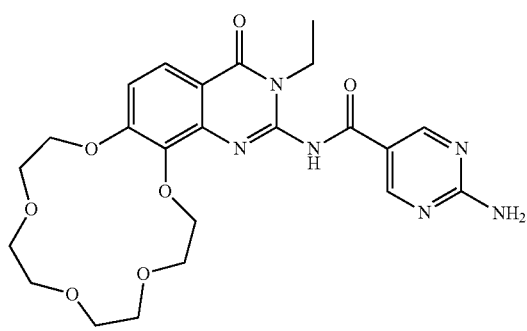 [SMILES: CCn1c(NC(=O)c2cnc(N)nc2)nc2c3c(ccc2c1=O)OCCOCCOCCOCCO3] |

| Compd. | Structure |
|---|---|
| 14b-12 | 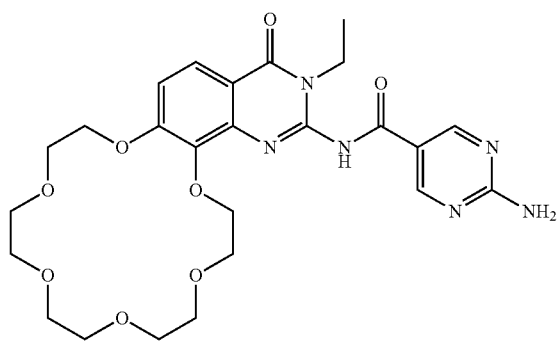 |
| 7'a-1 | 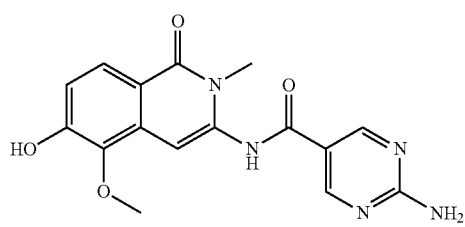 |
| 8a'-1 | 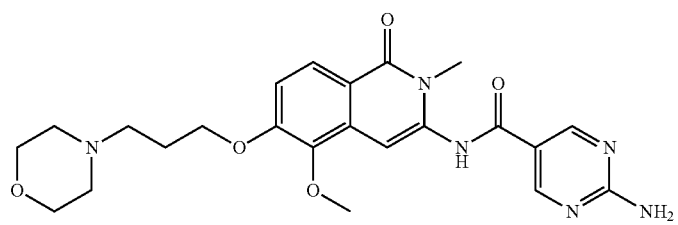 |
| 8a'-2 | 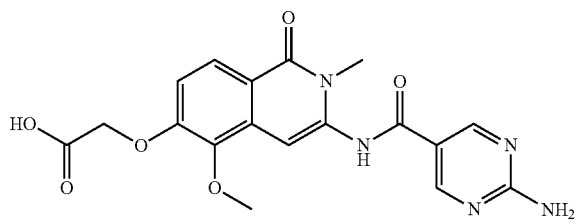 [SMILES: COc1c(OCC(=O)O)ccc2c(=O)n(C)c(NC(=O)c3cnc(N)nc3)cc12] |
| 8a'-3 | 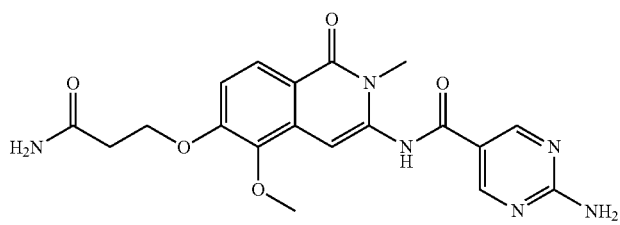 [SMILES: COc1c(OCCC(N)=O)ccc2c(=O)n(C)c(NC(=O)c3cnc(N)nc3)cc12] |
| 8a'-4 | 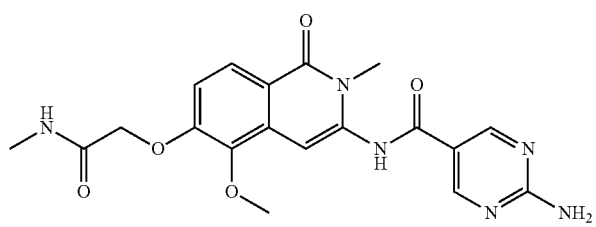 [SMILES: CNC(=O)COc1ccc2c(=O)n(C)c(NC(=O)c3cnc(N)nc3)cc2c1OC] |

| Compd. | Structure |
|---|---|
| 8a'-5 | 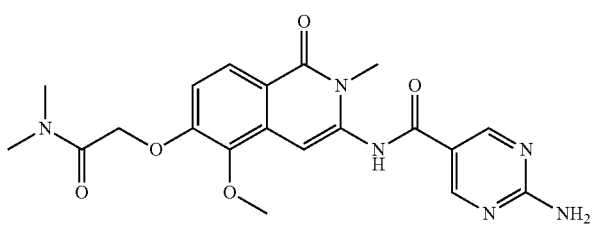 [SMILES: COc1c(OCC(=O)N(C)C)ccc2c(=O)n(C)c(NC(=O)c3cnc(N)nc3)cc12] |
| 8a'-6 | 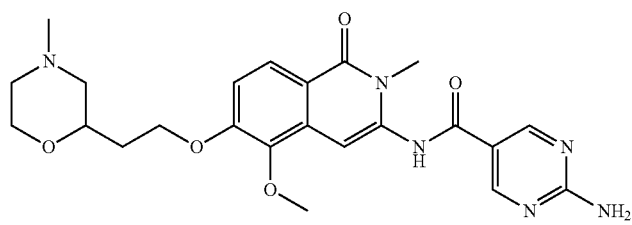 |
| 8a'-7 | 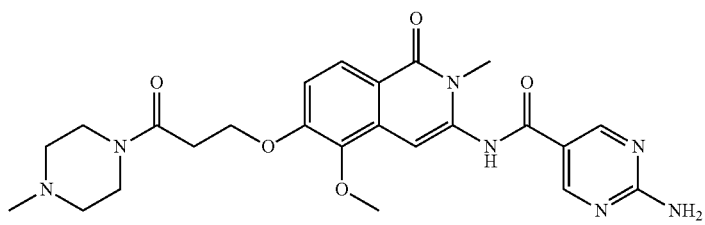 |
| 8a'-8 | 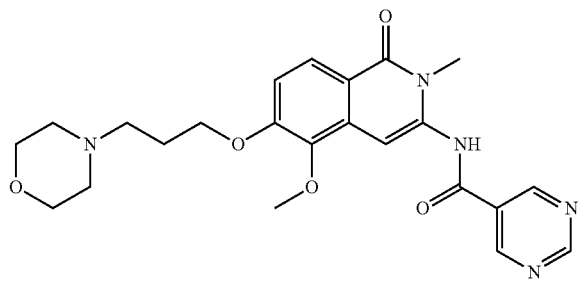 [SMILES: COc1c(OCCCN2CCOCC2)ccc2c(=O)n(C)c(NC(=O)c3cncnc3)cc12] |
| 8a'-9 | 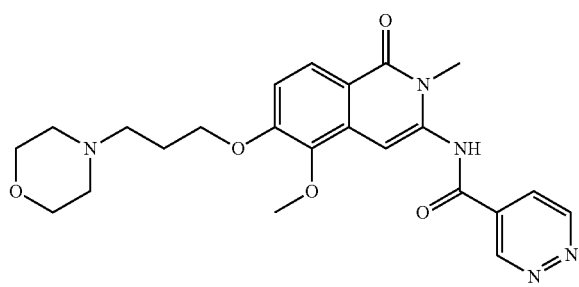 [SMILES: COc1c(OCCCN2CCOCC2)ccc2c(=O)n(C)c(NC(=O)c3ccnnc3)cc12] |
| 8a'-10 | 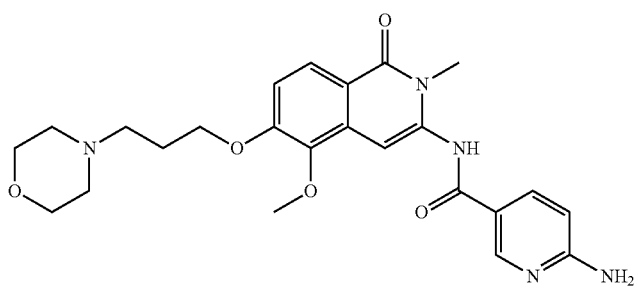 |

-continued

| Compd. | Structure |
|---|---|
| 8a'-11 | 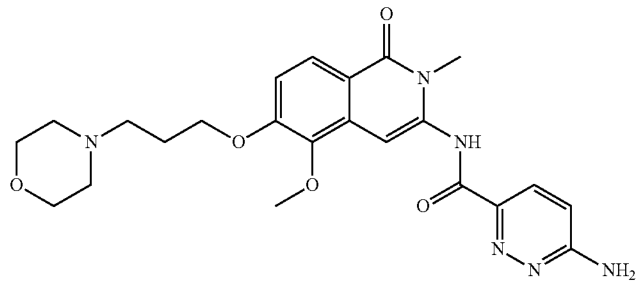 |
| 8a'-12 | 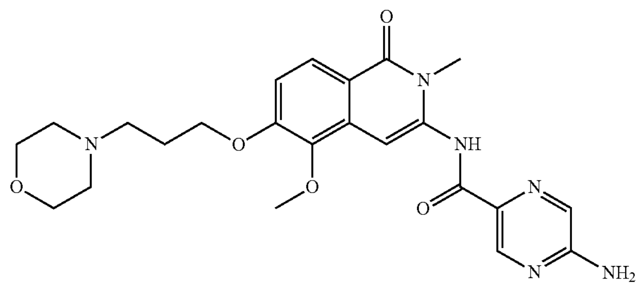 [SMILES: COc1c(OCCCN2CCOCC2)ccc2c(=O)n(C)c(NC(=O)c3cnc(N)cn3)cc12] |
| 8a'-13 | 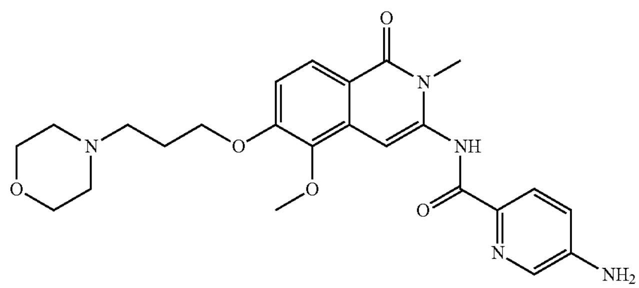 |
| 8a'-14 | 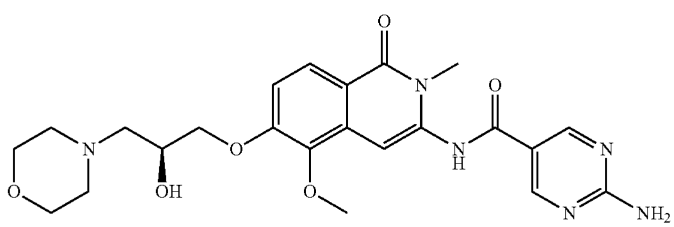 |
| 8a'-15 | 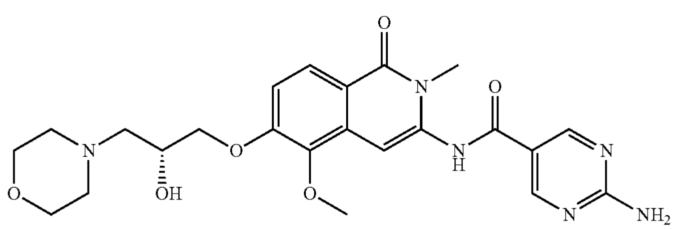 |
| 8a'-16 | 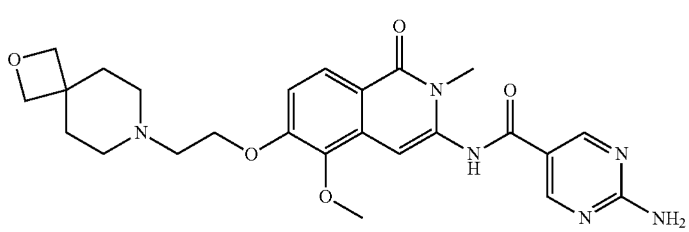 [SMILES: COc1c(OCCN2CCC3(CC2)COC3)ccc2c(=O)n(C)c(NC(=O)c3cnc(N)nc3)cc12] |

| Compd. | Structure |
|---|---|
| 8a'-17 | 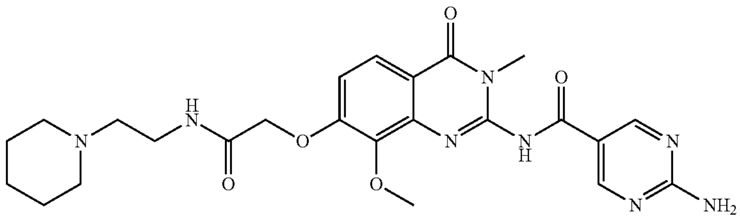 [SMILES: COc1c(OCC(=O)NCCN2CCCCC2)ccc2c(=O)n(C)c(NC(=O)c3cnc(N)nc3)nc12] |
| 8a'-18 | 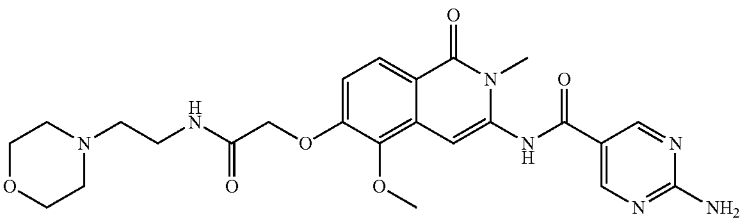 [SMILES: COc1c(OCC(=O)NCCN2CCOCC2)ccc2c(=O)n(C)c(NC(=O)c3cnc(N)nc3)cc12] |
| 8a'-19 | 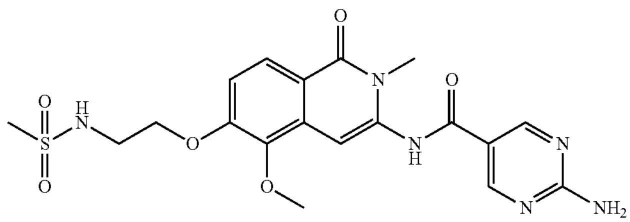 [SMILES: COc1c(OCCNS(C)(=O)=O)ccc2c(=O)n(C)c(NC(=O)c3cnc(N)nc3)cc12] |
| 7b'-1 | 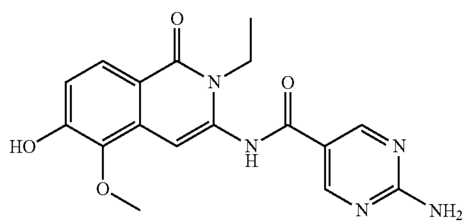 [SMILES: CCn1c(NC(=O)c2cnc(N)nc2)cc2c(OC)c(O)ccc2c1=O] |
| 8b'-1 | 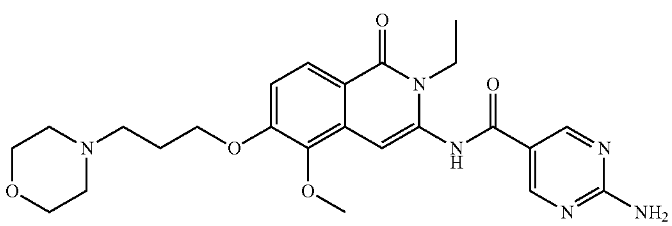 |
| 8b'-2 | 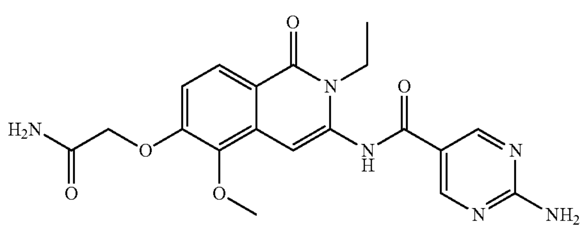 [SMILES: CCn1c(NC(=O)c2cnc(N)nc2)cc2c(OC)c(OCC(N)=O)ccc2c1=O] |
| 8b'-3 | 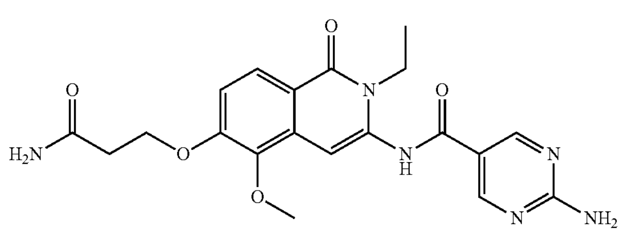 [SMILES: CCn1c(NC(=O)c2cnc(N)nc2)cc2c(OC)c(OCCC(N)=O)ccc2c1=O] |

| Compd. | Structure |
|---|---|
| 8b'-4 | 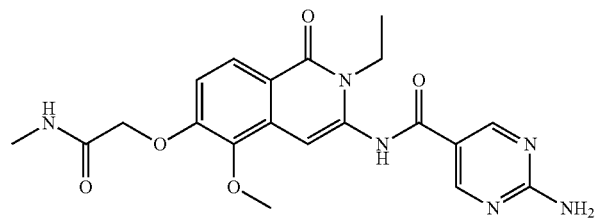 [SMILES: CCn1c(NC(=O)c2cnc(N)nc2)cc2c(OC)c(OCC(=O)NC)ccc2c1=O] |
| 8b'-5 | 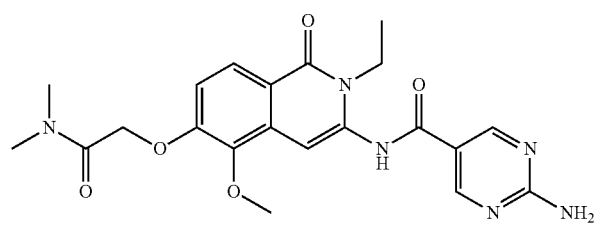 |
| 8b'-6 | 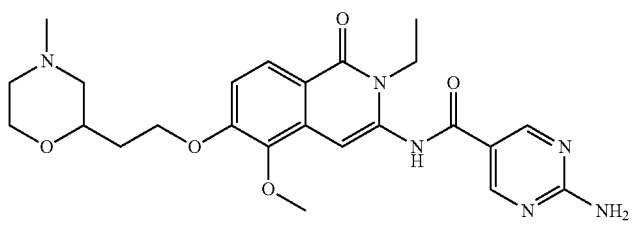 |
| 8b'-7 | 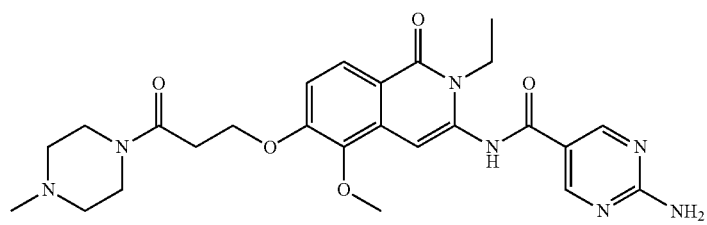 [SMILES: CCn1c(NC(=O)c2cnc(N)nc2)cc2c(OC)c(OCCC(=O)N3CCN(C)CC3)ccc2c1=O] |
| 8b'-8 | 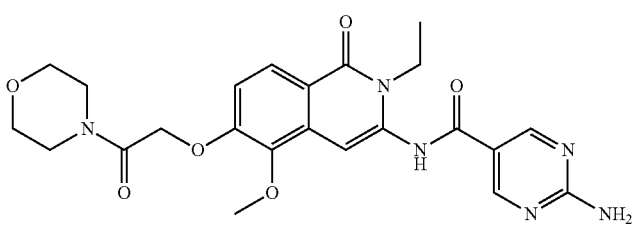 |
| 8b'-9 | 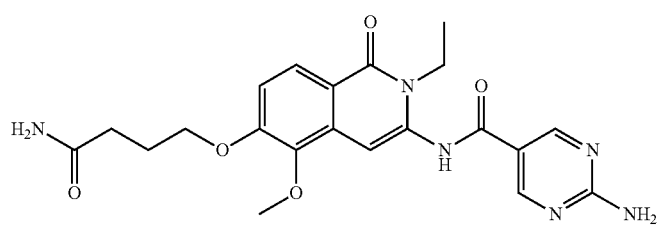 |

-continued

| Compd. | Structure |
|---|---|
| 8b'-10 | 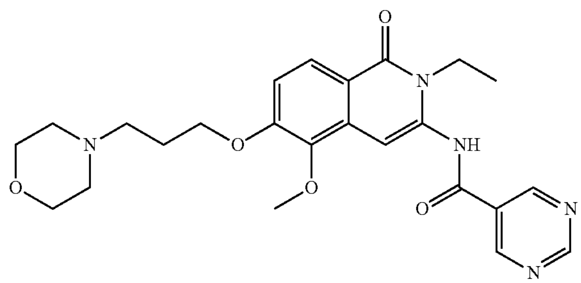 [SMILES: CCn1c(NC(=O)c2cncnc2)cc2c(OC)c(OCCCN3CCOCC3)ccc2c1=O] |
| 8b'-11 | 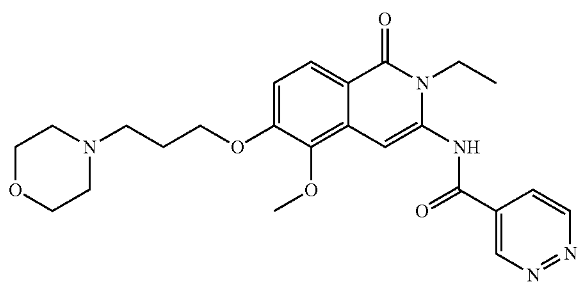 [SMILES: CCn1c(NC(=O)c2ccnnc2)cc2c(OC)c(OCCCN3CCOCC3)ccc2c1=O] |
| 8b'-12 | 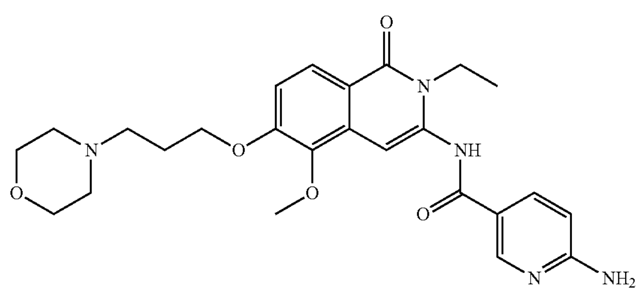 |
| 8b'-13 | 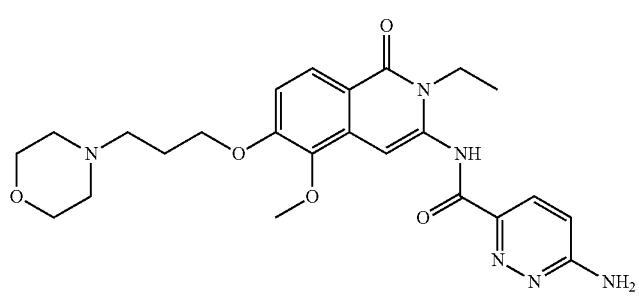 |
| 8b'-14 | 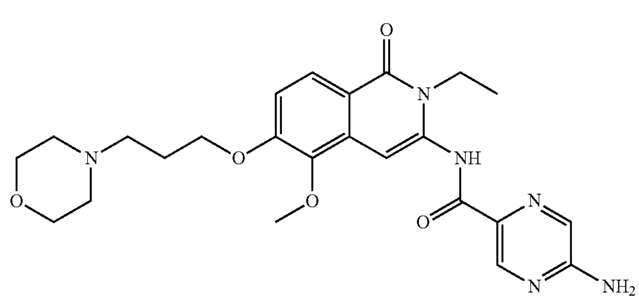 [SMILES: CCn1c(NC(=O)c2cnc(N)cn2)cc2c(OC)c(OCCCN3CCOCC3)ccc2c1=O] |

-continued
| Compd. | Structure |
|---|---|
| 8b'-15 | 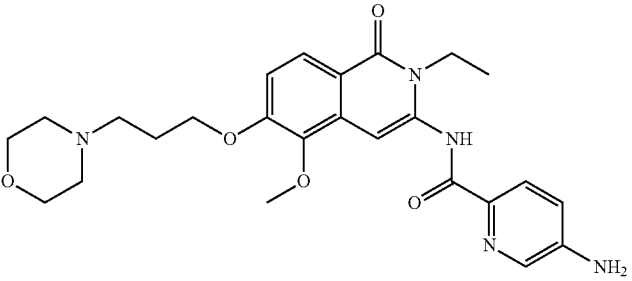 |
| 8b'-16 | 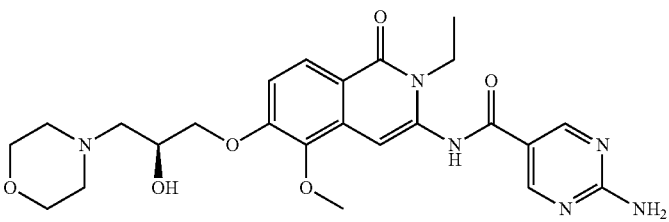 |
| 8b'-17 | 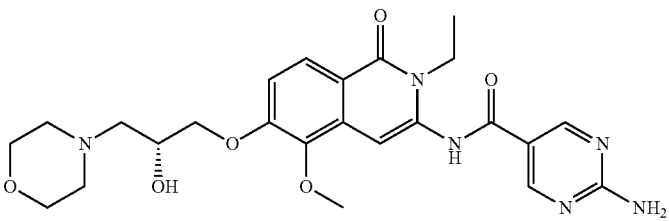 [SMILES: CCn1c(NC(=O)c2cnc(N)nc2)cc2c(OC)c(OC[C@H](O)CN3CCOCC3)ccc2c1=O] |
| 8b'-18 | 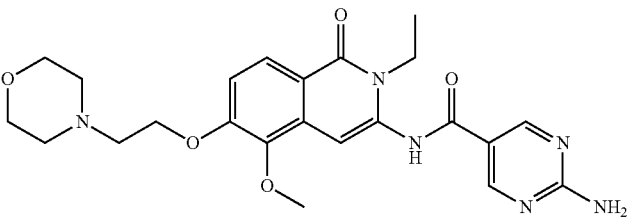 [SMILES: CCn1c(NC(=O)c2cnc(N)nc2)cc2c(OC)c(OCCN3CCOCC3)ccc2c1=O] |
| 8b'-19 | 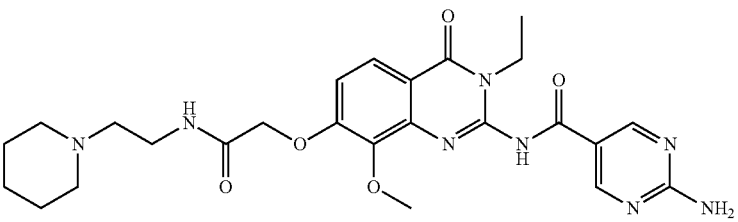 [SMILES: CCn1c(NC(=O)c2cnc(N)nc2)nc2c(OC)c(OCC(=O)NCCN3CCCCC3)ccc2c1=O] |
| 8b'-20 | 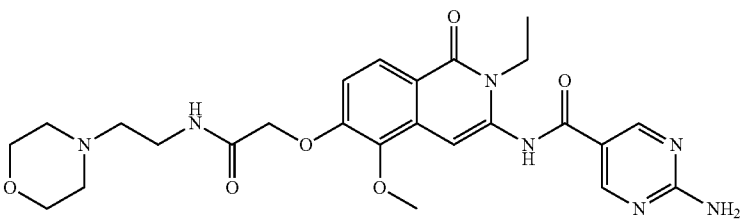 [SMILES: CCn1c(NC(=O)c2cnc(N)nc2)cc2c(OC)c(OCC(=O)NCCN3CCOCC3)ccc2c1=O] |

-continued
| Compd. | Structure |
|---|---|
| 8b'-21 | 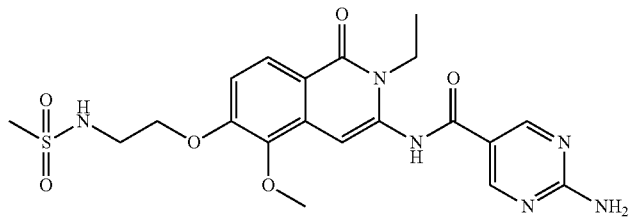 |
| 14a'-1 | 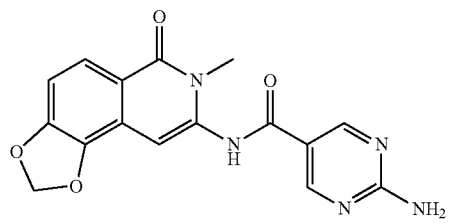 |
| 14a'-2 | 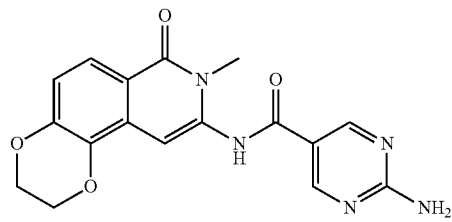 [SMILES: Cn1c(NC(=O)c2cnc(N)nc2)cc2c3c(ccc2c1=O)OCCO3] |
| 14a'-3 | 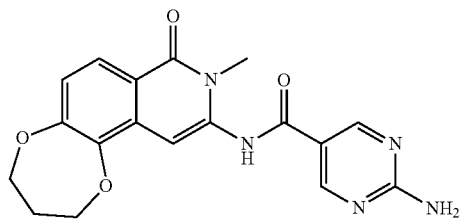 [SMILES: Cn1c(NC(=O)c2cnc(N)nc2)cc2c3c(ccc2c1=O)OCCCO3] |
| 14a'-4 | 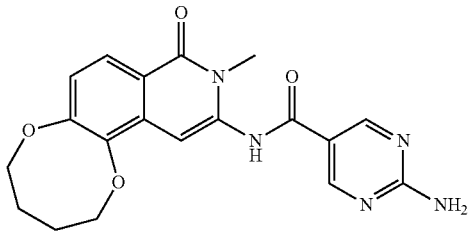 [SMILES: Cn1c(NC(=O)c2cnc(N)nc2)cc2c3c(ccc2c1=O)OCCCCO3] |
| 14a'-5 | 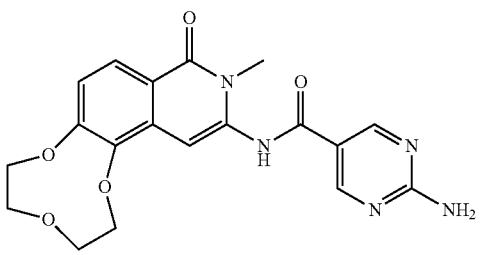 [SMILES: Cn1c(NC(=O)c2cnc(N)nc2)cc2c3c(ccc2c1=O)OCCOCCO3] |

| Compd. | Structure |
|---|---|
| 14a'-6 | 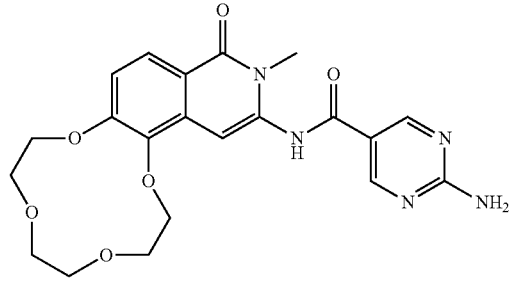 [SMILES: Cn1c(NC(=O)c2cnc(N)nc2)cc2c3c(ccc2c1=O)OCCOCCOCCO3] |
| 14a'-7 | 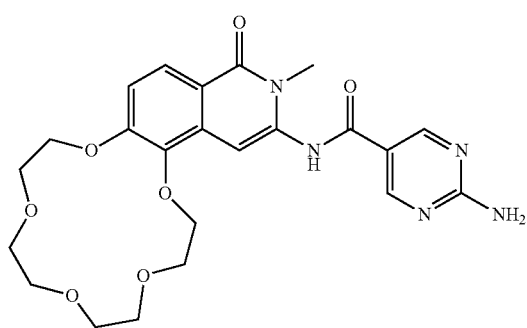 [SMILES: Cn1c(NC(=O)c2cnc(N)nc2)cc2c3c(ccc2c1=O)OCCOCCOCCOCCO3] |
| 14a'-8 | 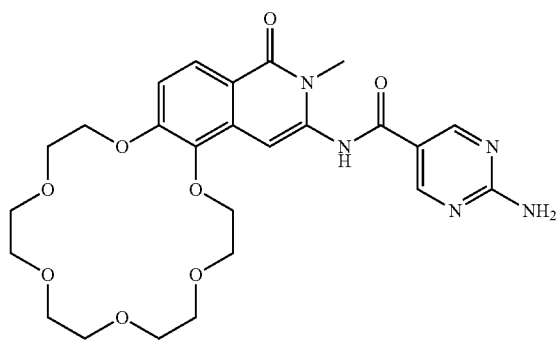 [SMILES: Cn1c(NC(=O)c2cnc(N)nc2)cc2c3c(ccc2c1=O)OCCOCCOCCOCCOCCO3] |
| 14b'-1 | 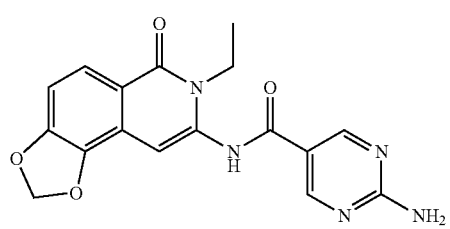 |
| 14b'-2 | 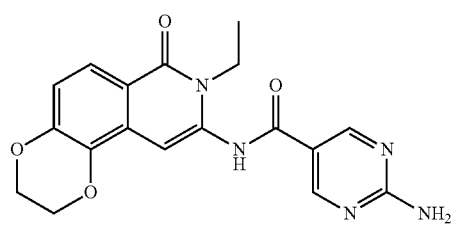 |

-continued

| Compd. | Structure |
|---|---|
| 14b'-3 | 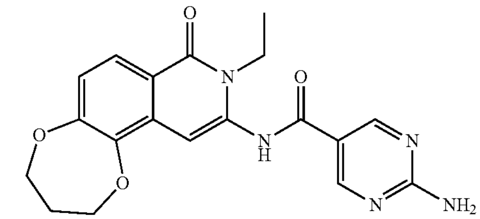 |
| 14b'-4 | 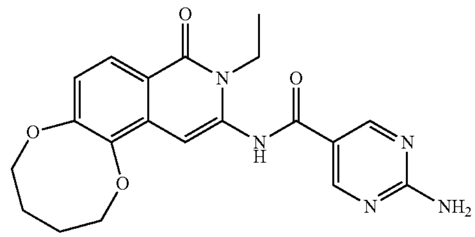 [SMILES: CCn1c(NC(=O)c2cnc(N)nc2)cc2c3c(ccc2c1=O)OCCCCO3] |
| 14b'-5 | 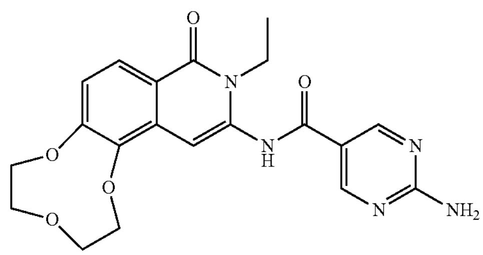 [SMILES: CCn1c(NC(=O)c2cnc(N)nc2)cc2c3c(ccc2c1=O)OCCOCCO3] |
| 14b'-6 | 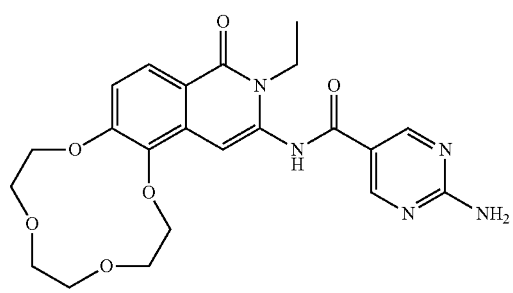 [SMILES: CCn1c(NC(=O)c2cnc(N)nc2)cc2c3c(ccc2c1=O)OCCOCCOCCO3] |
| 14b'-7 | 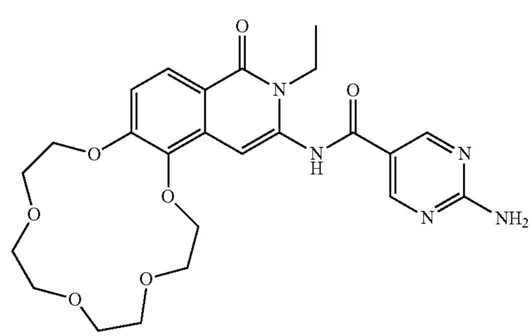 [SMILES: CCn1c(NC(=O)c2cnc(N)nc2)cc2c3c(ccc2c1=O)OCCOCCOCCOCCO3] |

| Compd. | Structure |
|---|---|
| 14b'-8 | 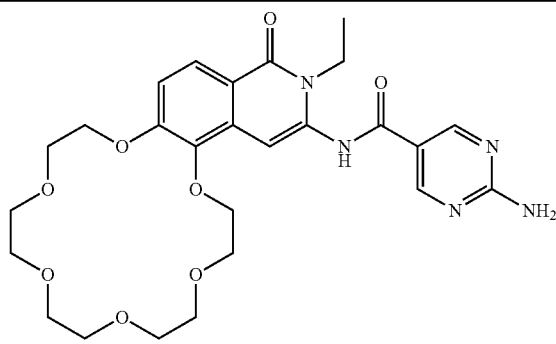 | or pharmaceutically acceptable salts of the above compounds.

Copanlisib is a 2,3-dihydroimidazo[1,2-c]-quinazoline derivative. Its tricyclic structure is essential for activity (ChemMedChem 2016, 11, 1517-1530), but this structure has greater rigidity, which affects the physicochemical properties of the entire molecule, especially the pharmacokinetic properties. The possible reason for the large volume of distribution of Copanlisib in the body is the tricyclic structure.

The present disclosure adopts the ring-opening strategy in medicinal chemistry to open the 2,3-dihydroimidazole ring of Copanlisib and introduce C1-C3 alkyl on the N atom of quinazoline, to improve the binding of the molecule to the PI3K protein, thus a new type of quinazolinone derivative with a new skeleton is obtained; and a bioelectronic isostere strategy is further adopted to replace the 1-position nitrogen atom of quinazolinone with a carbon atom, to design and synthesize isoquinolinone derivatives. The above structural optimization can effectively improve the physicochemical properties of the target molecule (such as increasing water solubility). The pharmacokinetic properties of the representative molecule are significantly improved compared with copanlisib, and thus has a good clinical prospect.

On the other hand, the development of selective PI3Kα inhibitors currently has made a good progress. Alpelisib and Taselisib (GDC-0032) have both entered phase III clinical trials for hematological tumors and a variety of solid tumors with PIK3C gene mutations, including breast cancer, colorectal cancer, gastric cancer, etc. Through molecular docking studies, we found that copanlisb binds closely to PI3Kα and PI3Kδ by its core structure, while the side chain propylmorpholine is located in the peripheral solvent region; and the molecular docking studies for the PI3Kα selective inhibitor Alpelisib (BYL719) and GDC-0032 have shown that the alkyl amide fragment of their side chains can form a strong hydrogen bond with the peripheral amino acid residue Gln859 of PI3Kα. Therefore, we modified and adjusted the side chains of the above two types of aminoquinazolinone and aminoisoquinolinone derivatives, introducing a variety of substituted alkyl amide functional groups to enhance the binding ability of the molecules to PI3Kα, weak the activity to PI3δ, and reduce the toxic and side effects caused by inhibiting PI3δ, thereby obtaining an inhibitor with a certain PI3Kα selectivity (inhibition of PI3Kα activity is more than five times higher than that of PI3δ).

The second object of the present disclosure is to provide a praparation method of the compounds.

I. Synthetic Method of Compounds of General Formula a (Including Analogs)

1. When $R_1$ is methyl:

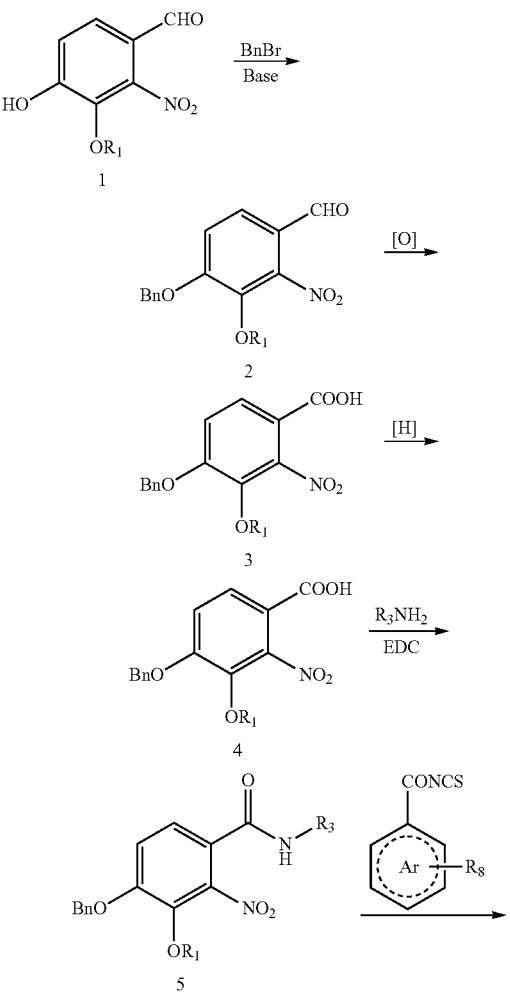

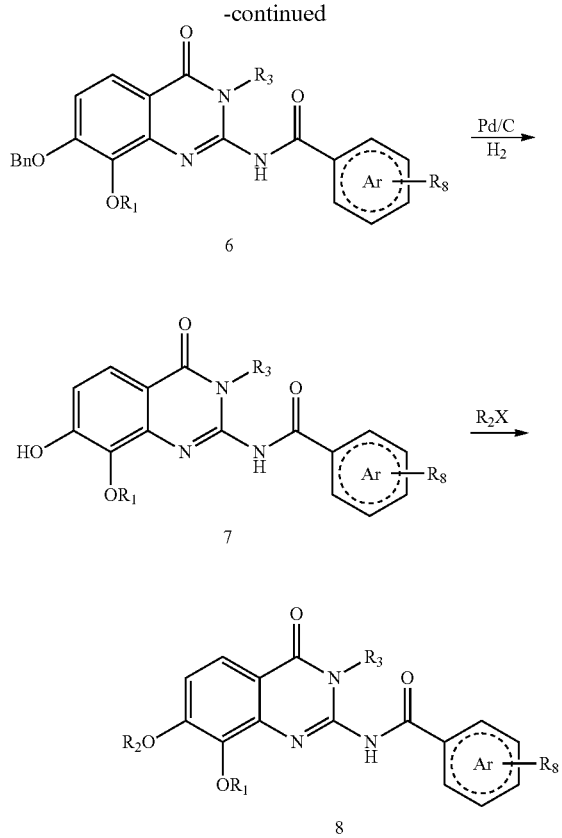

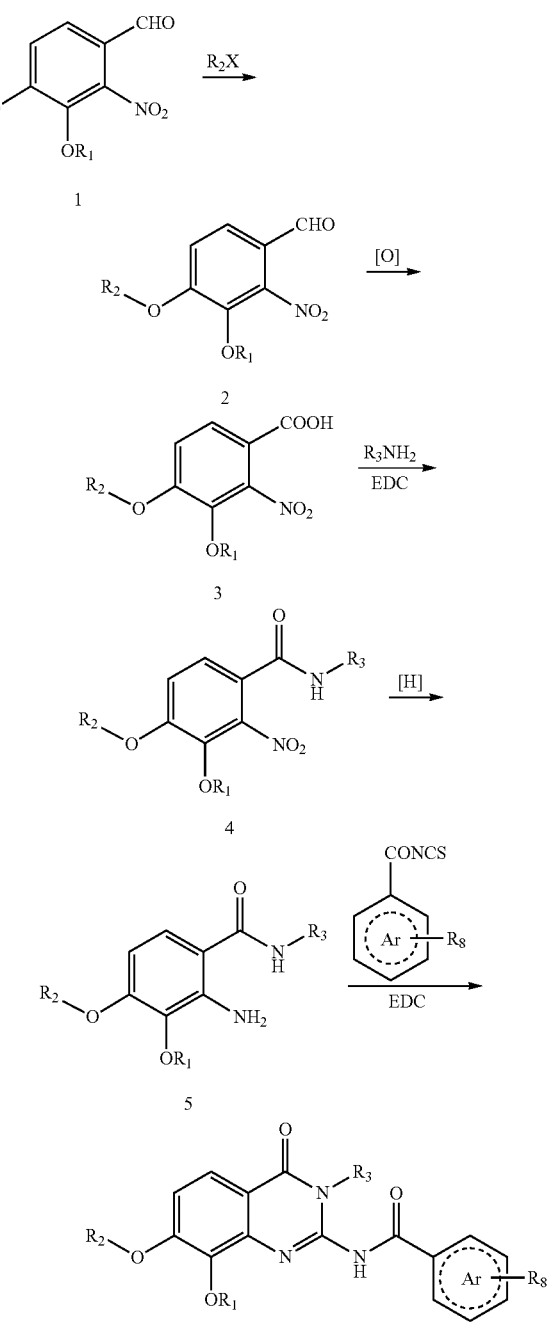

The specific reaction process can be:

Dissolving the substituted benzaldehyde (compound 1) in a solvent, and reacting with benzyl bromide or benzyl chloride under an alkaline condition to prepare the benzyl protected intermediate 2. The base used includes potassium carbonate, sodium carbonate, or cesium carbonate, and the solvent used includes acetonitrile, DMF, DMSO, etc.

Treating the benzaldehyde intermediate 2 with an oxidizing agent to obtain the benzoic acid intermediate 3. The oxidizing agent includes sodium hypochlorite, sodium chlorite, potassium permanganate, etc., and the solvent used is acetic acid, water, THF, dioxane, acetone, etc.

Treating the benzoic acid intermediate 3 with reducing agent to obtain anthranilic acid intermediate 4. The reducing agent includes iron powder, zinc powder, Pd/C-H$_2$, Raney Ni-H$_2$, etc.

Reacting the anthranilic acid intermediate 4 with the corresponding alkylamine by means of a condensing agent to prepare the benzamide intermediate 5. The condensing agent includes EDC, DCC, DIC, etc.

Cyclizing the anthranilamide intermediate 5 wiht the corresponding substituted aryl acyl isothiocyanate by means of a condensing agent to obtain the benzyl-protected aminoquinazolinone intermediate 6. The condensing agent includes EDC, DCC, DIC, etc.

Debenzylating the aminoquinazolinone intermediate 6 by the Pd/C-H$_2$ system to prepare intermediate 7.

Finally, undergoing a nucleophilic reaction for the intermediate 7 with the corresponding halogenated hydrocarbons (chlorinated and brominated) to prepare the target molecular product 8.

2. In addition, the target molecule 8 can also be synthesized by the following means:

Firatly reacting the substituted benzaldehyde 1 with halogenated hydrocarbon under an alkaline condition to introduce R$_2$ group to obtain intermediate 2. The alkaline reagent include potassium hydroxide, sodium hydroxide, cesium carbonate, potassium carbonate, sodium carbonate, etc.;

Treating the intermediate 2 with an oxidizing agent to obtain the benzoic acid intermediate 3; the oxidizing agent includes sulfamic acid+sodium chlorite, sodium hypochlorite, potassium permanganate, etc., and the solvent includes acetic acid, formic acid, water, acetone, dioxane, THF, etc.;

Condensing the benzoic acid intermediate 3 with amine to obtain the benzamide intermediate 4. The condensing agent used includes EDC, DCC, DIC, etc.;

Treating the benzamide intermediate 4 with a reducing agent to obtain the corresponding aminobenzamide intermediate 5. The reducing agent includes Fe/HAc, Pd/C-$H_2$, etc.;

Finally, cyclizing the intermediate 5 with different substituted aryl acyl isothiocyanates by means of a condensing agent to prepare the target molecule 8. The condensing agent includes EDC, DCC, DIC, etc.

3. For the target molecule with X=CH. the reaction formulas are as follows:

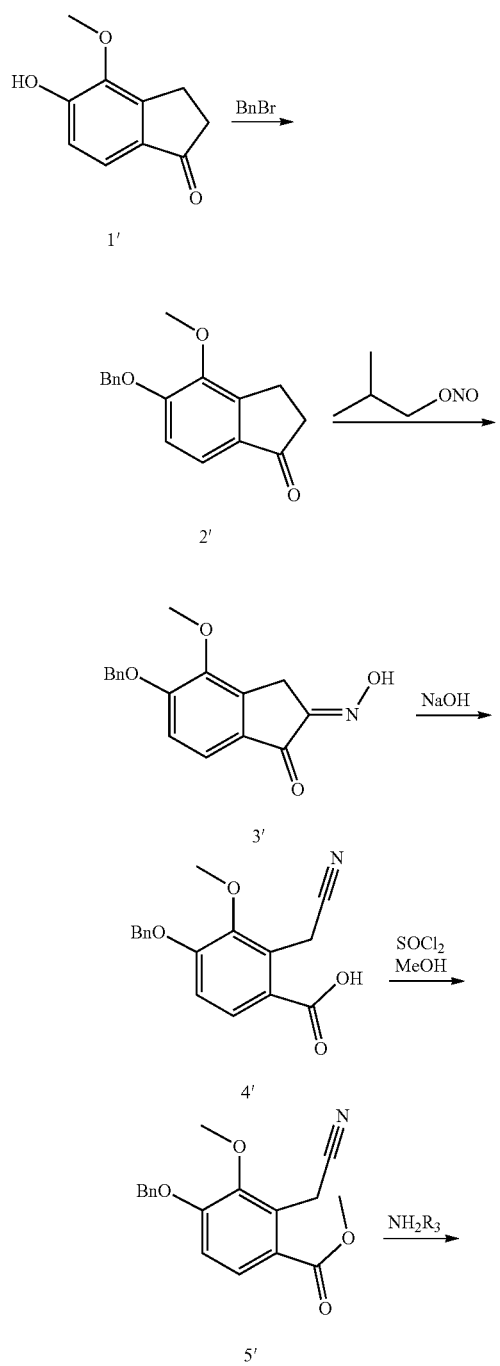

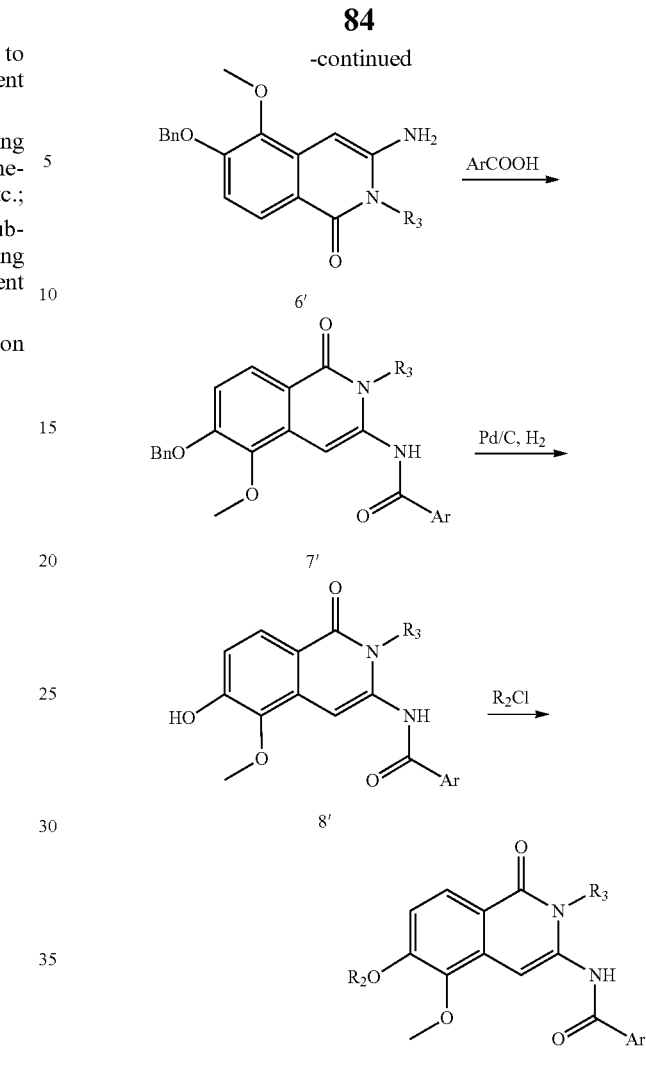

The specific reaction process can be:

Dissolving 5-Hydroxy-4-methoxy-1-indanone (Compound 1'), and adding dropwise benzyl bromide under an alkaline condition, stirring overnight at room temperature, and removing the solvent by rotary evaporation. Washing the obtained solid with water and petroleum successively, and undergoing a suction filtration to obtain the benzyl-protected intermediate 2'. The base used can be potassium carbonate, sodium carbonate, cesium carbonate, and the solvent used is generally acetonitrile or N,N-dimethyl formamide (DMF);

Dissolving 4-Methoxy-5-benzyloxy-1-indanone 2' in methyl tert-butyl ether, and adding dropwise isoamyl nitrite and trimethyl chlorosilane successively under stirring in an ice bath. And after the reaction is complete, undergoing a suction filtration to obtain the Hydroxime intermediate 3'.

Adding the hydroxyoxime intermediate 3' into 15% NaOH aqueous solution, stirring at room temperature, and undergoing a suction filtration after adjusting the pH. The obtained solid is o-carboxyphenylacetonitrile 4';

Dissolving the intermediate 4' in methanol, reacting by adding dropwise $SOCl_2$ in an ice bath, and extracting and concentrating to obtain methyl ester 5';

Dissolving the methyl ester intermediate 5', the corresponding alkylamine $R_3NH_2$ and triethylamine in water, reacting overnight in a sealed tank at 120° C., and extracting and concentrating to obtain the aminoisoquinolinone intermediate 6';

Dissolving the intermediate 6' and the corresponding aromatic carboxylic acid in DMF, and adding N,N-diisopropylethylamine (DPIEA), hexafluorophosphate benzotriazol-1-yl-oxytripyrrolidinyl phosphorus (PyBop) successively, reacting at room temperature, washing the solid obtained by suction filtration with ethyl acetate, and drying to obtain the benzyl-protected amide product 7';

Stirring the intermediate 7' at room temperature in a hydrogen and Pd/C system to debenzylate to obtain 6-hydroxy-5-methoxyisoquinolinone intermediate 8', and the solvent selects ethanol.

Reacting the intermediate 8' with the chloride of $R_2$ under an alkaline condition to prepare product 9'. The base used can be an organic base or an inorganic base. The organic base can select pyridine, triethylamine, or N,N-diisopropylethyl Amine, and the inorganic base can select potassium carbonate, sodium carbonate, or cesium carbonate, the solvent used is generally acetonitrile or N,N-dimethylformamide (DMF), the reaction temperature is between 40° C.-70° C., see the Examples for details.

II. Synthetic Method of Compounds of GENERAL Formula b (Including Analogs)

1. When X═N, the reaction formulas are as follows:

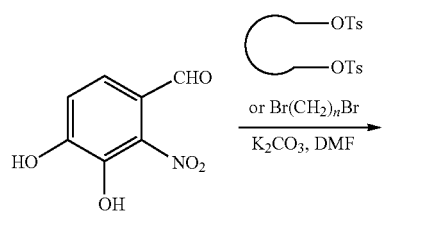

9

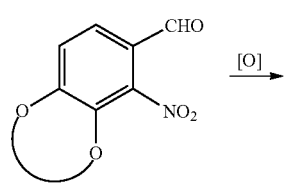

10

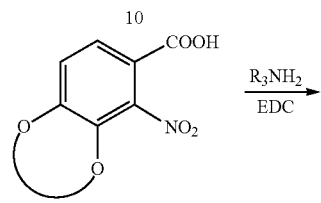

11

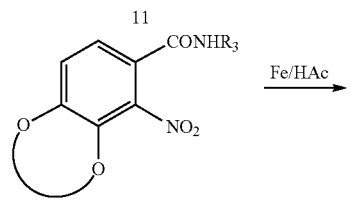

12

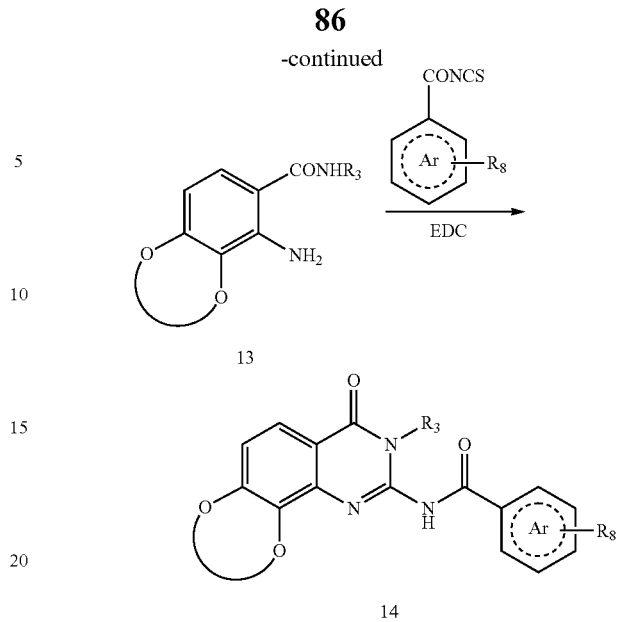

13

14

The specific reaction process can be:

Reacting the compound 9 with a reagents such as alkyl dibromide or ethylene glycol bis(p-toluenesulfonate), etc. with DMF as solvent by means of an alkaline reagent to obtain the intermediate 10 in which two oxygen atoms are ring-bonded.

Oxidizing the intermediate 10 (substituted benzaldehyde) with an oxidant to obtain the corresponding benzoic acid 11; the oxidant includes sodium hypochlorite, sodium chlorite, $KMnO_4$, etc.

Dissolving the substituted benzoic acid 11, different alkylamines and a condensing agent in dichloromethane, and stirring overnight at room temperature to obtain the amide intermediate 12; the condensing agent includes EDC, DCC, DIC, etc.

Reducing the intermediate 12 to the intermediate 13 using iron powder/acetic acid system. Finally, cyclizing the intermediate 13 with aryl acyl isothiocyanate by means of a condensing agent to obtain the target compound 14. The condensing agent includes EDC, DCC, DIC etc.

2. When X═CH, the reaction formulas are as follows:

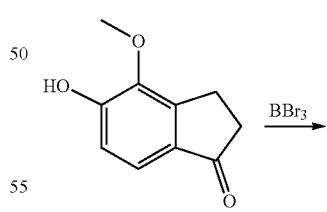

1'

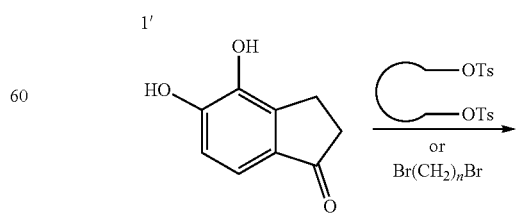

10'

-continued

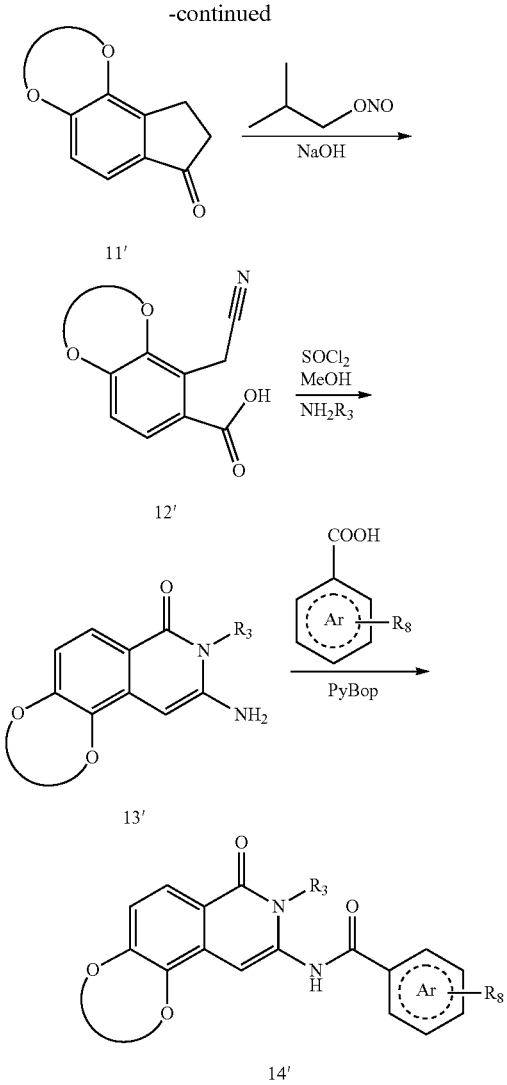

The specific reaction process can be:

Demethylating the compound 1' by means of BBr₃ to obtain the o-diphenol compound 10', and then reacting with alkyl dibromide or ethylene glycol bis(p-toluenesulfonate) to obtain the intermediate 11' in which two oxygen atoms are ring-bonded;

Reacting the intermediate 11' with isoamyl nitrite and trimethylchlorosilane, and then hydrolyzing with NaOH to obtain the o-carboxyphenylacetonitrile derivative 12';

Dissolving the intermediate 12' in methanol, reacting by adding dropwise SOCl₂ in an ice bath, and extracting and concentrating to obtain methyl ester, and then reacting with corresponding alkylamine R₃NH₂ to obtain the aminoisoquinolinone intermediate 13';

Dissolving the intermediate 13' and the corresponding aromatic carboxylic acid in DMF, and adding N,N-diisopropylethylamine (DPIEA), hexafluorophosphate benzotriazol-1-yl-oxytripyrrolidinyl phosphorus (PyBop) successively, reacting at room temperature, washing the solid obtained by suction filtration with ethyl acetate, and drying to obtain the target molecule 14'.

Another object of the present disclosure is to provide the application of the aminoquinazolinone and aminoisoquinolinone derivatives in the preparation of anti-tumor and anti-inflammatory drugs, and the drugs include the one prepared from any one or more of the derivatives and pharmaceutically acceptable salts thereof, and the solvates with a pharmaceutically acceptable carrier.

The "pharmaceutically acceptable carrier" refers to a conventional pharmaceutical carrier in the pharmaceutical field, including a conventional diluent or excipient such as water, etc., a filler such as starch, etc., a binder such as cellulose derivatives, gelatin, etc., a wetting agent such as glycerin, a disintegrating agent such as agar, calcium carbonate, etc., an absorption promoter such as quaternary ammonium compounds, a surfactants such as cetyl alcohol, an adsorption carrier such as kaolin and bentonite, a lubricant such as talc, etc. in the pharmaceutical field. If necessary a flavor, a sweetener, etc. also can be added.

The pharmaceutical formulation is suitable for administration by any appropriate manners, such as oral (including buccal or sublingual administration), rectal administration, nasal administration, and topical administration (including buccal, sublingual or transdermal administration)), vaginal administration or parenteral administration (including subcutaneous injection, intramuscular injection, intravenous injection or intradermal injection). These formulations can be prepared by any methods known in the pharmaceutical field, for example, by mixing the active ingredient with a carrier or an excipient.

The present disclosure provides the application of the combination of the compounds of the General Formulas a and b and the preferred compounds thereof, the pharmaceutically acceptable salts of the compounds, the solvates of the compounds, with other drugs in the preparation of anticancer drugs. Furthermore, the cancer is selected from breast cancer, sarcoma, lung cancer, prostate cancer, colon cancer, rectal cancer, kidney cancer, pancreatic cancer, blood cancer, neuroblastoma, glioma, head cancer, neck cancer, and thyroid cancer, liver cancer, ovarian cancer, vulvar cancer, cervical cancer, endometrial cancer, testicular cancer, bladder cancer, esophageal cancer, stomach cancer, nasopharyngeal cancer, buccal cancer, oral cancer, gastrointestinal stromal tumor, skin cancer, or multiple myeloma.

Anti-tumor drugs that can be used in combination with the compounds provided by the present disclosure or the pharmaceutically acceptable salts thereof include but not limited to at least one of the following categories: mitotic inhibitors (such as vinblastine, vindesine, and vinorelbine); tubulin Decomposition inhibitors (such as Taxol); alkylating reagents (such as cisplatin, carboplatin, and cyclophosphamide); antimetabolites (such as 5-fluorouracil, tegafur, methotrexate, cytarabine and hydroxy urea); insertable antibiotics (such as adriamycin, Mitomycin, and bleomycin); enzymes (such as aspartase); topoisomerase inhibitors (such as etoposide and camptothecin); biological response regulation agents (such as interferon); or proteasome inhibitors (such as bortezomib).

It has been confirmed through many experiments that the compounds synthesized in the present disclosure have excellent inhibitory effects on PI3Kα and PI3Kγ. Among them, most of the compounds have significant inhibitory effects on PI3Kα and show potent growth inhibitory effects on tumor cell lines such as PIK3CA mutant human breast cancer cell line (MCF7). Therefore, the compounds of the present disclosure can be used, as PI3Kα inhibitors, in the drugs for the treatment of tumors related to human or animal cell proliferation.

BRIEF DESCRIPTION OF DRAWINGS

FIG. 1 is the results of in vivo efficacy experiments.

DESCRIPTION OF EMBODIMENTS

The present disclosure will be further described in conjunction with the embodiments. The specific examples included below are for illustrative purposes and should not be construed as limiting the scope of the present disclosure. In addition, it should be noted that after reading the content described by the present disclosure, those skilled in the art can make various modifications or amendments to the present disclosure, and these equivalent forms also fall within the scope defined by the attached claims of the present disclosure.

Example 1: Preparation of 2-amino-N-(8-methoxy-3-methyl-7-(3-morpholinopropyl)-4-oxo-3,4-dihydroquina zolinone-2-yl) pyrimidine -5-formamide (Compound 8a-1)

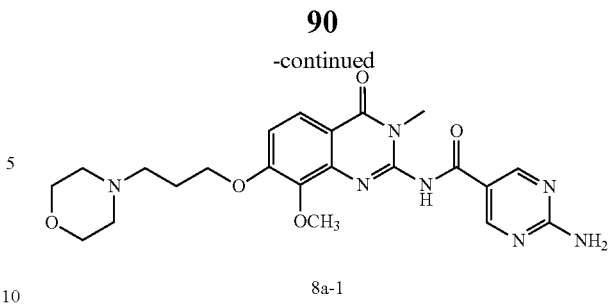

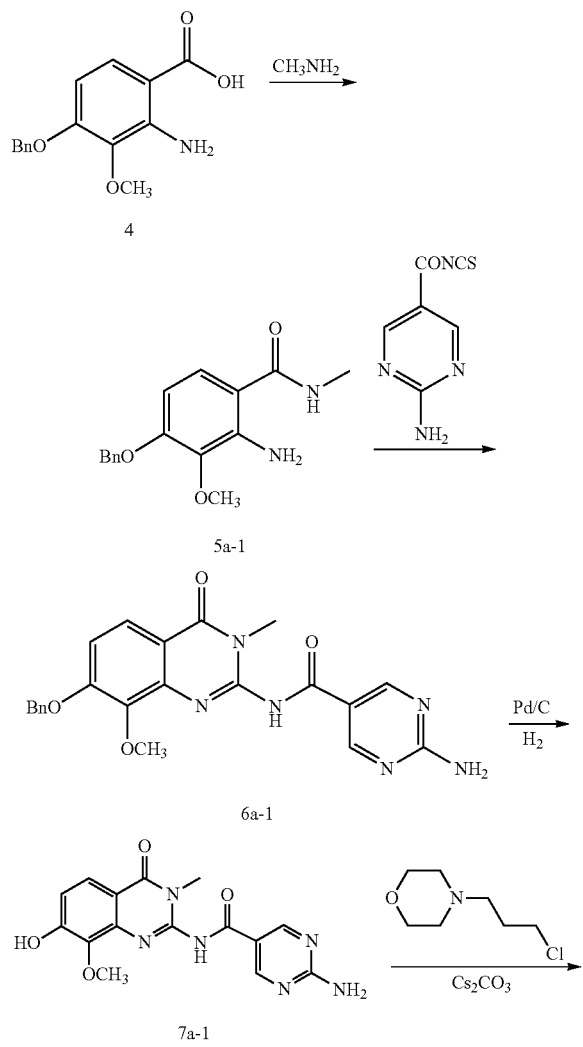

Step 1. Preparation of 2-amino-3-methoxy-4-benzyloxy-N-methylbenzamide (compound 5a-1)

2-amino-3-methoxy-4-benzyloxybenzoic acid (4, 546 mg, 2 mmol) was dissolved in 20 mL of DCM, and adding successively ethylamine hydrochloride (102 mg, 2.4 mmol), HOBT (405 mg, 3 mmol), DIC (378 mg, 3 mmol), and triethylamine (0.83 mL, 6 mmol). The mixture was stirred at room temperature for 2 h, then added water, and extracted with dichloromethane. The organic layers was combined, washed with saturated NaCl and dried over anhydrous $Na_2SO_4$. The solvent was recovered to obtain a white powder 0.48 g. Yield: 80%; ESI-MS: 287.1 $[M+H]^+$.

Step 2. Preparation of 2-Amino-N-(8-methoxy-3-methyl-7-benzyloxy-4-oxo-3,4-dihydroquinazolinone-2-yl) pyrimidine-5-formamide (compound 6a-1)

2-amino-3 -methoxy-4-benzyloxy-N-methylbenzamide (5a-1, 0.2 mmol), 2-aminopyrimidine-5-acylisothiocyanate (0.2 mmol) wre dissolved in 100 mL of anhydrous DMF, and adding EDC (0.3 mmol). The mixture was stirred at room temperature overnight, then underwent a suction filtration to obtain a precipitate. The precipitate was washed with ethyl acetate to obtain the target compound. Yield: 96%, ESI-MS: 433.2 $[M+H]^+$; $^1$H-NMR (δ, $CDCl_3/CD_3OD$=8:1): 13.96 (s, 1H), 9.10 (s, 2H), 7.89 (d, 1H, J=9.0 Hz), 7.46 (m, 5H), 7.00 (d, 1H, J=9.0 Hz), 5,84 (s, 2H), 5.26 (s, 2H), 4,43 (s, 3H), 4.8 (s, 3H).

Step 3. Preparation of 2-Amino-N-(8-methoxy-3-methyl-7-hydroxy-4-oxo-3,4-dihydroquinazolinone-2-yl) pyrimidine-5-carboxamide (compound 7a-1)

The compound 6a-1 (500 mg) was dissolved in 50 mL of EtOH, and adding 50 mg of 10% Pd/C. The mixture was stirred overnight at room temperature under $H_2$ atmosphere, then filtered through Celite. The filtrate was dried by rotary evaporation. The obtained solid was washed with ethanol. Yield: 90%, ESI-MS: 343.1 $[M+H]^+$; $^1$H-NMR (δ, DMSO-$d_6$): 13.95(s, 1H), 8.98(s, 1H), 8.94(s, 2H), 7.67(d, 1H, J=8.5 Hz), 7.47(s, 2H), 6.93(d, 1H, J=8.5 Hz), 4.27 (s, 3H), 3.92(s, 3H).

Step 4. Preparation of 2-Amino-N-(8-methoxy-3-methyl-7-(3-morpholinopropyl)-4-oxo-3,4-dihydroquinazolinone-2-yl) pyrimidine-5-carboxamide (compound 8a-1)

The compound 7a-1 (0.1 mmol) was dissolved in 10 mL of acetonitrile, and adding cesium carbonate (0.15 mmol). The mixture was stirred for 0.5 h, then the temperature was raised to 60° C. a N-(3-chloropropyl) morpholine (0.15 mmol) in 20 mL of acetonitrile solution was added dropwise thereto, reacting at 50° C. for 10 h. The solvent was removed by vacuum distillation. Water was added to precipitate a precipitate, which washed with methanol to obtain a pale yellow solid 8a-1. Yield: 78%, ESI-MS: 470.2 [M+H]$^+$; $^1$H-NMR (δ, CDCl$_3$/CD$_3$OD=10:1): 9.03 (s, 2H), 8.82 (s, 1H), 7.86 (d, 2H, J=8.5 Hz), 6.93 (d, 2H, J=8.5 Hz), 4.23 (t, 2H, J=6.0 Hz), 4.14 (t, 2H, J=6.0 Hz), 4.00 (s, 3H), 3.94 (m, 4H), 3.80 (s, 1H), 3.63 (s, 3H), 3.34 (m, 2H), 2.85 (s, 2H), 2.30 (m, 4H), 0.84 (t, 3H, J=6.5 Hz).

Preparation of salts of 8a-1:

100 mg of 8a-1 was dissolved in 20 mL of ethyl acetate saturated with hydrogen chloride. The solid was firstly dissolved, and then a white solid was precipitated out slowly to obtain 8a-1 hydrochloride;

According to a similar method, the target molecule 8a-1 was reacted with equimolar hydrobromic acid, fumaric acid, maleic acid, tartaric acid, etc. in a suitable solvent, so as to prepare the corresponding hydrobromide, fumarate, maleate and tartrate, etc of 8a-1, respectively.

Example 2: Synthesis of the Compounds 8a-2 TO 8a-13

The compound 7a-1 was used as a raw material. And chloroacetamide, chloropropionamide, N-methylchloroacetamide, N,N-dimethylchloroacetamide, 2-(2-chloroethyl)-4-methylmorpholine, 1-(3-chloro-propionyl)-4-methylpiperazine, chloroacetylmorpholine, 4-chlorobutanamide, difluorochloromethane, chloroethylsulfonamide, Togni reagent, or chloropropyl sulfonamide were used respectively to instead of N-(3-chloropropyl) morpholine to prepare the compounds 8a-2 to 8a-13.

The series of target molecules are shown in Table 1 below.

TABLE 1

| Compd. | Structure | MS (ESI) |
|---|---|---|
| 7a | 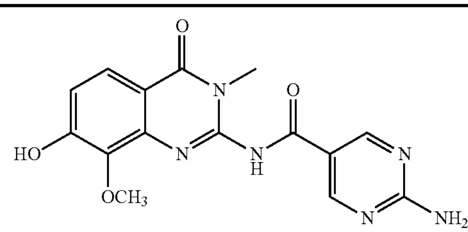 | 343.2 [M + H]$^+$ |
| 8a-1 | 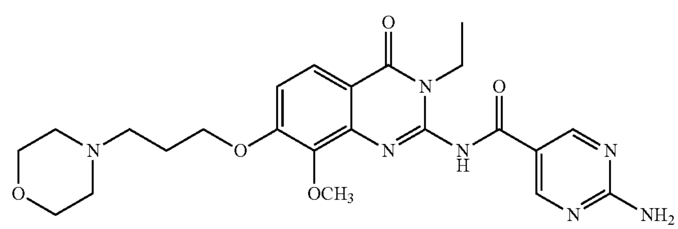 | 470.2 [M + H]$^+$ |
| 8a-2 | 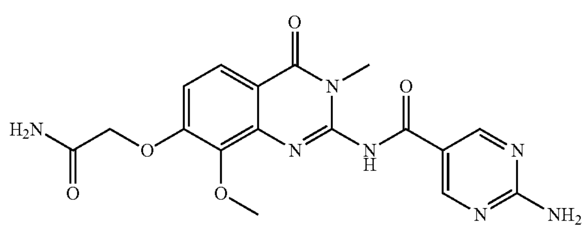 [SMILES: COc1c(OCC(N)=O)ccc2c(=O)n(C)c(NC(=O)c3cnc(N)nc3)nc12] | 400.2 [M + H]$^+$ |
| 8a-3 | 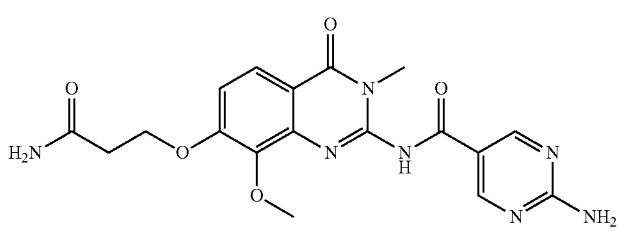 | 414.2 [M + H]$^+$ |
| 8a-4 | 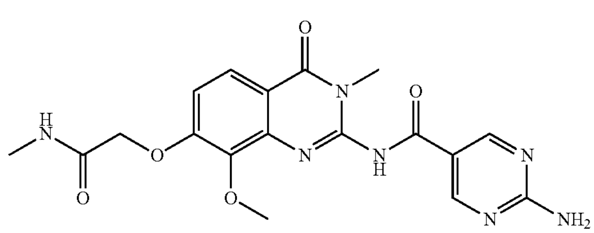 | 414.2 [M + H]$^+$ |

TABLE 1-continued

| Compd. | Structure | MS (ESI) |
|---|---|---|
| 8a-5 | 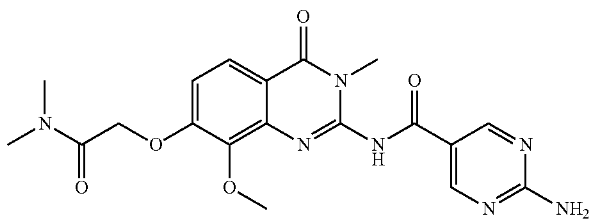 [SMILES: COc1c(OCC(=O)N(C)C)ccc2c(=O)n(C)c(NC(=O)c3cnc(N)nc3)nc12] | 428.2 [M + H]+ |
| 8a-6 | 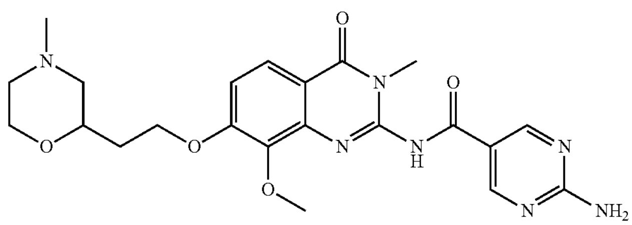 | 470.2 [M + H]+ |
| 8a-7 | 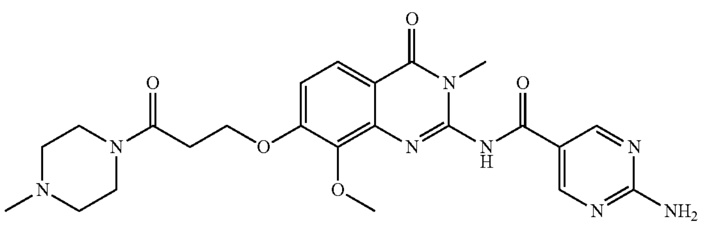 [SMILES: COc1c(OCCC(=O)N2CCN(C)CC2)ccc2c(=O)n(C)c(NC(=O)c3cnc(N)nc3)nc12] | 497.3 [M + H]+ |
| 8a-8 | 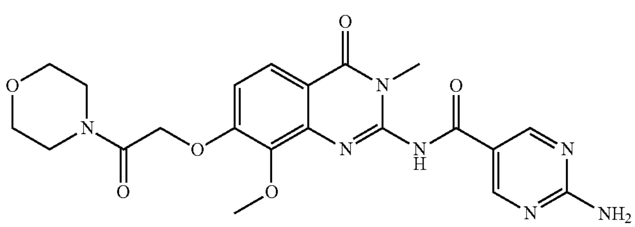 [SMILES: COc1c(OCC(=O)N2CCOCC2)ccc2c(=O)n(C)c(NC(=O)c3cnc(N)nc3)nc12] | 470.3 [M + H]+ |
| 8a-9 | 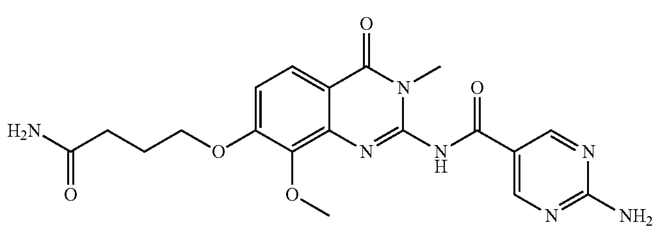 [SMILES: COc1c(OCCCC(N)=O)ccc2c(=O)n(C)c(NC(=O)c3cnc(N)nc3)nc12] | 428.2 [M + H]+ |
| 8a-10 | 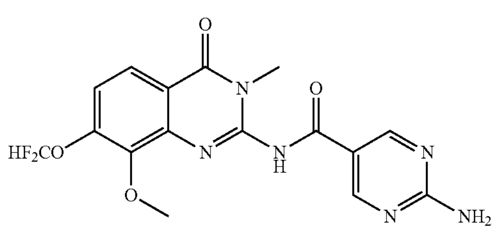 | 393.2 [M + H]+ |

TABLE 1-continued

| Compd. | Structure | MS (ESI) |
|---|---|---|
| 8a-11 | (structure) | 450.1 [M + H]+ |
| 8a-12 | (structure) | 411.2 [M + H]+ |
| 8a-13 | (structure) | 464.2 [M + H]+ |

Example 3: Synthesis of Compounds 8a-14 to 8a-26

The Synthetic Route is Shown as Follows

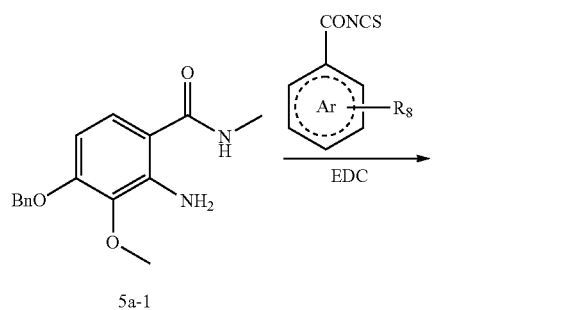

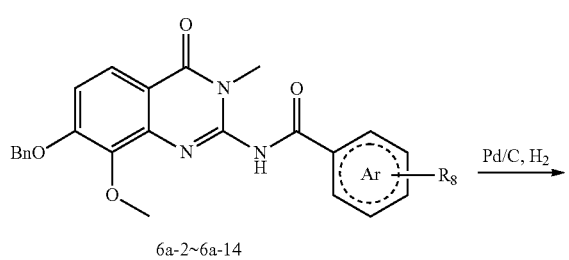

The compound 5a-1 was used as a raw material to firstly react respectively with pyrimidine-5-formyl isothiocyanate, pyridazine-4-formyl isothiocyanate, 2-amino-pyridine-5-formyl isothiocyanate, 6-amino-pyridazine-3-formyl isothiocyanate, 2-amino-pyrazine-5-formyl isothiocyanate, 5-aminopyridine-2-formyl isothiocyanate, 3-cyano-benzoyl isothiocyanate, pyrazine-2-formyl isothiocyanate, pyrazole-4-formyl isothiocyanate, thiazole-4-formyl isothiocyanate, purine-6-formyl isothiocyanate, benzimidazole-5-formyl isothiocyanate, or benzothiophene-5-formyl isothiocyanate, and then ring-bonded by the means of EDC to obtain the intermediates 6a-2 to 6a-14, and then debenzylated by Pd/C catalytic hydrogenation to obtain 7a-2 to 7a-14. Finally, they were reacted with N-(3-chloropropyl) morpholine to obtain the target molecules 8a-14 to 8a-26. The structural formulas of which are shown in Table 2 below.

TABLE 2

| Compd. | Structure | MS |
|---|---|---|
| 8a-14 | 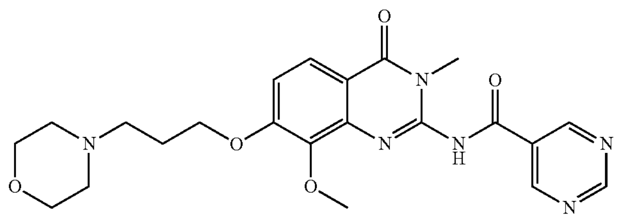 [SMILES: COc1c(OCCCN2CCOCC2)ccc2c(=O)n(C)c(NC(=O)c3cncnc3)nc12] | 455.3 [M + H]+ |
| 8a-15 | 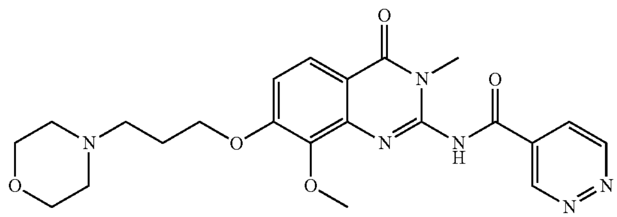 [SMILES: COc1c(OCCCN2CCOCC2)ccc2c(=O)n(C)c(NC(=O)c3ccnnc3)nc12] | 455.3 [M + H]+ |
| 8a-16 | 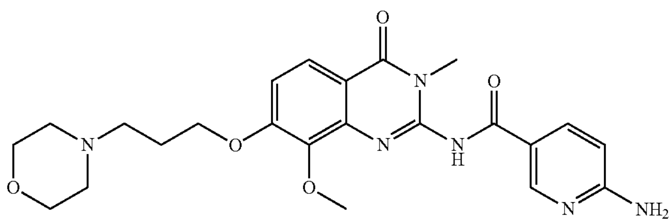 [SMILES: COc1c(OCCCN2CCOCC2)ccc2c(=O)n(C)c(NC(=O)c3ccc(N)nc3)nc12] | 469.3 [M + H]+ |
| 8a-17 | 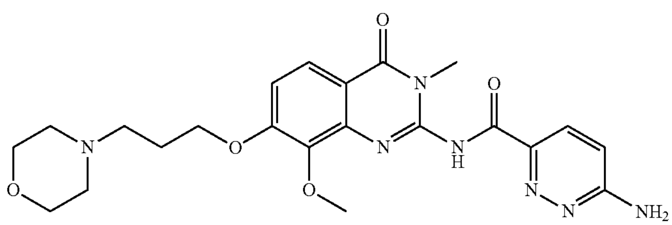 [SMILES: COc1c(OCCCN2CCOCC2)ccc2c(=O)n(C)c(NC(=O)c3ccc(N)nn3)nc12] | 470.2 [M + H]+ |
| 8a-18 | 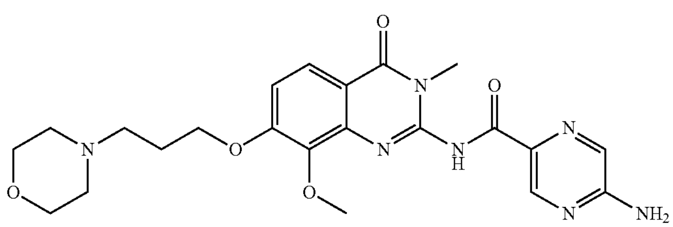 [SMILES: COc1c(OCCCN2CCOCC2)ccc2c(=O)n(C)c(NC(=O)c3cnc(N)cn3)nc12] | 470.2 [M + H]+ |
| 8a-19 | 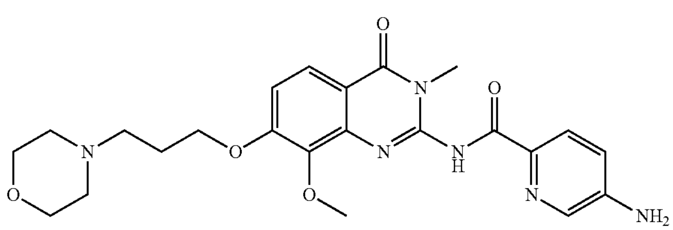 [SMILES: COc1c(OCCCN2CCOCC2)ccc2c(=O)n(C)c(NC(=O)c3ccc(N)cn3)nc12] | 469.3 [M + H]+ |
| 8a-20 | 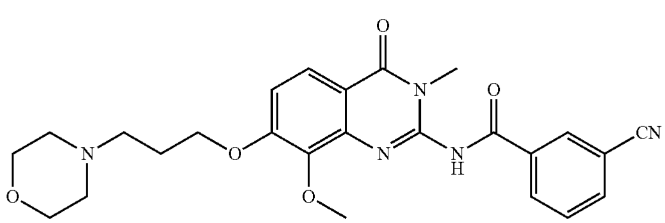 [SMILES: COc1c(OCCCN2CCOCC2)ccc2c(=O)n(C)c(NC(=O)c3cccc(C#N)c3)nc12] | 478.3 [M + H]+ |

TABLE 2-continued

| Compd. | Structure | MS |
|---|---|---|
| 8a-21 | 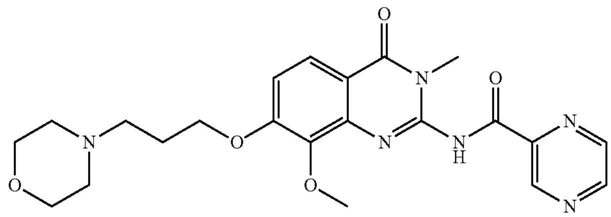 [SMILES: COc1c(OCCCN2CCOCC2)ccc2c(=O)n(C)c(NC(=O)c3cnccn3)nc12] | 455.3 [M + H]+ |
| 8a-22 | 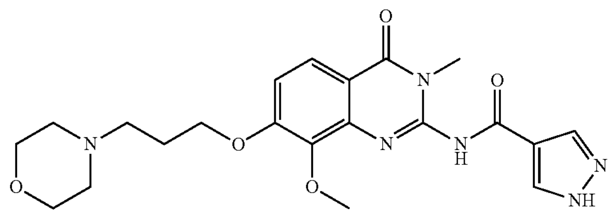 [SMILES: COc1c(OCCCN2CCOCC2)ccc2c(=O)n(C)c(NC(=O)c3cn[nH]c3)nc12] | 443.3 [M + H]+ |
| 8a-23 | 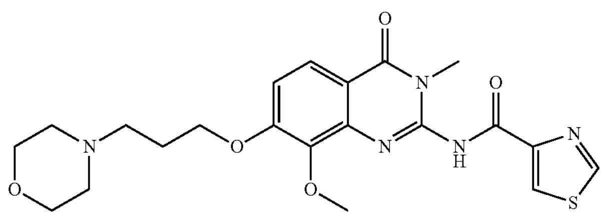 [SMILES: COc1c(OCCCN2CCOCC2)ccc2c(=O)n(C)c(NC(=O)c3cscn3)nc12] | 460.3 [M + H]+ |
| 8a-24 | 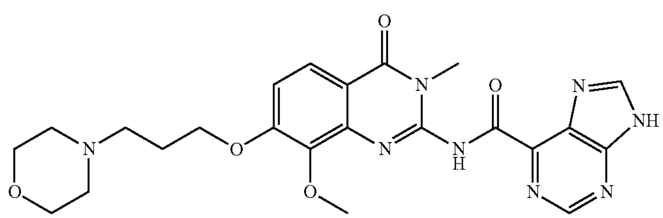 | 595.3 [M + H]+ |
| 8a-25 | 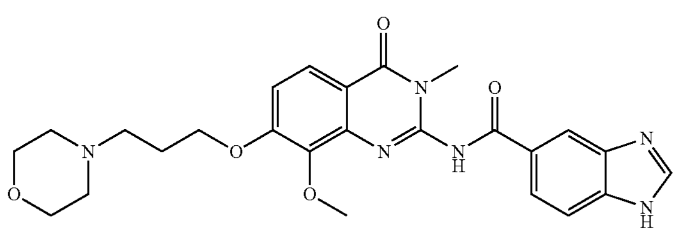 [SMILES: COc1c(OCCCN2CCOCC2)ccc2c(=O)n(C)c(NC(=O)c3ccc4[nH]cnc4c3)nc12] | 493.3 [M + H]+ |
| 8a-26 | 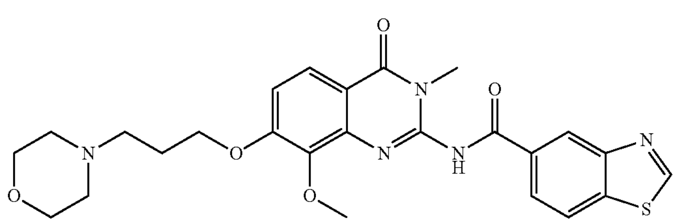 [SMILES: COc1c(OCCCN2CCOCC2)ccc2c(=O)n(C)c(NC(=O)c3ccc4scnc4c3)nc12] | 510.3 [M + H]+ |

Example 4: Synthesis of the Compounds 8a-27 to 8a-69

(S)-2-amino-N-(7-(2-hydroxy-3-morpholino-propoxy)-8-methoxy-3-methyl-4-oxo-3,4-dihydroquinazolin-2-yl) pyrimidine-5-carboxamide (compound 8a-27)

The preparation of the compound 8a-27 referred to the synthesis of 8a-1. N-chloropropyl morpholine was replaced with (S)-1-chloro-3-morpholinopropan-2-ol to obtain a white solid. Yield: 56.3%; ESI-MS: 486.2 [M+H]$^+$;$^1$H-NMR (δ, DMSO-d$_6$): 13.93 (s, 1H), 8.95 (s, 2H), 7.78 (d, 1H, J=9.0 Hz), 7.42 (s, 2H), 7.19 (d, 1H, J=9.0 Hz), 5.04 (d, 1H, J=5.0 Hz), 4,21 (dd, 1H, J$_1$=9.5 Hz, J$_2$=3.5 Hz), 4.11 (m, 2H), 3.98 (s, 3H), 3.58 (t, 4H, J=5.0 Hz), 3.54 (s, 3H), 2.47 (m, 6H).

(R)-2-amino-N-(7-(2-hydroxy-3-morpholino-propoxy)-8-methoxy-3-methyl-4-oxo-3,4-dihydroquinazolin-2-yl) pyrimidine-5-carboxamide (compound 8a-28)

The preparation of the compound 8a-28 referred to the synthesis of 8a-1. N-chloropropyl morpholine was replaced with (R)-1-chloro-3-morpholinopropan-2-ol to obtain a white solid. Yield: 48%; ES8a-MS: 486.2 [M+H]$^+$;$^1$H-NMR (δ, DMSO-d$_6$): 13.93 (s, 1H), 8.95 (s, 2H), 7.78 (d, 1H, J=9.0 Hz), 7.42 (s, 2H), 7.19 (d, 1H, J=9.0 Hz), 5.04 (d, 1H, J=5.0 Hz), 4,21 (dd, 1H, J$_1$=9.5 Hz, J$_2$=3.5 Hz), 4.11 (m, 2H), 3.98 (s, 3H), 3.58 (t, 4H, J=5.0 Hz), 3.54 (s, 3H), 2.47 (m, 6H).

2-((2-(2-aminopyrimidine-5-carboxamido)-8-methoxy-3-methyl-4-oxo-3,4-dihydroquinazolin-7-yl)oxy) ethyl acetate (compound 8a-29)

The preparation of the compound 8a-29 referred to the synthesis of 8a-1. N-chloropropyl morpholine was replaced with ethyl chloroacetate to obtain a white solid. Yield: 42%; ESI-MS: 453.1 [M+H]$^+$;$^1$H-NMR (δ, DMSO-d$_6$): 13.96 (s, 1H), 8.96 (s, 2H), 7.76 (d, 1H, J=9.0 Hz), 7.37 (d, 2H), 7.10 (d, 1H, J=9.0 Hz), 5.04 (s, 2H), 4.22 (m, 2H), 4.00 (s, 3H), 3.54 (s, 3H), 1.24 (m, 3H).

2-amino-N-(8-methoxy-3-methyl-7-(2-(methylsulfonamido)ethoxy)-4-oxo-3,4-dihydroquinazolin-2-yl) pyrimidine-5-carboxamide (compound 8a-30)

The preparation of the compound 8a-30 referred to the synthesis of 8a-1. N-chloropropyl morpholine was replaced with N-(2-bromoethyl) methanesulfonamide to obtain a white solid. Yield: 38%; ESI-MS: 464.1 [M+H]$^+$;$^1$H-NMR (δ, DMSO-d$_6$): 13.95 (s, 1H), 8.96 (s, 2H), 7.79 (d, 1H, J=9.0 Hz), 7.42 (s, 2H), 7.40 (t, 1H, J=6.0 Hz), 7.18 (d, J=8.5 Hz), 4.24 (t, 1H, J=5.5 Hz), 3.99 (s, 3H), 3.54 (s, 3H), 3.45 (q, 2H, J=5.5 Hz), 2.99 (s, 3H).

2-amino-N-(8-methoxy-3-methyl-7-(2-(methylamino)-2-oxoethoxy)-4-oxo-3,4-dihydroquinazolin-2-yl) pyrimidine-5-carboxamide (compound 8a-31)

The preparation of the compound 8a-31 referred to the synthesis of 8a-1. N-chloropropyl morpholine was replaced with 2-chloro-N-methylacetamide to obtain a white solid. Yield: 41%; ESI-MS: 414.1 [M+H]$^+$;$^1$H-NMR (δ, DMSO-d$_6$): 13.96 (s, 1H), 8.96 (s, 2H), 7.79 (d, 1H, J=9.0 Hz), 7.42 (m, 1H), 7.40 (t, 1H, J=6.0 Hz), 7.18 (d, J=8.5 Hz), 4.24 (t, 1H, J=5.5 Hz), 3.99 (s, 3H), 3.54 (s, 3H), 3.45 (q, 2H, J=5.5 Hz), 2.99 (s, 3H), 2.65 (d, 3H, J=4.5 Hz).

2-amino-N-(8-methoxy-3-methyl-4-oxo-7-(2-oxo-2-((2-(piperidin-1-yl)ethyl)amino)ethoxy) -3,4-dihydroquinazolin-2-yl) pyrimidine-5-carboxamide (compound 8a-32)

The preparation of the compound 8a-32 referred to the synthesis of 8a-1. N-chloropropyl morpholine was replaced with 2-chloro-N-(2-(piperidin-1-yl)ethyl)acetamide to obtain a white solid. Yield: 40%; ESI-MS: 511.1 [M+H]$^+$; $^1$H-NMR (δ, DMSO-d$_6$):14.01 (s, 1H), 8.96 (s, 2H), 7.77 (d, 1H, J=8.5 Hz), 7.05 (d, 1H, J=8.5 Hz), 6.73 (s, 2H), 4.74 (s, 2H), 4.00 (s, 3H), 3.55 (s, 3H), 3.27-3.23 (m, 2H), 2.36-2.32 (m, 6H), 1.49-1.45 (m, 4H), 1.39-1.35 (m, 2H).

2-amino-N-(8-methoxy-3-methyl-4-oxo-7-(2-oxo-2-((2-(morpholin-1-yl)ethyl)amino)ethoxy)-3,4-dihydroquinazolin-2-yl)pyrimidine-5-carboxamide (compound 8a-33)

The preparation of the compound 8a-33 referred to the synthesis of 8a-1. N-chloropropyl morpholine was replaced with 2-chloro-N-(2-(morpholin-1-yl)ethyl)acetamide to obtain a white solid. Yield: 39%; ESI-MS: 513.1 [M+H]$^+$; $^1$H-NMR (δ, DMSO-d$_6$, one drop TFA-d): 13.96 (s, 1H), 9.87 (s, 1H), 9.00 (s, 2H), 8.45 (t, 1H, J=6.0 Hz), 7.79 (d, 1H, J=8.5 Hz), 7.65 (s, 1H), 7.08 (d, J =9.0 Hz), 4.81 (s, 2H), 4.00 (s, 3H), 3.98 (s, 2H), 3.67 (t, 2H, J=12.5 Hz), 3.55 (s, 3H), 3.54 (m, 4H), 3.26 (t, 2H, J=6.5 Hz), 3.15 (m, 2H).

2-amino-N-(3-ethyl-8-methoxy-4-oxo-7-(2-(2-oxo-7-azaspiro [3.5] nonane-7-yl)ethoxy)-3,4-dihydroquinazolin-2-yl) pyrimidine-5-carboxamide (compound 8a-34)

The preparation of the compound 8a-34 referred to the synthesis of 8a-1. N-chloropropyl morpholine was replaced with 7-(2-chloroethyl)-7-azaspiro[3.5]nonane-2-one to obtain a white solid. Yield: 37%; ESI-MS: 508.2 [M+H]$^+$; $^1$H-NMR (δ, DMSO-d$_6$): 14.05(s, 1H), 8.61(s, 2H), 7.67(d, 1H, J=9.0 Hz), 7.36 (s, 2H), 7.22 (d, 1H, J=9.0 Hz), 4.07 (t, 2H, J=6.5 Hz), 3.83 (s, 3H), 3.54 (s, 3H), 2.91 (s, 4H), 2.64 (t, 2H, J=6.5 Hz), 2.45 (t, 4H, J=5.0 Hz), 1.38 (t, 4H, J=5.0 Hz).

5-amino-N-(8-methoxy-3-methyl-7-(3-morpholinopropoxy)-4-oxo-3,4-dihydroquinazolin-2-yl) pyrazine-2-carboxamide (compound 8a-35)

The preparation of the compound 8a-35 referred to the synthesis of 8a-1. 2-aminopyrimidine-5-acyl isothiocyanate was replaced with 5-aminopyrazine-2-acyl isothiocyanate to obtain a white solid. Yield: 44%; ESI-MS: 470.1 [M+H]$^+$; $^1$H-NMR (δ, DMSO-d$_6$): 14.03 (s, 1H), 8.92 (s, 1H), 7.95 (s, 1H), 7.79 (d, 1H, J=9.0 Hz), 7.17 (d, 1H, J=9.0 Hz), 4.23 (t, 2H, J=6.5 Hz), 3.95 (s, 3H), 3.59 (t, 4H, J=4.5 Hz), 3.54 (s, 3H), 2.47 (t, 2H, J=7.0 Hz), 2.39 (t, 4H, J=4.0 Hz), 1.99 (m, 2H).

N-(8-methoxy-3-methyl-7-(3-morpholinopropoxy)-4-oxo-3,4-dihydroquinazolin-2-yl)-1H-pyrrole [2,3-b]pyridine-5-carboxamide (compound 8a-36)

The preparation of the compound 8a-36 referred to the synthesis of 8a-1. 2-aminopyrimidine-5-acyl isothiocyanate was replaced with 1H-pyrrolo[2,3-b]pyridine-5-acyl isothiocyanate to obtain a white solid. Yield: 44%; ESI-MS: 493.1 [M+H]$^+$; $^1$H-NMR (δ, DMSO-d$_6$): 14.09 (s, 1H), 12.00 (s, 1H), 9.12 (s, 1H), 8.78 (s, 1H), 7.78 (d, 1H, J =8.5 Hz), 7.57-7.56 (m, 1H), 7.16 (d, 1H, J=9.0 Hz), 6.61 (s, 1H), 4.21 (t, 2H, J=6.5 Hz), 3.98 (s, 3H), 3.61 (m, 6H), 3.36 (s, 3H), 2.40 (m, 4H), 1.98 (t, 3H, J=7.5 Hz).

6-amino-N-(8-methoxy-3-methyl-7-(3-morpholinopropoxy)-4-oxo-3,4-dihydroquinazolin-2-yl) nicotinamide (compound 8a-37)

The preparation of the compound 8a-37 referred to the synthesis of 8a-1. 2-aminopyrimidine-5-acyl isothiocyanate was replaced with 6-aminopyridine-3-acyl isothiocyanate to obtain a white solid. Yield: 44%; ESI-MS: 469.1 [M+H]$^+$; $^1$-H-NMR (δ, DMSO-d$_6$): 14.05 (s, 1H), 8.83 (d, 1H, J=2.0 Hz), 8.11 (dd, 1H, =9.0 Hz, J$_2$ =2.5 Hz), 7.78 (d, 1H, J=9.0 Hz), 7.16 (d, 1H, J =9.0 Hz), 6.67 (s, 2H), 6.47 (d, 1H, J=9.0 Hz), 4.23 (d, 2H, J=6.5 Hz), 3.95 (s, 3H), 3.59 (t, 4H, J=5.0 Hz), 3.54 (s, 3H), 2.39 (s, 4H), 1.99 (m, 2H).

(S)-6-amino-N-(7-(2-hydroxy-3-morpholinopropoxy)-8-methoxy-3-methyl-4-oxo-3,4-dihydrouinazolin-2-yl) nicotinamide (compound 8a-38)

The preparation of the compound 8a-38 referred to the synthesis of 8a-27. 2-aminopyrimidine-5-acyl isothiocyanate was replaced with 6-aminopyridine-3-acyl isothiocyanate to obtain a white solid. Yield: 36%; ESI-MS: 485.1 [M+H]$^+$; $^1$H-NMR (δ, DMSO-d$_6$): 14.06 (s, 1H), 8.83 (d, 1H, J=2.5 Hz), 8.11 (dd, 1H, J$_1$=8.6 Hz, J$_2$=2.0 Hz), 7.78 (d, 1H, J=9.0 Hz), 7.17 (d, 1H, J=9.0 Hz), 6.72 (s, 2H), 6.47 (d, 1H, J=9.0 Hz), 5.03 (d, 2H, J=5.0 Hz), 4.21 (m, 2H), 4.11 (m, 2H), 3.97 (s, 3H), 3.58 (t, 4H, J=5.0 Hz), 3.54 (s, 3H), 2.43 (m, 4H).

(R)-6-amino-N-(7-(2-hydroxy-3-morpholinopropoxy)-8-methoxy-3-methyl-4-oxo-3,4-dihydroquinazolin-2-yl) nicotinamide (compound 8a-39)

The preparation of the compound 8a-39 referred to the synthesis of 8a-28. 2-aminopyrimidine-5-acyl isothiocyanate was replaced with 6-aminopyridine-3-acyl isothiocyanate to obtain a white solid. Yield: 38%; ESI-MS: 485.1 [M+H]$^+$; $^1$H-NMR (δ, DMSO-d$_6$): 14.06 (s, 1H), 8.83 (d, 1H, J=2.5 Hz), 8.11 (dd, 1H, J$_1$=8.6 Hz, J$_2$=2.0 Hz), 7.78 (d, 1H, J=9.0 Hz), 7.17 (d, 1H, J =9.0 Hz), 6.72 (s, 2H), 6.47 (d, 1H, J=9.0 Hz), 5.03 (d, 2H, J=5.0 Hz), 4.21 (m, 2H), 4.11 (m, 2H), 3.97 (s, 3H), 3.58 (t, 4H, J=5.0 Hz), 3.54 (s, 3H), 2.43 (m, 4H).

6-amino-N-(8-methoxy-3-methyl-7-(2-(methylsulfonamido)ethoxy)-4-oxo-3,4-dihydroquinazoline-2-yl) nicotinamide (compound 8a-40)

The preparation of the compound 8a-40 referred to the synthesis of 8a-41. 2-aminopyrimidine-5-acyl isothiocyanate was replaced with 6-aminopyridine-3-acyl isothiocyanate. Yield: 35%; ESI-MS: 463.1 [M+H]$^+$;$^1$H-NMR (δ, DMSO-d$_6$): 14.08 (s, 1H), 8.83 (s, 2H), 8.11 (dd, 1H, J$_1$=8.5 Hz, J$_2$=2.5 Hz), 7.78 (d, 1H, J=9.0 Hz), 7.40 (t, 1H, J=6.0 Hz), 7.17 (d, 1H, J=9.0 Hz), 6.72 (s, 2H), 6.47 (d, 1H, J=8.5 Hz), 4.24 (t, 1H, J=5.5 Hz), 3.99 (s, 3H), 3.54 (s, 3H), 3.45 (q, 2H, J=5.5 Hz), 2.99 (s, 3H).

2-amino-N-(8-methoxy-3-methyl-7-(3-morpholinopropoxy)-4-oxo-3,4-dihydroquinazolin-2-yl) pyrimidine-5-carboxamide (compound 8a-41)

The preparation of the compound 8a-41 referred to the synthesis of 8a-1. N-chloropropyl morpholine was replaced with N-chloroethylmorpholine to obtain a white solid. Yield: 36%; ESI-MS: 463.1 [M+H]$^+$;

(R)-2-amino-N-(8-methoxy-3-methyl-7-(2-(4-methylmorpholin-2-yl)ethoxy)-4-oxo-3,4-dihydroquinazolin-2-yl) pyrimidine-5-carboxamide (compound 8a-42)

The preparation of the compound 8a-42 referred to the synthesis of 8a-1. N-chloropropyl morpholine was replaced with (R)-2-(2-chloroethyl)-4-methylmorpholine to obtain a white solid. Yield: 35%; ESI-MS: 470.2 [M+H]$^+$;

(S)-2-amino-N-(8-methoxy-3-methyl-7-(2-(4-methylmorpholin-2-yl)ethoxy)-4-oxo-3,4-dihydroquinazolin-2-yl) pyrimidine-5-carboxamide (compound 8a-43)

The preparation of the compound 8a-43 referred to the synthesis of 8a-1. N-chloropropyl morpholine was replaced with (S)-2-(2-chloroethyl)-4-methylmorpholine to obtain a white solid. Yield: 33%; ESI-MS: 470.2 [M+H]$^+$;

2-amino-N-(8-methoxy-3-methyl-7-(2-(4-(methylsulfonyl)piperazin-1-yl)ethoxy)-4-oxo-3, 4-dihydroquinazolin-2-yl) pyrimidine-5-carboxamide (compound 8a-44)

The preparation of the compound 8a-44 referred to the synthesis of 8a-1. N-chloropropyl morpholine was replaced with 1-(2-chloroethyl)-4-(methylsulfonyl) piperazine to obtain a white solid. Yield: 42%; ESI-MS: 533.2 [M+H]$^+$;

2-amino-N-(8-methoxy-3-methyl-7-(3-(4-(methylsulfonyl)piperazin-1-yl)propoxy)-4-oxo-3,4-dihydroquinazolin-2-yl) pyrimidine-5-carboxamide (compound 8a-45)

The preparation of the compound 8a-45 referred to the synthesis of 8a-1. N-chloropropyl morpholine was replaced with 1-(3-chloropropyl)-4-(methylsulfonyl) piperazine to obtain a white solid. Yield: 24%; ESI-MS: 547.2 [M+H]$^+$;

2-amino-N-(8-methoxy-3-methyl-7-(2-(4-methylpiperazin-1-yl)ethoxy)-4-oxo-3,4-dihydro quinazolin-2-yl) pyrimidine-5-carboxamide (compound 8a-46)

The preparation of the compound 8a-46 referred to the synthesis of 8a-1. N-chloropropyl morpholine was replaced with 1-(2-chloroethyl)-4-methylpiperazine to obtain a white solid. Yield: 21%; ESI-MS: 469.2 [M+H]$^+$;

2-amino-N-(8-methoxy-3-methyl-7-(3-(4-methylpiperazin-1-yl)propoxy)-4-oxo-3,4-dihydr oquinazolin-2-yl) pyrimidine-5-carboxamide (compound 8a-47)

The preparation of the compound 8a-47 referred to the synthesis of 8a-1. N-chloropropyl morpholine was replaced with 1-(3-chloropropyl)-4-methylpiperazine to obtain a white solid. Yield: 33%; ESI-MS: 483.2 [M+H]$^+$;

2-amino-N-(8-methoxy-3-methyl-4-oxo-7-(2-(piperidin-1-yl)ethoxy)-3,4-dihydroquinazolin-2-yl) pyrimidine-5-carboxamide (compound 8a-48)

The preparation of the compound 8a-48 referred to the synthesis of 8a-1. N-chloropropyl morpholine was replaced with 1-(2-chloroethyl) piperidine to obtain a white solid. Yield: 27%; ESI-MS: 454.2 [M+H]$^+$;

2-amino-N-(8-methoxy-3-methyl-4-oxo-7-(3-(piperidin-1-yl)propoxy)-3,4-dihydroquinazolin-2-yl)pyrimidine-5-carboxamide (compound 8a-49)

The preparation of the compound 8a-49 referred to the synthesis of 8a-1. N-chloropropyl morpholine was replaced with1-(3-chloropropyl) piperidine to obtain a white solid. Yield: 35%; ESI-MS: 468.2 [M+H]$^+$;

2-amino-N-(8-methoxy-3-methyl-4-oxo-7-(2-(pyrrolidin-1-yl)ethoxy)-3,4-dihydroquinazolin-2-yl) pyrimidine-5-carboxamide (compound 8a-50)

The preparation of the compound 8a-50 referred to the synthesis of 8a-1. N-chloropropyl morpholine was replaced with 1-(2-chloroethyl)pyrrolidine to obtain a white solid. Yield: 22%; ESI-MS: 440.2 [M+H]$^+$;

2-amino-N-(8-methoxy-3-methyl-4-oxo-7-(3-(pyrrolidin-1-yl)propoxy)-3,4-dihydroquinazolin-2-yl) pyrimidine-5-carboxamide (compound 8a-51)

The preparation of the compound 8a-51 referred to the synthesis of 8a-1. N-chloropropyl morpholine was replaced with 1-(3-chloropropyl) pyrrolidine to obtain a white solid. Yield: 29%; ESI-MS: 454.2 [M+H]$^+$;

2-amino-N-(7-(2-(3,3-difluoropyrrolidin-1-yl)ethoxy)-8-methoxy-3-methyl-4-oxo-3,4-dihydroquinazolin-2-yl) pyrimidine-5-carboxamide (compound 8a-52)

The preparation of the compound 8a-52 referred to the synthesis of 8a-1. N-chloropropyl morpholine was replaced with 1-(2-chloroethyl)-3,3-difluoropyrrolidine to obtain a white solid. Yield: 28%; ESI-MS: 476.2 [M+H]$^+$;

2-amino-N-(7-(2-(2-(4,4-dimethylpiperidin-l-yl)ethoxy)-8-methoxy-3-methyl-4-oxo-3,4-dihydroquinazolin-2-yl) pyrimidine-5-carboxamide (compound 8a-53)

The preparation of the compound 8a-53 referred to the synthesis of 8a-1. N-chloropropyl morpholine was replaced with 1-(2-chloroethyl)-4,4-dimethylpiperidine to obtain a white solid. Yield: 26%; ESI-MS: 482.2 [M+H]$^+$;

N-(7-(2-(6-(6-azaspiro [2.5] octane-6-yl)ethoxy)-8-methoxy-3-methyl-4-oxo-3,4-dihydroquinazolin-2-yl)-2-aminopyrimidine-5-carboxamide (compound 8a-54)

The preparation of the compound 8a-54 referred to the synthesis of 8a-1. N-chloropropyl morpholine was replaced with 6-(2-chloroethyl)-6-azaspiro[2.5]octane to obtain a white solid. Yield: 32%; ESI-MS: 480.2 [M+H]$^+$;

2-amino-N-(8-methoxy-3-methyl-4-oxo-7-(2-(2-oxo-7-azaspiro [3.5] nonane-7-yl)ethoxy)-3, 4-dihydroquinazolin-2-yl) pyrimidine-5-carboxamide (compound 8a-55)

The preparation of the compound 8a-55 referred to the synthesis of 8a-1. N-chloropropyl morpholine was replaced with 7-(2-chloroethyl)-7-azaspiro[3.5]nonane-2-ol to obtain a white solid. Yield: 39%; ESI-MS: 508.2 [M+H]$^+$;

2-amino-N-(7-(2-(2-(2-hydroxy-7-azaspiro [3.5] nonane-7-yl)ethoxy)-8-methoxy-3-methyl-4-oxo-3,4-dihydroquinazolin-2-yl) pyrimidine-5-carboxamide (compound 8a-56)

The preparation of the compound 8a-56 referred to the synthesis of 8a-1. N-chloropropyl morpholine was replaced with 7-(2-chloroethyl)-7-azaspiro[3.5]nonane-2-ol to obtain a white solid. Yield: 41%; ESI-MS: 510.2 [M+H]$^+$;

N-(7-(2-(2-oxa-7-azaspiro [3.5] nonane-7-yl)ethoxy)-8-methoxy-3-methyl-4-oxo-3,4-dihydroquinazolin-2-yl-2-aminopyrimidine-5-carboxamide (compound 8a-57)

The preparation of the compound 8a-57 referred to the synthesis of 8a-1. N-chloropropyl morpholine was replaced with 7-(2-chloroethyl)-2-oxa-7-azaspiro[3.5]nonane to obtain a white solid. Yield: 35%; ESI-MS: 496.2 [M+H]$^+$;

N-(7-(2-(2-(2-oxa-8-azaspiro [4.5] octane-8-yl)ethoxy)-8-methoxy-3-methyl-4-oxo-3,4-dihydroquinazolin-2-yl)-2-aminopyrimidine-5-carboxamide (compound 8a-58)

The preparation of the compound 8a-58 referred to the synthesis of 8a-1. N-chloropropyl morpholine was replaced with 8-(2-chloroethyl)-2-oxa-8-azaspiro[4.5]decane to obtain a white solid. Yield: 38%; ESI-MS: 510.2 [M+H]$^+$;

Ethy 3-((2-(2-aminopyrimidine-5-carboxamido)-8-methoxy-3-methyl-4-oxo-3,4-dihydroquinazolin-7-yl)oxyl) propionate (compound 8a-59)

The preparation of the compound 8a-59 referred to the synthesis of 8a-1. N-chloropropyl morpholine was replaced with ethyl 3-chloropropionate to obtain a white solid. Yield: 28%; ESI-MS: 443.1[M+H]$^+$;

Ethyl 4-((2-(2-aminopyrimidine-5-carboxamido)-8-methoxy-3-methyl-4-oxo-3,4-dihydroquinazolin-7-yl)oxyl) butyrate (compound 8a-60)

The preparation of the compound 8a-60 referred to the synthesis of 8a-1. N-chloropropyl morpholine was replaced with ethyl 4-chlorobutyrate to obtain a white solid. Yield: 33%; ESI-MS: 457.2[M+H]$^+$;

2-amino-N-(7-(2-cyanoethoxy)-8-methoxy-3-methyl-4-oxo-3,4-dihydroquinazolin-2-yl) pyrimidine-5-carboxamide (compound 8a-61)

The preparation of the compound 8a-61 referred to the synthesis of 8a-1. N-chloropropyl morpholine was replaced with 3-chloropropionitrile to obtain a white solid. Yield: 37%; ESI-MS: 396.1 [M+H]+;

2-amino-N-(7-(2-(dimethylamino)-2-oxoethoxy)-8-methoxy-3-methyl-4-oxo-3,4-dihydroq uinazolin-2-yl) pyrimidine-5-carboxamide (compound 8a-62)

The preparation of the compound 8a-62 referred to the synthesis of 8a-1. N-chloropropyl morpholine was replaced with 2-chloro-N,N-dimethylacetamide to obtain a white solid. Yield: 22%; ESI-MS: 428.1[M+H]+;

2-amino-N-(7-(3-(dimethylamino)-3-oxopropoxy)-8-methoxy-3-methyl-4-oxo-3,4-dihydro quinazolin-2-yl) pyrimidine-5-carboxamide (compound 8a-63)

The preparation of the compound 8a-63 referred to the synthesis of 8a-1. N-chloropropyl morpholine was replaced with 3-chloro-N,N-dimethylacetamide to obtain a white solid. Yield: 28%; ESI-MS: 442.2[M+H]+;

2-amino-N-(7-(2-(isopropylamino)-2-oxoethoxy)-8-methoxy-3-methyl-4-oxo-3,4-dihydroq uinazolin-2-yl) pyrimidine-5-carboxamide (compound 8a-64)

The preparation of the compound 8a-64 referred to the synthesis of 8a-1. N-chloropropyl morpholine was replaced with 2-chloro-N-isopropylacetamide to obtain a white solid. Yield: 19%; ESI-MS: 442.2[M+H]+;

2-amino-N-(7-(2-(cyclopropylamino)-2-oxoethoxy)-8-methoxy-3-methyl-4-oxo-3,4-dihydr oquinazolin-2-yl) pyrimidine-5-carboxamide (compound 8a-65)

The preparation of the compound 8a-65 referred to the synthesis of 8a-1. N-chloropropyl morpholine was replaced with 2-chloro-N-cyclopropylacetamide to obtain a white solid. Yield: 26%; ESI-MS: 440.2[M+H]+;

2-amino-N-(8-methoxy-3-methyl-7-(2-morpholino-2-oxoethoxy)-4-oxo-3,4-dihydroquinaz olin-2-yl) pyrimidine-5-carboxamide (compound 8a-66)

The preparation of the compound 8a-66 referred to the synthesis of 8a-1. N-chloropropyl morpholine was replaced with 2-chloro-1-morpholino-1-one to obtain a white solid. Yield: 31%; ESI-MS: 470.2[M+H]+.

EXAMPLE 5: Preparation of 2-amino-N-(8-methoxy-3-ethyl-7-(3-morpholinopropyl)-4-oxo-3,4-dihydroquinazolinone-2-yl) pyrimidine-5-carboxamide (compound 8b-1)

The procedure is the same as the synthesis of the compound 8a-1. Ethylamine hydrochloride was used to instead of the methylamine hydrochloride to react with 2-amino-3-methoxy-4-benzyloxybenzoic acid (compound 4), to obtain 2-amino-3-methoxy-4-benzyloxy-N-ethylbenzamide (compound 5b-1). Then 5b-1 was condensed with 2-aminopyrimidine-5-acyl isothiocyanate to obtain 2-amino-N-(3-ethyl-7-benzyloxyhydroxy-8-methoxy-4-oxo-3,4-dihydroquinazolin-2-yl) pyrimidine-5-carboxamide (6b-1), then debenzylated by Pd/C-$H_2$ to obtain 2-amino-N-(3-ethyl-7-hydroxy-8-methoxy-4-oxo-3 ,4-dihydroquinazolin-2-yl) pyrimidine-5-carboxamide (7b-1), and finally reacted with N-(3-chloropropyl) morpholine to obtain the compound 8b-1. ESI-MS: 484.2 [M+H]+; $^1$H-NMR (δ, $CDCl_3$/$CD_3OD$=5:1): 8.96 (s, 2H), 7.78 (d, 1H, J=9.0 Hz), 6.88 (d, 1H, J=9.0 Hz), 4.31 (q, 2H, J=7.0 Hz), 4.13 (t, 2H, J=6.0 Hz), 3.95 (s, 3H), 3.64 (s, 4H), 3.25 (m, 2H), 2.49 (m, 5H), 1.99 (s, 2H), 1.27 (t, 3H, J=6.0 Hz), 1.14 (s, 2H).

EXAMPLE 6: Synthesis of the Compounds 8b-2 to 8b-13

The compound 2-amine-N-(3-ethyl-7-hydroxy-8-methoxy-4-oxo-3,4-dihydroquinazoline-2-yl) pyrimidine-5-formamide 7b-1 was used as a raw material. And chloroacetamide, chloropropionamide, N-methylchloroacetamide, N,N-dimethylchloroacetamide, 2-(2-chloroethyl)-4-methylmorpholine, 1-(3-chloro-propionyl)-4-methylpiperazine, chloroacetylmorpholine, 4-chlorobutanamide, difluorochloromethane, chloroethyl sulfonamide, $TMSCF_3$, or chloropropyl sulfonamide were used respectively to instead of N-(3-chloropropyl) morpholine to prepare the compounds 8b-2 to 8b-13. The structural formulas of the series of target molecules are shown in Table 3 below.

TABLE 3

| Compd. | Structure | MS |
| --- | --- | --- |
| 7b | 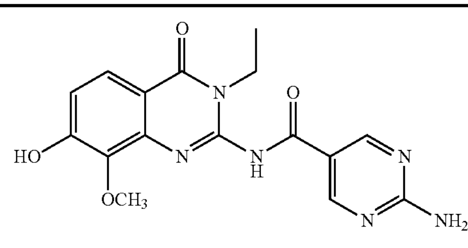 | 357.2 [M + H]+ |
| 8b-1 | 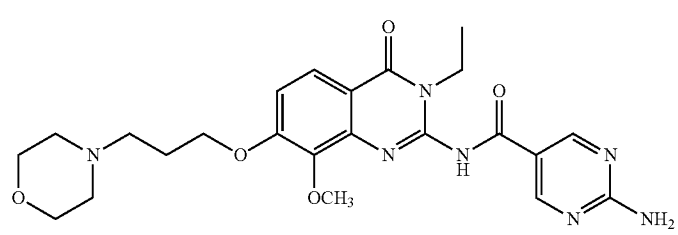 | 484.2 [M + H]+ |

TABLE 3-continued

| Compd. | Structure | MS |
|---|---|---|
| 8b-2 | 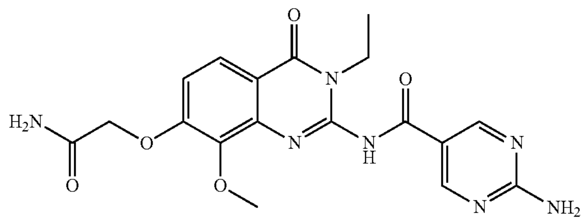 | 414.1 [M + H]+ |
| 8b-3 | 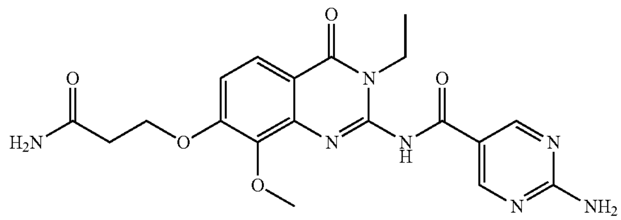 [SMILES: CCn1c(NC(=O)c2cnc(N)nc2)nc2c(OC)c(OCCC(N)=O)ccc2c1=O] | 428.2 [M + H]+ |
| 8b-4 | 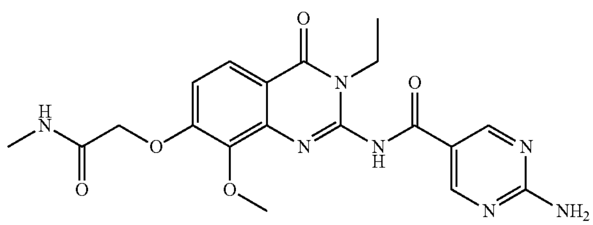 | 428.2 [M + H]+ |
| 8b-5 | 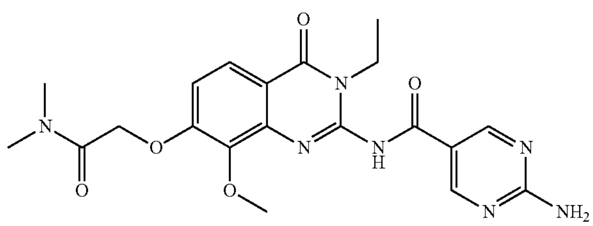 | 442.2 [M + H]+ |
| 8b-6 | 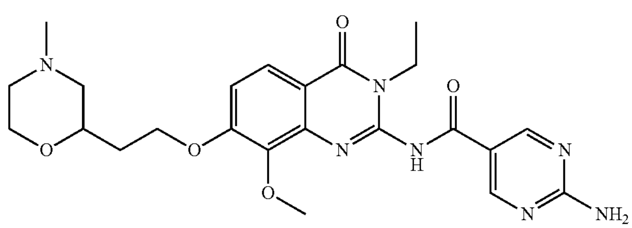 | 484.3 [M + H]+ |
| 8b-7 | 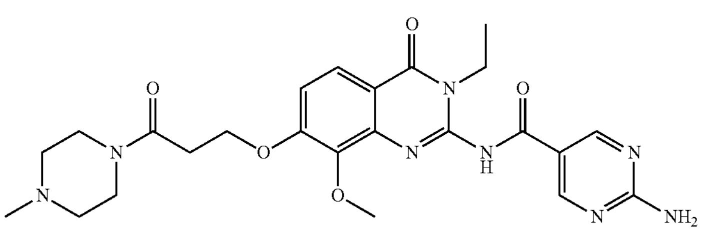 | 511.3 [M + H]+ |
| 8b-8 | 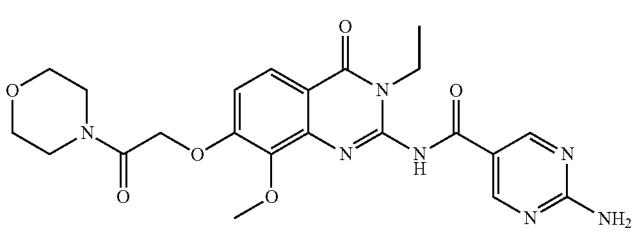 | 484.3 [M + H]+ |

TABLE 3-continued

| Compd. | Structure | MS |
| --- | --- | --- |
| 8b-9 | 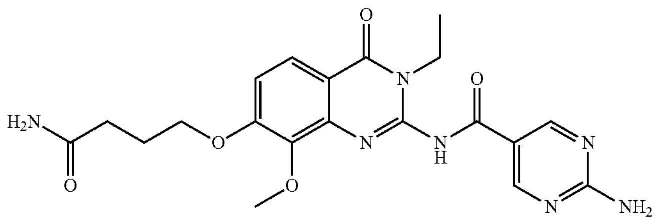 [SMILES: CCn1c(NC(=O)c2cnc(N)nc2)nc2c(OC)c(OCCCC(N)=O)ccc2c1=O] | 442.3 [M + H]$^+$ |
| 8b-10 | 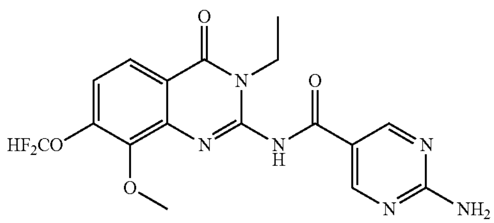 | 407.2 [M + H]$^+$ |
| 8b-11 | 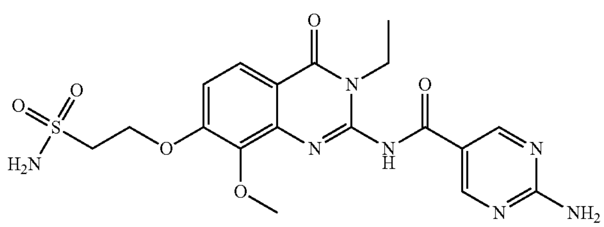 [SMILES: CCn1c(NC(=O)c2cnc(N)nc2)nc2c(OC)c(OCCS(N)(=O)=O)ccc2c1=O] | 464.1 [M + H]$^+$ |
| 8b-12 | 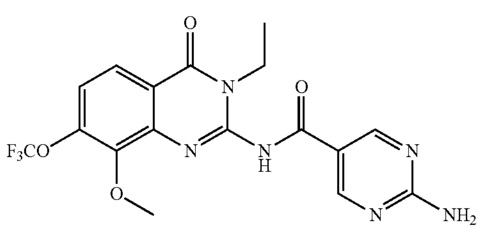 [SMILES: CCn1c(NC(=O)c2cnc(N)nc2)nc2c(OC)c(OC(F)(F)F)ccc2c1=O] | 425.2 [M + H]$^+$ |
| 8b-13 | 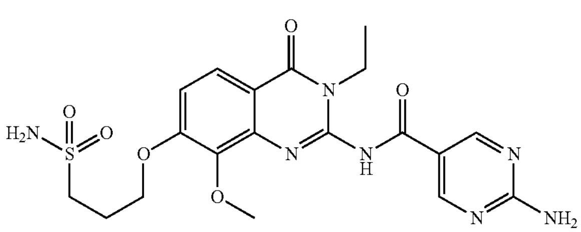 [SMILES: CCn1c(NC(=O)c2cnc(N)nc2)nc2c(OC)c(OCCCS(N)(=O)=O)ccc2c1=O] | 478.1 [M + H]$^+$ |

EXAMPLE 7: Synthesis of the Compounds 8b-14 to 8b-26 the Synthetic Route is Shown as Follows:

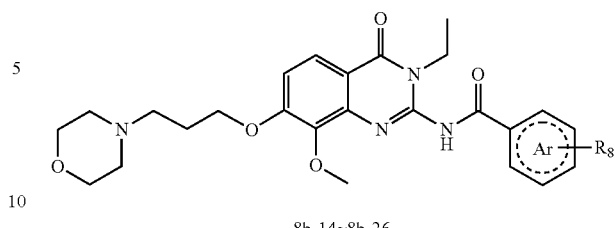

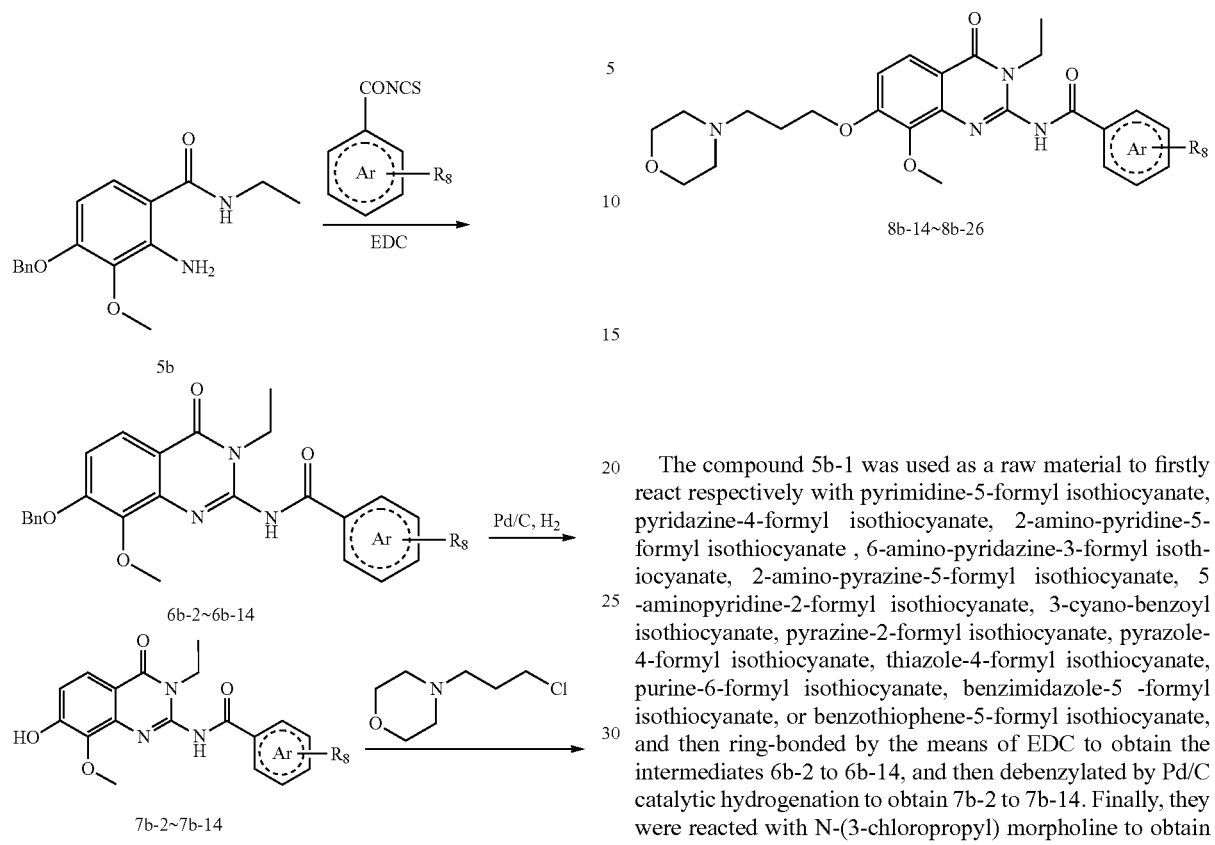

The compound 5b-1 was used as a raw material to firstly react respectively with pyrimidine-5-formyl isothiocyanate, pyridazine-4-formyl isothiocyanate, 2-amino-pyridine-5-formyl isothiocyanate, 6-amino-pyridazine-3-formyl isothiocyanate, 2-amino-pyrazine-5-formyl isothiocyanate, 5-aminopyridine-2-formyl isothiocyanate, 3-cyano-benzoyl isothiocyanate, pyrazine-2-formyl isothiocyanate, pyrazole-4-formyl isothiocyanate, thiazole-4-formyl isothiocyanate, purine-6-formyl isothiocyanate, benzimidazole-5-formyl isothiocyanate, or benzothiophene-5-formyl isothiocyanate, and then ring-bonded by the means of EDC to obtain the intermediates 6b-2 to 6b-14, and then debenzylated by Pd/C catalytic hydrogenation to obtain 7b-2 to 7b-14. Finally, they were reacted with N-(3-chloropropyl) morpholine to obtain the target molecules 8b-14 to 8b-26, as shown in Table 4.

TABLE 4

| Compd. | Structure | MS |
|---|---|---|
| 8b-14 | 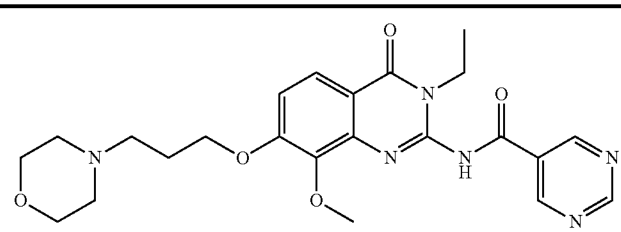 | 469.3 [M + H]$^+$ |
| 8b-15 | 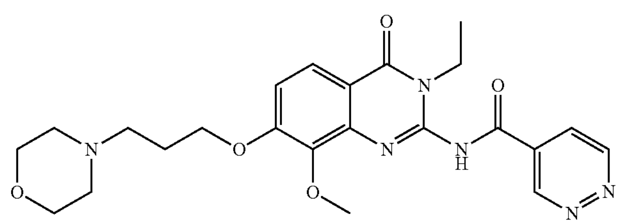 [SMILES: CCn1c(NC(=O)c2ccnnc2)nc2c(OC)c(OCCCN3CCOCC3)ccc2c1=O] | 469.3 [M + H]$^+$ |
| 8b-16 | 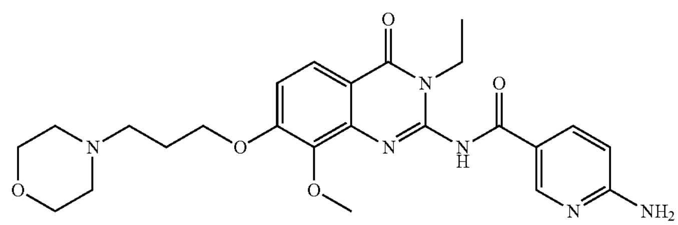 [SMILES: CCn1c(NC(=O)c2ccc(N)nc2)nc2c(OC)c(OCCCN3CCOCC3)ccc2c1=O] | 483.3 [M + H]$^+$ |

TABLE 4-continued

| Compd. | Structure | MS |
|---|---|---|
| 8b-17 | 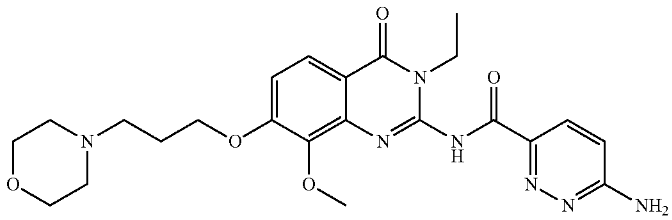 [SMILES: CCn1c(NC(=O)c2ccc(N)nn2)nc2c(OC)c(OCCCN3CCOCC3)ccc2c1=O] | 484.2 [M + H]+ |
| 8b-18 | 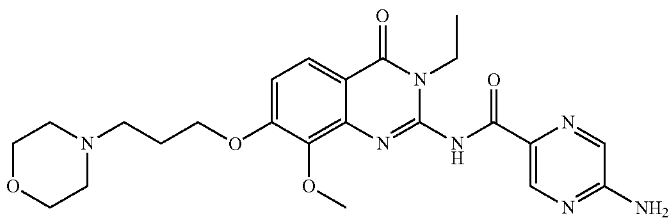 [SMILES: CCn1c(NC(=O)c2cnc(N)cn2)nc2c(OC)c(OCCCN3CCOCC3)ccc2c1=O] | 484.2 [M + H]+ |
| 8b-19 | 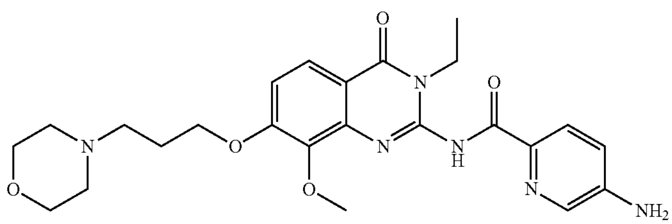 [SMILES: CCn1c(NC(=O)c2ccc(N)cn2)nc2c(OC)c(OCCCN3CCOCC3)ccc2c1=O] | 483.3 [M + H]+ |
| 8b-20 | 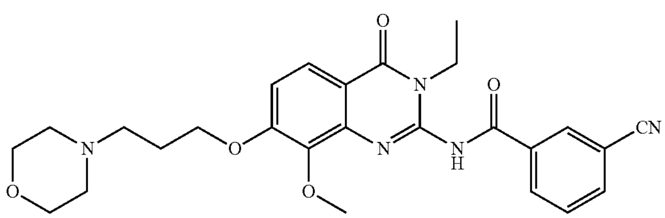 [SMILES: CCn1c(NC(=O)c2cccc(C#N)c2)nc2c(OC)c(OCCCN3CCOCC3)ccc2c1=O] | 492.3 [M + H]+ |
| 8b-21 | 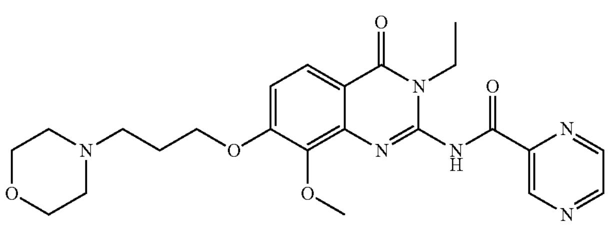 [SMILES: CCn1c(NC(=O)c2cnccn2)nc2c(OC)c(OCCCN3CCOCC3)ccc2c1=O] | 469.3 [M + H]+ |
| 8b-22 | 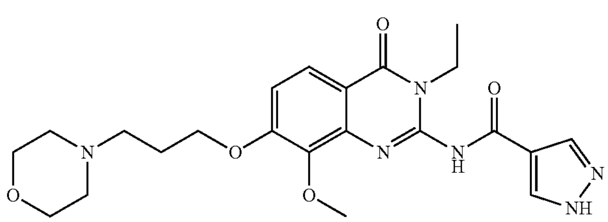 [SMILES: CCn1c(NC(=O)c2cn[nH]c2)nc2c(OC)c(OCCCN3CCOCC3)ccc2c1=O] | 457.3 [M + H]+ |
| 8b-23 | 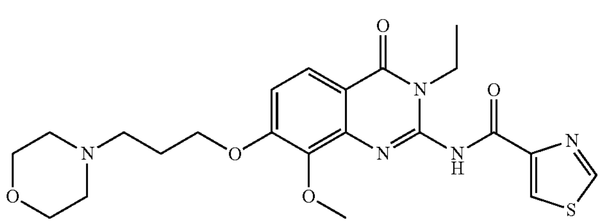 [SMILES: CCn1c(NC(=O)c2cscn2)nc2c(OC)c(OCCCN3CCOCC3)ccc2c1=O] | 474.3 [M + H]+ |

TABLE 4-continued

| Compd. | Structure | MS |
|---|---|---|
| 8b-24 | 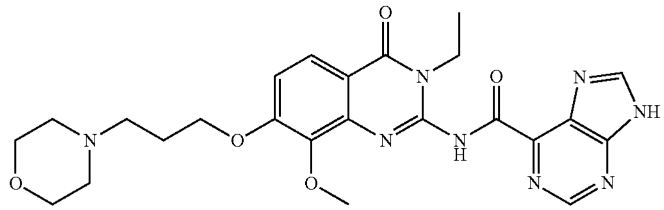 [SMILES: CCn1c(NC(=O)c2ncnc3[nH]cnc23)nc2c(OC)c(OCCCN3CCOCC3)ccc2c1=O] | 509.3 [M + H]⁺ |
| 8b-25 | 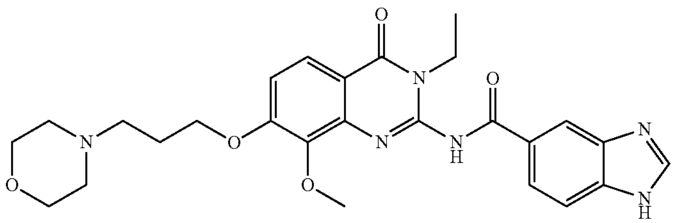 [SMILES: CCn1c(NC(=O)c2ccc3[nH]cnc3c2)nc2c(OC)c(OCCCN3CCOCC3)ccc2c1=O] | 507.3 [M + H]⁺ |
| 8b-26 | 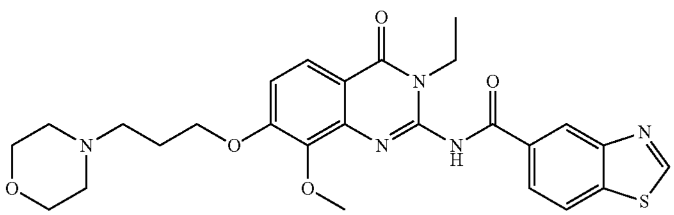 [SMILES: CCn1c(NC(=O)c2ccc3scnc3c2)nc2c(OC)c(OCCCN3CCOCC3)ccc2c1=O] | 524.3 [M + H]⁺ |

EXAMPLE 8: Synthesis of the Compounds 8b-27 to 8b-48

(S)-2-amino-N-(3-ethyl-7-(2-hydroxy-3-morpholinopropoxy)-8-methoxy-4-oxo-3,4-dihydr oquinazolin-2-yl) pyrimidine-5-carboxamide (compound 8b-27)

The preparation of the compound 8b-27 referred to the synthesis of 8b-1. N-chloropropyl morpholine was replaced with (S)-1-chloro-3-morpholinopropan-2-ol to obtain a white solid; ESI-MS: 500.2[M+H]⁺.

(R)-2-amino-N-(3-ethyl-7-(2-hydroxy-3-morpholinopropoxy)-8-methoxy-4-oxo-3,4-dihyd roquinazolin-2-yl) pyrimidine-5-carboxamide (compound 8b-28)

The preparation of the compound 8b-28 referred to the synthesis of 8b-1. N-chloropropyl morpholine was replaced with (R)-1-chloro-3-morpholinopropan-2-ol to obtain a white solid; ESI-MS: 500.2[M+H]⁺.

2-amino-N-(3-ethyl-8-methoxy-7-(2-(methylsulfonamido)ethoxy)-4-oxo-3,4-dihydroquina zolin-2-yl) pyrimidine-5-carboxamide (compound 8b-29)

The preparation of the compound 8b-29 referred to the synthesis of 8b-1. N-chloropropyl morpholine was replaced with N-(2-bromoethyl) methanesulfonamide to obtain a white solid; ESI-MS: 478.2 [M+H]⁺;¹H-NMIR (δ, DMSO-d₆): 13.95 (s, 1H), 8.94 (s, 2H), 7.80 (d, 1H, J=9.0 Hz), 7.36 (s, 2H), 7.35 (d, 1H, J=6.0 Hz), 7.19 (d, 1H, J=9.0 Hz), 4.30 (q, 2H, J=7.0 Hz), 4.25 (t, 2H, J=5.0 Hz), 3.99 (s, 3H), 3.45 (q, 2H, J=5.5 Hz), 2.98 (s, 3H), 1.29 (t, 3H, J=7.0 Hz).

2-amino-N-(3-ethyl-8-methoxy-7-(2-(methylsulfonamido)propoxy)-4-oxo-3,4-dihydroqui nazolin-2-yl) pyrimidine-5-carboxamide (compound 8b-30)

The preparation of the compound 8b-30 referred to the synthesis of 8b-1. N-chloropropyl morpholine was replaced with to N-(2-bromopropyl) methanesulfonamide to obtain a white solid; ESI-MS: 492.2 [M+H]⁺;¹H-NMIR (δ, DMSO-d₆): 13.95 (s, 1H), 8.94 (s, 2H), 7.81 (d, 1H, J=9.0 Hz), 7.36 (s, 2H), 7.19 (d, 1H, J=9.0 Hz), 7.10 (s, 1H), 4.29 (m, 2H), 3.96 (s, 3H), 3.18 (m, 2H), 2.91 (s, 3H), 2.02 (t, 2H, J=6.5 Hz), 1.29 (t, 3H, J=7.0 Hz).

2-amino-N-(3-ethyl-8-methoxy-7-(3-(4-methylpiperazin-1-yl)propoxy)-4-oxo-3,4-dihydro quinazolin-2-yl) pyrimidine-5-carboxamide (compound 8b-31)

The preparation of the compound 8b-31 referred to the synthesis of 8b-1. N-chloropropyl morpholine was replaced with 1-(3-chloropropyl)-4-methylpiperazine to obtain a white solid; ESI-MS: 497.3 [M+H]⁺.

2-amino-N-(3-ethyl-8-methoxy-4-oxo-7-(2-(piperidin-1-yl)ethoxy)-3,4-dihydroquinazolin-2-yl) pyrimidine-5-carboxamide (compound 8b-32)

The preparation of the compound 8b-32 referred to the synthesis of 8b-1. N-chloropropyl morpholine was replaced with 1-(2-chloroethyl) piperidine to obtain a white solid; ESI-MS: 468.2 [M+H]⁺.

2-amino-N-(3-ethyl-8-methoxy-4-oxo-7-(3-(piperidin-1-yl)propoxy)-3,4-dihydroquinazolin-2-yl)pyrimidine-5-carboxamide (compound 8b-33)

The preparation of the compound 8b-33 referred to the synthesis of 8b-1. N-chloropropyl morpholine was replaced with 1-(3-chloropropyl) piperidine to obtain a white solid; ESI-MS: 482.2 [M+H]$^+$.

2-amino-N-(3-ethyl-8-methoxy-4-oxo-7-(2-(pyrrolidin-1-yl)ethoxy)-3,4-dihydroquinazolin-2-yl)pyrimidine-5-carboxamide (compound 8b-34)

The preparation of the compound 8b-34 referred to the synthesis of 8b-1. N-chloropropyl morpholine was replaced with 1-(2-chloroethyl) pyrrolidine to obtain a white solid; ESI-MS: 454.2 [M+H]$^+$.

2-amino-N-(3-ethyl-8-methoxy-4-oxo-7-(3-(pyrrolidin-1-yl)propoxy)-3,4-dihydroquinazolin-2-yl)pyrimidine-5-carboxamide (compound 8b-35)

The preparation of the compound 8b-35 referred to the synthesis of 8b-1. N-chloropropyl morpholine was replaced with 1-(3-chloropropyl) pyrrolidine to obtain a white solid; ESI-MS: 469.2 [M+H]$^+$.

2-amino-N-(7-(2-(3,3-difluoropyrrolidin-1-yl)ethoxy)-3-ethyl-8-methoxy-4-oxo-3,4-dihydroquinazolin-2-yl) pyrimidine-5-carboxamide (compound 8b-36)

The preparation of the compound 8b-36 referred to the synthesis of 8b-1. N-chloropropyl morpholine was replaced with 1-(2-chloroethyl)-3,3-difluoropyrrolidine to obtain a white solid; ESI-MS: 490.2 [M+H]$^+$;

2-amino-N-(7-(2-(2-(4,4-dimethylpiperidin-1-yl)ethoxy)-3-ethyl-8-methoxy-4-oxo-3,4-dihydroquinazolin-2-yl) pyrimidine-5-carboxamide (compound 8b-37)

The preparation of the compound 8b-37 referred to the synthesis of 8b-1. N-chloropropyl morpholine was replaced with 1-(2-chloroethyl)-4,4-dimethylpiperidine to obtain a white solid; ESI-MS: 496.3 [M+H]$^+$;

N-(7-(2-(6-(6-azaspiro [2.5] octane-6-yl)ethoxy)-3-ethyl-8-methoxy-4-oxo-3,4-dihydroquinazolin-2-yl)-2-aminopyrimidine-5-carboxamide (compound 8b-38)

The preparation of the compound 8b-38 referred to the synthesis of 8b-1. N-chloropropyl morpholine was replaced with 6-(2-chloroethyl)-6-azaspiro[2.5]octane to obtain a white solid; ESI-MS: 494.2 [M+H]$^+$;

2-amino-N-(3-ethyl-7-(2-(2-hydroxy-7-azaspiro [3.5] nonane-7-yl)ethoxy)-8-methoxy-4-oxo -3,4-dihydroquinazolin-2-yl) pyrimidine-5-carboxamide (compound 8b-39)

The preparation of the compound 8b-39 referred to the synthesis of 8b-1. N-chloropropyl morpholine was replaced with 7-(2-chloroethyl)-7-azaspiro[3.5]nonane-2-ol to obtain a white solid; ESI-MS: 524.3 [M+H]$^+$.

N-(7-(2-(2-oxa-7-azaspiro [3.5] nonane-7-yl)ethoxy)-3-ethyl-8-methoxy-4-oxo-3,4-dihydroquinazolin-2-yl-2-aminopyrimidine-5-carboxamide (compound 8b-40)

The preparation of the compound 8b-40 referred to the synthesis of 8b-1. N-chloropropyl morpholine was replaced with 7-(2-chloroethyl)-2-oxa-7-azaspiro[3.5]nonane to obtain a white solid; ESI-MS: 510.2 [M+H]$^+$;

N-(7-(2-(2-oxa-8-azaspiro [4.5] decane-8-yl)ethoxy)-3-ethyl-8-methoxy-4-oxo-3,4-dihydroquinazolin-2-yl-2-aminopyrimidine-5-carboxamide (compound 8b-41)

The preparation of the compound 8b-41 referred to the synthesis of 8b-1. N-chloropropyl morpholine was replaced with 8-(2-chloroethyl)-2-oxa-8-azaspiro[4.5]decane to obtain a white solid; ESI-MS: 524.3 [M+H]$^+$;

2-amino-N-(7-(2-cyanoethoxy)-3-ethyl-8-methoxy-4-oxo-3,4-dihydroquinazolin-2-yl) pyrimidine-5-carboxamide (compound 8b-42)

The preparation of the compound 8b-42 referred to the synthesis of 8b-1. N-chloropropyl morpholine was replaced with 3-chloropropionitrile to obtain a white solid; ESI-MS: 410.2 [M+H]$^+$.

2-amino-N-(3-ethyl-7-(2-(isopropylamino)-2-oxoethoxy)-8-methoxy-4-oxo-3,4-dihydroquinazolin-2-yl) pyrimidine-5-carboxamide (compound 8b-43)

The preparation of the compound 8b-43 referred to the synthesis of 8b-1. N-chloropropyl morpholine was replaced with 2-chloro-N-isopropylacetamide to obtain a white solid; ESI-MS: 456.2 [M+H]$^+$.

2-amino-N-(7-(2-(cyclopropylamino)-2-oxoethoxy)-3-ethyl-8-methoxy-4-oxo-3,4-dihydroquinazolin-2-yl) pyrimidine-5-carboxamide (compound 8b-44)

The preparation of the compound 8b-44 referred to the synthesis of 8b-1. N-chloropropyl morpholine was replaced with 2-chloro-N-cyclopropylacetamide to obtain a white solid; ESI-MS: 454.2 [M+H]$^+$.

2-amino-N-(3-ethyl-8-methoxy-7-(3-morpholino-3-oxopropoxy)-4-oxo-3,4-dihydroquinazolin-2-yl) pyrimidine-5-carboxamide (compound 8b-45)

The preparation of the compound 8b-45 referred to the synthesis of 8b-1. N-chloropropyl morpholine was replaced with 3-chloro-1-morpholinopropan-1-one to obtain a white solid; ESI-MS: 498.2 [M+H]$^+$.

(S)-6-amino-N-(3-ethyl-7-(2-hydroxy-3-morpholinopropoxy)-8-methoxy-4-oxo-3,4-dihydroquinazolin-2-yl) nicotinamide (compound 8b-46)

The preparation of the compound 8b-46 referred to the synthesis of 8b-16. N-chloropropyl morpholine was replaced with (S)-1-chloro-3-morpholinopropan-2-ol to obtain a white solid; ESI-MS :499.2[M+H]⁺.

(R)-6-amino-N-(3-ethyl-7-(2-hydroxy-3-morpholinopropoxy)-8-methoxy-4-oxo-3,4-dihydroquinazolin-2-yl) nicotinamide (compound 8b-47)

The preparation of the compound 8b-47 referred to the synthesis of 8b-45. N-chloropropyl morpholine was replaced with (R)-1-chloro-3-morpholinopropan-2-ol to obtain a white solid; ESI-MS :499.2[M+H]⁺.

6-amino-N-(3-ethyl-8-methoxy-7-(2-((2-morpholinoethyl)amino)-2-oxoethoxy)-4-oxo-3,4-dihydroquinazolin -2-yl)nicotinamide (compound 8b-48)

The preparation of the compound 8b-48 referred to the synthesis of 8b-16. N-chloropropyl morpholine was replaced with 2-chloro-N-(2-morpholinoethyl) acetamide to obtain a white solid; ESI-MS:526.2[M+H]⁺.

Example 9: Preparation of 2-amino-N-(8-methoxy-3-isopropyl-7-(3-morpholinopropyl)-4-oxo-3,4-dihydroquinazolinone-2-yl) pyrimidine-5-carboxamide (compound 8c-1)

The procedure is the same as the synthesis of the compound 8a-1. An isopropylamine was used to instead of the methylamine hydrochloride to react with 2-amino-3-methoxy-4-benzyloxybenzoic acid (compound 4), to obtain 2-amino-3-methoxy-4-benzyloxy-N-isopropylbenzamide (compound 5c-1). Then 5c-1 was condensed with 2-aminopyrimidine-5-acyl isothiocyanate to obtain 2-amino-N-(3 sopropyl-7-benzyloxyhydroxy-8-methoxy-4-oxo-3 ,4-dihydroquinazolin-2-yl) pyrimidine-5-carboxamide (6c-1), then debenzylated by Pd/C-H₂ to obtain 2-amino-N-(3-isopropyl-7-hydroxy-8-methoxy-4-oxo-3,4-dihydroquinazolin-2-yl) pyrimidine-5-carboxamide (7c-1), and finally reacted with N-(3-chloropropyl) morpholine to obtain the compound 8c-1. ESI-MS: 498.3 [M+H]⁺; ¹H-NMR (δ, CDCl₃/CD₃OD=5:1): 9.07 (s, 2H), 7.81 (d, 1H, J=9.0 Hz), 6.88 (d, 1H, J=9.0 Hz), 5.71 (m, 1H), 4.17 (t, 2H, J=6.0 Hz), 3.98 (s, 3H), 3.73 (m, 5H), 2.53 (m, 6H), 2.08 (s, 2H), 1.59 (m, 8H).

Example 10: Synthesis of the Target Compounds 8c-2 to 8c-9

The compound 2-amine-N-(3 sopropyl-7-hydroxy-8-methoxy-4-oxo-3 ,4-dihydroquinazoline-2-yl) pyrimidine-5-formamide (7c-1) was used as a raw material. And chloroacetamide, chloropropionamide, N-methylchloroacetamide, N,N-dimethylchloroacetamide, 2-(2-chloroethyl)-4-methylmorpholine, 1-(3-chloro-propionyl)-4-methylpiperazine, chloroacetylmorpholine, or 4-chlorobutanamide were used respectively to instead of N-(3-chloropropyl) morpholine to prepare the compounds 8c-2 to 8c-9. The structural formulas of the series of compounds are shown in Table 5 below.

TABLE 5

| Compd. | Structure | MS |
| --- | --- | --- |
| 7c-1 | 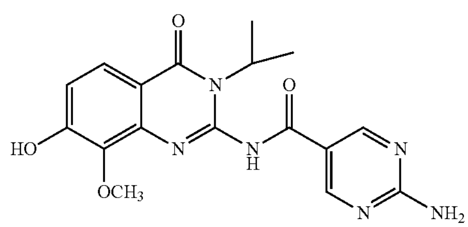 [SMILES: COc1c(O)ccc2c(=O)n(C(C)C)c(NC(=O)c3cnc(N)nc3)nc12] | 371.2 [M + H]⁺ |
| 8c-1 | 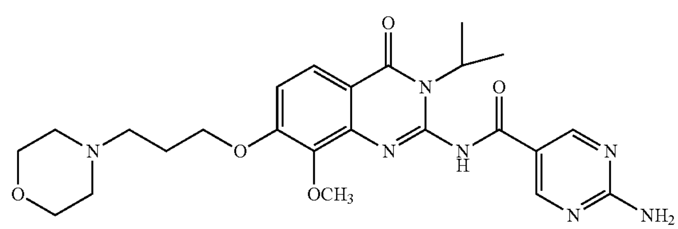 [SMILES: COc1c(OCCCN2CCOCC2)ccc2c(=O)n(C(C)C)c(NC(=O)c3cnc(N)nc3)nc12] | 498.3 [M + H]⁺ |
| 8c-2 | 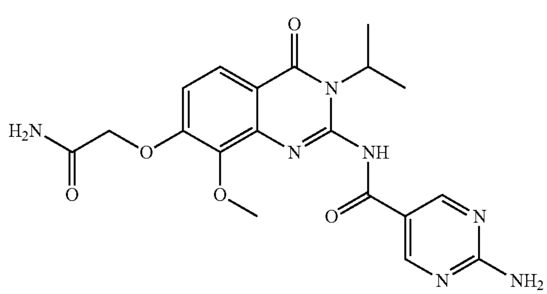 [SMILES: COc1c(OCC(N)=O)ccc2c(=O)n(C(C)C)c(NC(=O)c3cnc(N)nc3)nc12] | 428.2 [M + H]⁺ |

TABLE 5-continued

| Compd. | Structure | MS |
|---|---|---|
| 8c-3 | 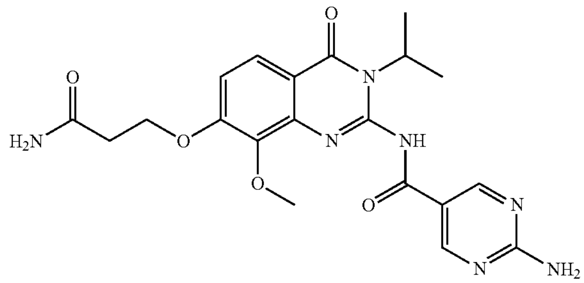 [SMILES: COc1c(OCCC(N)=O)ccc2c(=O)n(C(C)C)c(NC(=O)c3cnc(N)nc3)nc12] | 442.2 [M + H]+ |
| 8c-4 | 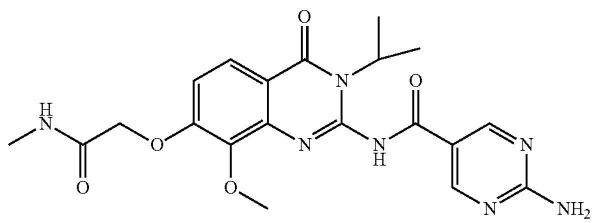 [SMILES: CNC(=O)COc1ccc2c(=O)n(C(C)C)c(NC(=O)c3cnc(N)nc3)nc2c1OC] | 442.2 [M + H]+ |
| 8c-5 | 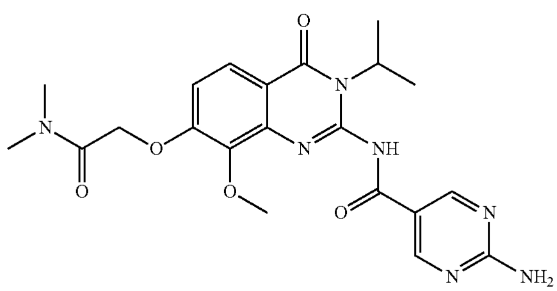 [SMILES: COc1c(OCC(=O)N(C)C)ccc2c(=O)n(C(C)C)c(NC(=O)c3cnc(N)nc3)nc12] | 456.2 [M + H]+ |
| 8c-6 | 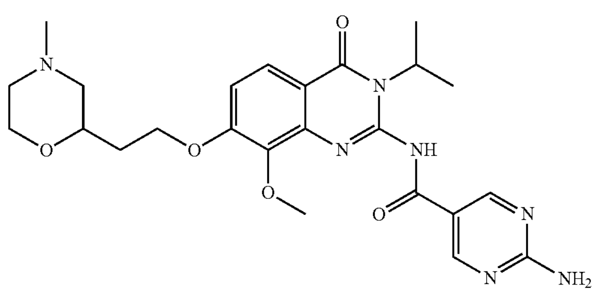 [SMILES: COc1c(OCCC2CN(C)CCO2)ccc2c(=O)n(C(C)C)c(NC(=O)c3cnc(N)nc3)nc12] | 498.2 [M + H]+ |
| 8c-7 | 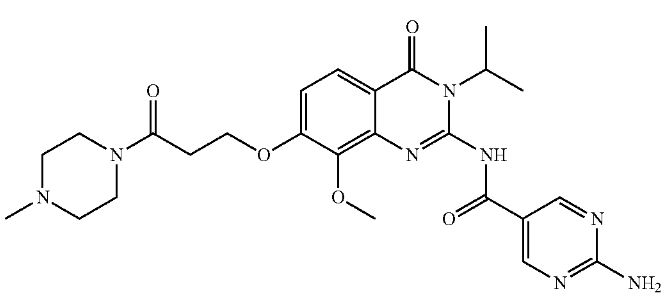 [SMILES: COc1c(OCCC(=O)N2CCN(C)CC2)ccc2c(=O)n(C(C)C)c(NC(=O)c3cnc(N)nc3)nc12] | 525.2 [M + H]+ |

TABLE 5-continued

| Compd. | Structure | MS |
|---|---|---|
| 8c-8 | 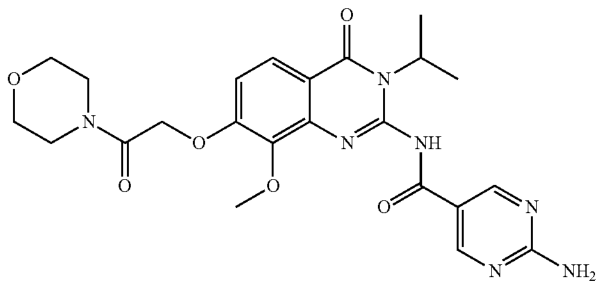 [SMILES: COc1c(OCC(=O)N2CCOCC2)ccc2c(=O)n(C(C)C)c(NC(=O)c3cnc(N)nc3)nc12] | 498.2 [M + H]+ |
| 8c-9 | 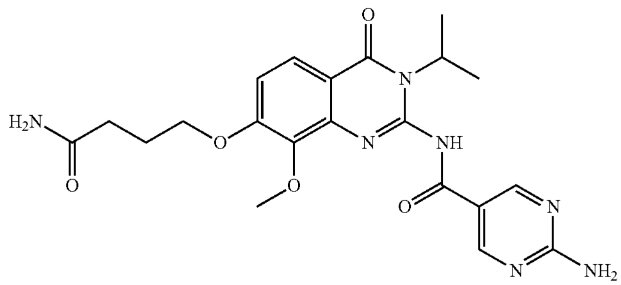 [SMILES: COc1c(OCCCC(N)=O)ccc2c(=O)n(C(C)C)c(NC(=O)c3cnc(N)nc3)nc12] | 456.2 [M + H]+ |

Example 11: Preparation of 2-amino-N-(8-methoxy--3-cyclopropyl-7-(3-morpholinopropyl)-4-oxo-3,4-dihydroquinazolino n-2-yl) pyrimidine-5-carboxamide (compound 8d-1)

The procedure is the same as the synthesis of the compound 8a-1. A cyclopropylamine was used to instead of the methylamine hydrochloride to react with 2-amino-3-methoxy-4-benzyloxybenzoic acid (compound 4), to obtain 2-amino-3-methoxy-4-benzyloxy-N-cyclopropylbenzamide (compound 5d-1). Then 5d-1 was condensed with 2-aminopyrimidine-5 -acyl isothiocyanate to obtain 2-amino-N-(3 -cyclopropyl-7-benzyloxyhydroxy-8-methoxy-4-oxo-3,4-dihydroquinazolin-2-yl) pyrimidine-5-carboxamide (6d-1), then debenzylated by Pd/C-H₂ to obtain 2-amino-N-(3 -cyclopropyl-7-hydroxy-8-methoxy-4-oxo-3,4-dihydroquinazolin-2-yl) pyrimidine-5-carboxamide (7d-1), and finally reacted with N-(3-chloropropyl) morpholine to obtain the compound 8d-1.ESI-MS: 496.2 [M+H]+.

Example 12: Synthesis of the Compounds 8d-2 to 8d-5

2-amino-N-(3 -cyclopropyl-7-hydroxy-8-methoxy-4-oxo-3,4-dihydroquinazolin-2-yl) pyrimidine-5-carboxamide (7d-1) was used as a raw material. And chloroacetamide, chloropropionamide, N-m ethylchloroacetamide, or N,N-dimethylchloroacetamide were used respectively to instead of N-(3-chloropropyl) morpholine to prepare the compounds 8d-2 to 8d-5. The structural formulas of which are shown in Table 6 below.

TABLE 6

| Compd. | Structure | MS |
|---|---|---|
| 7d-1 | 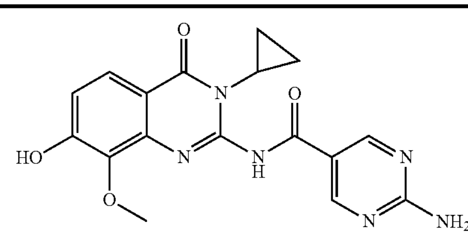 | 369.2 [M + H]+ |
| 8d-1 | 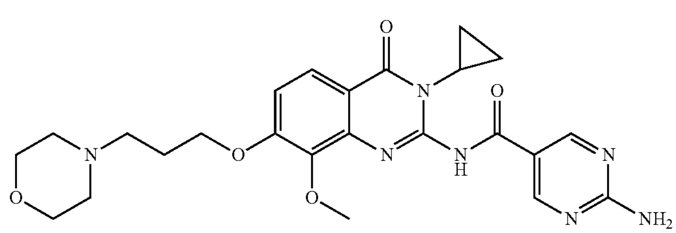 [SMILES: COc1c(OCCCN2CCOCC2)ccc2c(=O)n(C3CC3)c(NC(=O)c3cnc(N)nc3)nc12] | 496.2 [M + H]+ |

TABLE 6-continued

| Compd. | Structure | MS |
|---|---|---|
| 8d-2 | 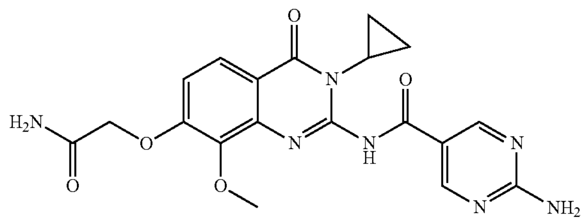 [SMILES: COc1c(OCC(N)=O)ccc2c(=O)n(C3CC3)c(NC(=O)c3cnc(N)nc3)nc12] | 426.1 [M + H]+ |
| 8d-3 | 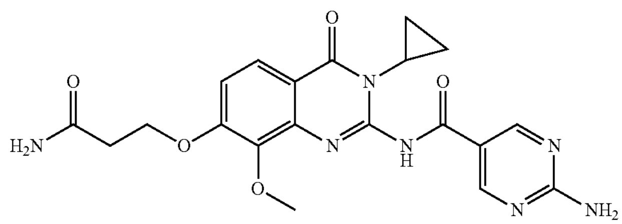 [SMILES: COc1c(OCCC(N)=O)ccc2c(=O)n(C3CC3)c(NC(=O)c3cnc(N)nc3)nc12] | 440.2 [M + H]+ |
| 8d-4 | 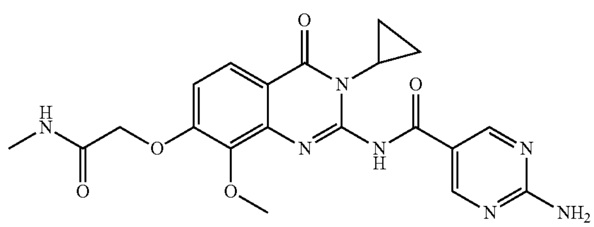 | 440.2 [M + H]+ |
| 8d-5 | 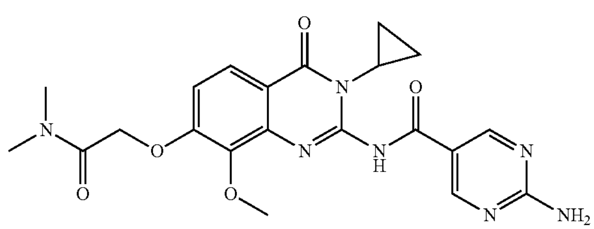 [SMILES: COc1c(OCC(=O)N(C)C)ccc2c(=O)n(C3CC3)c(NC(=O)c3cnc(N)nc3)nc12] | 454.2 [M + H]+ |

Example 13: Preparation of 2-amino-N-(8-methoxy-7-(3-morpholinopropyl)-4-oxo-3-(2,2,2-trifluoroethyl)-3,4-dihydroqui nazolinon-2-yl) pyrimidine-5-carboxamide (compound 8e-1)

The procedure is the same as the synthesis of the compound 8a-1. 2,2,2-trifluoroethylamine was used to instead of the methylamine hydrochloride to react with 2-amino-3-methoxy-4-benzyloxybenzoicacid (compound 4), to obtain 2-amino-3-methoxy-4-benzyloxy-N-trifluoroethylaminobenzamide (compound 5e-1). Then 5e-1 was condensed with 2-aminopyrimidine-5-acyl isothiocyanate to obtain 2-amino-N-(3 -trifluoroethyl -7-benzyloxyhydroxy-8-methoxy-4-oxo-3 ,4-dihydroquinazolin-2-yl) pyrimidine-5-carboxamide (6e-1), then debenzylated by Pd/C-H₂ to obtain 2-amino-N-(3-trifluoroethyl-7-hydroxy-8-methoxy-4-oxo-3,4-dihydroquinazolin-2-yl) pyrimidine-5-carboxamide (7e-1), and finally reacted with N-(3-chloropropyl) morpholine to obtain the compound 8e-1, which was a white solid. ESI-MS: 538.2 [M+H]+; $^1$H NMR (δ, CDCl₃/CD₃OD=5:1): 8.96 (s, 2H), 7.78 (d, 1H, J=9.0 Hz), 6.88 (d, 1H, J=9.0 Hz), 5.31 (s, 2H), 4.13 (t, 2H, J=6.0 Hz), 3.95 (s, 3H), 3.64 (s, 4H), 3.25 (m, 2H), 2.49 (m, 5H), 1.99 (s, 2H), 1.14 (s, 2H).

Example 14: Synthesis of the Compounds 8e-2 to 8e-5

The compound 7e-1 was used as a raw material. And chloroacetamide, chloropropionamide, N-methylchloroacetamide, or chloroacetylmorpholine were used respectively to instead of N-(3-chloropropyl) morpholine to prepare the compounds 8e-2 to 8e-5. The structural formulas of which are shown in Table 7 below.

TABLE 7

| Compd. | Structure | MS |
|---|---|---|
| 7e-1 | 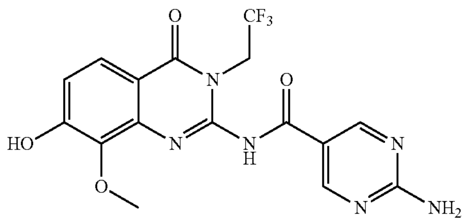 [SMILES: COc1c(O)ccc2c(=O)n(CC(F)(F)F)c(NC(=O)c3cnc(N)nc3)nc12] | 411.2 [M + H]⁺ |
| 8e-1 | 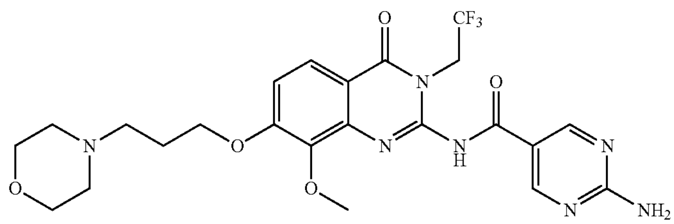 [SMILES: COc1c(OCCCN2CCOCC2)ccc2c(=O)n(CC(F)(F)F)c(NC(=O)c3cnc(N)nc3)nc12] | 538.3 [M + H]⁺ |
| 8e-2 | 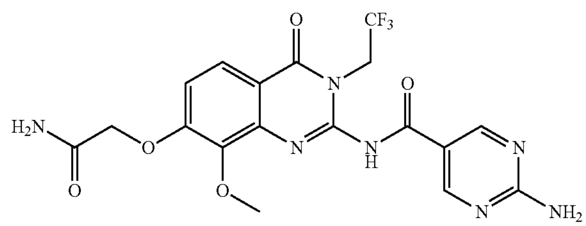 [SMILES: COc1c(OCC(N)=O)ccc2c(=O)n(CC(F)(F)F)c(NC(=O)c3cnc(N)nc3)nc12] | 450.1 [M + H]⁺ |
| 8e-3 | 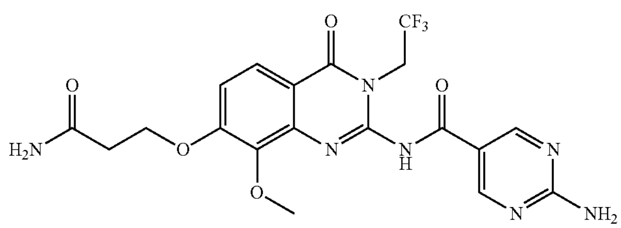 [SMILES: COc1c(OCCC(N)=O)ccc2c(=O)n(CC(F)(F)F)c(NC(=O)c3cnc(N)nc3)nc12] | 464.1 [M + H]⁺ |
| 8e-4 | 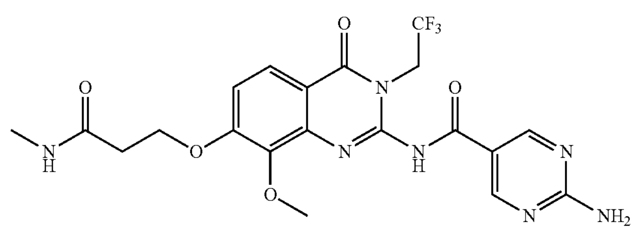 [SMILES: CNC(=O)CCOc1ccc2c(=O)n(CC(F)(F)F)c(NC(=O)c3cnc(N)nc3)nc2c1OC] | 478.1 [M + H]⁺ |
| 8e-5 | 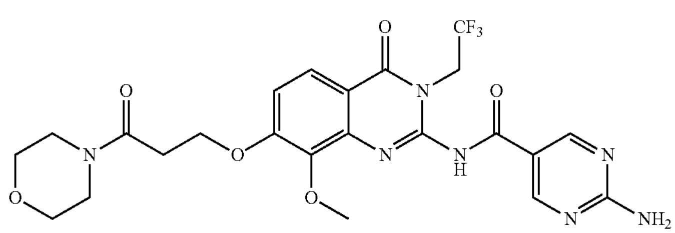 [SMILES: COc1c(OCCC(=O)N2CCOCC2)ccc2c(=O)n(CC(F)(F)F)c(NC(=O)c3cnc(N)nc3)nc12] | 534.2 [M + H]⁺ |

Example 15: Preparation of 2-amino-N-(8-methoxy-7-(3-morpholinopropyl)-4-oxo-3-(2,2-difluoroethyl)-3,4-dihydroquinaz olinon-2-yl) pyrimidine-5-carboxamide (compound 8f-1)

2,2-difluoroethylamine was used to instead of the methylamine hydrochloride to react with 2-amino-3-methoxy-4-benzyloxybenzoic acid (compound 4), to obtain 2-amino-3-methoxy-4-benzyloxy-N-difluoroethylaminobenzamide (compound 5f-1). Then 5f-1 was condensed with 2-aminopyrimidine-5-acyl isothiocyanate to obtain 2-amino-N-(3-difluoroethyl-7-benzyloxyhydroxy-8-methoxy-4-oxo-3,4-dihydroquinazolin-2-yl) pyrimidine-5-carboxamide (6f-1), then debenzylated by Pd/C-H₂ to obtain 2-amino-N-(3 -difluoroethyl-7-hydroxy-8-methoxy-4-oxo-3 ,4-dihydroquinazolin-2-yl) pyrimidine-5-carboxamide (7f-1), and finally reacted with N-(3-chloropropyl) morpholine to obtain the compound, which was a white solid. ESI-MS: 520.2

[M+H]⁺;¹H-NMR (δ, DMSO-d₆): 13.87 (s, 1H), 8.92 (s, 2H), 7.82 (d, 1H, J=9.0 Hz), 7.26 (s, 2H), 7.21 (d, 1H, J=9.0 Hz), 6.52 (tt, 1H, J₁=56.0 Hz, J₂=4.0 Hz), 4.71 (td, 2H, J₁=14.0 Hz, J₂=4.0 Hz), 4.25 (t, 2H, J=6.5 Hz), 3.96 (s, 3H), 3.59 (t, 4H, J=5.0 Hz), 2.48 (t, 2H, J=7.0 Hz)2.38 (s, 4H), 2.00 (m, 2H).

Example 16: Synthesis of the Compounds 8f-2 to 8f-3

The compound 2-amino-N-(3-difluoroethyl-7-hydroxy-8-methoxy-4-oxo-3,4-dihydroquinazolin-2-yl) pyrimidine-5-carboxamide (7f-1) was used as a raw material. And chloroacetamide or chloropropionamide were used respectively to instead of N-(3-chloropropyl) morpholine to prepare the compounds 8f-2 to 8f-3. The structural formulas of the series of compounds are shown in Table 8 below.

Example 17: Preparation of 2-amino-N-(7-ethyl-6-oxo-6,7-dihydro-[1,3] dioxolo[4,5-H] quinazoline-8-yl)pyrimidine-5-carboxamide (compound 14a-1)

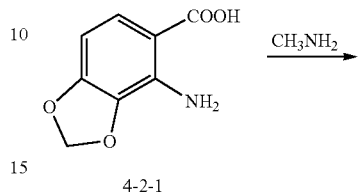

4-2-1

TABLE 8

| Compd. | Structure | MS |
|---|---|---|
| 8f-1 | | 393.2 [M + H]⁺ |
| 8f-1 | | 520.2 [M + H]⁺ |
| 8f-2 | 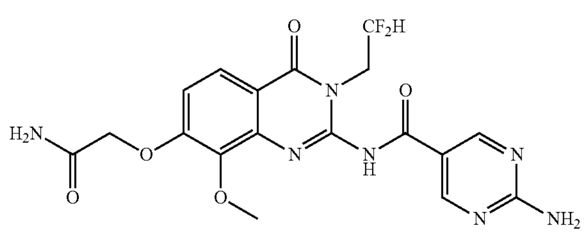 | 450.2 [M + H]⁺ |
| 8f-3 | 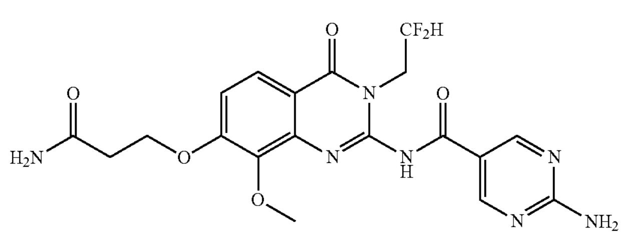 [SMILES: COc1c(OCCC(N)=O)ccc2c(=O)n(CC(F)F)c(NC(=O)c3cnc(N)nc3)nc12] | 464.1 [M + H]⁺ |

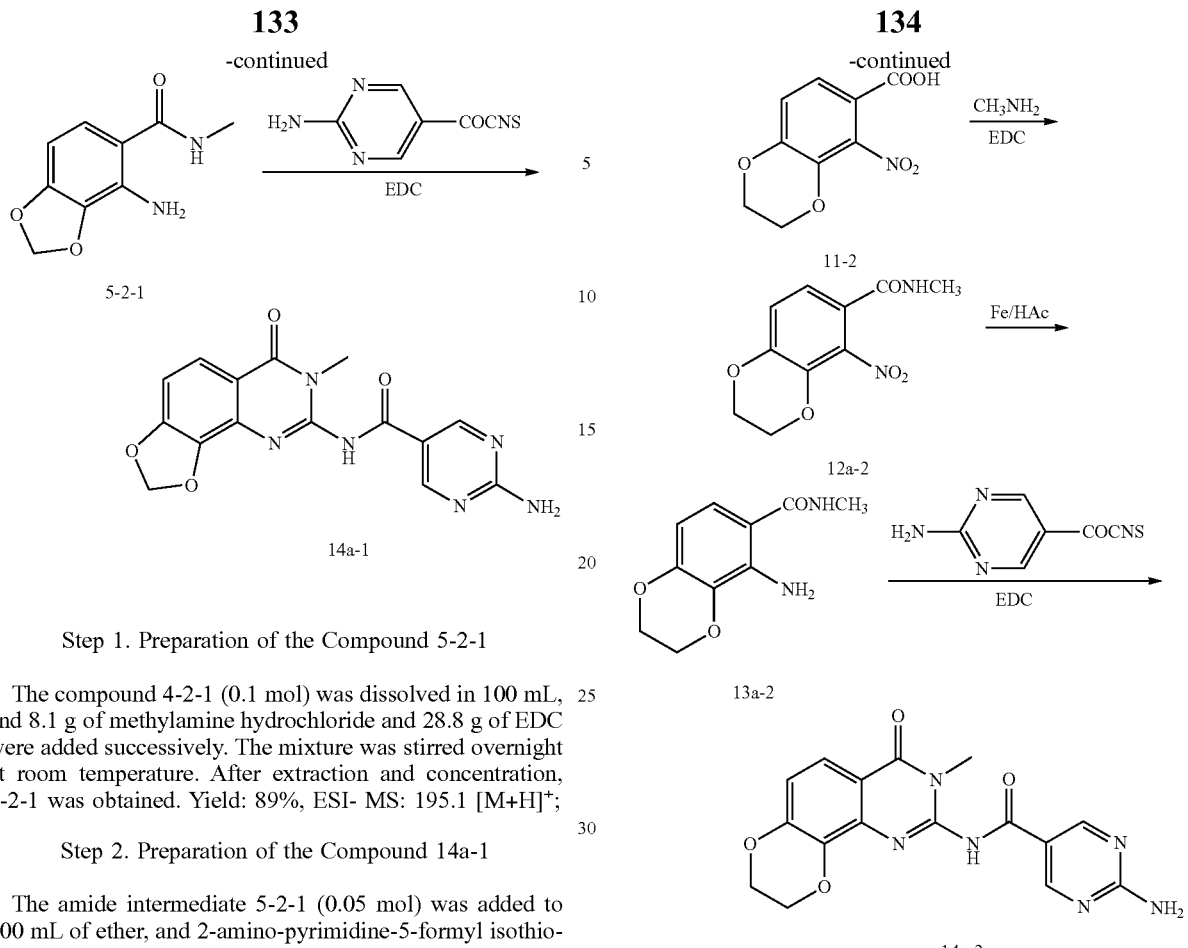

Step 1. Preparation of the Compound 5-2-1

The compound 4-2-1 (0.1 mol) was dissolved in 100 mL, and 8.1 g of methylamine hydrochloride and 28.8 g of EDC were added successively. The mixture was stirred overnight at room temperature. After extraction and concentration, 5-2-1 was obtained. Yield: 89%, ESI- MS: 195.1 [M+H]$^+$;

Step 2. Preparation of the Compound 14a-1

The amide intermediate 5-2-1 (0.05 mol) was added to 200 mL of ether, and 2-amino-pyrimidine-5-formyl isothiocyanate (0.05 mol) in acetone was added dropwise thereto. After stirring at room temperature overnight, a precipitate precipitated. The powdery white precipitate obtained by suction filtration was dissolved in anhydrous DCM and then added with EDC (0.05 mmol). After stirring at room temperature overnight, a precipitate was obtain by suction filtration, and washed with methanol several times to obtain the target compound. Yield: 80%, ESI-MS: 341.1 [M+H]$^+$.

Example 18: Preparation of 2-amino-N-(3-methyl-4-oxo-3,4,8,9-tetrahydro-[1,4]dioxino[2,3-H) quinazolin-2-yl)pyrimidine-5-carboxamide (compound 14a-2)

The synthetic route is as follows:

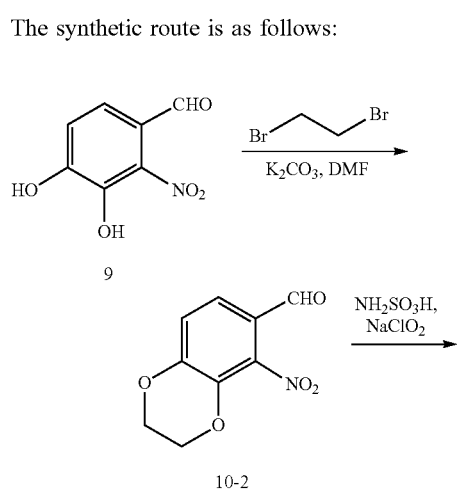

Step 1. Preparation of the Compound 10-2

3,4-dihydroxy-2-nitrobenzaldehyde (compound 9, 0.1 mol) was dissolved in 100 mL of DMF, 55.2 g of potassium carbonate was added, and then 1,2-dibromoethane (0.11 mol) was added dropwise, and the temperature was raised to 60° C. for reaction. After the reaction was complete, water and ethyl acetate were added for extraction. The ethyl acetate layer was washed with saturated brine, dried over anhydrous sodium sulfate, and then concentrated to obtain the compound 10-2. Yield: 62%, ESI-MS: 210.1 [M+H]$^+$;

Step 2. Preparation of the Compound 11-2

The compound 10-2 (0.06 mol) was dissolved in 100 mL of glacial acetic acid, and sulfamic acid (0.08 mol) and NaClO$_2$ solution (0.12 mol) were added. After reacting at low temperature for 4 hours, a large amount of water was added to precipitate a precipitate, and the compound 11-2 was obtained by suction filtration. Yield: 88%, ESI-MS: 226.2 [M+H]$^+$;

Step 3. Preparation of the Compound 12a-2

The compound 11-2 (0.04 mol) was dissolved in 100 mL of dichloromethane, and methylamine hydrochloride (0.05 mol) and EDC (0.06 mol) were added successively. The mixture was stirred overnight at room temperature. A NaHCO$_3$ solution was added to separate the organic layer, which was washed with saturated NaCl solution, dried over anhydrous sodium sulfate, and the compound 12a-2 was obtained by recovering solvent under reduced pressure. Yield; 80%, ESI-MS: 239.2[M+H]$^+$;

Step 4. Preparation of the Compound 13a-2

The compound 12a-2 (0.03 mol) was dissolved in 100 mL ethanol, and reduced iron powder (0.05 mol) andglacial acetic acid (0.06 mol) were added. The mixture was heated to 60° C. and reacted for 8 h, then removed the iron powder by suction filtration, vacuum distilled to remove ethanol after adding water, and adjusted the pH=10, and the product 13a-2 was obtained by suction filtration. Yield; 78%, ESI-MS: 209.1 [M+H]$^+$;

Step 5. Preparation of the Compound 14a-2

The compound 13a-1 (0.005 mol) was added to 100 mL of ether, and 2-amino-pyrimidine-5-formyl isothiocyanate (0.005 mol) in acetone was added dropwise thereto. After stirring at room temperature overnight, a precipitate precipitated. The solid obtained by suction filtration was dissolved in 100 mL of DCM, and then added with EDC (0.008 mmol). After stirring at room temperature overnight, a precipitate was obtain by suction filtration, and washed with methanol several times to obtain the target compound 14a-2. Yield: 48%, ESI-MS: 355.1 [M+H]$^+$.

Example 19: Synthesis of the Compounds 14a-3 to 14a-8

The procedure is the same as the synthesis of compound 14a-2. 9a was used as a raw material to react respectively with 1,3-dibromopropane, 1,4-dibromobutane, 1,5-dibromopentane, 1,6-dibromohexane, 1,7-dibromoheptane, or 1,8-dibromooctane by means of an alkaline reagent, to obtain etherified benzaldehyde intermediates 10-2 to 10-7. And then their aldehyde group was oxidized to obtain etherified benzaldehyde intermediates 11-2 to 11-7, which was underwent methylamination to obtain benzamide derivatives 12a-2 to 12a-7, and then reduced nitro to obtain 13a-2 to 13a-7, and finally condensed with 2-amino-pyrimidine-5-formyl isothiocyanate to obtain the compounds 14a-3 to 14a-8. The structural formulas of the series of compounds are shown in Table 9 below.

TABLE 9

| Compd. | Structure | MS |
| --- | --- | --- |
| 14a-1 | 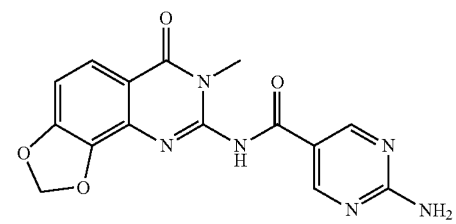 [SMILES: Cn1c(NC(=O)c2cnc(N)nc2)nc2c3c(ccc2c1=O)OCO3] | 341.1 [M + H]$^+$ |
| 14a-2 | 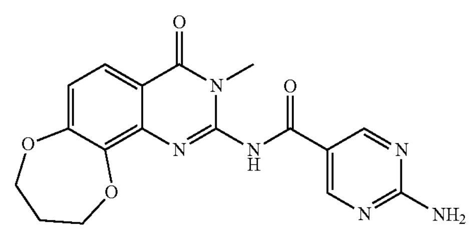 | 355.1 [M + H]$^+$ |
| 14a-3 | 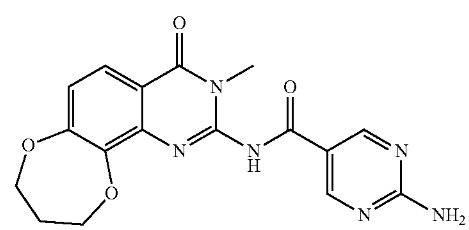 [SMILES: Cn1c(NC(=O)c2cnc(N)nc2)nc2c3c(ccc2c1=O)OCCCO3] | 369.1 [M + H]$^+$ |
| 14a-4 | 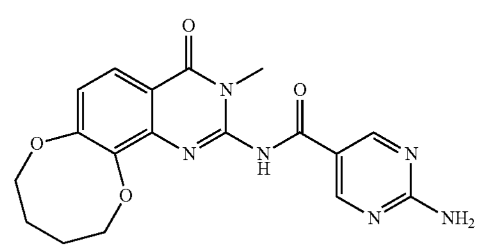 | 383.1 [M + H]$^+$ |

TABLE 9-continued

| Compd. | Structure | MS |
|---|---|---|
| 14a-5 | 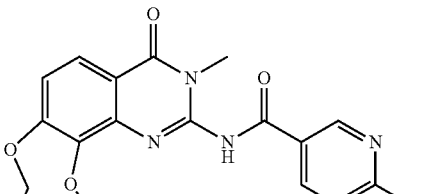 | 397.2 [M + H]+ |
| 14a-6 | 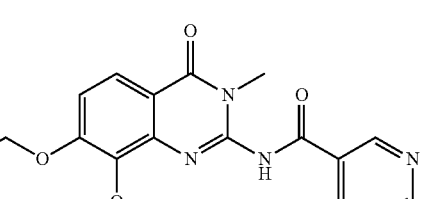 | 411.1 [M + H]+ |

Example 20: Preparation of 2-amino-N-(3-methyl-4-oxo-3,4,8,9,11,12-hexahydro-[1,4,7]trioxo [2,3-H] quinazolin-2-yl) pyrimidine-5-formamide (compound 14a-9)

The synthetic route is as follows:

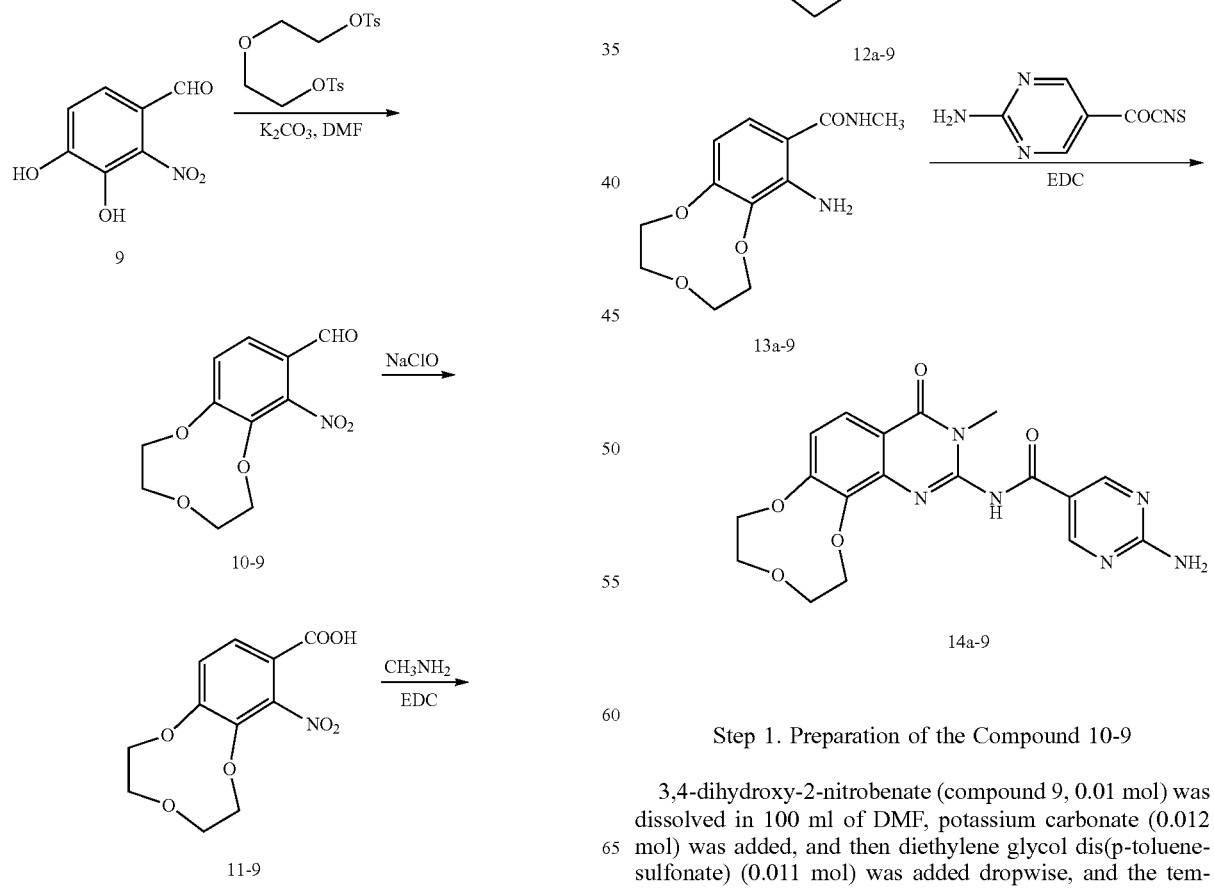

Step 1. Preparation of the Compound 10-9

3,4-dihydroxy-2-nitrobenate (compound 9, 0.01 mol) was dissolved in 100 ml of DMF, potassium carbonate (0.012 mol) was added, and then diethylene glycol dis(p-toluene-sulfonate) (0.011 mol) was added dropwise, and the temperature was raised to 60° C. for reaction. After the reaction was complete, water and ethyl acetate were added. The ethyl acetate layer was washed with saturated brine, dried over anhydrous sodium sulfate, and then concentrated to obtain the compound 10-9. Yield: 62%, ESI-MS: 254.1 [M+H]$^+$;

Step 2. Preparation of the Compound 11-9

The compound 10-9 (0.006 mol) was dissolved in 80 mL of dichloromethane, and 50 ml of 15% NaOH solution was added, the temperature was raised to 55° C., then a NaClO aqueous solution (0.012 mol) was dropped into. After reacting for 4 hours, methanol was removed by vacuum distillation. The system was adjusts pH to 2-3 by 6N HCl to precipitate a precipitate, and the compound 11-9 was obtained by suction filtration.Yield: 88%, ESI-MS: 270.1 [M+H]$^+$;

Step 3. Preparation of the Compound 12a-9

The compound 11-9 (0.004 mol) was dissolved in 100 mL of dichloromethane, methylamine hydrochloride (0.006 mol), EDC (0.006 mol) and triethylamine (0.006 mol) were added successively. The mixture was stirred overnight at room temperature. A NaHCO$_3$ solution was added for washing, dried over anhydrous sodium sulfate, and the compound 12a-9 was obtained by concentrating organic layer. Yield: 80%, ESI-MS: 283.1[M+H]$^+$;

Step 4. Preparation of the Compound 13a-9

The compound 12a-9 (0.003 mol) is dissolved in 100 mL of ethanol, and reduced iron powder (0.008 mol) and 20 ml of glacial acetic acid were added. The mixture was reacted under mechanically stirring for 8 h, then removed the iron powder by suction filtration, vacuum distilled to remove ethanol after adding water, and adjusted the pH to 10, and the product 13a-9 was obtained by suction filtration. Yield: 78%, ESI-MS: 253.1 [M+H]$^+$;

Step 5. Preparation of the Compound 14a-9

The compound 13a-9 was reacted with 2-amino-pyrimidine-5-formylisocyanate, then condened with EDC to obtain 14a-9. Yield: 48%, ESI-MS: 399.1 [M+H]$^+$.

Example 21: Synthesis of the Compounds 14a-10 to 14a-12

The procedure is the same as the synthesis of compound 14a-9. The compound 9 was used as a raw material to react respectively with corresponding triethylene glycol dis(p-toluenesulfonate), tetraethylene glycol dis(p-toluenesulfonate), or pentaethylene glycol dis(p-toluenesulfonate), to prepare etherified intermediates 10-9 to 10-11. And then their aldehyde group was oxidized to obtain benzoic acid derivative 11-9 toll-11, which was condensed with methylamine to obtain N-methylbenzamide derivatives 12a-9 to 12a-11, and then reduced nitro to obtain 13a-9 to 13a-11, and finally condensed with 2-amino-pyrimidine-5-formylisocyanate to obtain the compounds 14a-10 to 14a-12. The structural formulas of the series of compounds are shown in Table 10 below.

TABLE 10

| Compd. | Structure | MS |
| --- | --- | --- |
| 14a-9 | 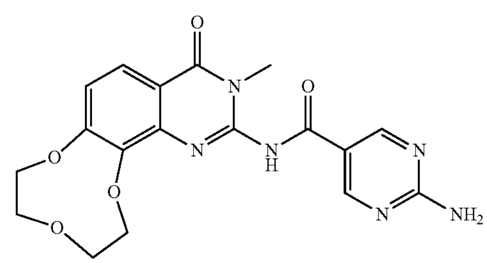 [SMILES: Cn1c(NC(=O)c2cnc(N)nc2)nc2c3c(ccc2c1=O)OCCOCCO3] | 399.2 [M + H]$^+$ |
| 14a-10 | 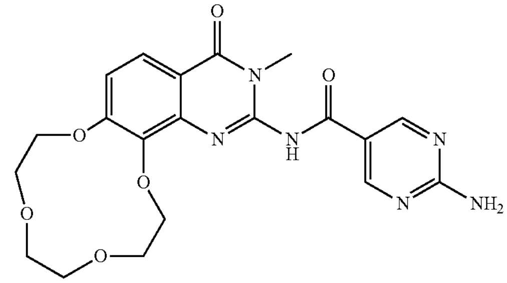 [SMILES: Cn1c(NC(=O)c2cnc(N)nc2)nc2c3c(ccc2c1=O)OCCOCCOCCO3] | 443.2 [M + H]$^+$ |

TABLE 10-continued

| Compd. | Structure | MS |
|---|---|---|
| 14a-11 | 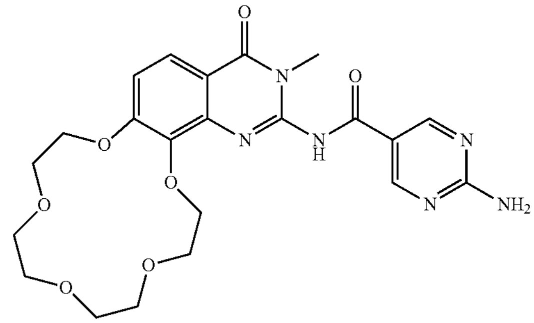 [SMILES: Cn1c(NC(=O)c2cnc(N)nc2)nc2c3c(ccc2c1=O)OCCOCCOCCOCCO3] | 487.2 [M + H]+ |
| 14a-12 | 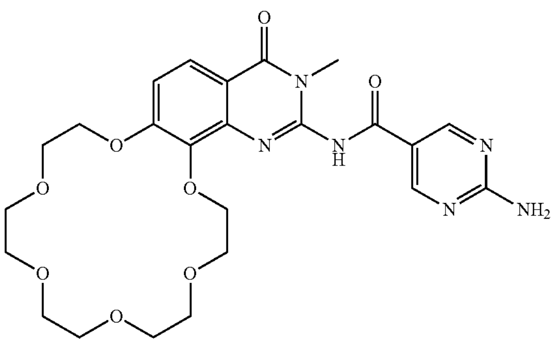 [SMILES: Cn1c(NC(=O)c2cnc(N)nc2)nc2c3c(ccc2c1=O)OCCOCCOCCOCCOCCO3] | 531.2 [M + H]+ |

Example 22: Preparation of 2-amino-N-(7-ethyl-6-oxo-6,7-dihydro-[1,3]dioxolo[4,5-H]quinazoline-8-yl)pyrimidine-5-carb oxamide (compound 14b-1)

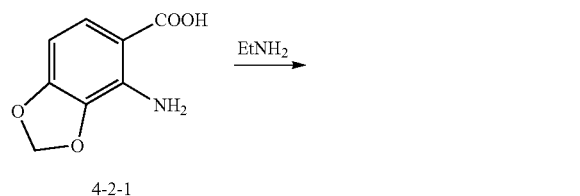

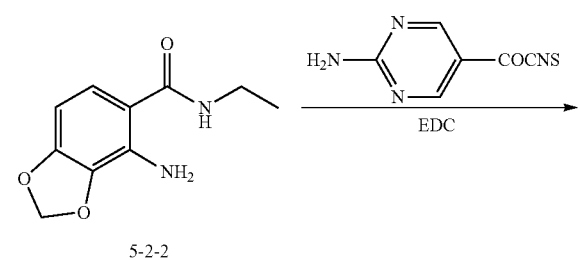

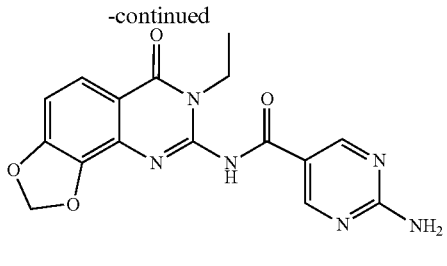

The reaction steps were as shown above, which was the same as the synthesis of the compound 14a-1. 4-2-1 was used as a raw material to firstly react with ethylamine, to obtain the benzoylanamine intermediate 5-2-2, which then condensed with 2-amino-pyrimidine-5-formyl isothiocyanate to obtain the product 14b-1. ESI-MS: 355.1[M+H]+.

Example 23: Preparation of the Compounds 14b-2 TO 14b-8

The procedure is the same as the synthesis of compound 14a-2. The benzoal aldehyde intermediates 11-1 to 11-7 were used to condense with ethylamine to obtain the intermediates 12-1 to 12-7, which then were reduced nitro to obtain 13-2 to 13-7, and finally condensed with 2-amino-pyrimidine-5-formyl isothiocyanate to obtain white solids 14b-2 to 14b-8, which as shown in Table 11.

TABLE 11

| Compd. | Structure | MS |
|---|---|---|
| 14b-1 | 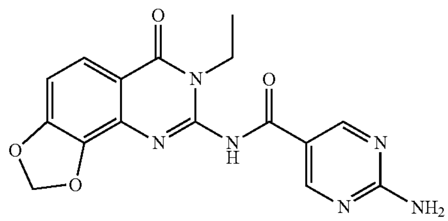 | 355.2 [M + H]+ |
| 14b-2 | 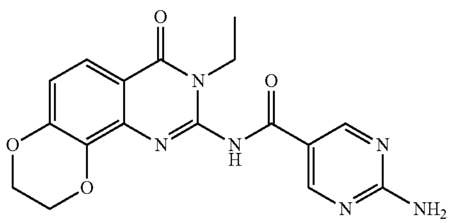 [SMILES: CCn1c(NC(=O)c2cnc(N)nc2)nc2c3c(ccc2c1=O)OCCO3] | 369.2 [M + H]+ |
| 14b-3 | 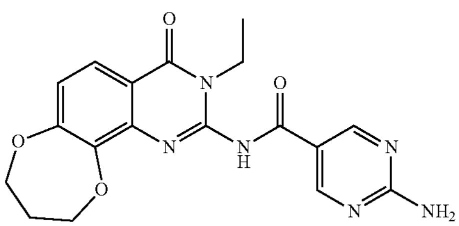 [SMILES: CCn1c(NC(=O)c2cnc(N)nc2)nc2c3c(ccc2c1=O)OCCCO3] | 383.1 [M + H]+ |
| 14b-4 | 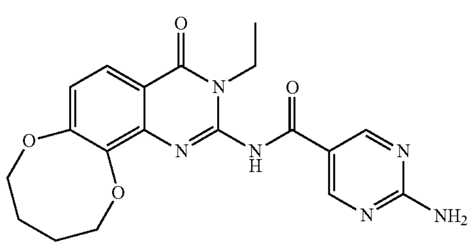 [SMILES: CCn1c(NC(=O)c2cnc(N)nc2)nc2c3c(ccc2c1=O)OCCCCO3] | 397.2 [M + H]+ |
| 14b-5 | 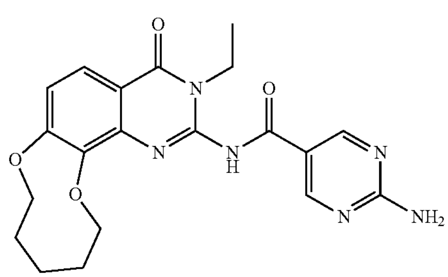 [SMILES: CCn1c(NC(=O)c2cnc(N)nc2)nc2c3c(ccc2c1=O)OCCCCCO3] | 411.2 [M + H]+ |
| 14b-6 | 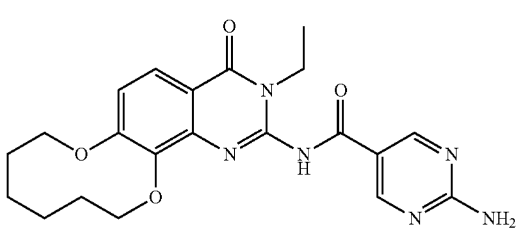 [SMILES: CCn1c(NC(=O)c2cnc(N)nc2)nc2c3c(ccc2c1=O)OCCCCCCO3] | 425.2 [M + H]+ |

TABLE 11-continued

| Compd. | Structure | MS |
|---|---|---|
| 14b-7 | 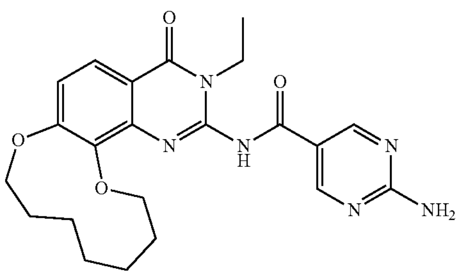 [SMILES: CCn1c(NC(=O)c2cnc(N)nc2)nc2c3c(ccc2c1=O)OCCCCCCCO3] | 439.2 [M + H]+ |
| 14b-8 | 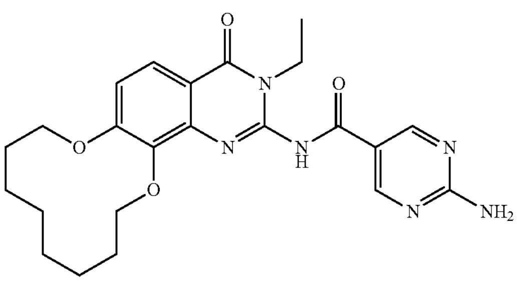 [SMILES: CCn1c(NC(=O)c2cnc(N)nc2)nc2c3c(ccc2c1=O)OCCCCCCCCO3] | 453.2 [M + H]+ |

Example 24: Synthesis of the Compound 14b-9 to 14b-12

The procedure is the same as the synthesis of compound 14a-9. The benzoic acid derivatives 11-9 to 11-11 were condensed with ethylamine to obtain the N-methylbenzamide derivatives 12b-9 to 12b-11, which then were reduced nitro to obtain 13b-9 to 13b-11, and finally condensed with 2-amino-pyrimidine-5-formyl isocyanate to obtain the compounds 14b-10 to 14b-12. The structural formulas of which are shown in Table 12 below.

TABLE 12

| Compd. | Structure | MS |
|---|---|---|
| 14b-9 | 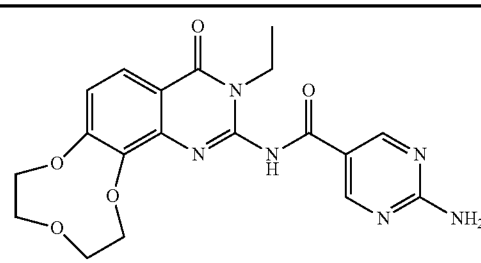 | 413.1 [M + H]+ |
| 14b-10 | 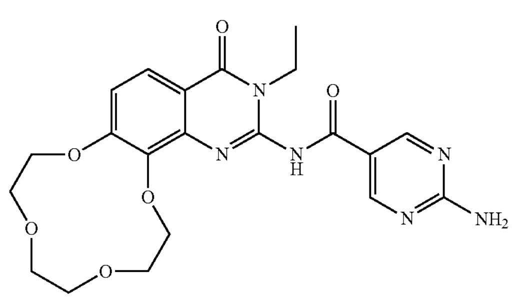 [SMILES: CCn1c(NC(=O)c2cnc(N)nc2)nc2c3c(ccc2c1=O)OCCOCCOCCO3] | 457.2 [M + H]+ |

| Compd. | Structure | MS |
|---|---|---|
| 14b-11 | 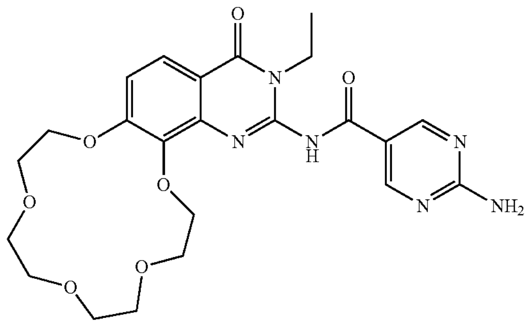 [SMILES: CCn1c(NC(=O)c2cnc(N)nc2)nc2c3c(ccc2c1=O)OCCOCCOCCOCCO3] | 501.2 [M + H]+ |
| 14b-12 | 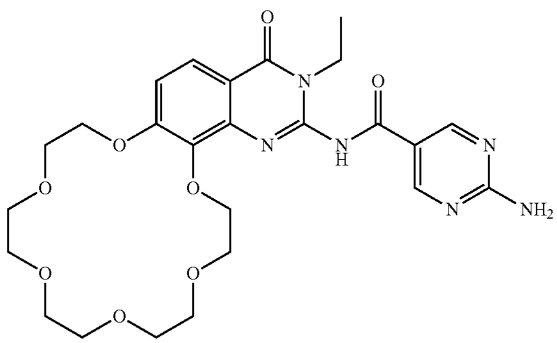 | 545.2 [M + H]+ |
Example 25: Preparation of 2-amino-N-(2-methyl-5-methoxy-6-(3-morpholino)-1-oxo-1,2-dihydroisoquinolin-3-yl) pyrimidin-5-formamide (compound 8a'-1)
The synthetic route is shown as follows:
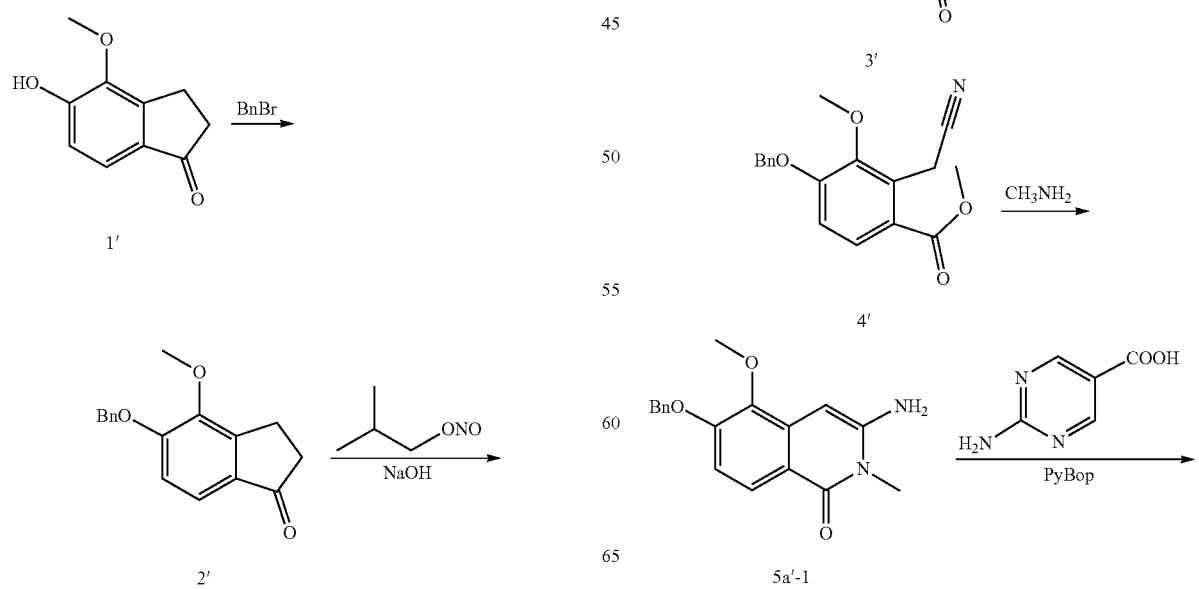

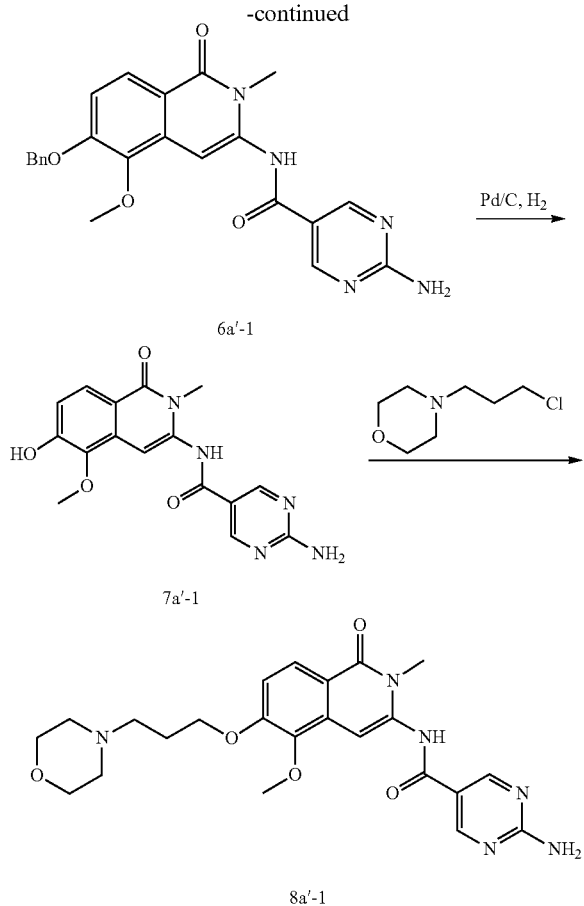

Step 1. Synthesis of 5-(benzyloxy)-4-methoxy-2,3-dihydro-1-antleanone (compound 2')

5-(benzyloxy)-4-hydroxy-2,3-dihydro-1-antleanone (10 mmol) and potassium carbonate (3.45 g) were dissolved in DMF (30 mL), and benzyl bromide (11 mmol) was added dropwise. The mixture was stirred at room temperature overnight, and extracted and concentrated to obtain the compound 2' after the reaction was complete. Yield: 92%, ESI-MS: 269.1 [M+H]$^+$;

Step 2. Synthesis of 4-(benzyloxy)-2-(cyanomethyl)-3-methoxybenzoic acid (compound 3')

5-(benzyloxy)-4-methoxy-2,3-dihydro-1-antleanone (9 mmol) was dissolved in methyl tert-butyl ether (30 mL), and isoamyl nitrite (13.5 mmol) and trimethyl chlorosilane (13.5 mmol) were added dropwise successively in an ice bath. The reaction was cooled to room temperature after compleiteing, then underwent a suction filtration to obtain a solid. The solid was added to 15% NaOH solution (20 mL), stirred at room temperature overnight, adjusted pH to 2-3, and underwent a suction filtration. The resulting solid was the carboxylic acid product. Yield: 56%, ESI-MS: 298.1 [M+H]$^+$;

Step 3 Synthesis of methyl 4-(benzyloxy)-2-(cyanomethyl)-3-methoxybenzoate (compound 4')

The carboxylic acid intermediate 3' (5 mmol) was dissolved in anhydrous methanol (10 mmol), and thionyl chloride (15 mmol) was added dropwise in an ice bath. The mixture was stirred at room temperature for 8 h, then vacuum distilled, and extracted with water and ethyl acetate. The ethyl acetate layer was washed with saturated brine, and drying with anhydrous sodium sulfate to obtain the product. Yield: 99%, ESI-MS: 312.1 [M+H]$^+$;

Step 4. Synthesis of methyl 4-(benzyloxy)-2-(cyanomethyl)-3-methoxybenzoate (compound 5a'-1)

The compound 4a' (5 mmol) was dissolved in methylamine aqueous solution (10 mmol), and raised the temperature to 120° C. to react for 12 hours in a sealed tank. The mixture was extracted with water and ethyl acetate. The organic layer was washed with saturated brine and dried over anhydrous sodium sulfate, and the compound 5a'was obtained by concentration under reduced pressure. Yield: 88%, ESI-MS: 311.1 [M+H]$^+$;

Step 5. Preparation of 2-amino-N-(6-(benzyloxy)-2-methyl-5-methoxy-1-oxo-1,2-dihydroisoquinolin-3-yl) pyrimidine-5-formamide (Compound 6a'-1)

3-amino-6-(benzyloxy)-5-methoxy-2-methylisoquinoline-1-(2H)-one (compound 5a'-1) and 2-amino-pyrimidine-5-carboxylic acid were dissolved in DMF, and N,N-diisopropylethylamine (DPIEA), hexafluorophosphate benzotriazol-1-yl-oxytripyrrolidinyl phosphorus (PyBop) were added successively. The mixture was reacted at room temperature for 2 days, and underwent a suction filtration, and the obtained solid was washed with ethyl acetate and dried to obtain the benzyl-protected amide intermediate 6a'-1. Yield: 40%, ESI-MS: 432.2 [M+H]$^+$;

Step 6. Preparation of 2-amino-N-(2-methyl-6-hydroxy-5-methoxy-1-oxo-1,2-dihydroisoquinolin-3-yl) pyrimidine-5-carboxamide (Compound 7a'-1)

The intermediate 6a'-1 (3.0 mmol), 10% Pd/C (50 mg) and 30 mL of ethanol were fed into a reaction flask connected with a hydrogen reduction device, vacuumized and input hydrogen for three times. The mixture was reacted at room temperature for 6 hours, and then removed Pd/C by suction filtration through diatomite. The filtrate was concentrated under reduced pressure to obtain a white solid. Yield: 88%, ESI-MS: 342.1 [M+H]$^+$;

Step 7. Preparation of 2-amino-N-(2-methyl-5-methoxy-6-(3-morpholino)-1-oxo-1,2-dihydroisoquinolin-3-yl) pyrimidine-5-carboxamide (compound 8a'-1)

The compound 7a'-1 (1.0 eq) was dissolved in acetonitrile, and cesium carbonate (2.5 eq) was added. The mixture was stirred for 0.5h, added N-chloropropylmorpholine, and reacted overnight at 60° C., then distilled under reduced pressure, and washed the precipitate with water to obtain a white solid. Yield: 83%, ESI-MS: 469.2 [M+H]$^+$.

Example 26: Synthesis of the Compounds 8a'-2 to 8a'-7

The compound 7a'-1 was used as a raw material. And chloroacetamide, chloropropionamide, N-methylchloroacetamide, N,N-dim ethylchloroacetamide, 2-(2-chloroethyl)-4-methylmorpholine, or 1-(3-chloro-propionyl)-4-methylpiperazine were used respectively to instead of N-(3-chloropropyl) morpholine to prepare the compounds 8a'-2 to 8a'-7.

In addition, the 5'a-1 was used as a raw material. And pyrimidine-5-carboxylic acid, pyridazine-4-carboxylic acid, 2-amino-pyridine-5-carboxylic acid, 6-amino-pyridazine-3-carboxylicacid, 2-amino-pyrazine-5-carboxylic acid, or 5-aminopyridine-2-carboxylic acid were used respectively to instead of 2-amino-pyrimidine-5carboxylic acid for condensation reaction to obtain 6'a-2 to 6'a-7, which were further deprotected by Pd/C-H$_2$ to obtain 7'a-2 to 7'a-7, and finally reacted with N-chloropropylmorpholine to synthesize 8a'-8 to 8a'12. The structural formulas of which are shown in Table 13 below.

TABLE 13

| Compd. | Structure | MS |
| --- | --- | --- |
| 7a'-1 | 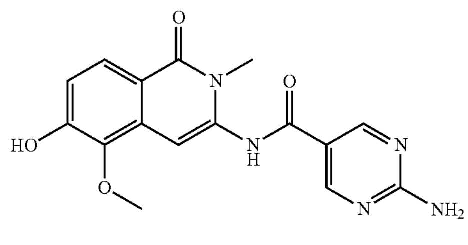 [SMILES: COc1c(O)ccc2c(=O)n(C)c(NC(=O)c3cnc(N)nc3)cc12] | 342.1 [M + H]$^+$ |
| 8a'-1 | 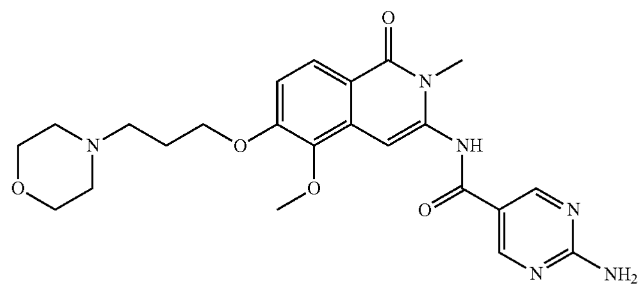 | 469.2 [M + H]$^+$ |
| 8a'-2 | 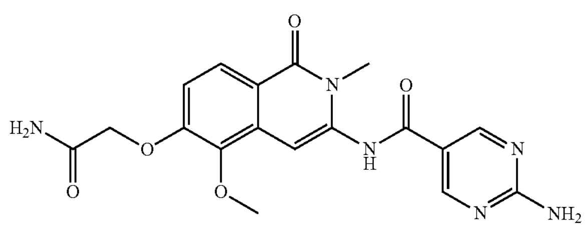 | 399.1 [M + H]$^+$ |
| 8a'-3 | 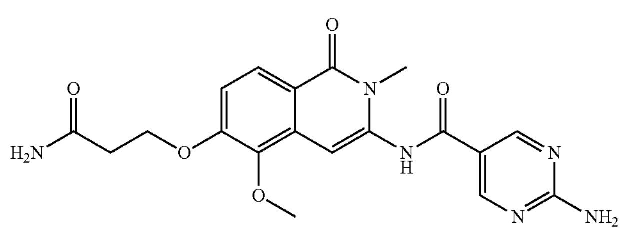 [SMILES: COc1c(OCCC(N)=O)ccc2c(=O)n(C)c(NC(=O)c3cnc(N)nc3)cc12] | 413.1 [M + H]$^+$ |
| 8a'-4 | 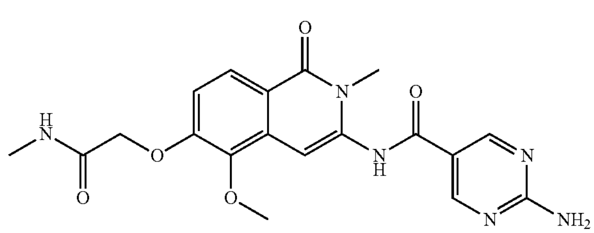 [SMILES: CNC(=O)COc1ccc2c(=O)n(C)c(NC(=O)c3cnc(N)nc3)cc2c1OC] | 413.1 [M + H]$^+$ |

TABLE 13-continued

| Compd. | Structure | MS |
|---|---|---|
| 8a'-5 | 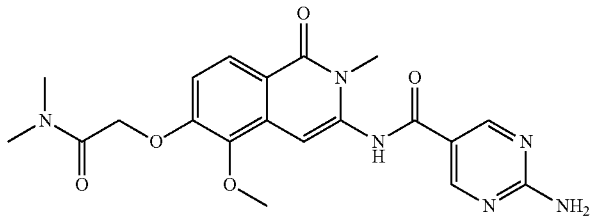 | 427.2 [M + H]+ |
| 8a'-6 | 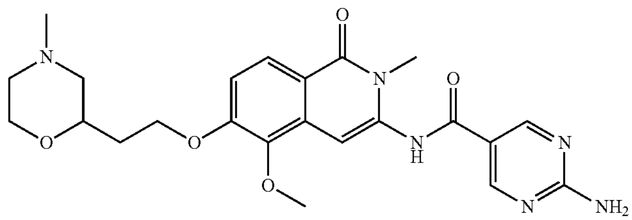 [SMILES: COc1c(OCCC2CN(C)CCO2)ccc2c(=O)n(C)c(NC(=O)c3cnc(N)nc3)cc12] | 469.2 [M + H]+ |
| 8a'-7 | 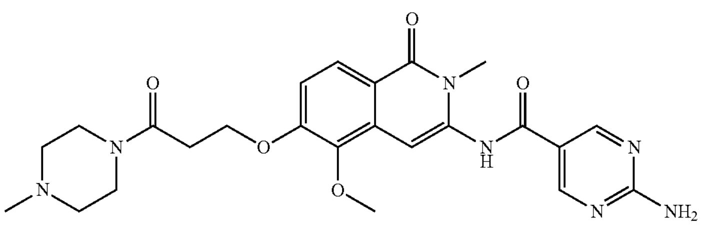 [SMILES: COc1c(OCCC(=O)N2CCN(C)CC2)ccc2c(=O)n(C)c(NC(=O)c3cnc(N)nc3)cc12] | 496.2 [M + H]+ |
| 8a'-8 | 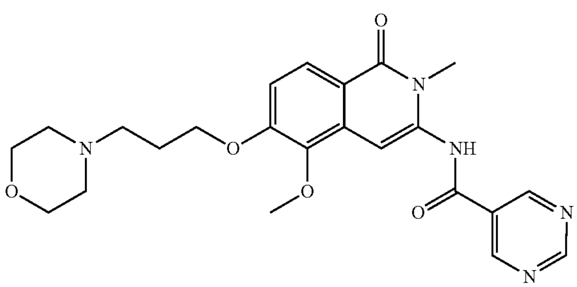 [SMILES: COc1c(OCCCN2CCOCC2)ccc2c(=O)n(C)c(NC(=O)c3cncnc3)cc12] | 454.2 [M + H]+ |
| 8a'-9 | 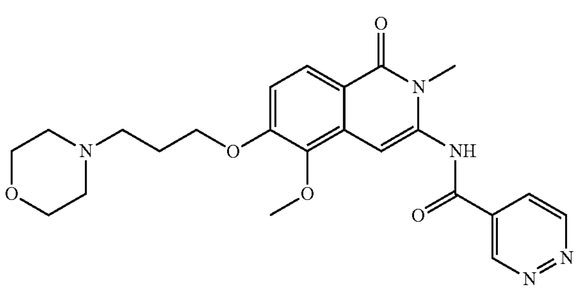 [SMILES: COc1c(OCCCN2CCOCC2)ccc2c(=O)n(C)c(NC(=O)c3ccnnc3)cc12] | 454.2 [M + H]+ |
| 8a'-10 | 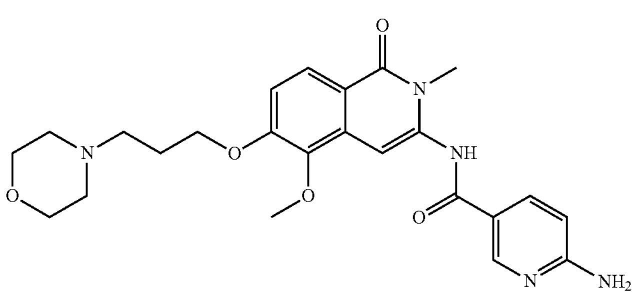 | 468.2 [M + H]+ |

TABLE 13-continued

| Compd. | Structure | MS |
|---|---|---|
| 8a'-11 | 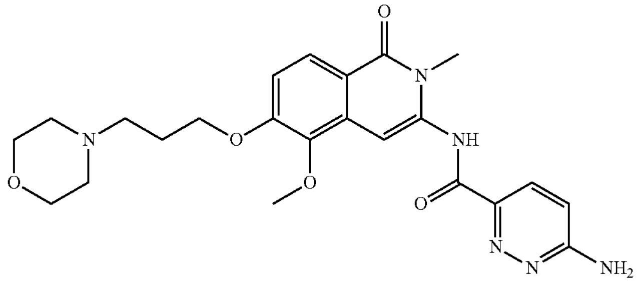 | 469.2 [M + H]+ |
| 8a'-12 | 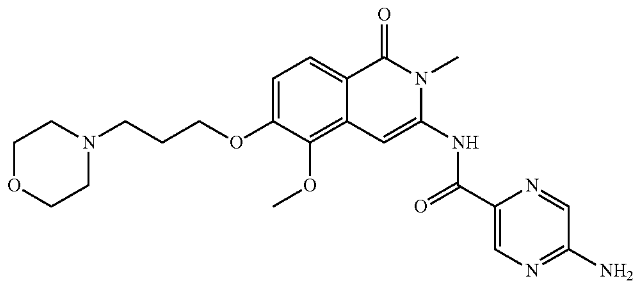 | 469. [M + H]+ |
| 8a'-13 | 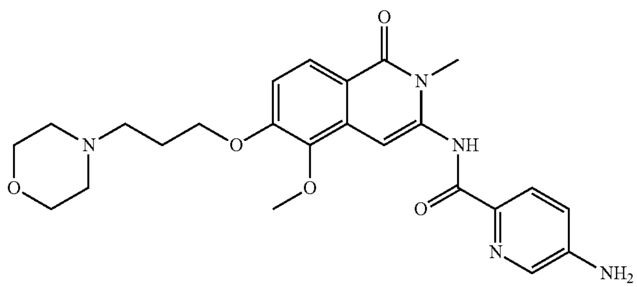 | 468.2 [M + H]+ |

Example 27: Synthesis of the Compounds 8a'-14 to 8a'-19 PREPARATION OF (S)-2-amino-N-(6-(2-hydroxy-3-morpholino-propoxy)-5-methoxy-2-methyl-1-oxo-1,2-dihydroisoquinolin-3-yl) pyrimidine-5-carboxamide (compound 8a'-14)

According to the preparation method of the compound 8a'-1, (S)-1-chloro-3-morpholinopropane-2-ol were used to instead of N-chloropropylmorpholine to prepare the target product. ESI-MS: 485.2 [M+H]+.

(R)-2-amino-N-(6-(2-hydroxy-3-morpholino-propoxy)-5-methoxy-2-methyl-1-oxo-1,2-dihydroisoquinolin-3-yl) pyrimidine-5-carboxamide (compound 8a'-15)

According to the preparation method of the compound 8a'-1, (R)-1-chloro-3-morpholinopropane-2-ol were used to instead of N-chloropropylmorpholine to prepare the target product. ESI-MS: 485.2 [M+H]+.

Preparation of N-(6-(2-(2-oxa-7-azaspiro [3.5] nonane-7-yl)ethoxy)-5-methoxy-2-methyl-1-oxo-1,2-dihydroisoq uinolin-3-yl-2-aminopyrimidine-5-carboxamide (compound 8a'-16)

According to the preparation method of the compound 8a'-1, N-chloropropylmorpholine was replaced to 7-(2-chloroethyl)-2-oxa-7-azaspiro[3.5]nonane to prepare the target product. ESI-MS: 495.2 [M+H]+.

Preparation of 2-amino-N-(8-methoxy-3-methyl-4-oxo-7-(2-oxo-2-((2-(piperidin-1-yl)ethyl)amino) ethoxy)-3,4 -dihydroquinazolin-2-yl) pyrimidine-5-carboxamide (compound 8a'-17)

According to the preparation method of the compound 8a'-1, N-chloropropylmorpholine was replaced to 2-chloro-N-(2-(piperidin-1-yl)ethyl)acetamide to prepare the target product. ESI-MS: 511.2 [M+H]+.

Preparation of 2-amino-N-(5-methoxy-2-methyl-6-(2-((2-morpholinoethyl)amino)-2-oxoethoxy)-1-oxo-1,2,2-d ihydroisoquinolin-3-yl) pyrimidine-5-carboxamide (compound 8a'-18)

According to the preparation method of the compound 8a'-1, N-chloropropylmorpholine was replaced to 2-chloro-N-(2-morpholinoethyl)acetamide to prepare the target product. ESI-MS: 511.2 [M+H]+. ESI-MS: 512.2 [M+H]+.

Preparation of 2-amino-N-(5-methoxy-2-methyl-6-(2-(methylsulfonamido)ethoxy)-1-oxo-1,2-dihydroisoquinolin-3-yl) pyrimidine-5-carboxamide (compound 8a'-19)

According to the preparation method of the compound 8a'-1, N-chloropropylmorpholine was replaced to N-(2-chloroethyl) methanesulfonamide to prepare the target product. ESI-MS: 463.1 [M+H]⁺.

Example 28: Preparation of 2-amino-N-(2-methyl-5-methoxy-6-(3-morpholino)-1-oxo-1,2-dihydroisoquinolin-3-yl) pyrimidine-5-carboxamide (compound 8b'-1)

The procedure is the same as the synthesis of compound 8a'-1. 3-amino-6-(benzyloxy)-5-methoxy-2-ethylisoquinolin-1-(2H)-one (5b'-1) was used to instead of 3-amino-6-(benzyloxy)-5-methoxy-2-methylisoquinoline-1-(2H)-one (5a'-1) to firstly conden with 2-amino-pyrimidine-5-formic acid to obtain 2-amino-N-(2-ethyl-6-benzyloxy-5-methoxy-1-oxo-1,2-dihydroisoquinolin-3-yl) pyrimidine-5-carboxamide (6b'-1), then deprotected by Pd/C-H₂ to obtain 2-amino-N-(2-ethyl-6-hydroxy-5-methoxy-1-oxo-1,2-dihydroisoquinolin-3-yl) pyrimidine-5-carboxamide (7b'-1), and finally condensed with (N-chloropropyl)-morpholine to obtain the white solid 8b'-1. ESI-MS: 483.2[M+H]⁺.

Example 29: Synthesis of the Compounds 8b'-2 to 8b'-7

The compound 2-amino-N-(2-ethyl-6-hydroxy-5-methoxy--oxo-1,2-dihydroisoquinolin-3-yl) pyrimidine-5-carboxamide 7b'-1 was used as a raw material. And chloroacetamide, chloropropionamide, N-methylchloroacetamide, N,N-dim ethylchloroacetamide, 2-(2-chloroethyl)-4-methylmorpholine, 1-(3-chloro-propionyl)-4-methylpiperazine, chloroacetyl-morpholine, or 4-chlorobutanamide were used respectively to instead of N-(3-chloropropyl) morpholine to prepare the compounds 8b'-2 to 8b'-9.

In addition, the 5b'-1 was used as a raw material. And pyrimidine-5-carboxylic acid, pyridazine-4-carboxylic acid, 2-amino-pyridine-5-carboxylic acid, 6-amino-pyridazine-3-carboxylic acid, 2-amino-pyrazine-5-carboxylic acid, or 5-aminopyridine-2-carboxylic acid were used respectively to instead of 2-amino-pyrimidine-5carboxylic acid for condensation reaction to obtain 6'b-2 to 6'b-7, which were further deprotected by Pd/C-H₂ to obtain 7'b-2 to 7'b-7, and finally reacted with N-chloropropylmorpholine to synthesize 8b'-8 to 8b'-12. The structural formulas of which are shown in Table 14 below.

TABLE 14

| Compd. | Structure | MS |
| --- | --- | --- |
| 7b'-1 | 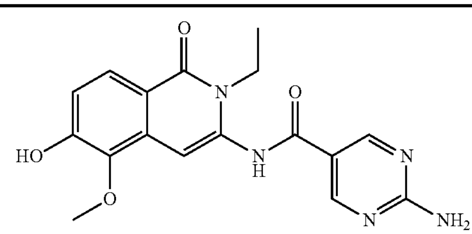 | 356.2 [M + H]⁺ |
| 8b'-1 | 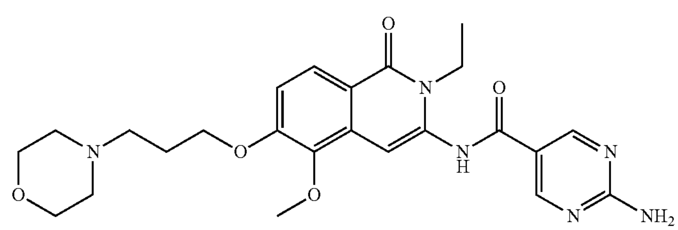 [SMILES: CCn1c(NC(=O)c2cnc(N)nc2)cc2c(OC)c(OCCCN3CCOCC3)ccc2c1=O] | 483.2 [M + H]⁺ |
| 8b'-2 | 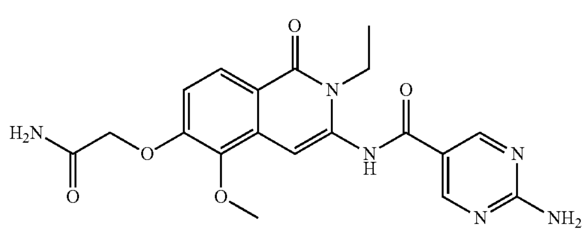 | 413.1 [M + H]⁺ |
| 8b'-3 | 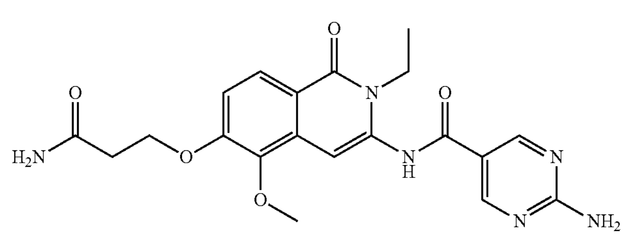 | 427.2 [M + H]⁺ |

TABLE 14-continued

| Compd. | Structure | MS |
| --- | --- | --- |
| 8b'-4 | 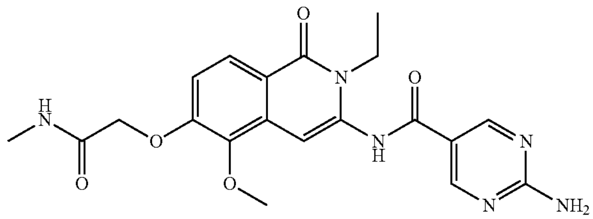 [SMILES: CCn1c(NC(=O)c2cnc(N)nc2)cc2c(OC)c(OCC(=O)NC)ccc2c1=O] | 427.2 [M + H]+ |
| 8b'-5 | 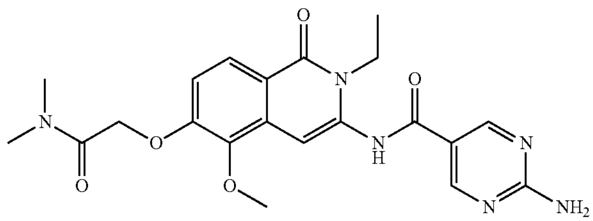 [SMILES: CCn1c(NC(=O)c2cnc(N)nc2)cc2c(OC)c(OCC(=O)N(C)C)ccc2c1=O] | 441.2 [M + H]+ |
| 8b'-6 | 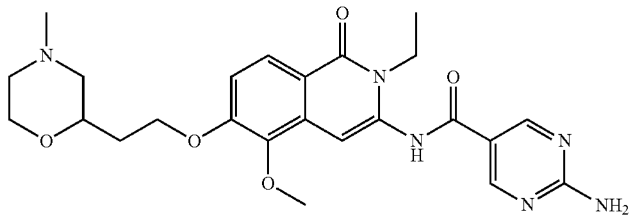 [SMILES: CCn1c(NC(=O)c2cnc(N)nc2)cc2c(OC)c(OCCC3CN(C)CCO3)ccc2c1=O] | 483.2 [M + H]+ |
| 8b'-7 | 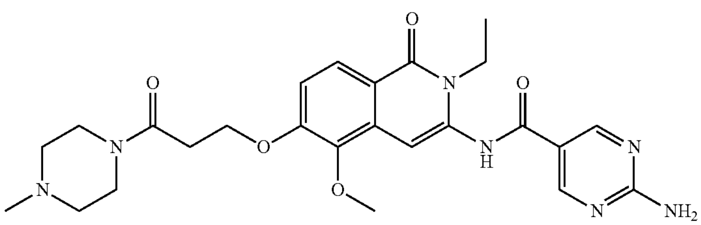 [SMILES: CCn1c(NC(=O)c2cnc(N)nc2)cc2c(OC)c(OCCC(=O)N3CCN(C)CC3)ccc2c1=O] | 510.2 [M + H]+ |
| 8b'-8 | 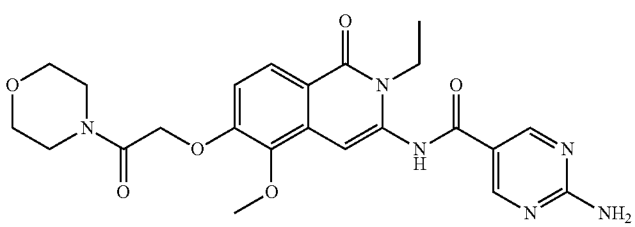 [SMILES: CCn1c(NC(=O)c2cnc(N)nc2)cc2c(OC)c(OCC(=O)N3CCOCC3)ccc2c1=O] | 483.2 [M + H]+ |
| 8b'-9 | 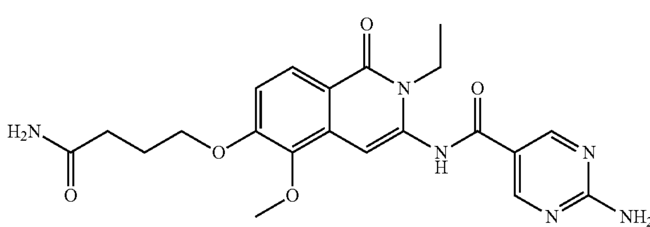 [SMILES: CCn1c(NC(=O)c2cnc(N)nc2)cc2c(OC)c(OCCCC(N)=O)ccc2c1=O] | 441.2 [M + H]+ |

TABLE 14-continued

| Compd. | Structure | MS |
|---|---|---|
| 8b'-10 | 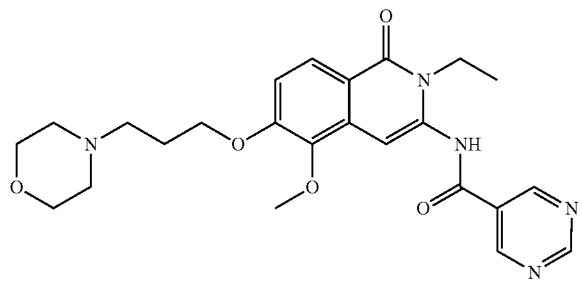 [SMILES: CCn1c(NC(=O)c2cncnc2)cc2c(OC)c(OCCCN3CCOCC3)ccc2c1=O] | 468.2 [M + H]+ |
| 8b'-11 | 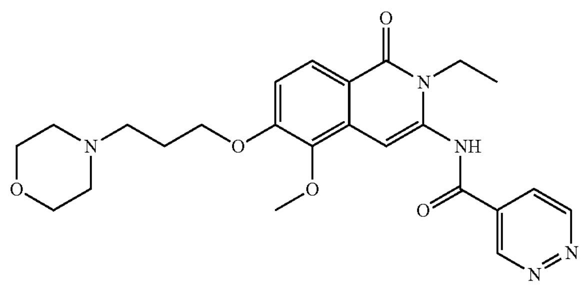 [SMILES: CCn1c(NC(=O)c2ccnnc2)cc2c(OC)c(OCCCN3CCOCC3)ccc2c1=O] | 468.2 [M + H]+ |
| 8b'-12 | 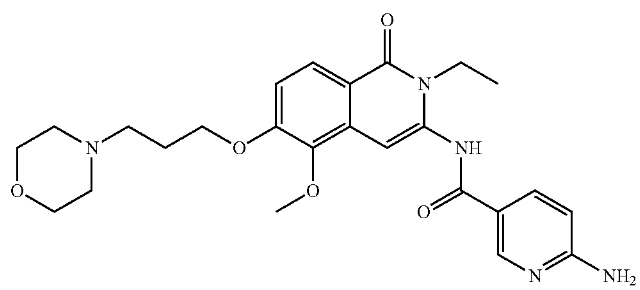 [SMILES: CCn1c(NC(=O)c2ccc(N)nc2)cc2c(OC)c(OCCCN3CCOCC3)ccc2c1=O] | 482.2 [M + H]+ |
| 8b'-13 | 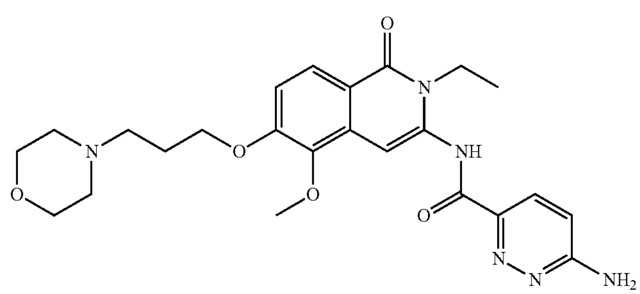 [SMILES: CCn1c(NC(=O)c2ccc(N)nn2)cc2c(OC)c(OCCCN3CCOCC3)ccc2c1=O] | 483.2 [M + H]+ |
| 8b'-14 | 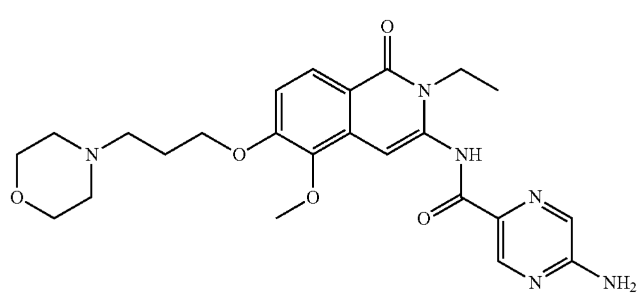 [SMILES: CCn1c(NC(=O)c2cnc(N)cn2)cc2c(OC)c(OCCCN3CCOCC3)ccc2c1=O] | 483.2 [M + H]+ |

TABLE 14-continued

| Compd. | Structure | MS |
|---|---|---|
| 8b'-15 | 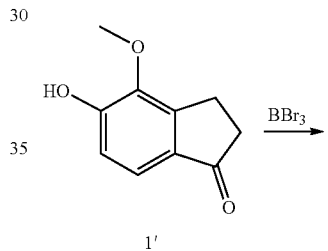 | 482.2 [M + H]+ |

Example 30: Synthesis of the Compounds 8b'-16 to 8b'-21

Preparation of (S)-2-amino-N-(6-(2-hydroxy-3-morpholinopropoxy)-5-methoxy-2-methyl-1-oxo-1,2-dihydrois oquinolin-3-yl) pyrimidine-5-carboxamide (compound 8b'-16)

According to the preparation method of the compound 8b'-1, (S)-1-chloro-3-morpholinopropane-2-ol were used to instead of N-chloropropylmorpholine to prepare the target product. ESI-MS: 485.2 [M+H]+.

Preparation of (R)-2-amino-N-(6-(2-hydroxy-3-morpholinopropoxy)-5-methoxy-2-methyl-1-oxo-1,2-dihydroi soquinolin-3-yl) pyrimidine-5-carboxamide (compound 8b'-17)

According to the preparation method of the compound 8b'-1, (R)-1-chloro-3-morpholinopropane-2-ol were used to instead of N-chloropropylmorpholine to prepare the target product. ESI-MS: 485.2 [M+H]+.

Preparation of N-(6-(2-(2-oxa-7-azaspiro [3.5] nonane-7-yl)ethoxy)-5-methoxy-2-methyl-1-oxo-1, 2-dihydroisoq uinolin-3-yl-2-aminopyrimidine-5-carboxamide (compound 8b'-18)

According to the preparation method of the compound 8b'-1, N-chloropropylmorpholine was replaced to 7-(2-chloroethyl)-2-oxa-7-azaspiro[3.5]nonane to prepare the target product. ESI-MS: 495.2 [M+H]+.

Preparation of 2-amino-N-(8-methoxy-3-methyl-4-oxo-7-(2-oxo-2-((2-(piperidin-1-yl)ethyl)amino) ethoxy)-3,4 -dihydroquinazolin-2-yl) pyrimidine-5-carboxamide (compound 8b'-19)

According to the preparation method of the compound 8b'-1, N-chloropropylmorpholine was replaced to 2-chloro-N-(2-(piperidin-1-yl)ethyl)acetamide to prepare the target product. ESI-MS: 511.2 [M+H]+.

Preparation of 2-amino-N-(5-methoxy-2-methyl-6-(2-((2-morpholinoethyl)amino)-2-oxoethoxy)-1-oxo-1,2,2-d ihydroisoquinolin-3-yl) pyrimidine-5-carboxamide (compound 8b'-20)

According to the preparation method of the compound 8b'-1, N-chloropropylmorpholine was replaced to 2-chloro-N-(2-morpholinoethyl)acetamide to prepare the target product. ESI-MS: 512.2 [M+H]+.

Preparation of 2-amino-N-(5-methoxy-2-methyl-6-(2-(methylsulfonamido)ethoxy)-1-oxo-1,2-dihydroisoquino lin-3-yl) pyrimidine-5-carboxamide (compound 8b'-21)

According to the preparation method of the compound 8b'-1, N-chloropropylmorpholine was replaced to N-(2-chloroethyl) methanesulfonamide to prepare the target product. ESI-MS: 463.1 [M+H]+.

Example 31: Preparation of the Compound 14'a-2

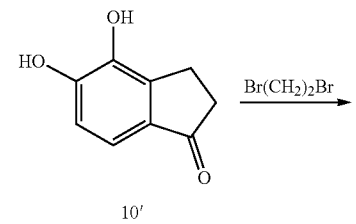

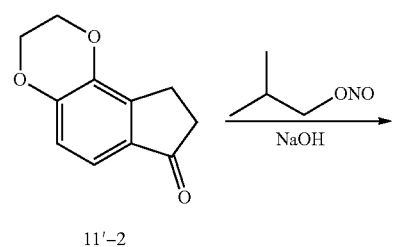

-continued

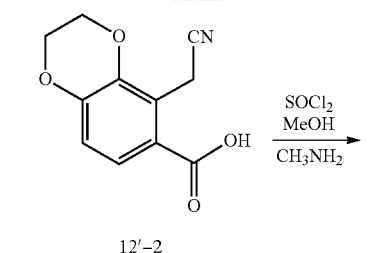

12'-2

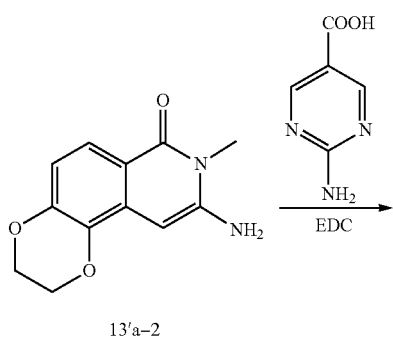

13'a-2

-continued

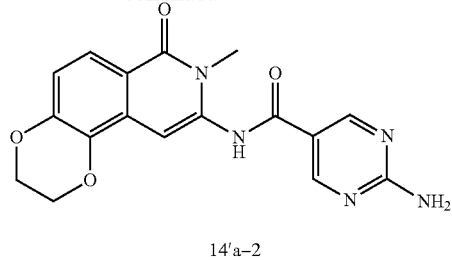

14'a-2

The compound 1' was demethylated by BBr$_3$ to obtain o-diphenol 10', which was condensed with dibromoethane to obtain the compound 11'-2, and then hydrolyzed with isobutyl nitrite and sodium hydroxide to obtain compound 12'-2, then chlorinated with thionyl chloride and condensed with an alkylamino to obtain 13'a-2, and finally condensed with an aromatic carboxyl to obtain the target molecule 14'a-2.

The target molecules 14a'-1 and 14a'-3 to 14a'-8 could be synthesized by changing the length of the ether bond in a similar way.

The structural formulas of the series of molecules are shown in Table 15 below.

TABLE 15

| Compd. | Structure | MS |
|---|---|---|
| 14a'-1 | 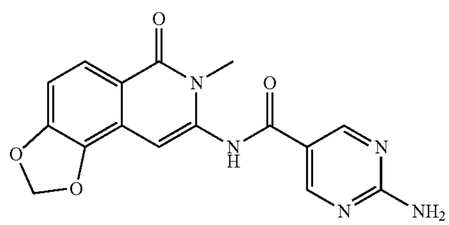 [SMILES: Cn1c(NC(=O)c2cnc(N)nc2)cc2c3c(ccc2c1=O)OCO3] | 340.1 [M + H]$^+$ |
| 14a'-2 | 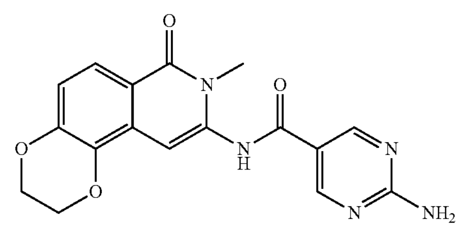 [SMILES: Cn1c(NC(=O)c2cnc(N)nc2)cc2c3c(ccc2c1=O)OCCO3] | 354.1 [M + H]$^+$ |
| 14a'-3 | 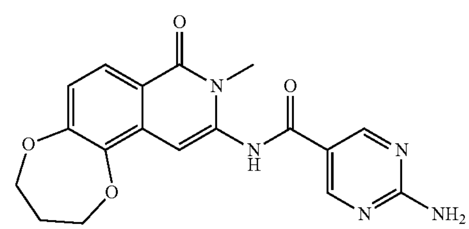 [SMILES: Cn1c(NC(=O)c2cnc(N)nc2)cc2c3c(ccc2c1=O)OCCCO3] | 368.1 [M + H]$^+$ |
| 14a'-4 | 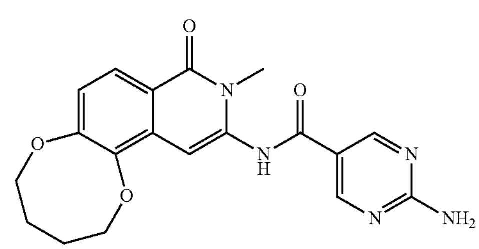 [SMILES: Cn1c(NC(=O)c2cnc(N)nc2)cc2c3c(ccc2c1=O)OCCCCO3] | 382.2 [M + H]$^+$ |

TABLE 15-continued

| Compd. | Structure | MS |
|---|---|---|
| 14a'-5 | 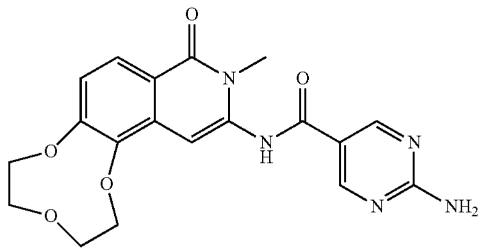 [SMILES: Cn1c(NC(=O)c2cnc(N)nc2)cc2c3c(ccc2c1=O)OCCOCCO3] | 398.2 [M + H]+ |
| 14a'-6 | 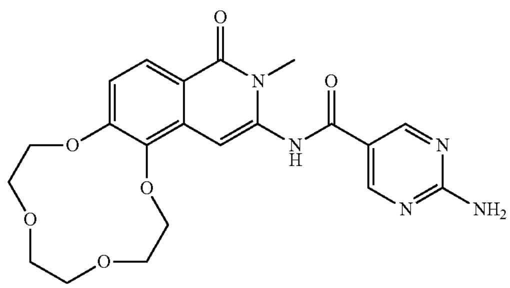 | 442.2 [M + H]+ |
| 14a'-7 | 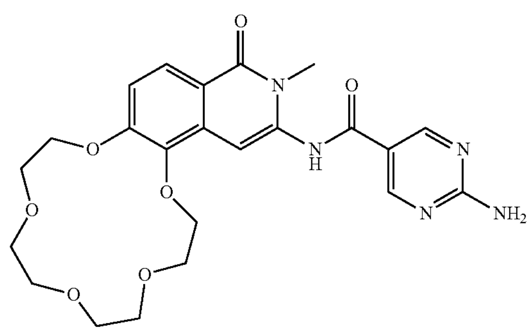 | 486.2 [M + H]+ |
| 14a'-8 | 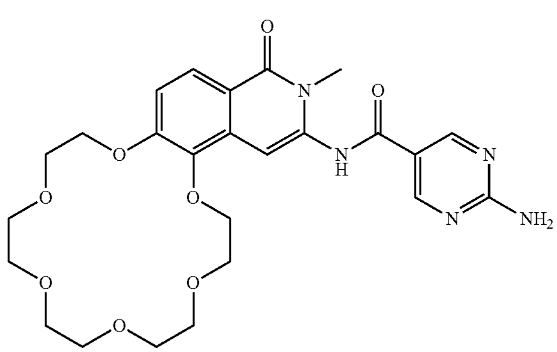 [SMILES: Cn1c(NC(=O)c2cnc(N)nc2)cc2c3c(ccc2c1=O)OCCOCCOCCOCCOCCO3] | 530.2 [M + H]+ |

Example 32: Synthesis of the Compounds 14b'-3~14b'-8

The procedure is the same as the synthesis of compound 14a'-2, and the compounds 14b'-1 to 14b'-8 were prepared. The structural formulas of which are shown in Table 16 below.

TABLE 16

| Compd. | Structure | MS |
|---|---|---|
| 14b'-1 | 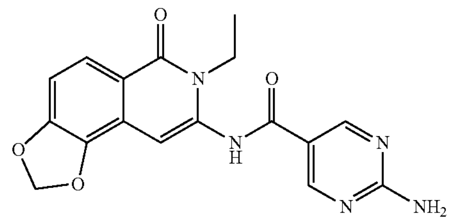 [SMILES: CCn1c(NC(=O)c2cnc(N)nc2)cc2c3c(ccc2c1=O)OCO3] | 354.1 [M + H]+ |
| 14b'-2 | 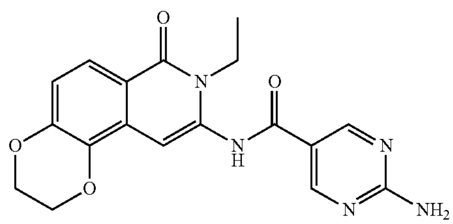 [SMILES: CCn1c(NC(=O)c2cnc(N)nc2)cc2c3c(ccc2c1=O)OCCO3] | 368.1 [M + H]+ |
| 14b'-3 | 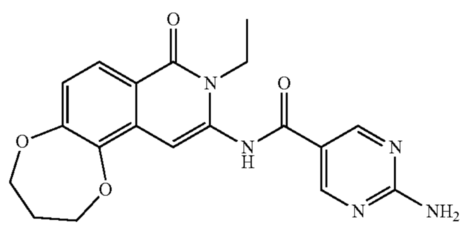 [SMILES: CCn1c(NC(=O)c2cnc(N)nc2)cc2c3c(ccc2c1=O)OCCCO3] | 382.1 [M + H]+ |
| 14b'-4 | 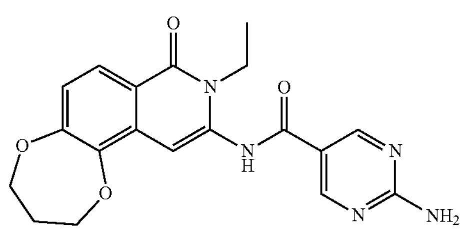 | 396.2 [M + H]+ |
| 14b'-5 | 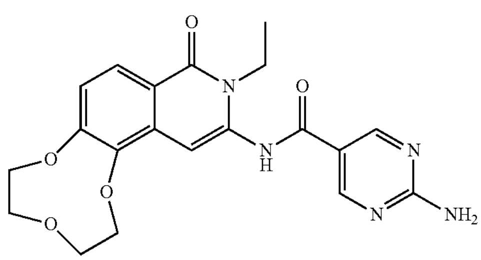 [SMILES: CCn1c(NC(=O)c2cnc(N)nc2)cc2c3c(ccc2c1=O)OCCOCCO3] | 412.2 [M + H]+ |

TABLE 16-continued

| Compd. | Structure | MS |
|---|---|---|
| 14b'-6 | 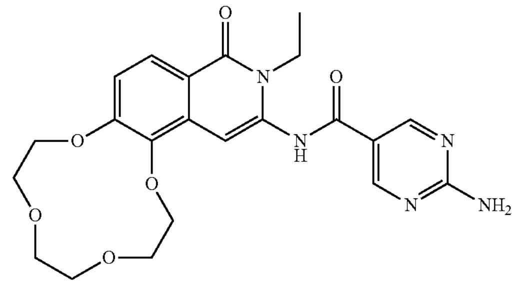 | 456.2 [M + H]+ |
| 14b'-7 | 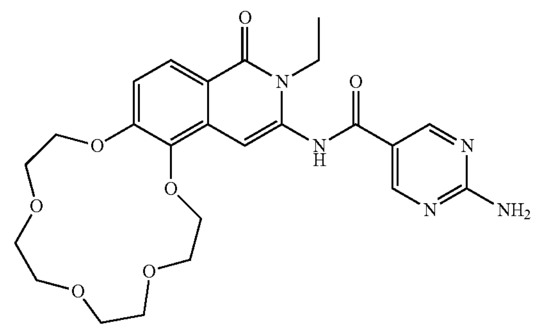 [SMILES: CCn1c(NC(=O)c2cnc(N)nc2)cc2c3c(ccc2c1=O)OCCOCCOCCOCCO3] | 500.2 [M + H]+ |
| 14b'-8 | 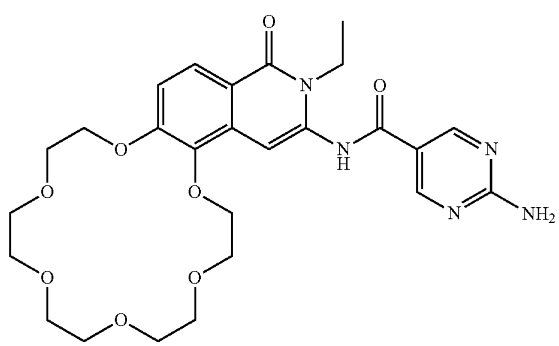 [SMILES: CCn1c(NC(=O)c2cnc(N)nc2)cc2c3c(ccc2c1=O)OCCOCCOCCOCCOCCO3] | 544.2 [M + H]+ |

Example 33: Inhibitory Effects of the Aminoquinazolinone and Aminoisoquinolinone Derivatives on PI3K Activity in Vitro 1. Experimental Methods Instrument: ELISA Reader Envision™ (PerkinElmer, USA)

Materials: Human recombinant PI3K and PI3Kδ proteins, purchased from Carna Bioscience; ADP-GLO kit, purchased from Promega.

Sample processing: The sample was dissolved in DMSO, stored at low temperature, and diluted gradually, and the concentration of DMSO in the final system was controlled within the range that does not affect the activity detection. The positive compounds used in the experiment were Copanlisib and Alpelisib.

Take the PI3Kα Molecular Activity Test as an Example to Describe the Text Method of the PI3K Subtypes PI3K-α recombinant protein and substrate ATP were diluted with kinase reaction buffer (50 mM Tris-HCl, pH 7.4, 2.1 mM DTT, 0.05% Tween-20, 10 mM $MgCl_2$). 1 μL of the compound with gradient concentration was added into the 384 reaction plate (ProxiPlate™-384 Plus, PerkinElmer). The specific reaction system was 2% of DMSO, 0.8 ng/μL PI3K-α, and 100 μM ATP, the positive compound control groups and control wells were set, and there were 3 multiple-wells for each concentration of each sample. After incubating for 2 hours at room temperature, ADP-GLO Reagent and Kinase Detection Reagent were added respectively, and then Envision™ was used to detect the fluorescence readings. The activity rate of the samples were calculated by the sample readings, and the calculation formula was: activity rate=$(OD_{compound}-OD_{control})/(OD_{DMSO}-OD_{contro})\times 100\%$. The activity rate was nonlinearly fitted to the sample concentrations to obtain IC50, the software used for calculation was Graphpad Prism 5, the model used for fitting was sigmoidal dose-response (varible slope), and the bottom and top of the fitting curve were set to 0 and 100, respectively.

2. Experimental Results: See Table 17 for Specific Results

TABLE 17

The inhibitory effects of some the compounds on PI3Kα/PI3Kδ activity

| No. | PI3Kα IC$_{50}$ (nM) | PI3Kδ IC$_{50}$ (nM) | Selectivity (PI3Kδ IC$_{50}$/PI3KαIC$_{50}$) |
|---|---|---|---|
| Copanlisib | ++++ | ++++ | I |
| Alpelisib | ++++ | +++ | III |
| 7a | ++++ | +++ | III |
| 7b | ++++ | +++ | II |
| 7e | +++ | +++ | I |
| 7f | +++ | +++ | I |
| 8a-1 | ++++ | ++++ | II |
| 8a-2 | ++++ | ++++ | III |
| 8a-3 | ++++ | +++ | III |
| 8a-4 | ++++ | +++ | II |
| 8a-5 | ++++ | +++ | II |
| 8a-8 | ++++ | +++ | II |
| 8a-9 | ++++ | +++ | III |
| 8a-14 | ++++ | +++ | II |
| 8a-15 | ++++ | +++ | II |
| 8a-16 | ++++ | +++ | II |
| 8a-27 | ++++ | +++ | II |
| 8a-28 | ++++ | +++ | II |
| 8a-29 | ++++ | ++ | III |
| 8a-30 | ++++ | +++ | II |
| 8a-38 | ++++ | +++ | II |
| 8a-39 | ++++ | +++ | II |
| 8a-40 | ++++ | +++ | II |
| 8b-2 | ++++ | +++ | III |
| 8b-3 | ++++ | +++ | III |
| 8b-9 | ++++ | +++ | III |
| 8b-11 | ++++ | ++++ | II |
| 8b-14 | +++ | ++++ | II |
| 8b-27 | ++++ | ++ | II |
| 8b-28 | ++++ | ++ | II |
| 8b-29 | ++++ | ++ | III |
| 8b-30 | ++++ | ++ | II |
| 8b-46 | ++++ | ++ | II |
| 8b-47 | ++++ | ++ | II |
| 8b-48 | ++++ | ++ | II |
| 8c-2 | +++ | +++ | I |
| 8c-3 | +++ | +++ | I |
| 8d-2 | +++ | +++ | I |
| 8e-3 | +++ | +++ | I |
| 14a-4 | ++++ | ++++ | I |
| 14a-5 | ++++ | +++ | II |
| 14a-6 | ++++ | +++ | II |
| 14a-7 | ++++ | +++ | II |
| 14a-8 | ++++ | ++++ | I |
| 14b-4 | +++ | +++ | I |
| 14b-8 | ++++ | ++++ | I |
| 14b-11 | +++ | +++ | I |
| 8a'-3 | ++++ | +++ | III |
| 8a'-8 | ++++ | +++ | III |
| 8a'-9 | ++++ | +++ | III |
| 8b'-1 | ++++ | ++++ | I |
| 8b'-2 | ++++ | +++ | III |
| 8b'-3 | ++++ | +++ | III |
| 14a'-2 | ++++ | +++ | II |
| 14a'-4 | ++++ | +++ | II |
| 14a'-5 | ++++ | +++ | II |
| 14a'-6 | ++++ | +++ | II |
| 14a'-7 | ++++ | +++ | II |

TABLE 17-continued

The inhibitory effects of some the compounds on PI3Kα/PI3Kδ activity

| No. | PI3Kα IC$_{50}$ (nM) | PI3Kδ IC$_{50}$ (nM) | Selectivity (PI3Kδ IC$_{50}$/PI3KαIC$_{50}$) |
|---|---|---|---|
| 14b'-2 | ++++ | ++++ | I |
| 14b'-4 | +++ | +++ | I |
| 14b'-6 | ++++ | ++++ | I |

"++++" represents <20 nM; "+++" represents 20-200 nM; ""++" represents 200-1000 nM; "+" represents >1000 nM; and "—"represents untested.
The selectivity of PI3Kα was calculated by PI3Kδ IC$_{50}$/PI3Kα IC$_{50}$, wherein "I" represents <5 times, "II" represents 5-10 times, and "III" represents >10 times.

Example 34: Inhibitory Activity of the Aminoquinazolinone and Aminoisoquinolinone Derivatives on Tumor Cell Proliferation 1. Experimental Methods and Results The CCK8 method was used, and copanlisib and alpelisib were used as positive controls, so as to test the inhibitory effects of the different compounds on the proliferation of the four tumor lines. The IC$_{50}$ value was calculated using Graphpad Prism V5.0 software. The results were shown in Table 18 below.

TABLE 18

The inhibitory effects of some the compounds on the proliferation of different tumor cells

| No. | MCF7 (PIK3CA mut) | KPL4 (PIK3CA mut) | SW48 (PIK3CA mut) | ZR-75-1 (PTEN loss) |
|---|---|---|---|---|
| Copanlisib | ++++ | ++++ | ++++ | ++++ |
| Alpelisib | ++++ | +++ | +++ | +++ |
| 7b | ++++ | +++ | ++++ | +++ |
| 8a-1 | ++++ | ++++ | ++++ | ++++ |
| 8a-2 | ++++ | ++++ | ++++ | ++++ |
| 8a-3 | ++++ | ++++ | ++++ | ++++ |
| 8a-27 | ++++ | +++ | +++ | ++ |
| 8a-28 | ++++ | +++ | +++ | ++ |
| 8a-29 | ++++ | +++ | +++ | ++ |
| 8a-30 | ++++ | +++ | +++ | ++ |
| 8a-38 | ++++ | +++ | +++ | ++ |
| 8a-39 | ++++ | +++ | +++ | ++ |
| 8a-40 | ++++ | +++ | +++ | ++ |
| 8b-1 | ++++ | ++++ | ++++ | ++++ |
| 8b-2 | ++++ | +++ | +++ | +++ |
| 8b-11 | ++++ | ++++ | +++ | +++ |
| 8b-27 | ++++ | +++ | +++ | ++ |
| 8b-28 | ++++ | +++ | +++ | ++ |
| 8b-29 | ++++ | +++ | +++ | ++ |
| 8b-30 | ++++ | +++ | +++ | ++ |
| 8b-46 | ++++ | +++ | +++ | ++ |
| 8b-47 | ++++ | +++ | +++ | ++ |
| 8b-48 | ++++ | +++ | +++ | ++ |
| 8e-2 | +++ | ++ | +++ | ++ |
| 8f-1 | ++++ | +++ | +++ | ++ |
| 8g-1 | ++++ | +++ | +++ | ++ |
| 14a-4 | +++ | ++ | ++ | ++ |
| 14a-5 | +++ | ++ | ++ | ++ |
| 14a-6 | +++ | ++ | ++ | ++ |
| 14a-7 | +++ | ++ | ++ | ++ |
| 14a-8 | ++++ | +++ | +++ | +++ |
| 14b-4 | ++++ | +++ | ++ | ++ |
| 14b-8 | ++++ | +++ | ++ | ++ |
| 14b-11 | ++++ | +++ | ++ | ++ |

TABLE 18-continued

The inhibitory effects of some the compounds
on the proliferation of different tumor cells

| No. | MCF7 (PIK3CA mut) | KPL4 (PIK3CA mut) | SW48 (PIK3CA mut) | ZR-75-1 (PTEN loss) |
|---|---|---|---|---|
| 8b'-1 | ++++ | +++ | +++ | +++ |
| 8b'-2 | ++++ | +++ | +++ | +++ |
| 14b'-6 | ++++ | +++ | +++ | +++ |

"++++" represents <20 nM; "+++" represents 20-200 nM; "++" represents 200-1000 nM; and "+" represents >1000 nM.

Example 35 Pharmacokinetic Determination of the Representative Molecules In Vivo:

Healthy SD rats weighing 200±20 g, male, were randomly divided into groups with 6 rats in each group, and were administered by tail vein injection at a dose of 1 mg/kg. The blood sampling time points for pharmacokinetic analysis: 5 min, 15 min, 30 min, 2 h, 4 h, 6 h, 8 h, 24 h, and 48 h after administration. About 0.3 mL of whole blood was collected via the orbit and placed in a heparinized test tube, centrifugalized at 6000 rpm for 10 min to separate the plasma, and store at −80° C. for testing. The plasma concentrations of the each compounds were detected with an Agilent liquid mass spectrometry (LC-MS/MS, Agilent Jet Stream Electrometric spray ion), and the relevant pharmacokinetic parameters were calculated using the WinNonLin 7.0 pharmacokinetic software non-compartment model method. The results were shown in Table 19 below.

TABLE 19

The pharmacokinetic results of the representative compounds

| Compd. | administration | $T_{1/2}$ (h) | Vd (L/kg) | CL (L/h/kg) |
|---|---|---|---|---|
| Copanlisib | intravenous | 8.9 | 33.5 | 2.2 |
| 8a-1 | intravenous | 5.3 | 4.2 | 2.0 |
| 8a-2 | intravenous | 4.9 | 3.2 | 1.8 |
| 8b-1 | intravenous | 5.2 | 3.8 | 1.9 |
| 8b-9 | intravenous | 4.2 | 3.9 | 1.6 |
| 14b-3 | intravenous | 4.7 | 2.4 | 2.3 |
| 8'a-3 | intravenous | 6.7 | 2.9 | 2.5 |
| 14'b-1 | intravenous | 4.2 | 3.9 | 3.9 |

The pharmacokinetic experiments shown that the volume of distribution of Copanlisib in rats was very large with reaching 33.5 L/kg, which was prone to drug accumulation, resulting in toxic and side effects. The representative compounds of the present disclosure had significantly reduced volume of distributions with values of Vss (L/kg) between 2.4-4.2 L/h/kg and a reduced $T_{1/2}$ of about 4 hours. Therefore, the above compounds are not easy to accumulate in rats, and are not easy to cause side effects caused by drug accumulation. Therefore, it can be concluded that compared with Copanlisib, the above compounds may show better pharmacokinetic characteristics in clinical practice, reduce the accumulation of drugs in a human body, and reduce toxic and side effects.

Example 36 Efficacy Determination of the Representative Molecules In Vivo:

Female nude mice, weighing 20±3 g, were inoculated subcutaneously with Kasumi-1 cell line in their right axilla. The cell inoculation accounted for $1 \times 10^7$/mouse. After tumor formation, the diameter of the transplanted tumor was measured with a vernier caliper. When the tumor grown to 100-300 mm$^3$, the animals were divided into a model control group and administration groups with 6 rats in each group depending on body weight and tumor volume. The model control group was given the same amount of blank solvent. After grouping, the drugs were administered daily (qd) with a doge of 10 mg/Kg for 21 consecutive days. During the experiment, the diameter of the transplanted tumor and the weight of the mice were measured twice a week. The calculation formula of the tumor volume (TV) was: TV=½× a×b$^2$, where a and b represented length and width respectively. The relative tumor volume (RTV) was calculated from the measurement results, the calculation formula was: RTV=$V_t/V_0$, where $V_0$ was the tumor volume measured as grouping and administering (i.e. $d_0$), and $V_t$ was the tumor volume at each measurement. The evaluation index of anti-tumor activity was the relative tumor proliferation rate T/C(%), and the calculation formula was as follows: T/C (%)=(TRTV/CRTV)×100%, where TRTV: RTV of the treatment group; and CRTV: RTV of the negative control group. The tumor weight inhibition rate, the calculation formula was as follows: tumor weight inhibition rate %=(Wc-WT)/ Wc×100%, where Wc: the tumor weight of the control group, WT: the tumor weight of the treatment group. The results are shown in FIG. 1. From the pharmacodynamic activity data in vivo in the figure, it can be seen that the compounds 8a-27 and 8a-28 exhibit strong tumor growth inhibitory activity, which is comparable to positive copanlisib, and therefore has good application prospects.

What is claimed is:

1. An aminoquinazolinone or aminoisoquinolinone having the following Structural General Formulas a or b, or pharmaceutically acceptable salts, stereoisomers or solvates thereof:

Structural General Formula a

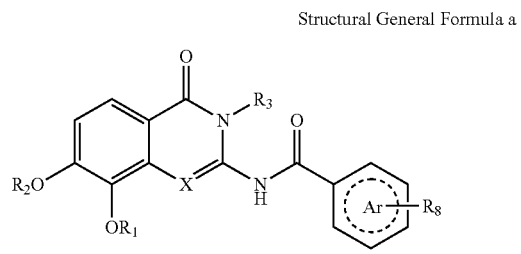

Structural General Formula b

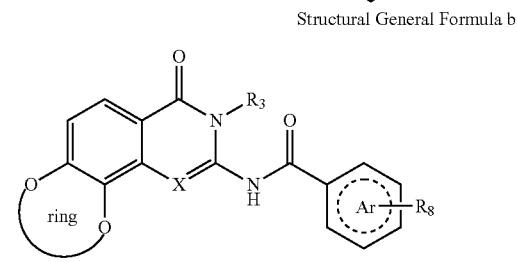

wherein (1) For Structural General Formula a:

X=N or CH;

$R_1$ is selected from hydrogen, $C_{1-6}$ alkyl, cycloalkyl, or fluoroalkyl, $R_2$ is selected from hydrogen, $C_{1-12}$ alkyl, cycloalkyl, fluoroalkyl, —(CH$_2$)$_n$NR$_5$R$_6$, —(CH$_2$)$_n$—CONR$_5$R$_6$, —(CH$_2$)$_n$—SO$_2$NR$_5$R$_6$, or —(CH$_2$)$_n$OR$_5$, wherein n is an integer selected from 1 to 8, $R_5$ and $R_6$ are independent of each other, may be the same or different, and are selected from hydrogen, $C_{1-4}$ alkyl, or $C_{1-4}$ cycloalkyl, or $NR_5R_6$ is a 4-8 membered cyclic amine, including but not limited to morpholine, piperazine, pyrrolidine, piperidine, or a cyclic amine substituted with $R_7$ which is selected from hydrogen, $C_{1-6}$ alkyl, $C_{1-6}$ alkoxy, $C_{2-6}$ unsaturated aliphatic chain hydrocarbon group, $C_{3-8}$ cycloalkyl, $C_{3-8}$ unsaturated alicyclic group, $C_{3-8}$ saturated aliphatic heterocyclic group, halogen, amino, or cyano;

$R_3$ is selected from $C_{1-6}$ alkyl, cycloalkyl, or fluoroalkyl;

Ar is an aromatic heterocyclic ring, including but not limited to benzene ring, furan ring, thiophene ring, pyrrole ring, thiazole ring, pyrazole ring, oxazole ring, pyridine ring, pyrimidine ring, pyridazine ring, pyrazine ring, purine ring, azapurine ring, azaindole ring, indole ring, quinoline ring, quinazoline ring, quinoxaline ring, or indazole ring;

$R_8$ is selected from hydrogen, halogen, cyano, hydroxyl, $C_{1-6}$ alkoxy, amino, $C_{1-6}$ alkylamino, $C_{1-6}$ dialkylamino, $C_{1-6}$ alkyl, $C_{2-6}$-unsaturated fat chain hydrocarbon group, $C_{3-8}$ cycloalkyl, $C_{3-8}$ unsaturated alicyclic group, $C_{3-8}$ saturated aliphatic heterocyclic group, or $C_{1-6}$ haloalkyl; and (2) For Structural General Formula b:

The two adjacent oxygen atoms on the benzene ring of the quinazoline or quinoline are connected by different chains to form a 5-21 membered ring, and the chain contains 2-7 oxygen atoms; the rest of the structure has the same definition as the Structural General Formula a.

2. The aminoquinazolinone or aminoisoquinolinone compound according to claim 1, characterized in that, for the Structural General Formulas a, when $R_1$ is a methyl, $R_2$ is selected from the following groups:

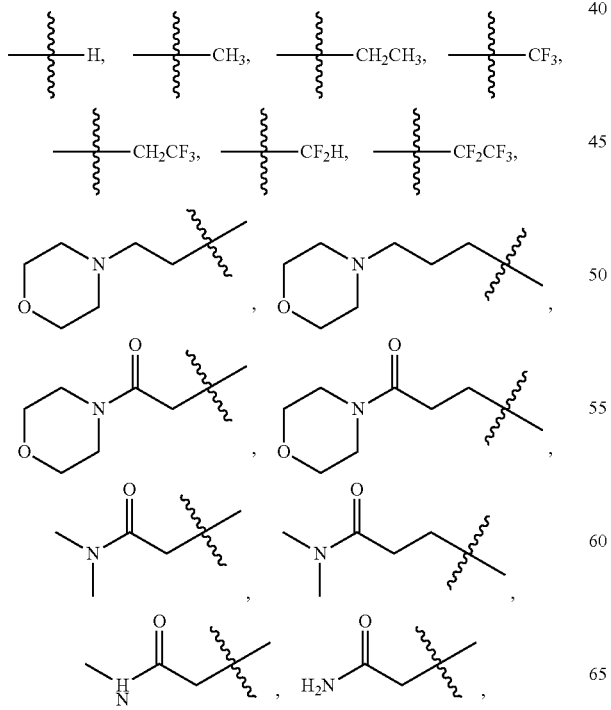

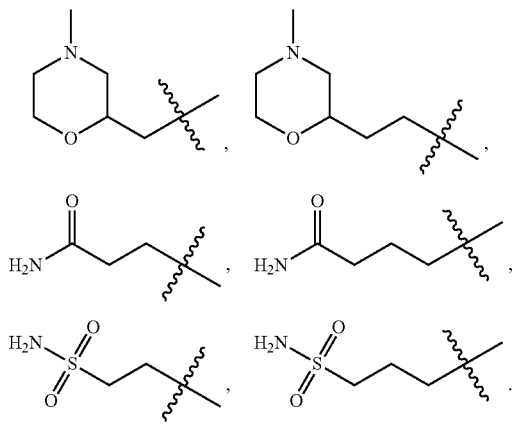

3. The aminoquinazolinone or aminoisoquinolinone compound according to claim 1, characterized in that, the 5-21 membered ring formed by connecting the two oxygen atoms on the benzene ring by chains described for the Structural General Formula b is selected from the following groups:

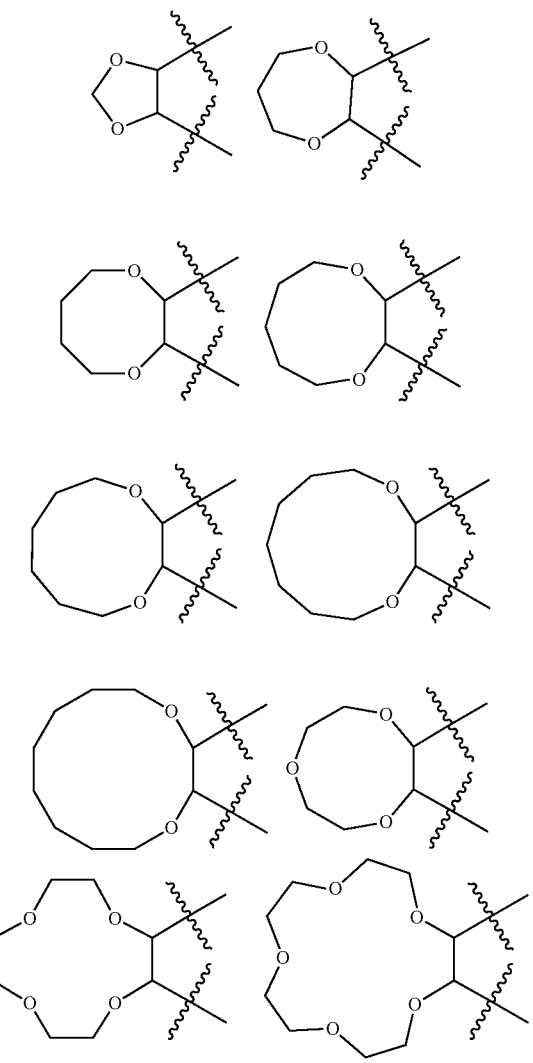

-continued

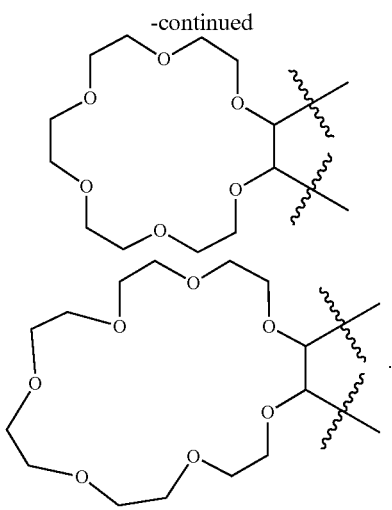

4. The aminoquinazolinone or aminoisoquinolinone compound according to claim 1, characterized in that, $R_3$ is selected from —$CH_3$, —$CH_2CH_3$, —$CH_2CH_2CH_3$, —$CH(CH_3)_2$, cyclopropyl, —$CH_2CF_3$, or —$CH_2CF_2H$.

5. The aminoquinazolinone or aminoisoquinolinone compound according to claim 1, characterized in that, Ar is selected from 4-methoxyphenyl, p-aminophenyl, 5-amino-pyrazol-3-yl, 2-amino-imidazol-4-yl, 2-amino-thiazol-4-yl, 2-amino-oxazol-4-yl, pyridin-3-yl, pyridin-2-yl, 2-amino-pyridin-5-yl, 2-amino-pyrimidin-5-yl, 2-amino -pyrazin-5-yl, or 3-amino-pyridazin-6-yl; and $R_8$ is selected from amino, methylamino, hydroxyl, methoxy, dimethylamino, cyano, or 3,4-dimethoxy.

6. The aminoquinazolinone or aminoisoquinolinone compound according to claim 1, characterized in that, the compound is selected from the following compounds or pharmaceutically acceptable salts or solvates thereof:

| Compd. | Structure |
|---|---|
| 7a-1 | 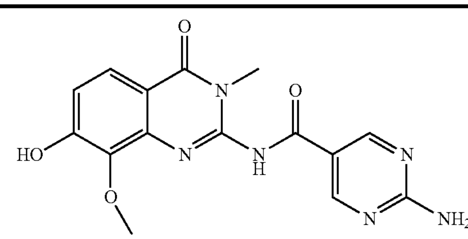 |
| 8a-1 | 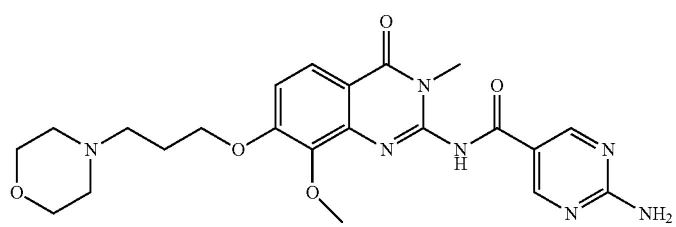 [SMILES: COc1c(OCCCN2CCOCC2)ccc2c(=O)n(C)c(NC(=O)c3cnc(N)nc3)nc12] |
| 8a-2 | 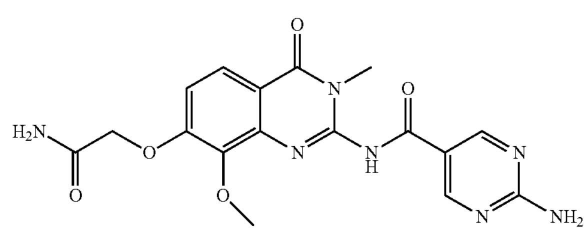 [SMILES: COc1c(OCC(N)=O)ccc2c(=O)n(C)c(NC(=O)c3cnc(N)nc3)nc12] |
| 8a-3 | 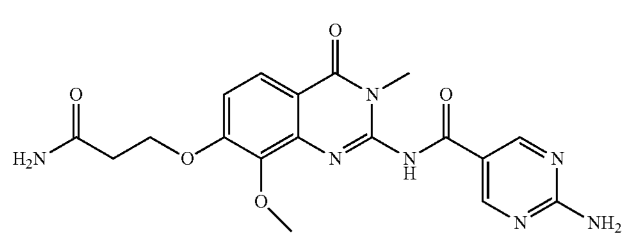 |

| Compd. | Structure |
|---|---|
| 8a-4 | 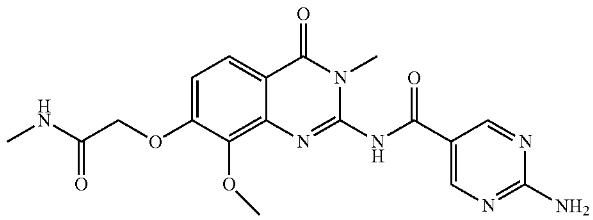 [SMILES: CNC(=O)COc1ccc2c(=O)n(C)c(NC(=O)c3cnc(N)nc3)nc2c1OC] |
| 8a-5 | 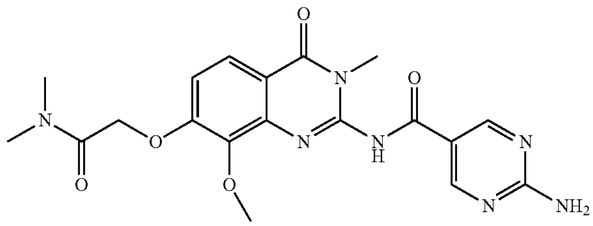 [SMILES: COc1c(OCC(=O)N(C)C)ccc2c(=O)n(C)c(NC(=O)c3cnc(N)nc3)nc12] |
| 8a-6 | 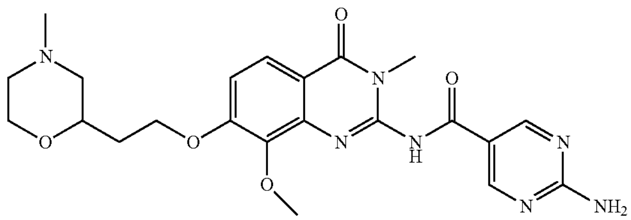 [SMILES: COc1c(OCCC2CN(C)CCO2)ccc2c(=O)n(C)c(NC(=O)c3cnc(N)nc3)nc12] |
| 8a-7 | 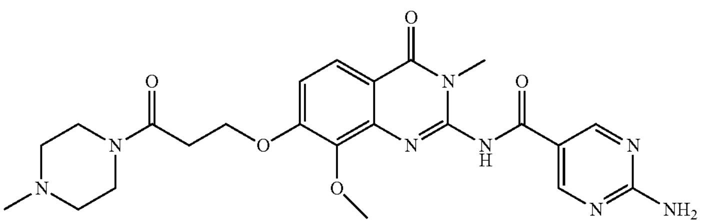 |
| 8a-8 | 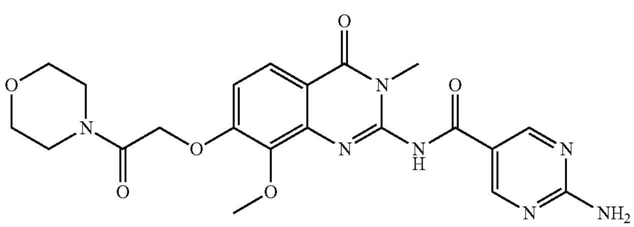 [SMILES: COc1c(OCC(=O)N2CCOCC2)ccc2c(=O)n(C)c(NC(=O)c3cnc(N)nc3)nc12] |
| 8a-9 | 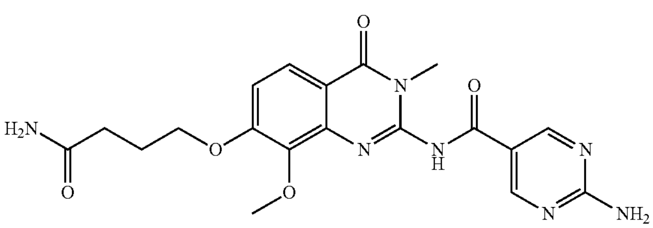 [SMILES: COc1c(OCCCC(N)=O)ccc2c(=O)n(C)c(NC(=O)c3cnc(N)nc3)nc12] |
| 8a-10 | 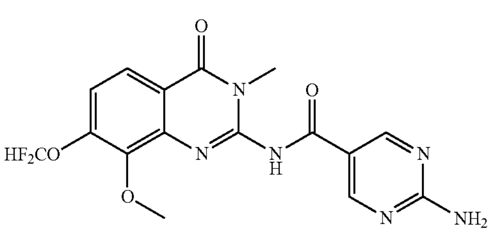 |

| Compd. | Structure |
|---|---|
| 8a-11 | 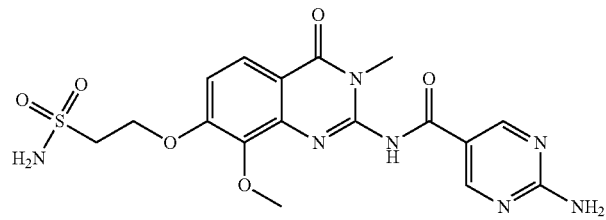 |
| 8a-12 | 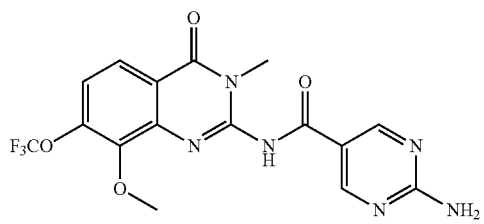 |
| 8a-13 | 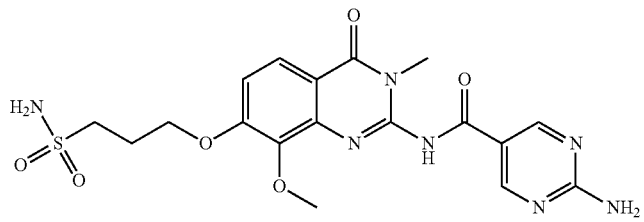 [SMILES: COc1c(OCCCS(N)(=O)=O)ccc2c(=O)n(C)c(NC(=O)c3cnc(N)nc3)nc12] |
| 8a-14 | 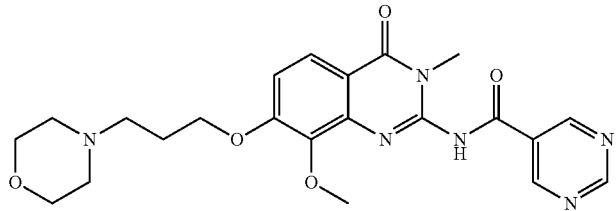 [SMILES: COc1c(OCCCN2CCOCC2)ccc2c(=O)n(C)c(NC(=O)c3cncnc3)nc12] |
| 8a-15 | 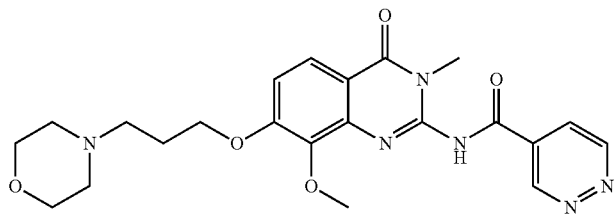 [SMILES: COc1c(OCCCN2CCOCC2)ccc2c(=O)n(C)c(NC(=O)c3ccnnc3)nc12] |
| 8a-16 | 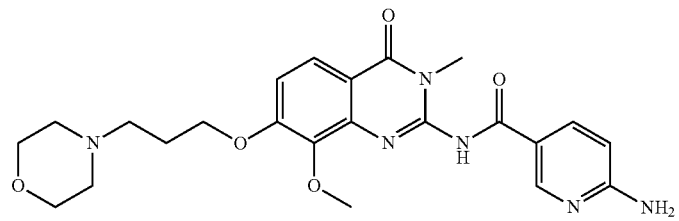 [SMILES: COc1c(OCCCN2CCOCC2)ccc2c(=O)n(C)c(NC(=O)c3ccc(N)nc3)nc12] |

| Compd. | Structure |
|---|---|
| 8a-17 | 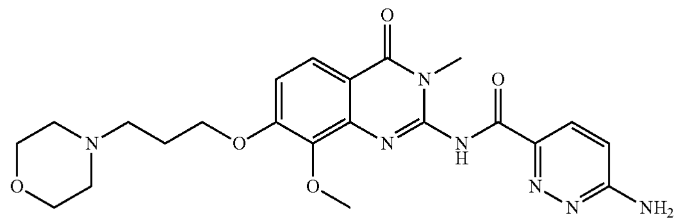 [SMILES: COc1c(OCCCN2CCOCC2)ccc2c(=O)n(C)c(NC(=O)c3ccc(N)nn3)nc12] |
| 8a-18 | 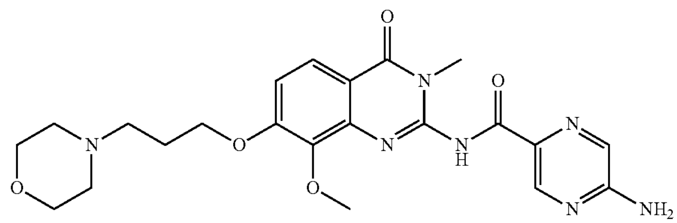 [SMILES: COc1c(OCCCN2CCOCC2)ccc2c(=O)n(C)c(NC(=O)c3cnc(N)cn3)nc12] |
| 8a-19 | 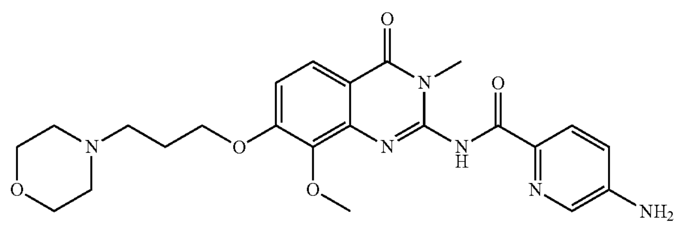 [SMILES: COc1c(OCCCN2CCOCC2)ccc2c(=O)n(C)c(NC(=O)c3ccc(N)cn3)nc12] |
| 8a-20 | 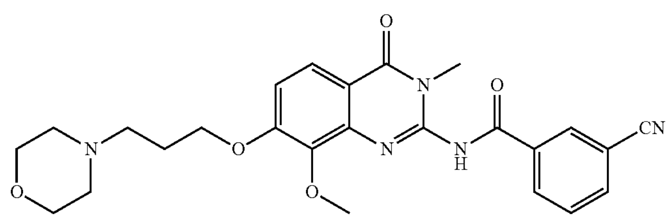 [SMILES: COc1c(OCCCN2CCOCC2)ccc2c(=O)n(C)c(NC(=O)c3cccc(C#N)c3)nc12] |
| 8a-21 | 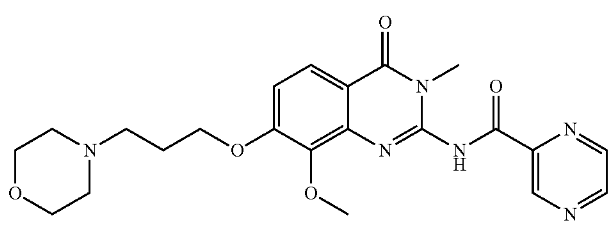 [SMILES: COc1c(OCCCN2CCOCC2)ccc2c(=O)n(C)c(NC(=O)c3cnccn3)nc12] |
| 8a-22 | 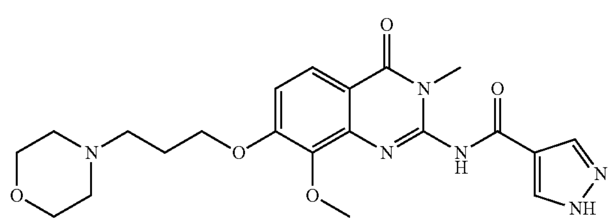 [SMILES: COc1c(OCCCN2CCOCC2)ccc2c(=O)n(C)c(NC(=O)c3cn[nH]c3)nc12] |
| 8a-23 | 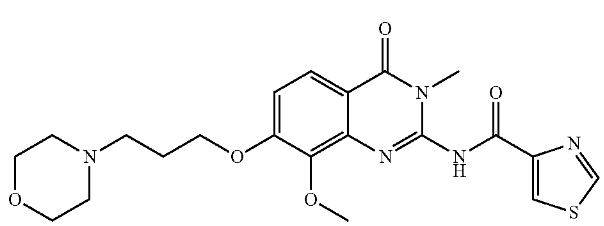 [SMILES: COc1c(OCCCN2CCOCC2)ccc2c(=O)n(C)c(NC(=O)c3cscn3)nc12] |

| Compd. | Structure |
|---|---|
| 8a-24 | 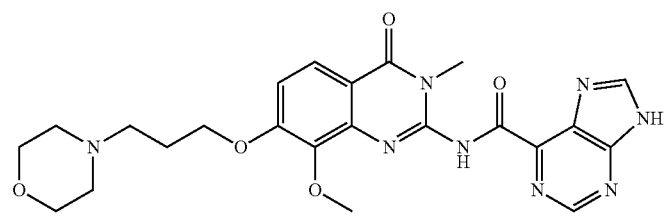 [SMILES: COc1c(OCCCN2CCOCC2)ccc2c(=O)n(C)c(NC(=O)c3ncnc4[nH]cnc34)nc12] |
| 8a-25 | 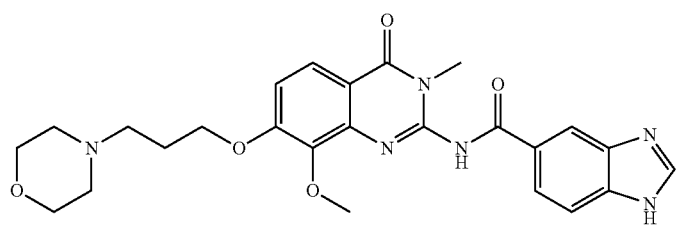 [SMILES: COc1c(OCCCN2CCOCC2)ccc2c(=O)n(C)c(NC(=O)c3ccc4[nH]cnc4c3)nc12] |
| 8a-26 | 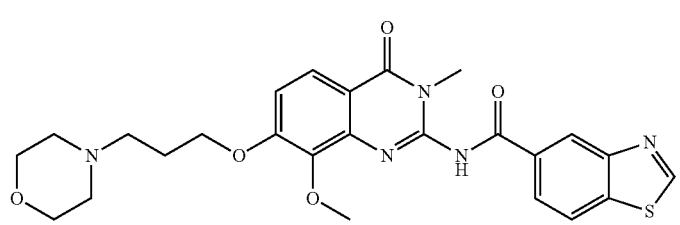 [SMILES: COc1c(OCCCN2CCOCC2)ccc2c(=O)n(C)c(NC(=O)c3ccc4scnc4c3)nc12] |
| 8a-27 | 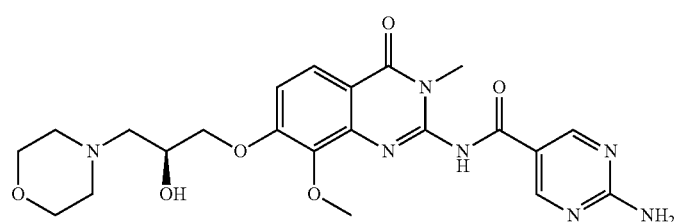 |
| 8a-28 | 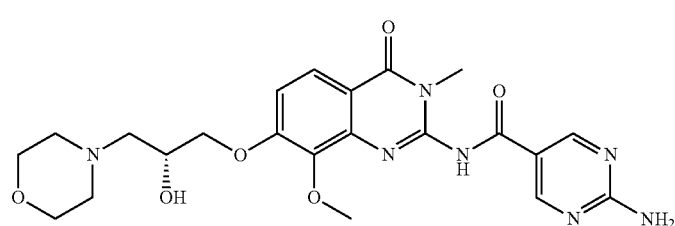 |
| 8a-29 | 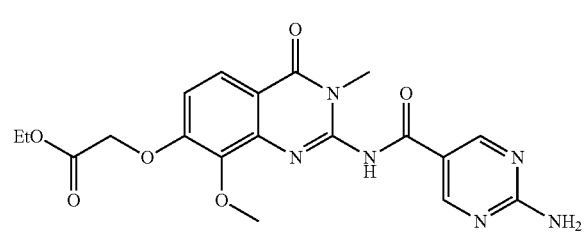 [SMILES: CCOC(=O)COc1ccc2c(=O)n(C)c(NC(=O)c3cnc(N)nc3)nc2c1OC] |
| 8a-30 | 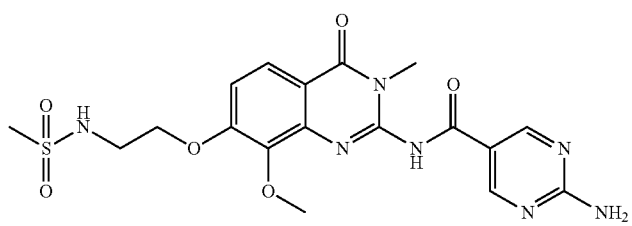 [SMILES: COc1c(OCCNS(C)(=O)=O)ccc2c(=O)n(C)c(NC(=O)c3cnc(N)nc3)nc12] |

| Compd. | Structure |
|---|---|
| 8a-31 | 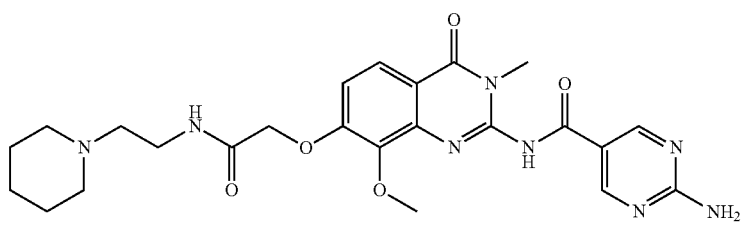 |
| 8a-32 | 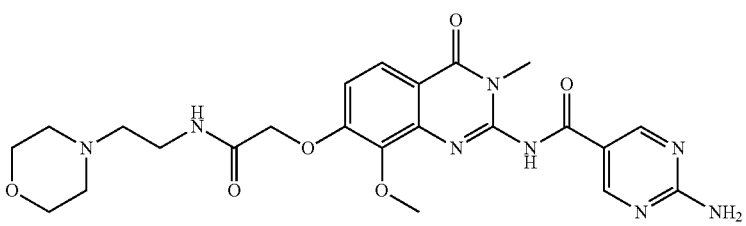 |
| 8a-33 | 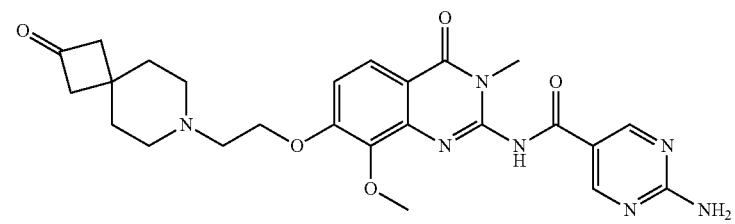 [SMILES: COc1c(OCCN2CCC3(CC2)CC(=O)C3)ccc2c(=O)n(C)c(NC(=O)c3cnc(N)nc3)nc12] |
| 8a-34 | 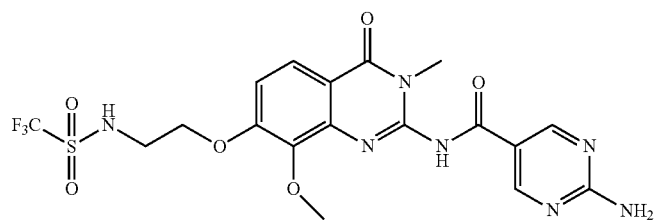 [SMILES: COc1c(OCCNS(=O)(=O)C(F)(F)F)ccc2c(=O)n(C)c(NC(=O)c3cnc(N)nc3)nc12] |
| 8a-35 | 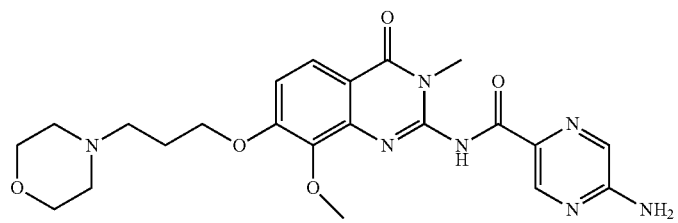 [SMILES: COc1c(OCCCN2CCOCC2)ccc2c(=O)n(C)c(NC(=O)c3cnc(N)cn3)nc12] |
| 8a-36 | 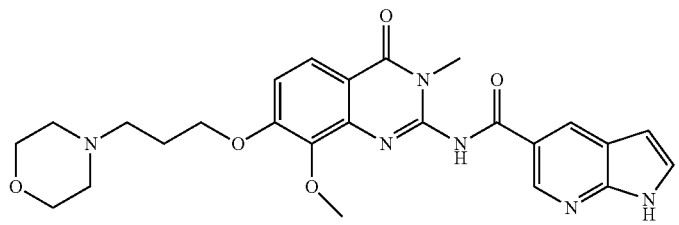 [SMILES: COc1c(OCCCN2CCOCC2)ccc2c(=O)n(C)c(NC(=O)c3cnc4[nH]ccc4c3)nc12] |
| 8a-37 | 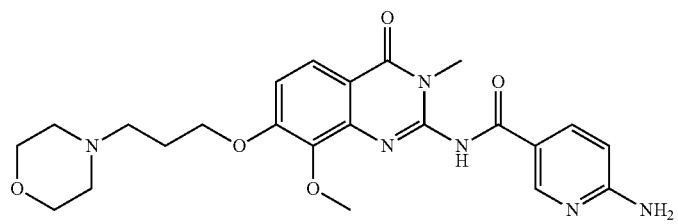 [SMILES: COc1c(OCCCN2CCOCC2)ccc2c(=O)n(C)c(NC(=O)c3ccc(N)nc3)nc12] |

| Compd. | Structure |
|---|---|
| 8a-38 | 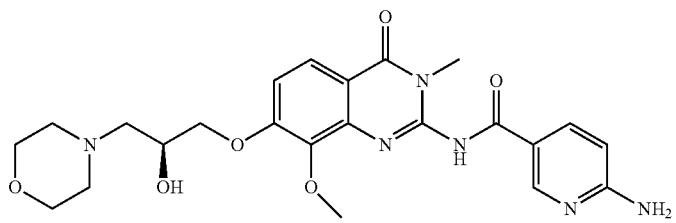 [SMILES: COc1c(OC[C@@H](O)CN2CCOCC2)ccc2c(=O)n(C)c(NC(=O)c3ccc(N)nc3)nc12] |
| 8a-39 | 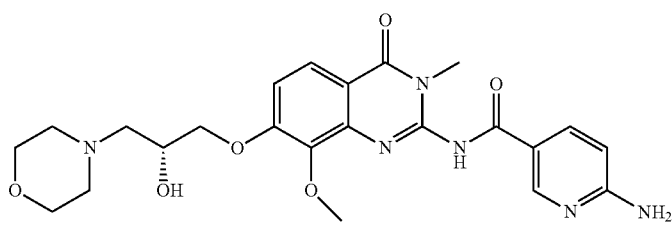 [SMILES: COc1c(OC[C@H](O)CN2CCOCC2)ccc2c(=O)n(C)c(NC(=O)c3ccc(N)nc3)nc12] |
| 8a-40 | 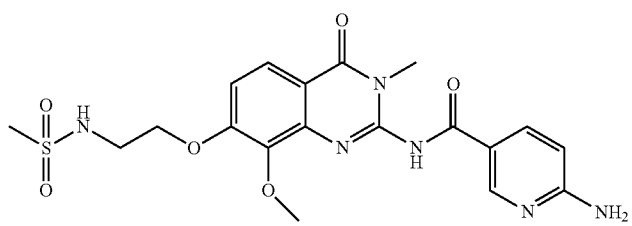 [SMILES: COc1c(OCCNS(C)(=O)=O)ccc2c(=O)n(C)c(NC(=O)c3ccc(N)nc3)nc12] |
| 8a-41 | 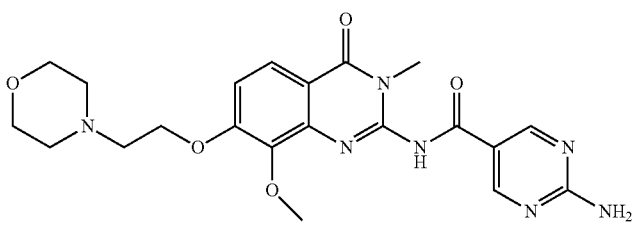 [SMILES: COc1c(OCCN2CCOCC2)ccc2c(=O)n(C)c(NC(=O)c3cnc(N)nc3)nc12] |
| 8a-42 | 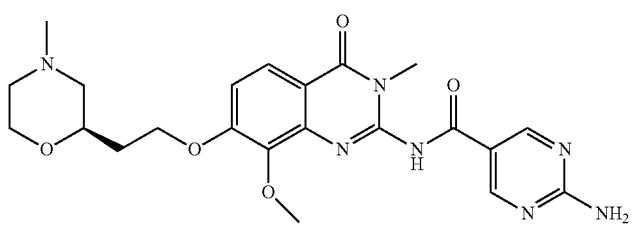 [SMILES: COc1c(OCC[C@@H]2CN(C)CCO2)ccc2c(=O)n(C)c(NC(=O)c3cnc(N)nc3)nc12] |
| 8a-43 | 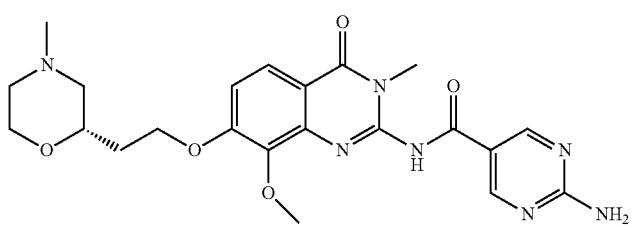 |

| Compd. | Structure |
|---|---|
| 8a-44 | 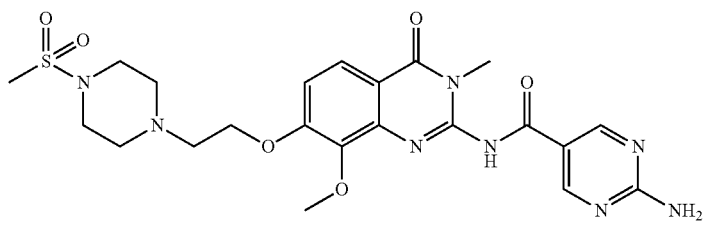 [SMILES: COc1c(OCCN2CCN(S(C)(=O)=O)CC2)ccc2c(=O)n(C)c(NC(=O)c3cnc(N)nc3)nc12] |
| 8a-45 | 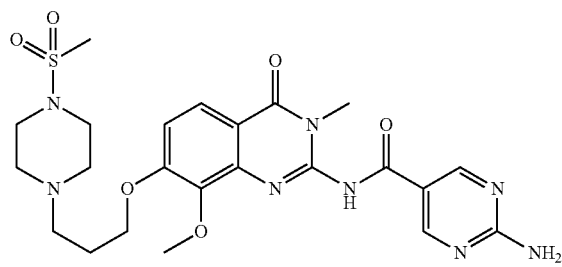 [SMILES: COc1c(OCCCN2CCN(S(C)(=O)=O)CC2)ccc2c(=O)n(C)c(NC(=O)c3cnc(N)nc3)nc12] |
| 8a-46 | 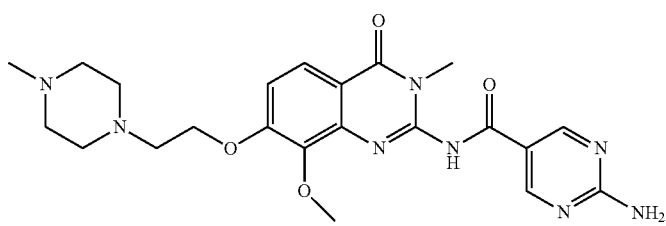 [SMILES: COc1c(OCCN2CCN(C)CC2)ccc2c(=O)n(C)c(NC(=O)c3cnc(N)nc3)nc12] |
| 8a-47 | 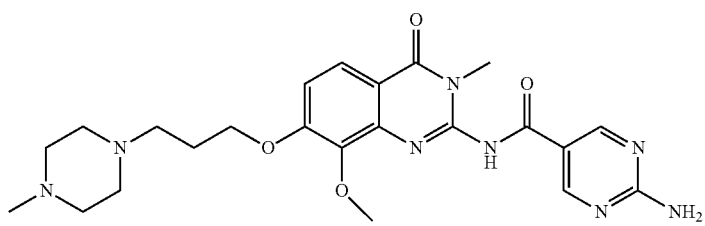 [SMILES: COc1c(OCCCN2CCN(C)CC2)ccc2c(=O)n(C)c(NC(=O)c3cnc(N)nc3)nc12] |
| 8a-48 | 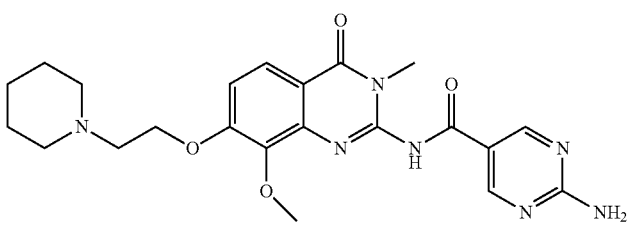 [SMILES: COc1c(OCCN2CCCCC2)ccc2c(=O)n(C)c(NC(=O)c3cnc(N)nc3)nc12] |
| 8a-49 | 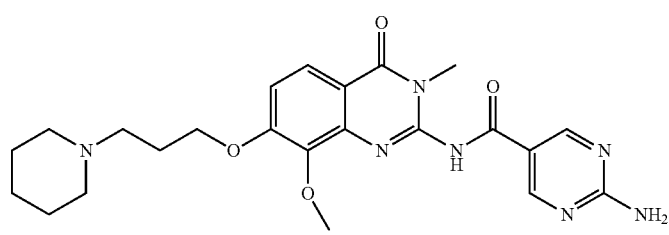 [SMILES: COc1c(OCCCN2CCCCC2)ccc2c(=O)n(C)c(NC(=O)c3cnc(N)nc3)nc12] |

| Compd. | Structure |
|---|---|
| 8a-50 | 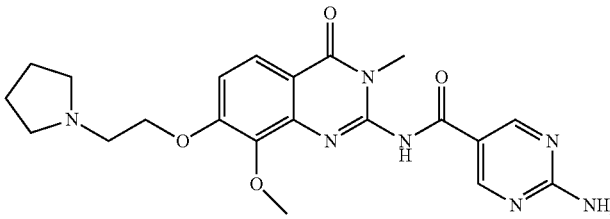 |
| 8a-51 | 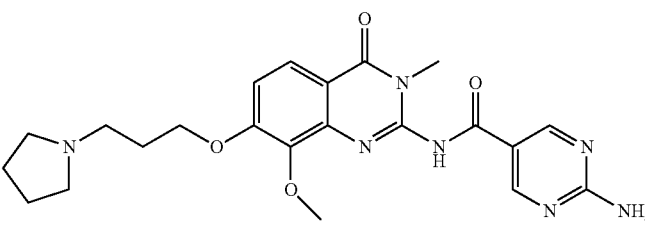 |
| 8a-52 | 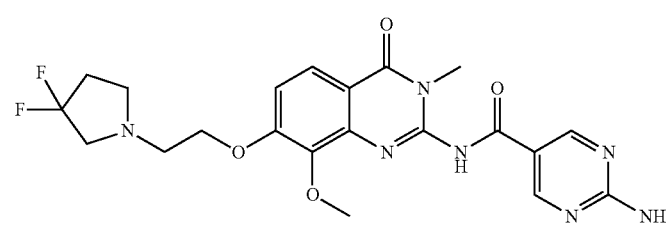 |
| 8a-53 | 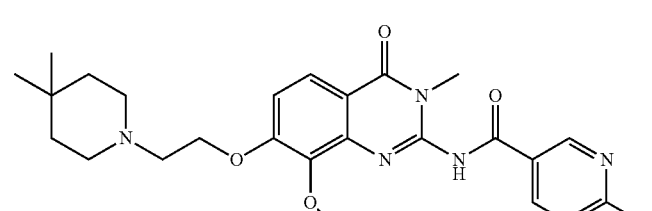 |
| 8a-54 | 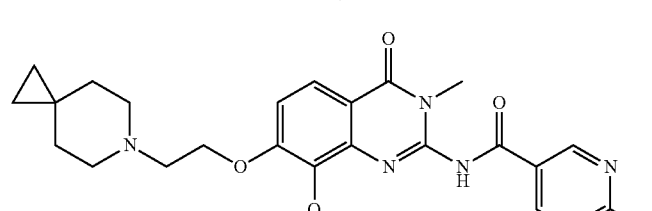 |
| 8a-55 | 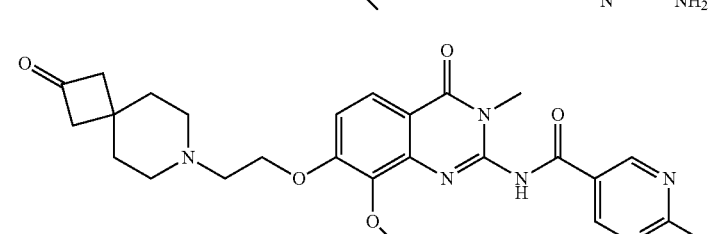 |
| 8a-56 | 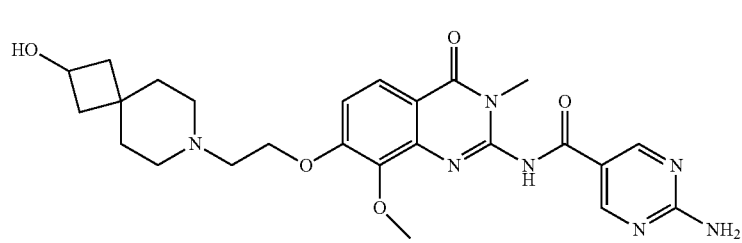 [SMILES: COc1c(OCCN2CCC3(CC2)CC(O)C3)ccc2c(=O)n(C)c(NC(=O)c3cnc(N)nc3)nc12] |

| Compd. | Structure |
|---|---|
| 8a-57 | 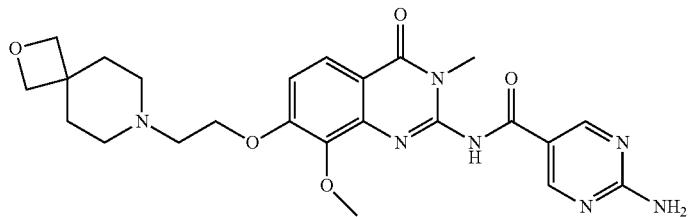 [SMILES: COc1c(OCCN2CCC3(CC2)COC3)ccc2c(=O)n(C)c(NC(=O)c3cnc(N)nc3)nc12] |
| 8a-58 | 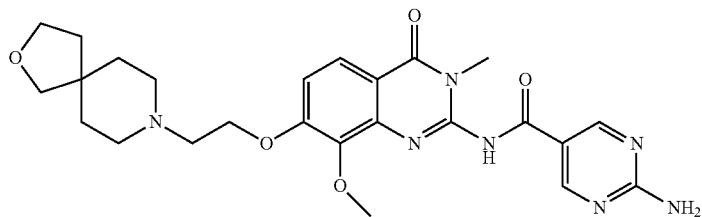 |
| 8a-59 | 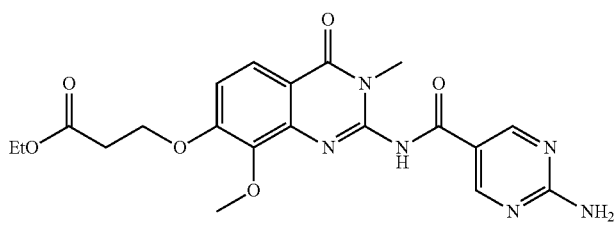 [SMILES: CCOC(=O)CCOc1ccc2c(=O)n(C)c(NC(=O)c3cnc(N)nc3)nc2c1OC] |
| 8a-60 | 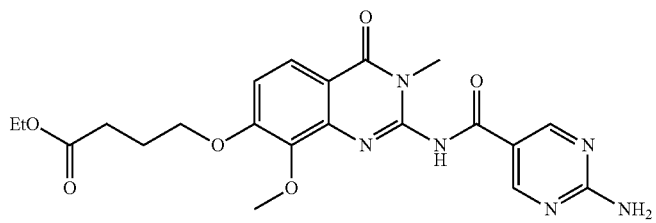 [SMILES: CCOC(=O)CCCOc1ccc2c(=O)n(C)c(NC(=O)c3cnc(N)nc3)nc2c1OC] |
| 8a-61 | 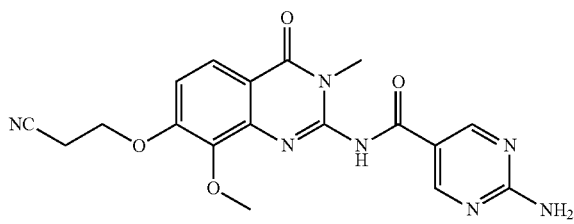 [SMILES: COc1c(OCCC#N)ccc2c(=O)n(C)c(NC(=O)c3cnc(N)nc3)nc12] |
| 8a-62 | 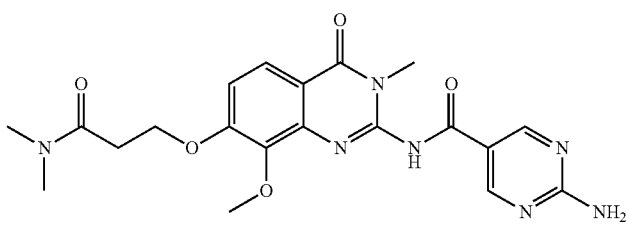 [SMILES: COc1c(OCCC(=O)N(C)C)ccc2c(=O)n(C)c(NC(=O)c3cnc(N)nc3)nc12] |

| Compd. | Structure |
|---|---|
| 8a-63 | 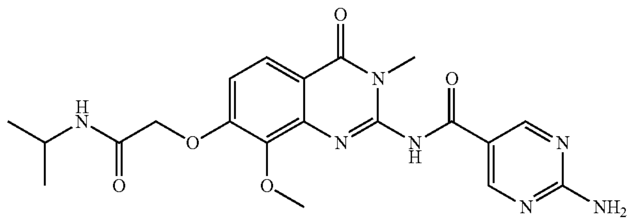 [SMILES: COc1c(OCC(=O)NC(C)C)ccc2c(=O)n(C)c(NC(=O)c3cnc(N)nc3)nc12] |
| 8a-64 | 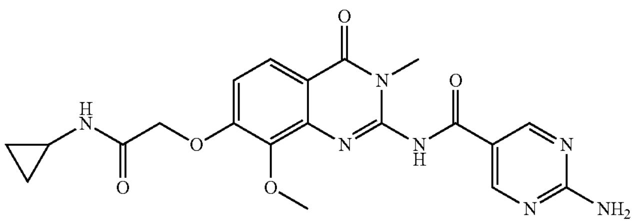 [SMILES: COc1c(OCC(=O)NC2CC2)ccc2c(=O)n(C)c(NC(=O)c3cnc(N)nc3)nc12] |
| 8a-65 | 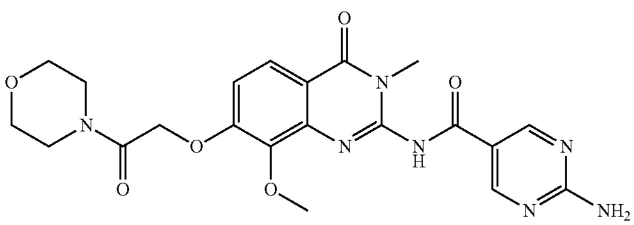 [SMILES: COc1c(OCC(=O)N2CCOCC2)ccc2c(=O)n(C)c(NC(=O)c3cnc(N)nc3)nc12] |
| 8a-66 | 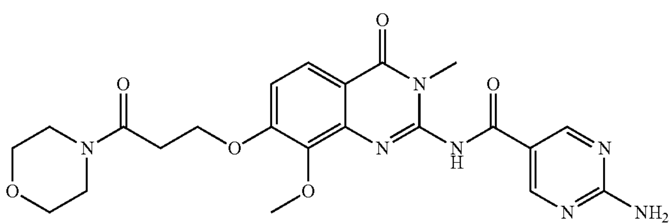 [SMILES: COc1c(OCCC(=O)N2CCOCC2)ccc2c(=O)n(C)c(NC(=O)c3cnc(N)nc3)nc12] |
| 7b-1 | 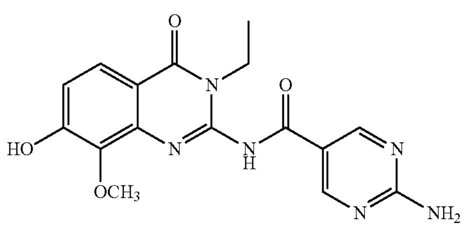 [SMILES: CCn1c(NC(=O)c2cnc(N)nc2)nc2c(OC)c(O)ccc2c1=O] |
| 8b-1 | 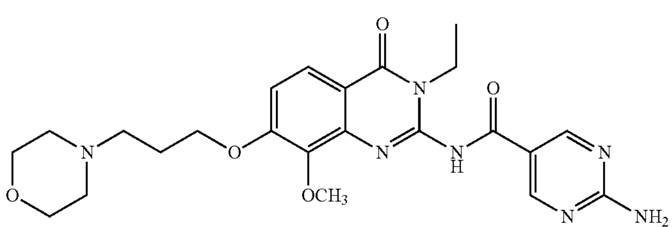 [SMILES: CCn1c(NC(=O)c2cnc(N)nc2)nc2c(OC)c(OCCCN3CCOCC3)ccc2c1=O] |
| 8b-2 | 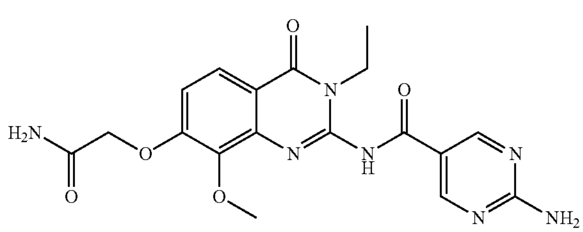 [SMILES: CCn1c(NC(=O)c2cnc(N)nc2)nc2c(OC)c(OCC(N)=O)ccc2c1=O] |

| Compd. | Structure |
|---|---|
| 8b-3 | 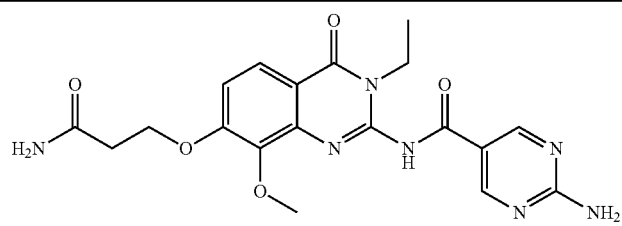 |
| 8b-4 | 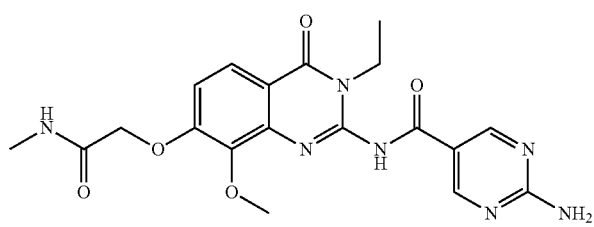 |
| 8b-5 | 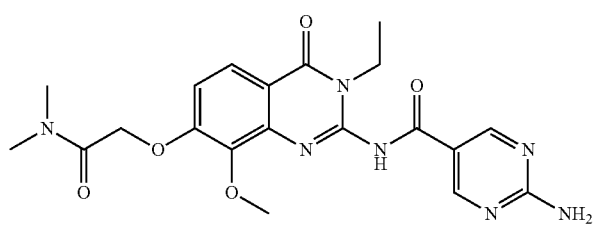 |
| 8b-6 | 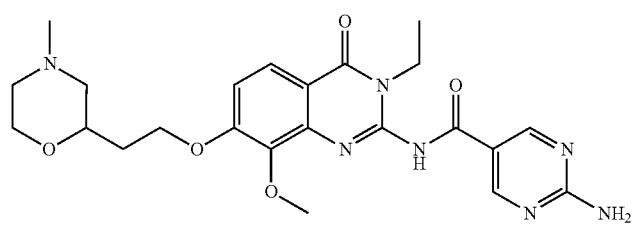 [SMILES: CCn1c(NC(=O)c2cnc(N)nc2)nc2c(OC)c(OCCC3CN(C)CCO3)ccc2c1=O] |
| 8b-7 | 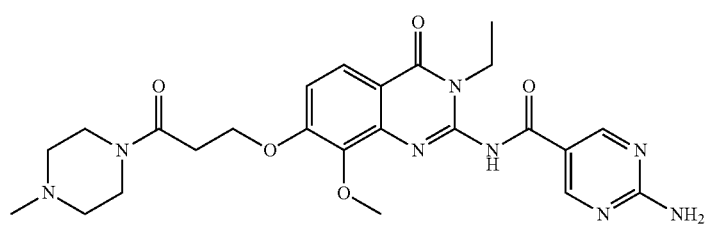 |
| 8b-8 | 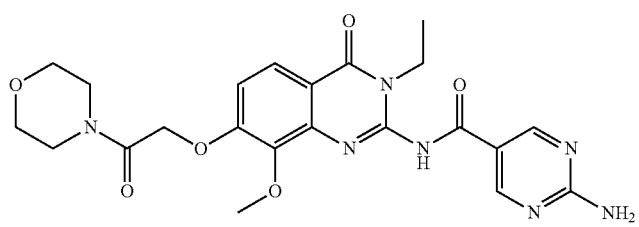 |
| 8b-9 | 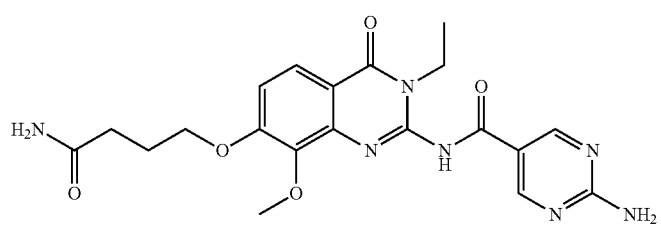 [SMILES: CCn1c(NC(=O)c2cnc(N)nc2)nc2c(OC)c(OCCCC(N)=O)ccc2c1=O] |

| Compd. | Structure |
|---|---|
| 8b-10 | 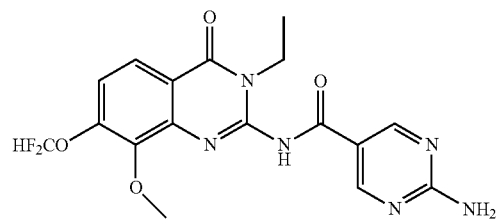 |
| 8b-11 | 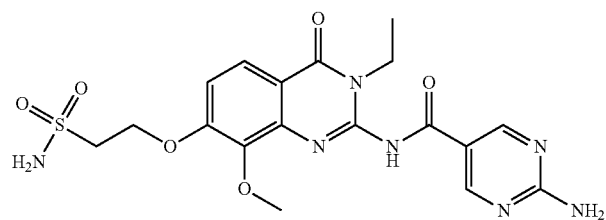 [SMILES: CCn1c(NC(=O)c2cnc(N)nc2)nc2c(OC)c(OCCS(N)(=O)=O)ccc2c1=O] |
| 8b-12 | 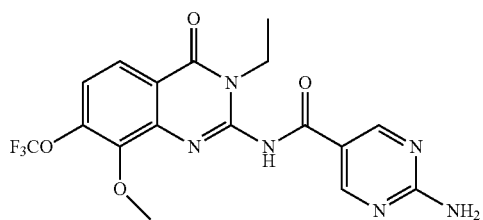 [SMILES: CCn1c(NC(=O)c2cnc(N)nc2)nc2c(OC)c(OC(F)(F)F)ccc2c1=O] |
| 8b-13 | 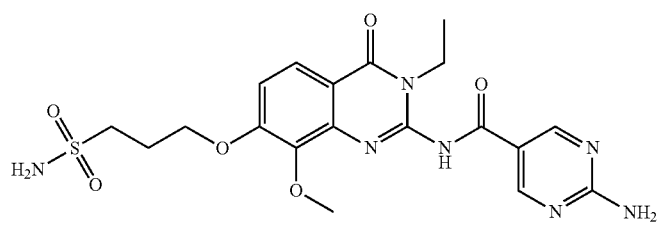 [SMILES: CCn1c(NC(=O)c2cnc(N)nc2)nc2c(OC)c(OCCCS(N)(=O)=O)ccc2c1=O] |
| 8b-14 | 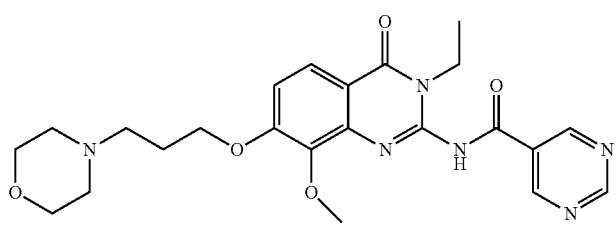 [SMILES: CCn1c(NC(=O)c2cncnc2)nc2c(OC)c(OCCCN3CCOCC3)ccc2c1=O] |
| 8b-15 | 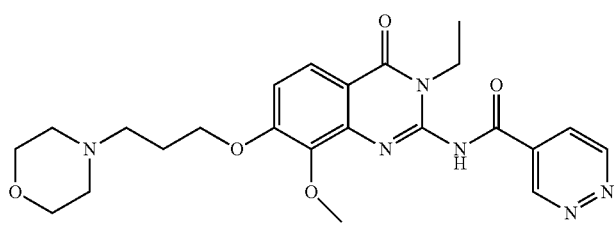 [SMILES: CCn1c(NC(=O)c2ccnnc2)nc2c(OC)c(OCCCN3CCOCC3)ccc2c1=O] |

| Compd. | Structure |
|---|---|
| 8b-16 | 4-oxo-3-ethyl-7-(3-morpholinopropoxy)-8-methoxy-quinazolin-2-yl N-(5-aminopyridin-3-ylcarbonyl)amide |
| 8b-17 | 4-oxo-3-ethyl-7-(3-morpholinopropoxy)-8-methoxy-quinazolin-2-yl N-(6-aminopyridazin-3-ylcarbonyl)amide |
| 8b-18 | 4-oxo-3-ethyl-7-(3-morpholinopropoxy)-8-methoxy-quinazolin-2-yl N-(5-aminopyrazin-2-ylcarbonyl)amide |
| 8b-19 | 4-oxo-3-ethyl-7-(3-morpholinopropoxy)-8-methoxy-quinazolin-2-yl N-(5-aminopyridin-2-ylcarbonyl)amide |
| 8b-20 | 4-oxo-3-ethyl-7-(3-morpholinopropoxy)-8-methoxy-quinazolin-2-yl N-(3-cyanobenzoyl)amide |
| 8b-21 | 4-oxo-3-ethyl-7-(3-morpholinopropoxy)-8-methoxy-quinazolin-2-yl N-(pyrazin-2-ylcarbonyl)amide |
| 8b-22 | 4-oxo-3-ethyl-7-(3-morpholinopropoxy)-8-methoxy-quinazolin-2-yl N-(1H-pyrazol-4-ylcarbonyl)amide |

| Compd. | Structure |
|---|---|
| 8b-23 | 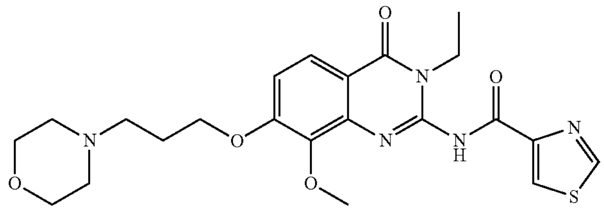 [SMILES: CCn1c(NC(=O)c2cscn2)nc2c(OC)c(OCCCN3CCOCC3)ccc2c1=O] |
| 8b-24 | 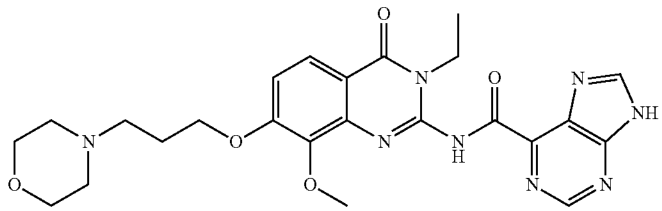 [SMILES: CCn1c(NC(=O)c2ncnc3[nH]cnc23)nc2c(OC)c(OCCCN3CCOCC3)ccc2c1=O] |
| 8b-25 | 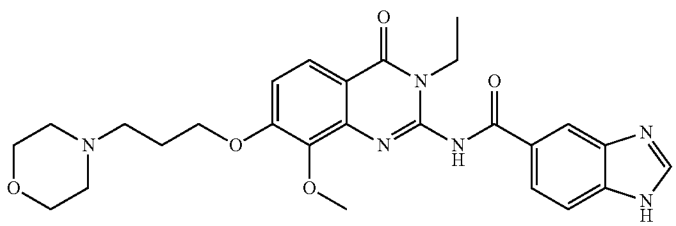 [SMILES: CCn1c(NC(=O)c2ccc3[nH]cnc3c2)nc2c(OC)c(OCCCN3CCOCC3)ccc2c1=O] |
| 8b-26 | 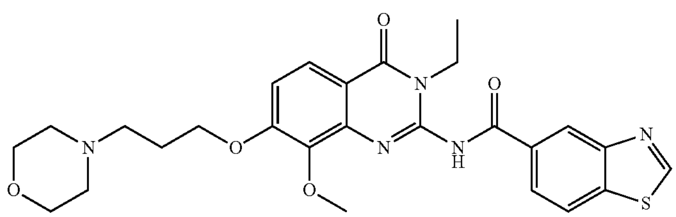 [SMILES: CCn1c(NC(=O)c2ccc3scnc3c2)nc2c(OC)c(OCCCN3CCOCC3)ccc2c1=O] |
| 8b-27 | 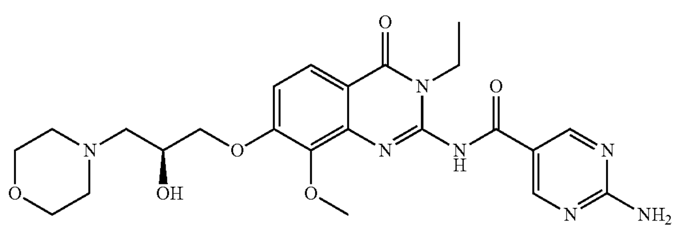 [SMILES: CCn1c(NC(=O)c2cnc(N)nc2)nc2c(OC)c(OC[C@@H](O)CN3CCOCC3)ccc2c1=O] |
| 8b-28 | 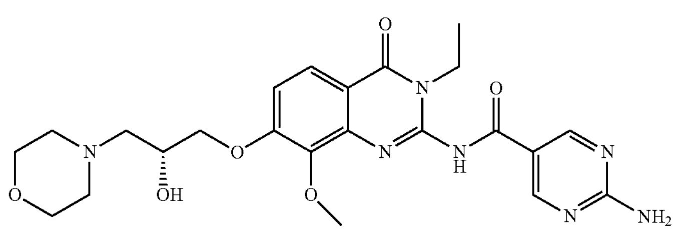 [SMILES: CCn1c(NC(=O)c2cnc(N)nc2)nc2c(OC)c(OC[C@H](O)CN3CCOCC3)ccc2c1=O] |
| 8b-29 | 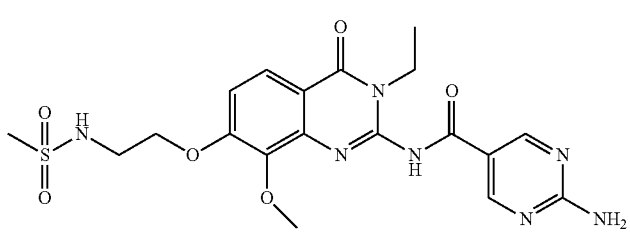 [SMILES: CCn1c(NC(=O)c2cnc(N)nc2)nc2c(OC)c(OCCNS(C)(=O)=O)ccc2c1=O] |

| Compd. | Structure |
|---|---|
| 8b-29 | 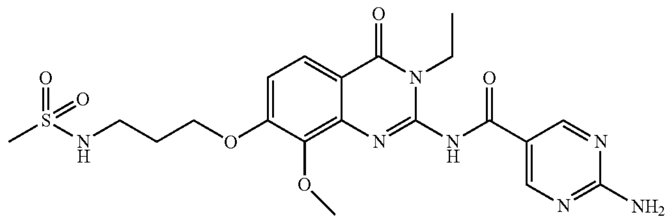 [SMILES: CCn1c(NC(=O)c2cnc(N)nc2)nc2c(OC)c(OCCCNS(C)(=O)=O)ccc2c1=O] |
| 8b-31 | 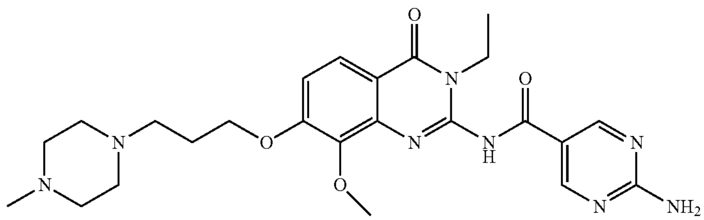 [SMILES: CCn1c(NC(=O)c2cnc(N)nc2)nc2c(OC)c(OCCCN3CCN(C)CC3)ccc2c1=O] |
| 8b-32 | 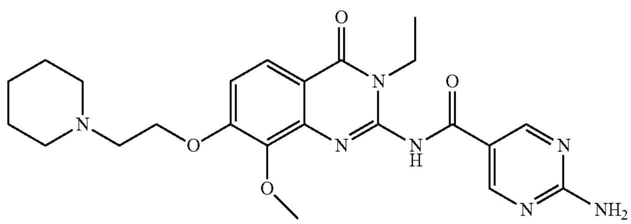 [SMILES: CCn1c(NC(=O)c2cnc(N)nc2)nc2c(OC)c(OCCN3CCCCC3)ccc2c1=O] |
| 8b-33 | 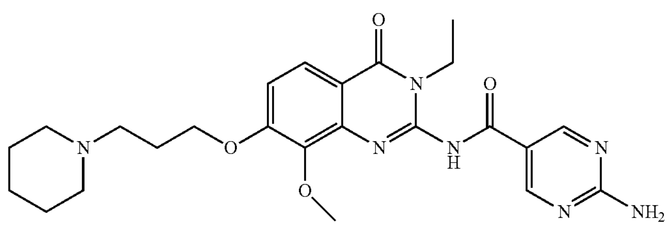 [SMILES: CCn1c(NC(=O)c2cnc(N)nc2)nc2c(OC)c(OCCCN3CCCCC3)ccc2c1=O] |
| 8b-34 | 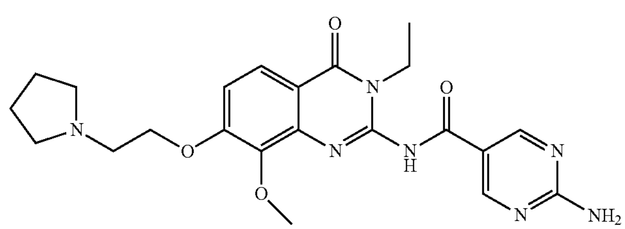 [SMILES: CCn1c(NC(=O)c2cnc(N)nc2)nc2c(OC)c(OCCN3CCCC3)ccc2c1=O] |
| 8b-35 | 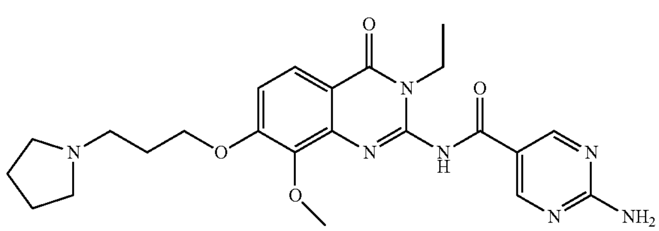 [SMILES: CCn1c(NC(=O)c2cnc(N)nc2)nc2c(OC)c(OCCCN3CCCC3)ccc2c1=O] |
| 8b-36 | 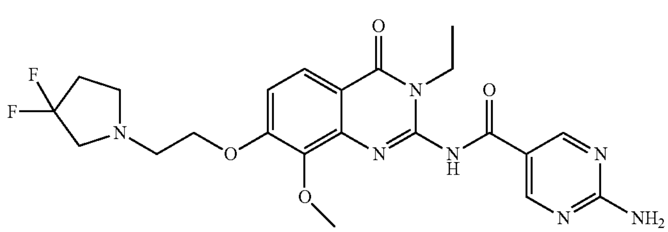 [SMILES: CCn1c(NC(=O)c2cnc(N)nc2)nc2c(OC)c(OCCN3CCC(F)(F)C3)ccc2c1=O] |

| Compd. | Structure |
|---|---|
| 8b-37 | 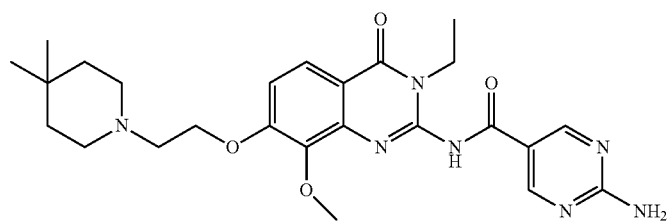 [SMILES: CCn1c(NC(=O)c2cnc(N)nc2)nc2c(OC)c(OCCN3CCC(C)(C)CC3)ccc2c1=O] |
| 8b-38 | 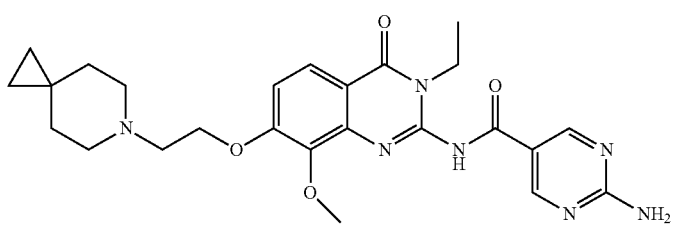 [SMILES: CCn1c(NC(=O)c2cnc(N)nc2)nc2c(OC)c(OCCN3CCC4(CC3)CC4)ccc2c1=O] |
| 8b-39 | 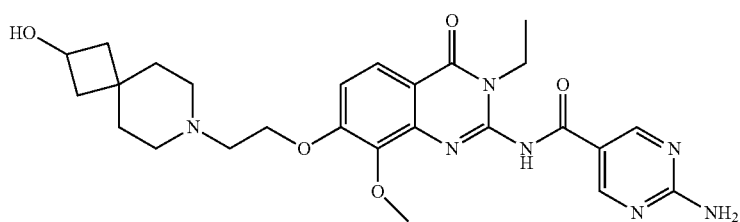 |
| 8b-40 | 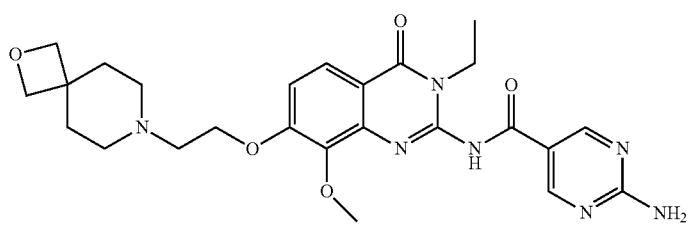 |
| 8b-41 | 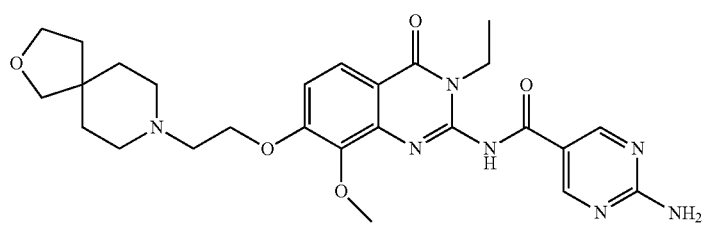 [SMILES: CCn1c(NC(=O)c2cnc(N)nc2)nc2c(OC)c(OCCN3CCC4(CCOC4)CC3)ccc2c1=O] |
| 8b-42 | 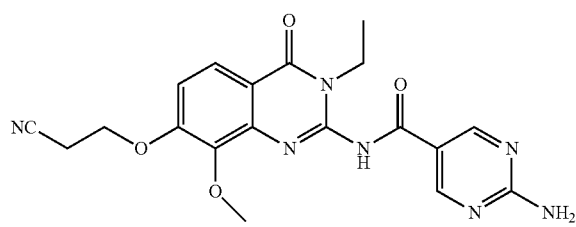 [SMILES: CCn1c(NC(=O)c2cnc(N)nc2)nc2c(OC)c(OCCC#N)ccc2c1=O] |

-continued

| Compd. | Structure |
|---|---|
| 8b-43 | 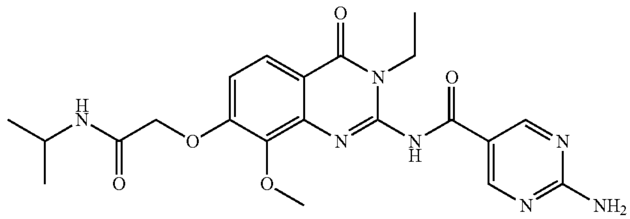 [SMILES: CCn1c(NC(=O)c2cnc(N)nc2)nc2c(OC)c(OCC(=O)NC(C)C)ccc2c1=O] |
| 8b-44 | 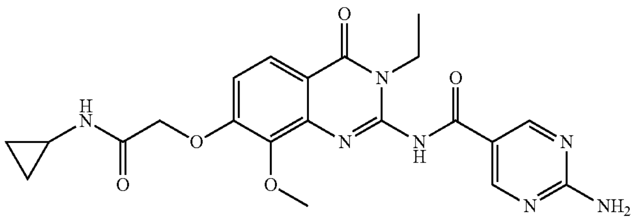 [SMILES: CCn1c(NC(=O)c2cnc(N)nc2)nc2c(OC)c(OCC(=O)NC3CC3)ccc2c1=O] |
| 8b-45 | 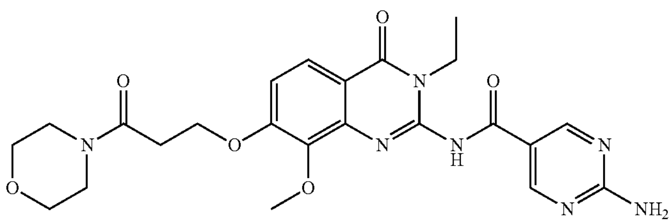 |
| 8b-46 | 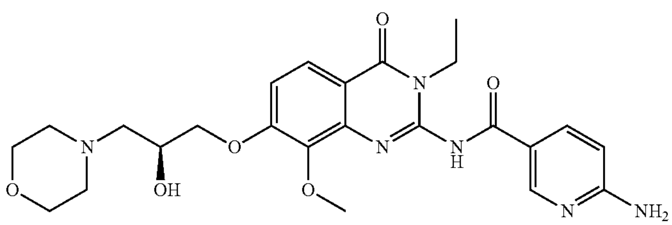 [SMILES: CCn1c(NC(=O)c2ccc(N)nc2)nc2c(OC)c(OC[C@@H](O)CN3CCOCC3)ccc2c1=O] |
| 8b-47 | 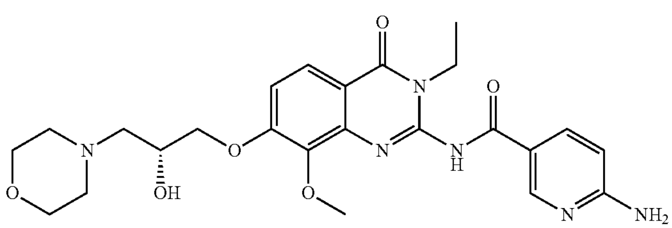 [SMILES: CCn1c(NC(=O)c2ccc(N)nc2)nc2c(OC)c(OC[C@H](O)CN3CCOCC3)ccc2c1=O] |
| 8b-48 | 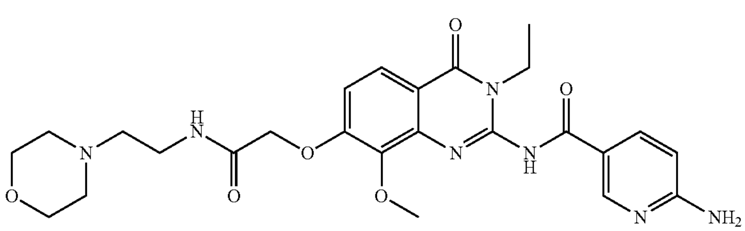 [SMILES: CCn1c(NC(=O)c2ccc(N)nc2)nc2c(OC)c(OCC(=O)NCCN3CCOCC3)ccc2c1=O] |
| 8b-49 | 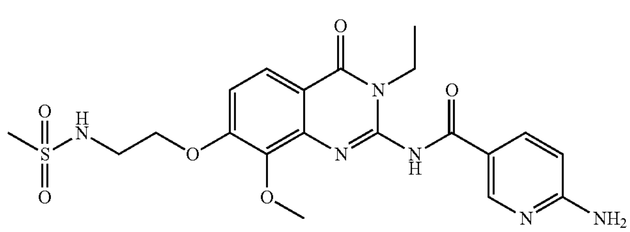 |

-continued
| Compd. | Structure |
|---|---|
| 8b-50 | 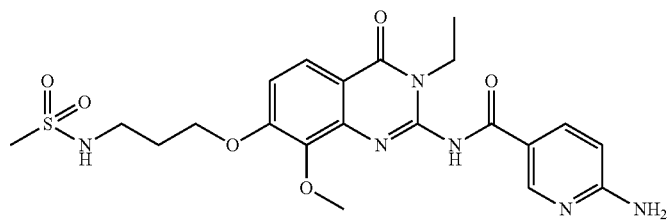 [SMILES: CCn1c(NC(=O)c2ccc(N)nc2)nc2c(OC)c(OCCCNS(C)(=O)=O)ccc2c1=O] |
| 7c-1 | 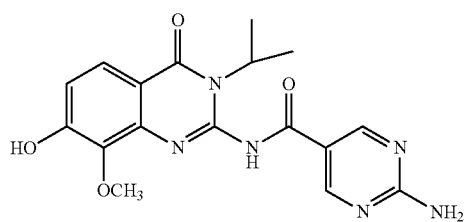 |
| 8c-1 | 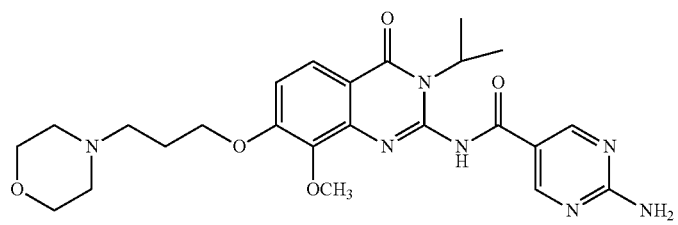 [SMILES: COc1c(OCCCN2CCOCC2)ccc2c(=O)n(C(C)C)c(NC(=O)c3cnc(N)nc3)nc12] |
| 8c-2 | 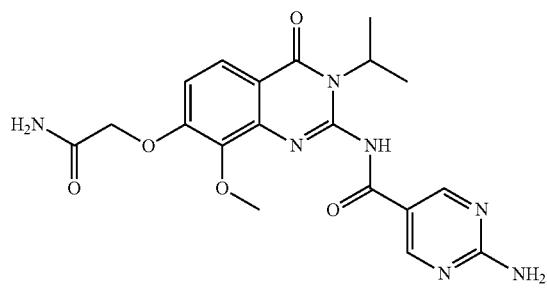 [SMILES: COc1c(OCC(N)=O)ccc2c(=O)n(C(C)C)c(NC(=O)c3cnc(N)nc3)nc12] |
| 8c-3 | 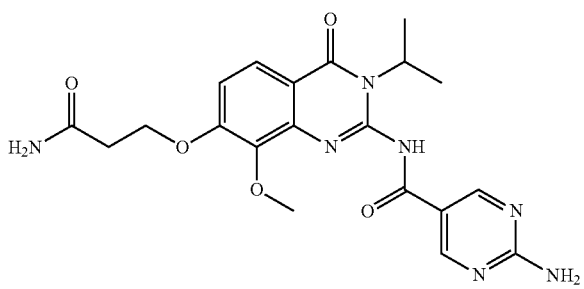 [SMILES: COc1c(OCCC(N)=O)ccc2c(=O)n(C(C)C)c(NC(=O)c3cnc(N)nc3)nc12] |
| 8c-4 | 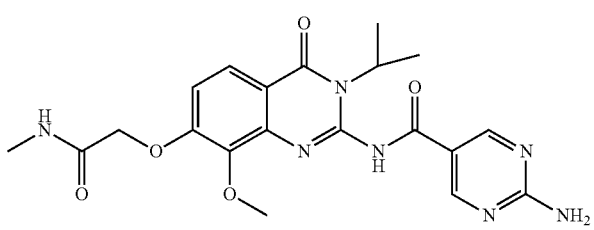 |

-continued
| Compd. | Structure |
|---|---|
| 8c-5 | 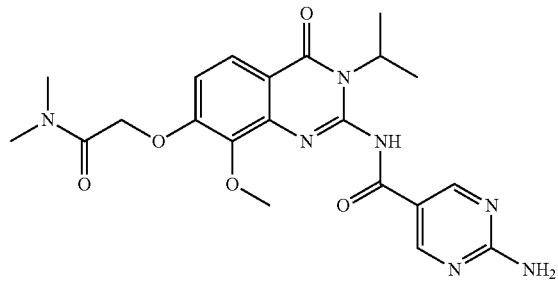 [SMILES: COc1c(OCC(=O)N(C)C)ccc2c(=O)n(C(C)C)c(NC(=O)c3cnc(N)nc3)nc12] |
| 8c-6 | 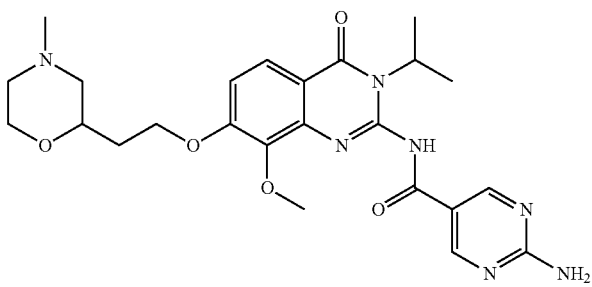 [SMILES: COc1c(OCCC2CN(C)CCO2)ccc2c(=O)n(C(C)C)c(NC(=O)c3cnc(N)nc3)nc12] |
| 8c-7 | 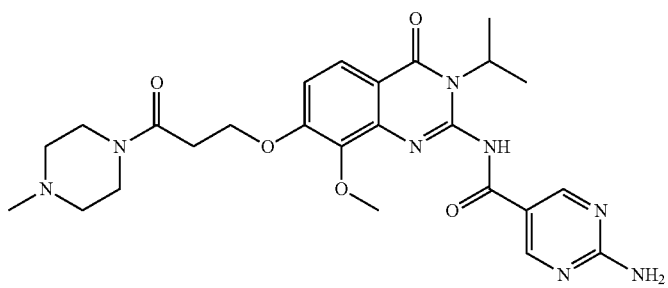 [SMILES: COc1c(OCCC(=O)N2CCN(C)CC2)ccc2c(=O)n(C(C)C)c(NC(=O)c3cnc(N)nc3)nc12] |
| 8c-8 | 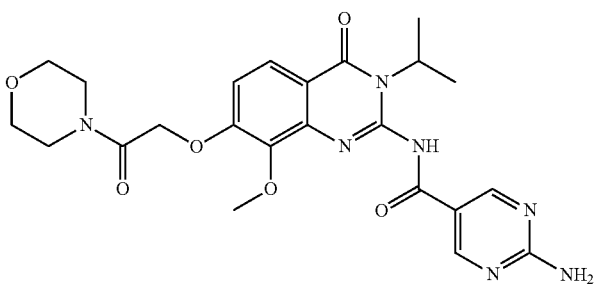 [SMILES: COc1c(OCC(=O)N2CCOCC2)ccc2c(=O)n(C(C)C)c(NC(=O)c3cnc(N)nc3)nc12] |
| 8c-9 | 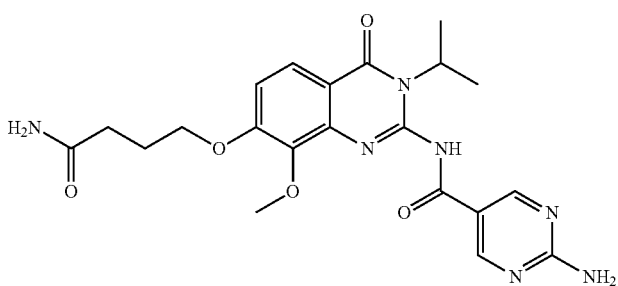 [SMILES: COc1c(OCCCC(N)=O)ccc2c(=O)n(C(C)C)c(NC(=O)c3cnc(N)nc3)nc12] |

| Compd. | Structure |
|---|---|
| 7d-1 | (structure) |
| 8d-1 | (structure) |
| 8d-2 | (structure) |
| 8d-3 | (structure) |
| 8d-4 | (structure) |
| 8d-5 | (structure) |
| 7e-1 | (structure) |

| Compd. | Structure |
|---|---|
| 8e-1 | 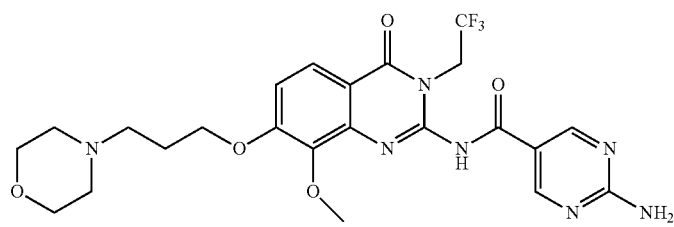 |
| 8e-2 | 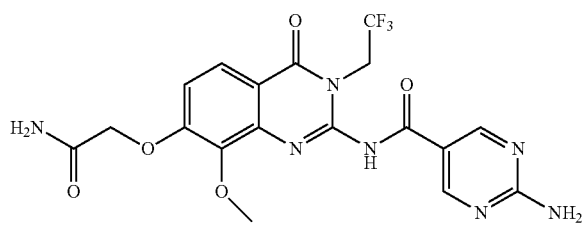 [SMILES: COc1c(OCC(N)=O)ccc2c(=O)n(CC(F)(F)F)c(NC(=O)c3cnc(N)nc3)nc12] |
| 8e-3 | 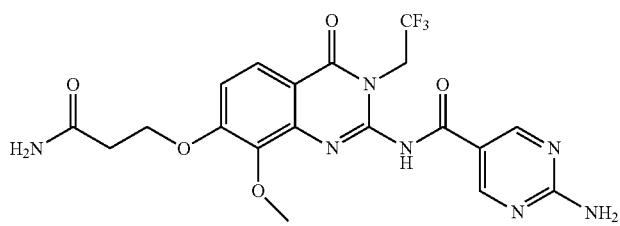 [SMILES: COc1c(OCCC(N)=O)ccc2c(=O)n(CC(F)(F)F)c(NC(=O)c3cnc(N)nc3)nc12] |
| 8e-4 | 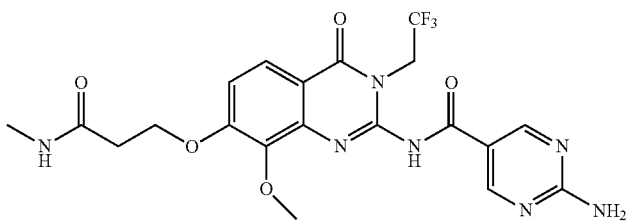 [SMILES: CNC(=O)CCOc1ccc2c(=O)n(CC(F)(F)F)c(NC(=O)c3cnc(N)nc3)nc2c1OC] |
| 8e-5 | 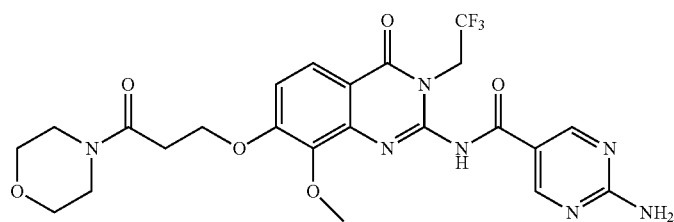 [SMILES: COc1c(OCCC(=O)N2CCOCC2)ccc2c(=O)n(CC(F)(F)F)c(NC(=O)c3cnc(N)nc3)nc12] |
| 7f-1 | 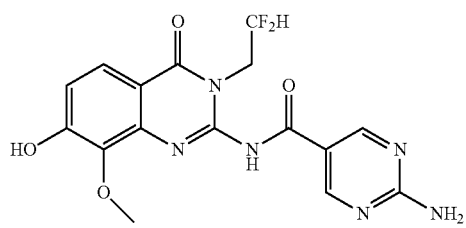 [SMILES: COc1c(O)ccc2c(=O)n(CC(F)F)c(NC(=O)c3cnc(N)nc3)nc12] |

-continued

| Compd. | Structure |
|---|---|
| 8f-1 | 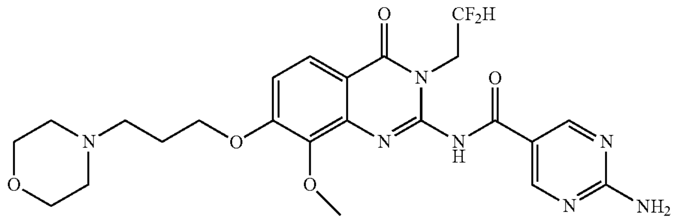 [SMILES: COc1c(OCCCN2CCOCC2)ccc2c(=O)n(CC(F)F)c(NC(=O)c3cnc(N)nc3)nc12] |
| 8f-2 | 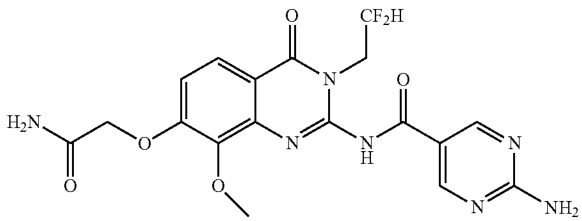 [SMILES: COc1c(OCC(N)=O)ccc2c(=O)n(CC(F)F)c(NC(=O)c3cnc(N)nc3)nc12] |
| 8f-3 | 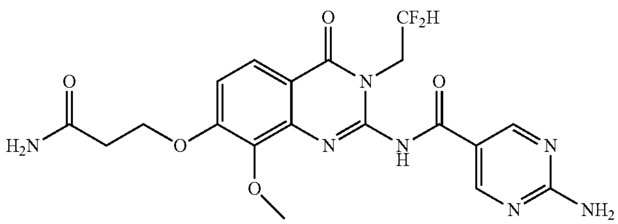 [SMILES: COc1c(OCCC(N)=O)ccc2c(=O)n(CC(F)F)c(NC(=O)c3cnc(N)nc3)nc12] |
| 7g-1 | 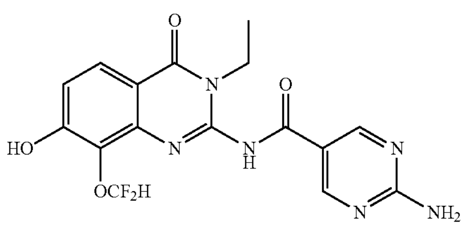 |
| 8g-1 | 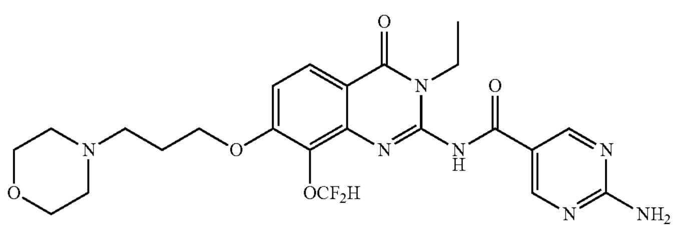 |
| 8g-2 | 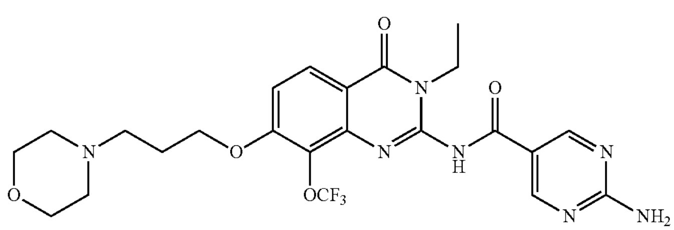 |
| 8g-3 | 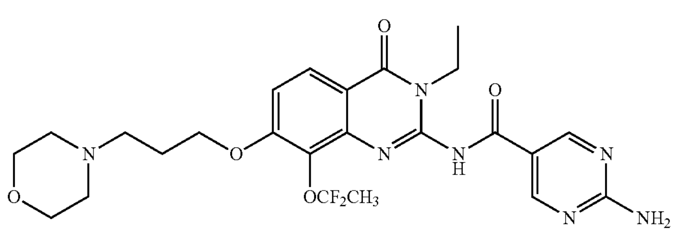 |

| Compd. | Structure |
|---|---|
| 8g-4 | 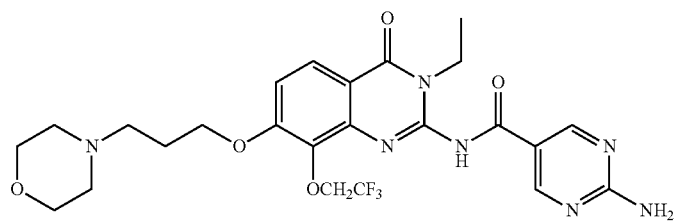 |
| 8g-5 | 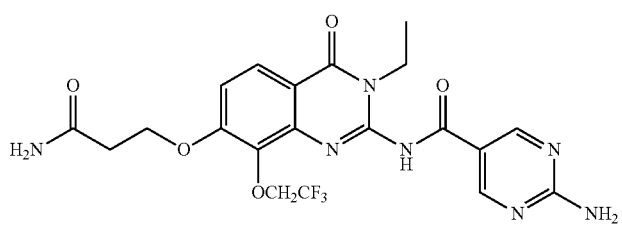 |
| 14a-1 | 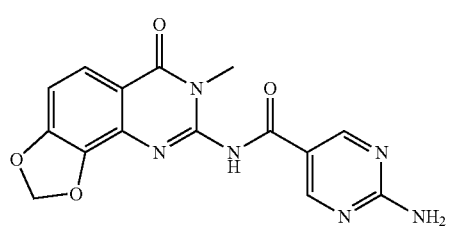 [SMILES: Cn1c(NC(=O)c2cnc(N)nc2)nc2c3c(ccc2c1=O)OCO3] |
| 14a-2 | 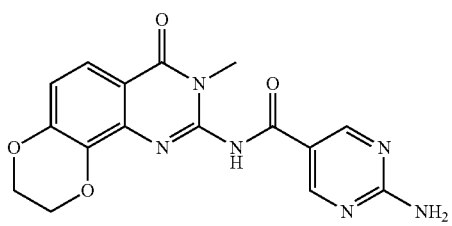 [SMILES: Cn1c(NC(=O)c2cnc(N)nc2)nc2c3c(ccc2c1=O)OCCO3] |
| 14a-3 | 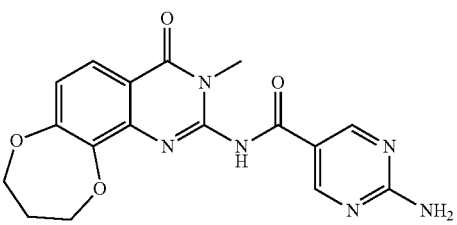 [SMILES: Cn1c(NC(=O)c2cnc(N)nc2)nc2c3c(ccc2c1=O)OCCCO3] |
| 14a-4 | 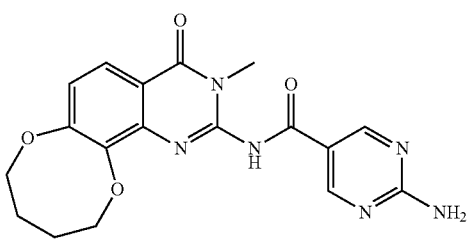 |

| Compd. | Structure |
|---|---|
| 14a-5 | 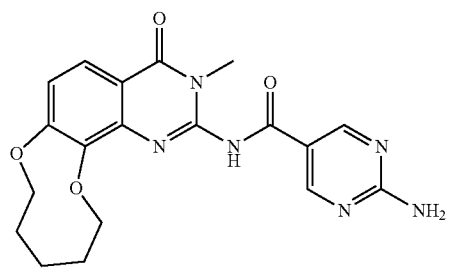 [SMILES: Cn1c(NC(=O)c2cnc(N)nc2)nc2c3c(ccc2c1=O)OCCCCCO3] |
| 14a-6 | 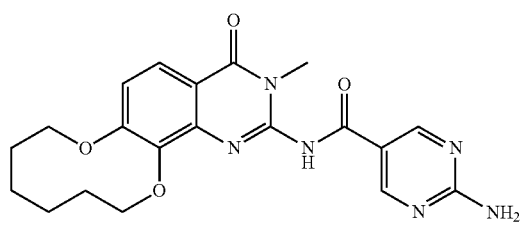 [SMILES: Cn1c(NC(=O)c2cnc(N)nc2)nc2c3c(ccc2c1=O)OCCCCCCO3] |
| 14a-7 | 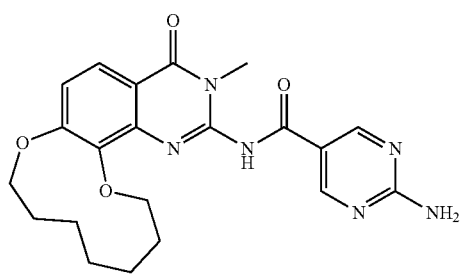 [SMILES: Cn1c(NC(=O)c2cnc(N)nc2)nc2c3c(ccc2c1=O)OCCCCCCCO3] |
| 14a-8 | 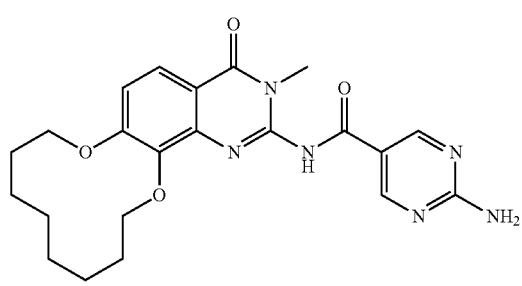 [SMILES: Cn1c(NC(=O)c2cnc(N)nc2)nc2c3c(ccc2c1=O)OCCCCCCCCO3] |
| 14a-9 | 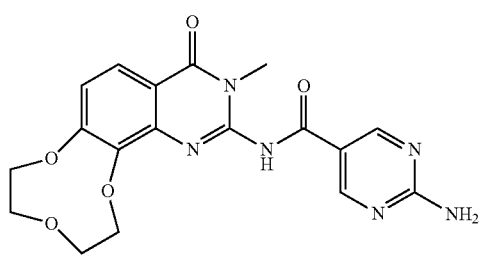 [SMILES: Cn1c(NC(=O)c2cnc(N)nc2)nc2c3c(ccc2c1=O)OCCOCCO3] |
| 14a-10 | 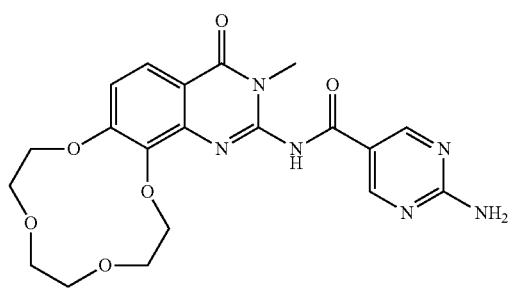 |

| Compd. | Structure |
|---|---|
| 14a-11 | 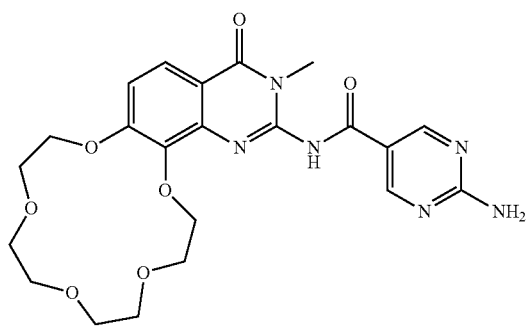 |
| 14a-12 | 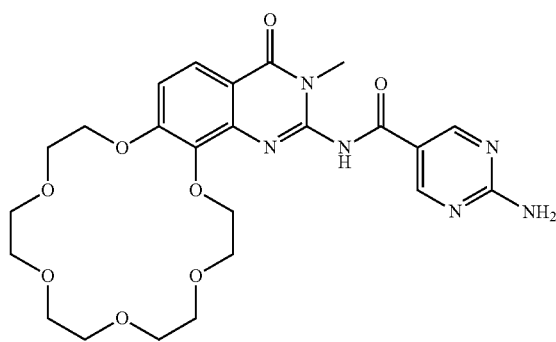 [SMILES: Cn1c(NC(=O)c2cnc(N)nc2)nc2c3c(ccc2c1=O)OCCOCCOCCOCCOCCO3] |
| 14b-1 | 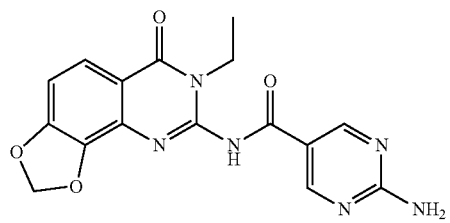 [SMILES: CCn1c(NC(=O)c2cnc(N)nc2)nc2c3c(ccc2c1=O)OCO3] |
| 14b-2 | 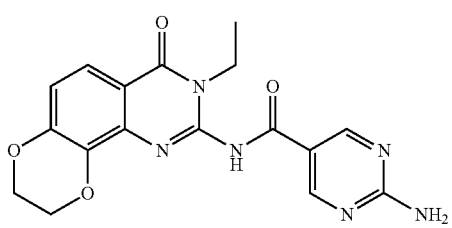 [SMILES: CCn1c(NC(=O)c2cnc(N)nc2)nc2c3c(ccc2c1=O)OCCO3] |
| 14b-3 | 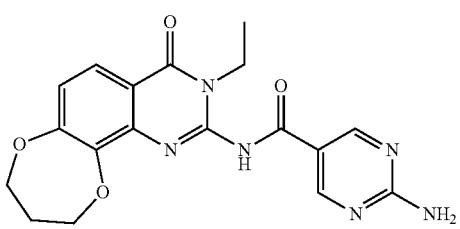 |

| Compd. | Structure |
|---|---|
| 14b-4 | 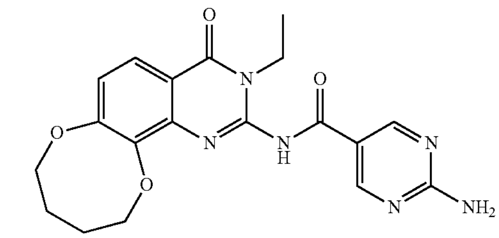 [SMILES: CCn1c(NC(=O)c2cnc(N)nc2)nc2c3c(ccc2c1=O)OCCCCO3] |
| 14b-5 | 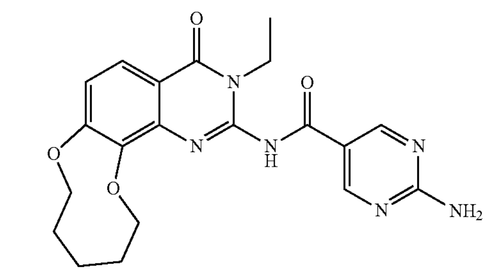 [SMILES: CCn1c(NC(=O)c2cnc(N)nc2)nc2c3c(ccc2c1=O)OCCCCCO3] |
| 14b-6 | 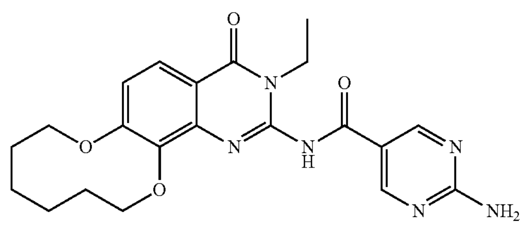 |
| 14b-7 | 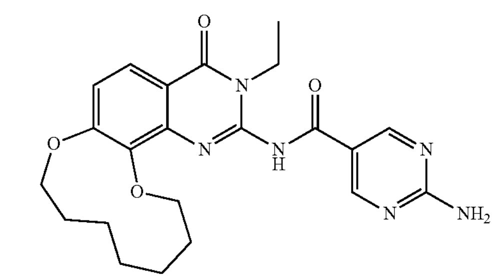 |
| 14b-8 | 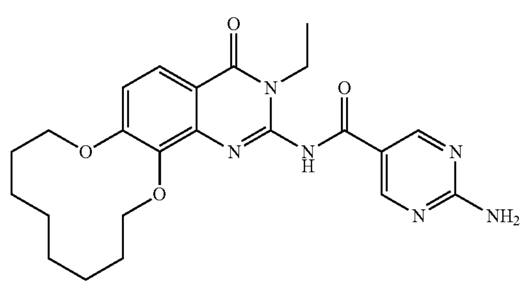 [SMILES: CCn1c(NC(=O)c2cnc(N)nc2)nc2c3c(ccc2c1=O)OCCCCCCCCO3] |
| 14b-9 | 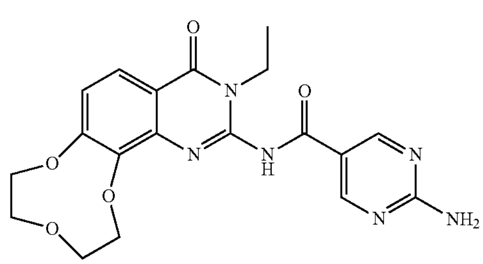 |

| Compd. | Structure |
|---|---|
| 14b-10 | 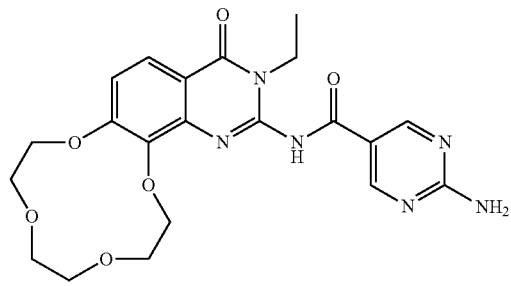 |
| 14b-11 | 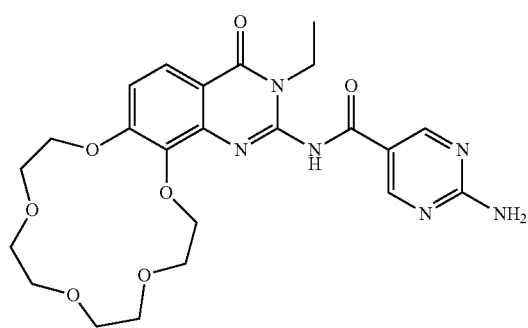 [SMILES: CCn1c(NC(=O)c2cnc(N)nc2)nc2c3c(ccc2c1=O)OCCOCCOCCOCCO3] |
| 14b-12 | 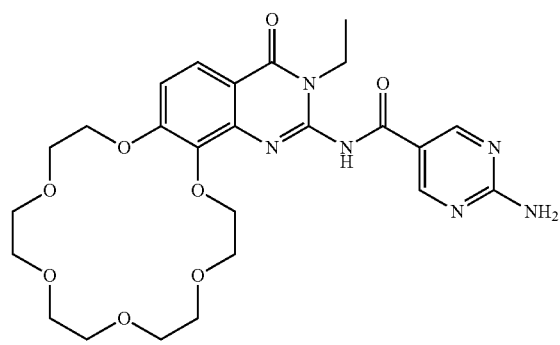 |
| 7'a-1 | 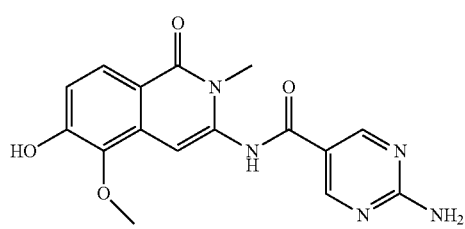 [SMILES: COc1c(O)ccc2c(=O)n(C)c(NC(=O)c3cnc(N)nc3)cc12] |
| 8a'-1 | 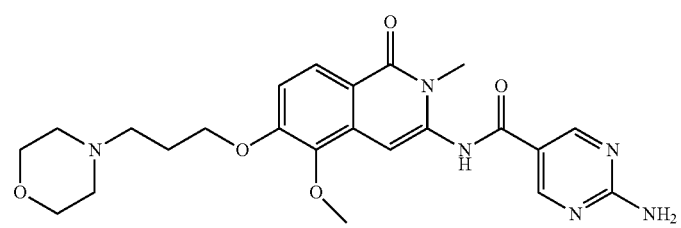 |

-continued
| Compd. | Structure |
|---|---|
| 8a'-2 | 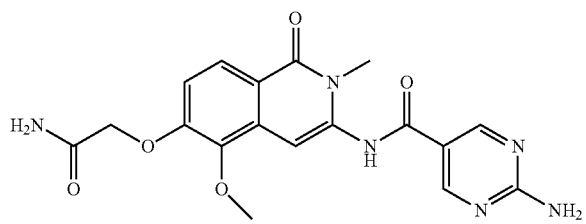 |
| 8a'-3 | 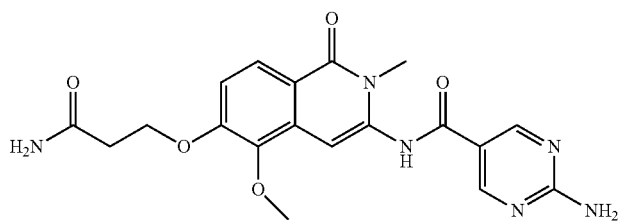 [SMILES: COc1c(OCCC(N)=O)ccc2c(=O)n(C)c(NC(=O)c3cnc(N)nc3)cc12] |
| 8a'-4 | 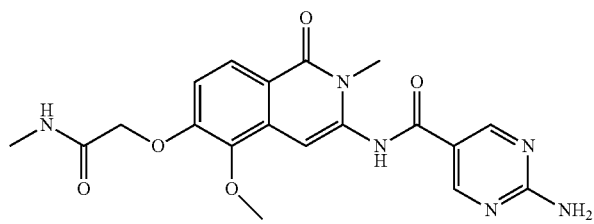 [SMILES: CNC(=O)COc1ccc2c(=O)n(C)c(NC(=O)c3cnc(N)nc3)cc2c1OC] |
| 8a'-5 | 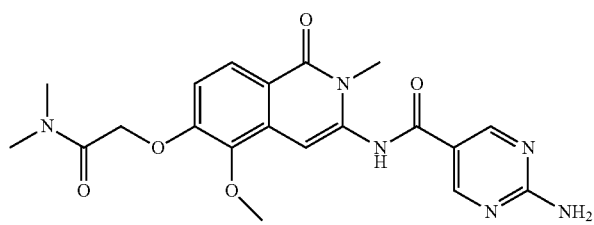 [SMILES: COc1c(OCC(=O)N(C)C)ccc2c(=O)n(C)c(NC(=O)c3cnc(N)nc3)cc12] |
| 8a'-6 | 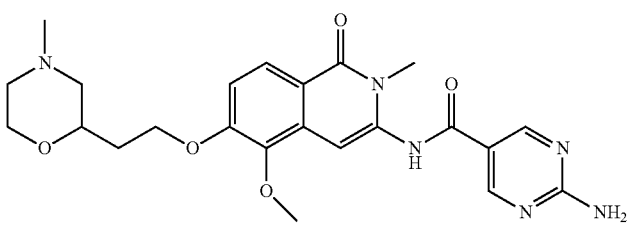 [SMILES: COc1c(OCCC2CN(C)CCO2)ccc2c(=O)n(C)c(NC(=O)c3cnc(N)nc3)cc12] |
| 8a'-7 | 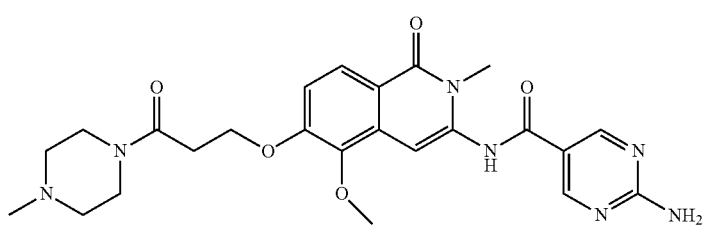 [SMILES: COc1c(OCCC(=O)N2CCN(C)CC2)ccc2c(=O)n(C)c(NC(=O)c3cnc(N)nc3)cc12] |

| Compd. | Structure |
|---|---|
| 8a'-8 | 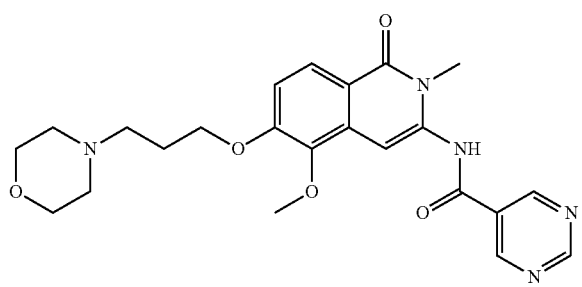 [SMILES: COc1c(OCCCN2CCOCC2)ccc2c(=O)n(C)c(NC(=O)c3cncnc3)cc12] |
| 8a'-9 | 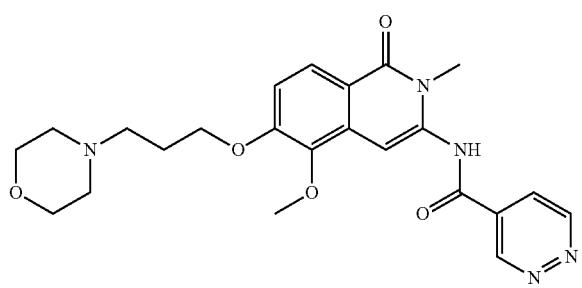 [SMILES: COc1c(OCCCN2CCOCC2)ccc2c(=O)n(C)c(NC(=O)c3ccnnc3)cc12] |
| 8a'-10 | 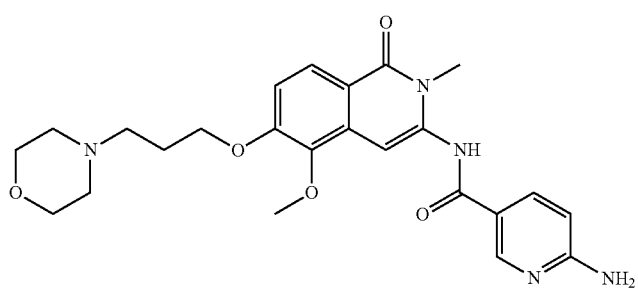 [SMILES: COc1c(OCCCN2CCOCC2)ccc2c(=O)n(C)c(NC(=O)c3ccc(N)nc3)cc12] |
| 8a'-11 | 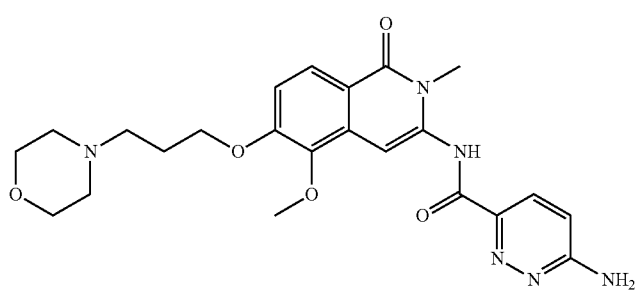 [SMILES: COc1c(OCCCN2CCOCC2)ccc2c(=O)n(C)c(NC(=O)c3ccc(N)nn3)cc12] |
| 8a'-12 | 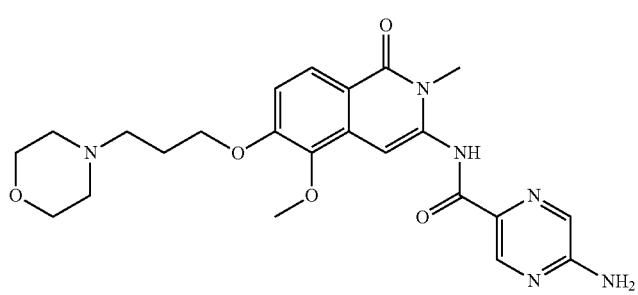 [SMILES: COc1c(OCCCN2CCOCC2)ccc2c(=O)n(C)c(NC(=O)c3cnc(N)cn3)cc12] |

| Compd. | Structure |
|---|---|
| 8a'-13 | 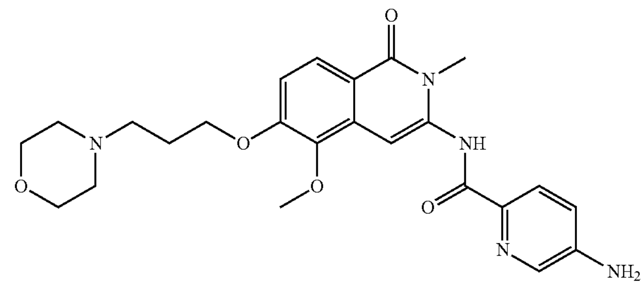 [SMILES: COc1c(OCCCN2CCOCC2)ccc2c(=O)n(C)c(NC(=O)c3ccc(N)cn3)cc12] |
| 8a'-14 | 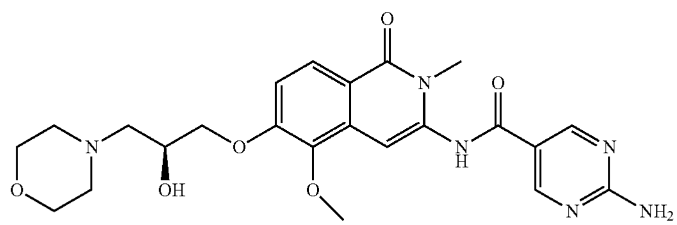 |
| 8a'-15 | 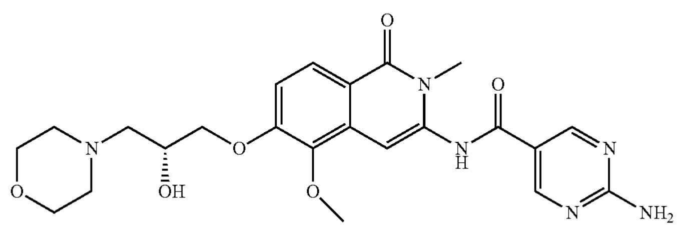 [SMILES: COc1c(OC[C@H](O)CN2CCOCC2)ccc2c(=O)n(C)c(NC(=O)c3cnc(N)nc3)cc12] |
| 8a'-16 | 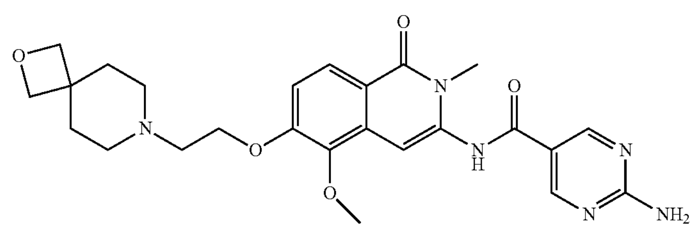 |
| 8a'-17 | 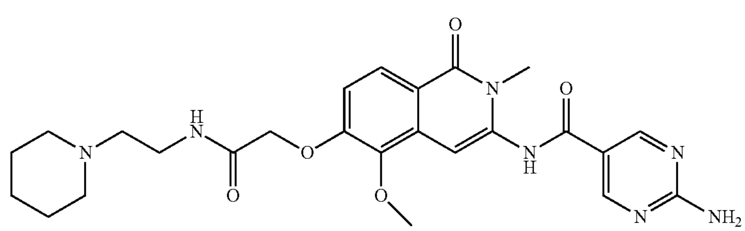 [SMILES: COc1c(OCC(=O)NCCN2CCCCC2)ccc2c(=O)n(C)c(NC(=O)c3cnc(N)nc3)cc12] |
| 8a'-18 | 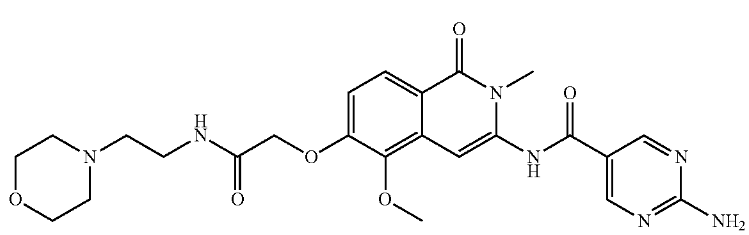 [SMILES: COc1c(OCC(=O)NCCN2CCOCC2)ccc2c(=O)n(C)c(NC(=O)c3cnc(N)nc3)cc12] |

| Compd. | Structure |
|---|---|
| 8a'-19 | 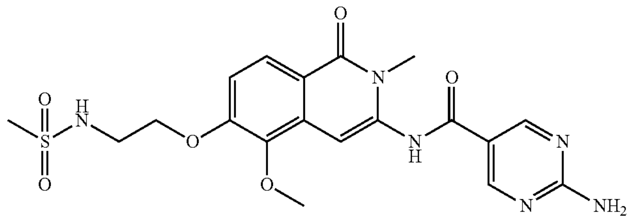 [SMILES: COc1c(OCCNS(C)(=O)=O)ccc2c(=O)n(C)c(NC(=O)c3cnc(N)nc3)cc12] |
| 7b'-1 | 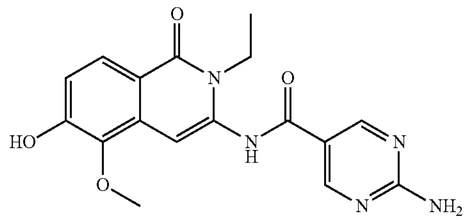 [SMILES: CCn1c(NC(=O)c2cnc(N)nc2)cc2c(OC)c(O)ccc2c1=O] |
| 8b'-1 | 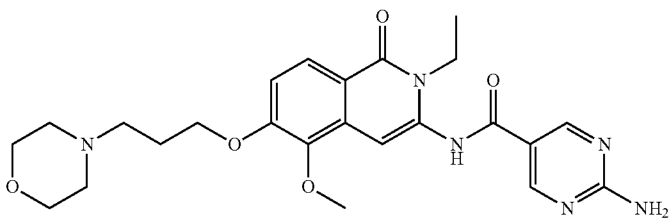 [SMILES: CCn1c(NC(=O)c2cnc(N)nc2)cc2c(OC)c(OCCCN3CCOCC3)ccc2c1=O] |
| 8b'-2 | 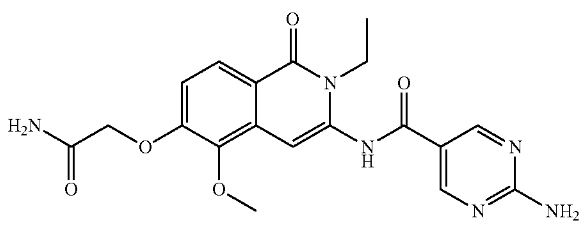 [SMILES: CCn1c(NC(=O)c2cnc(N)nc2)cc2c(OC)c(OCC(N)=O)ccc2c1=O] |
| 8b'-3 | 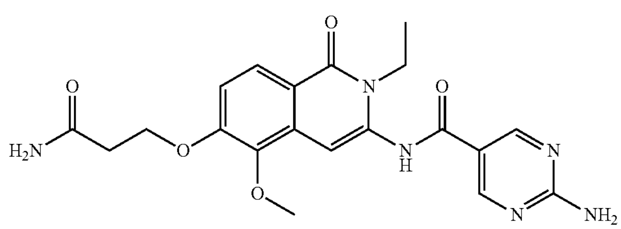 [SMILES: CCn1c(NC(=O)c2cnc(N)nc2)cc2c(OC)c(OCCC(N)=O)ccc2c1=O] |
| 8b'-4 | 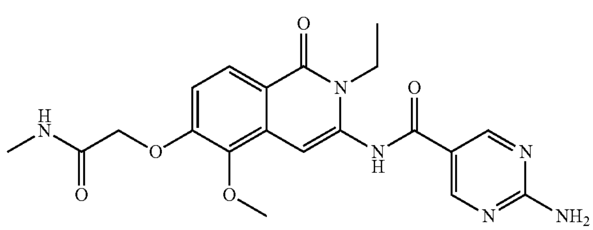 |
| 8b'-5 | 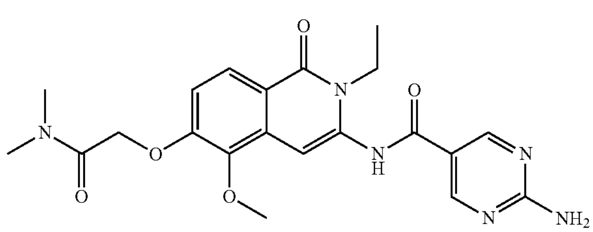 |

| Compd. | Structure |
|---|---|
| 8b'-6 | 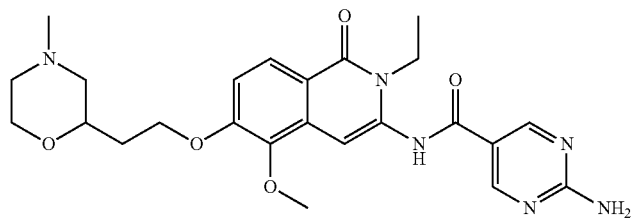 [SMILES: CCn1c(NC(=O)c2cnc(N)nc2)cc2c(OC)c(OCCC3CN(C)CCO3)ccc2c1=O] |
| 8b'-7 | 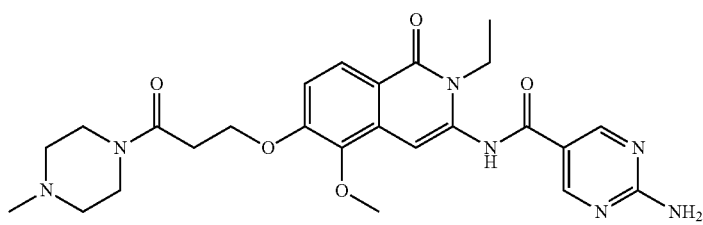 [SMILES: CCn1c(NC(=O)c2cnc(N)nc2)cc2c(OC)c(OCCC(=O)N3CCN(C)CC3)ccc2c1=O] |
| 8b'-8 | 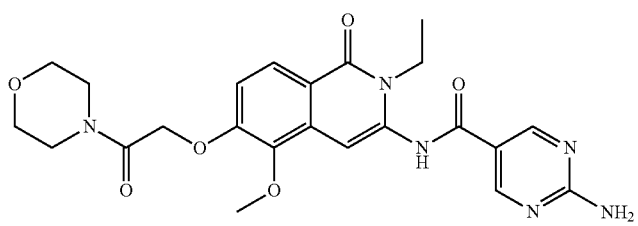 [SMILES: CCn1c(NC(=O)c2cnc(N)nc2)cc2c(OC)c(OCC(=O)N3CCOCC3)ccc2c1=O] |
| 8b'-9 | 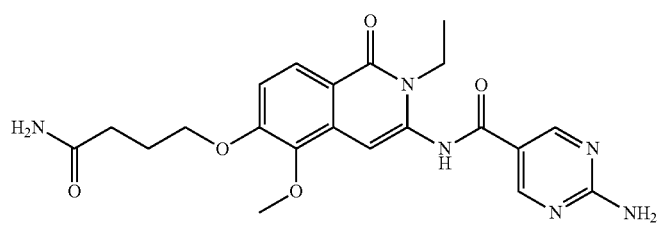 [SMILES: CCn1c(NC(=O)c2cnc(N)nc2)cc2c(OC)c(OCCCC(N)=O)ccc2c1=O] |
| 8b'-10 | 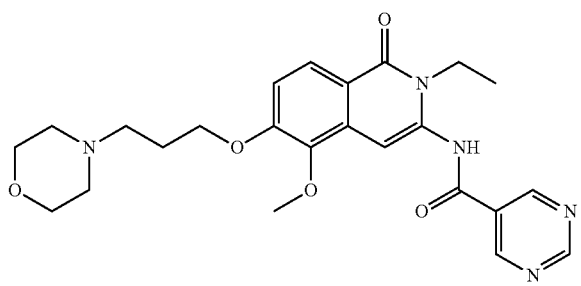 [SMILES: CCn1c(NC(=O)c2cncnc2)cc2c(OC)c(OCCCN3CCOCC3)ccc2c1=O] |
| 8b'-11 | 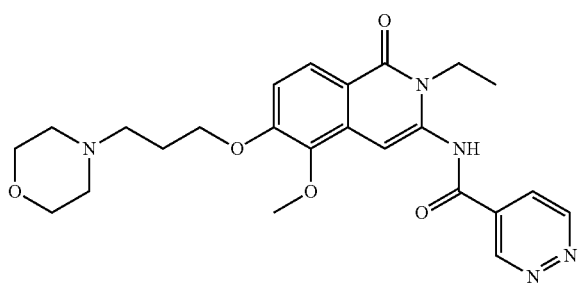 [SMILES: CCn1c(NC(=O)c2ccnnc2)cc2c(OC)c(OCCCN3CCOCC3)ccc2c1=O] |

-continued
| Compd. | Structure |
|---|---|
| 8b'-12 | 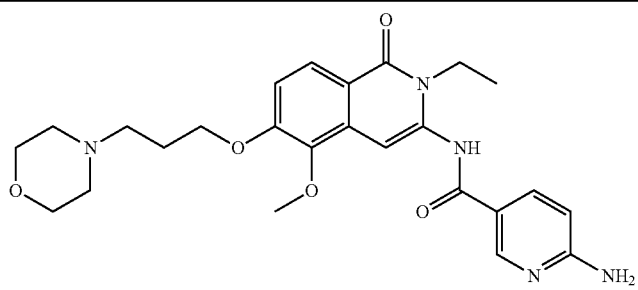 |
| 8b'-13 | 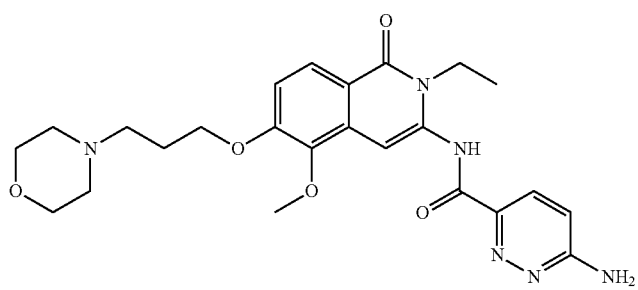 |
| 8b'-14 | 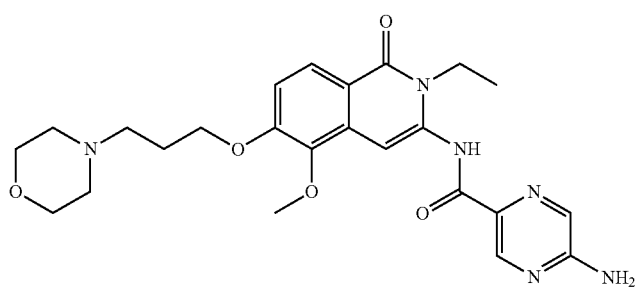 [SMILES: CCn1c(NC(=O)c2cnc(N)cn2)cc2c(OC)c(OCCCN3CCOCC3)ccc2c1=O] |
| 8b'-15 | 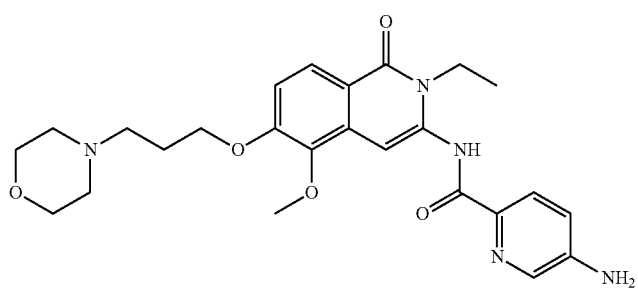 |
| 8b'-16 | 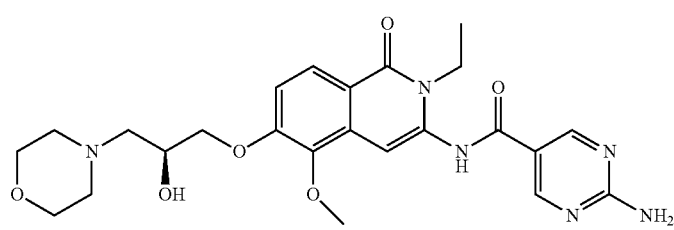 [SMILES: CCn1c(NC(=O)c2cnc(N)nc2)cc2c(OC)c(OC[C@@H](O)CN3CCOCC3)ccc2c1=O] |
| 8b'-17 | 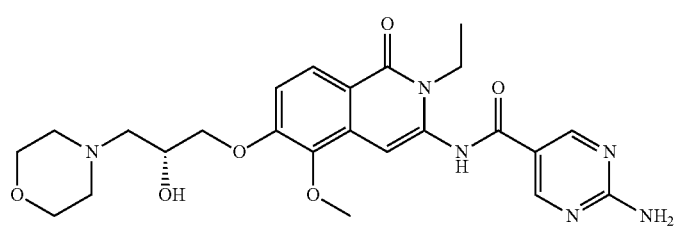 [SMILES: CCn1c(NC(=O)c2cnc(N)nc2)cc2c(OC)c(OC[C@H](O)CN3CCOCC3)ccc2c1=O] |

| Compd. | Structure |
|---|---|
| 8b'-18 | 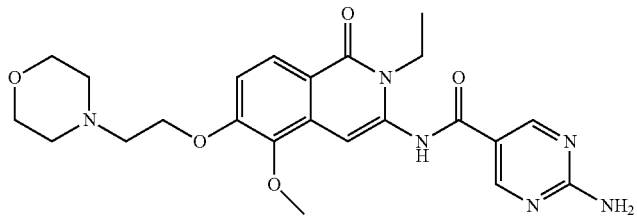 [SMILES: CCn1c(NC(=O)c2cnc(N)nc2)cc2c(OC)c(OCCN3CCOCC3)ccc2c1=O] |
| 8b'-19 | 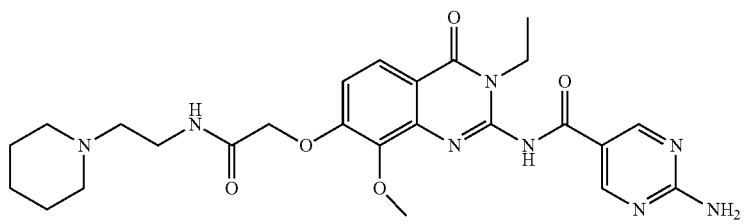 [SMILES: CCn1c(NC(=O)c2cnc(N)nc2)nc2c(OC)c(OCC(=O)NCCN3CCCCC3)ccc2c1=O] |
| 8b'-20 | 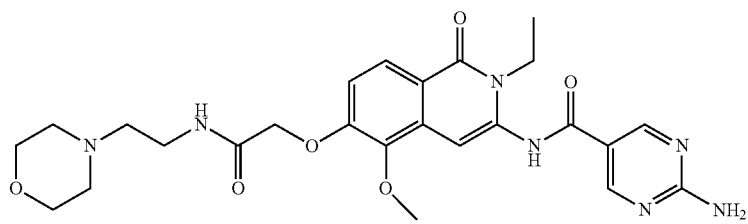 [SMILES: CCn1c(NC(=O)c2cnc(N)nc2)cc2c(OC)c(OCC(=O)NCCN3CCOCC3)ccc2c1=O] |
| 8b'-21 | 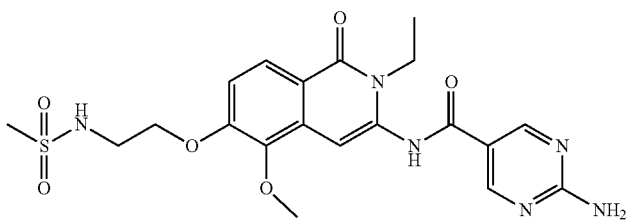 |
| 14a'-1 | 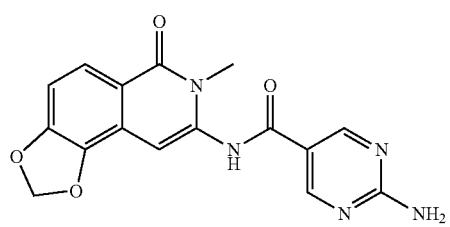 |
| 14a'-2 | 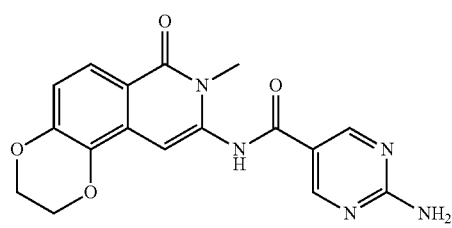 |

| Compd. | Structure |
|---|---|
| 14a'-3 | 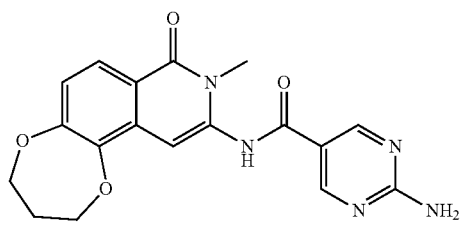 |
| 14a'-4 | 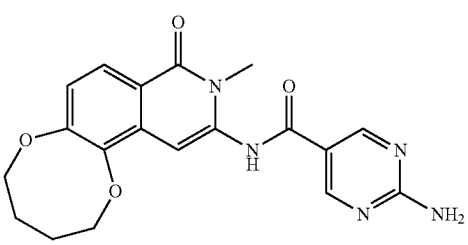 [SMILES: Cn1c(NC(=O)c2cnc(N)nc2)cc2c3c(ccc2c1=O)OCCCCO3] |
| 14a'-5 | 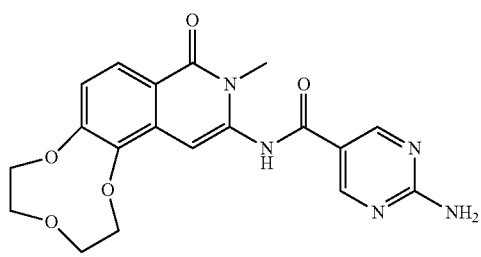 [SMILES: Cn1c(NC(=O)c2cnc(N)nc2)cc2c3c(ccc2c1=O)OCCOCCO3] |
| 14a'-6 | 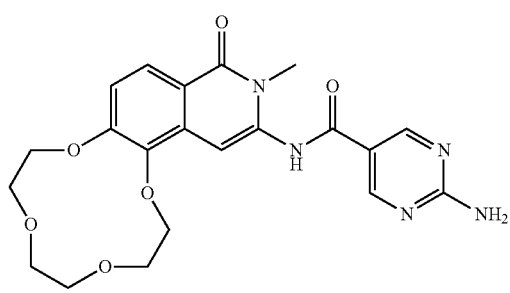 |
| 14a'-7 | 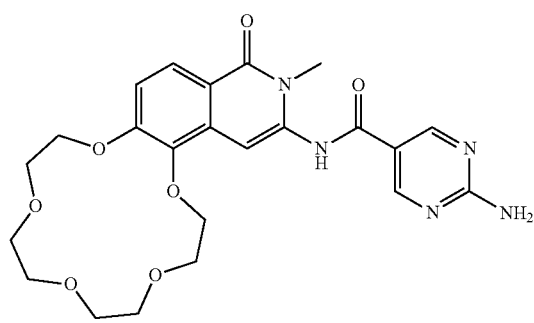 [SMILES: Cn1c(NC(=O)c2cnc(N)nc2)cc2c3c(ccc2c1=O)OCCOCCOCCOCCO3] |

-continued
| Compd. | Structure |
|---|---|
| 14a'-8 | 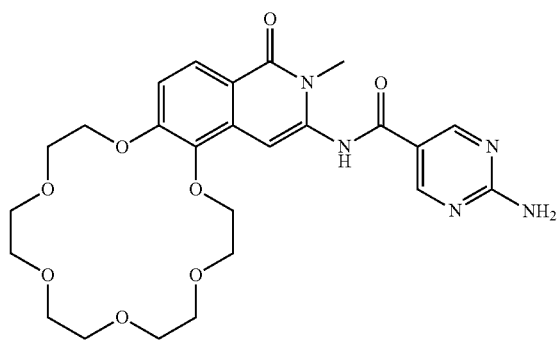 |
| 14b'-1 | 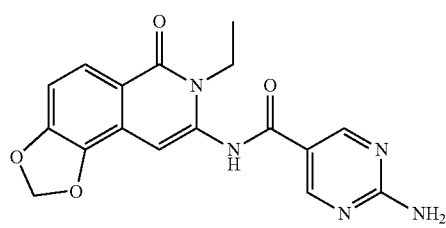 |
| 14b'-2 | 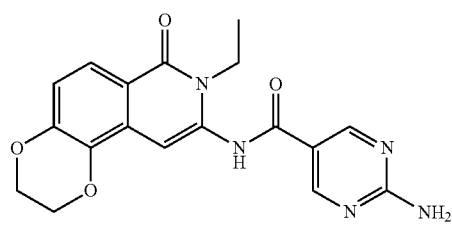 [SMILES: CCn1c(NC(=O)c2cnc(N)nc2)cc2c3c(ccc2c1=O)OCCO3] |
| 14b'-3 | 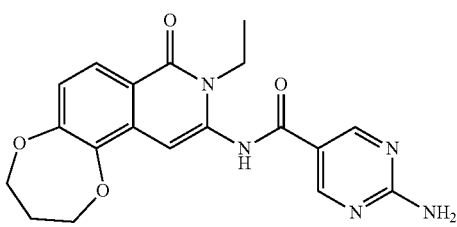 |
| 14b'-4 | 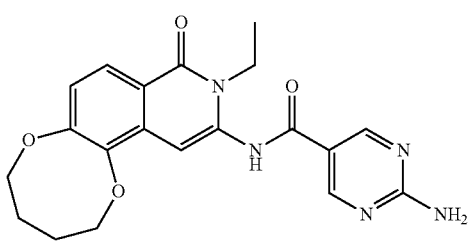 [SMILES: CCn1c(NC(=O)c2cnc(N)nc2)cc2c3c(ccc2c1=O)OCCCCO3] |
| 14b'-5 | 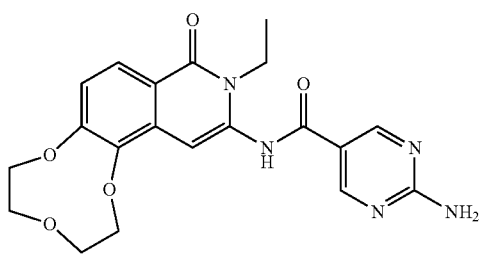 [SMILES: CCn1c(NC(=O)c2cnc(N)nc2)cc2c3c(ccc2c1=O)OCCOCCO3] |

| Compd. | Structure |
|---|---|
| 14b'-6 | (structure) |
| 14b'-7 | (structure) |
| 14b'-8 | (structure) |

7. The aminoquinazolinone or aminoisoquinolinone compound according to claim 1, characterized in that the salts formed with the compounds comprise hydrochloride, hydrobromide, methanesulfonate, sulfate, fumerate, tartrate, maleate, malate, or citrate.

8. A method for treating tumor and inflammation, comprising administration of the aminoquinazolinone or aminoisoquinolinone compound according to claim 1 to a patient in need, wherein the tumor is leukemia, lymphoma, myelodysplasia, non-Hodgkin's lymphoma tumor, multiple myeloma, breast cancer, sarcoma, lung cancer, prostate cancer, colon cancer, rectal cancer, kidney cancer, pancreatic cancer, neuroblastoma, glioma, head cancer, neck cancer, thyroid cancer, liver cancer, ovarian cancer, cervical cancer, endometrial cancer, testicular cancer, bladder cancer, esophageal cancer, gastric cancer, nasopharyngeal cancer, buccal cancer, oral cancer, gastrointestinal stromal tumor, or skin cancer; the inflammatory diseases are allergy, asthma, rheumatoid arthritis, osteoarthritis, allergic conjunctivitis, allergic keratitis, chronic obstructive pulmonary disease, lupus erythematosus, psoriasis, multiple sclerosis and end-stage renal disease; the compounds comprise pharmaceutically acceptable salts and solvates.

* * * * *